(12) United States Patent
Fan et al.

(10) Patent No.: US 11,713,307 B2
(45) Date of Patent: Aug. 1, 2023

(54) HETEROARYL-BIPHENYL AMIDES FOR THE TREATMENT OF PD-L1 DISEASES

(71) Applicant: CHEMOCENTRYX, INC., Mountain View, CA (US)

(72) Inventors: Pingchen Fan, Fremont, CA (US); Christopher W. Lange, Hayward, CA (US); Rebecca M. Lui, Mountain View, CA (US); Darren J. McMurtrie, Sunnyvale, CA (US); Ryan J. Scamp, Fremont, CA (US); Ju Yang, Palo Alto, CA (US); Yibin Zeng, Foster City, CA (US); Penglie Zhang, Foster City, CA (US)

(73) Assignee: CHEMOCENTRYX, INC., Thousand Oaks, CA (US)

( * ) Notice: Subject to any disclaimer, the term of this patent is extended or adjusted under 35 U.S.C. 154(b) by 13 days.

(21) Appl. No.: 17/071,077

(22) Filed: Oct. 15, 2020

(65) Prior Publication Data

US 2021/0130325 A1   May 6, 2021

Related U.S. Application Data

(60) Provisional application No. 63/057,460, filed on Jul. 28, 2020, provisional application No. 63/042,796, filed on Jun. 23, 2020, provisional application No. 62/915,779, filed on Oct. 16, 2019.

(51) Int. Cl.

| | | |
|---|---|---|
| *C07D 401/12* | (2006.01) | |
| *C07D 401/14* | (2006.01) | |
| *C07D 403/14* | (2006.01) | |
| *C07D 405/14* | (2006.01) | |
| *C07D 487/10* | (2006.01) | |

(52) U.S. Cl.
CPC ......... *C07D 401/14* (2013.01); *C07D 401/12* (2013.01); *C07D 403/14* (2013.01); *C07D 405/14* (2013.01); *C07D 487/10* (2013.01)

(58) Field of Classification Search
CPC .. C07D 401/12; C07D 401/14; C07D 403/14; C07D 405/14

See application file for complete search history.

(56) References Cited

U.S. PATENT DOCUMENTS

| | | | |
|---|---|---|---|
| 10,654,815 | B2 | 5/2020 | Yang et al. |
| 10,815,208 | B2 | 10/2020 | Feng et al. |
| 10,882,833 | B2 | 1/2021 | Feng et al. |
| 10,941,129 | B2 | 3/2021 | Feng et al. |
| 10,975,049 | B2 | 4/2021 | Feng et al. |
| 2014/0275077 | A1 | 9/2014 | Dandu et al. |
| 2014/0349998 | A1 | 11/2014 | Ahern et al. |
| 2017/0107216 | A1 | 4/2017 | Wu et al. |
| 2017/0145025 | A1 | 5/2017 | Li et al. |
| 2017/0174671 | A1 | 6/2017 | Wu et al. |
| 2017/0174679 | A1 | 6/2017 | Lajkiewicz et al. |
| 2018/0118718 | A1 | 5/2018 | Fabritius et al. |
| 2018/0179197 | A1 | 6/2018 | Wu et al. |
| 2019/0308957 | A1 | 10/2019 | Wang et al. |
| 2020/0383979 | A1 | 12/2020 | Fan et al. |
| 2020/0392083 | A1 | 12/2020 | Jiang et al. |
| 2021/0002229 | A1 | 1/2021 | Malathong et al. |
| 2021/0032270 | A1 | 2/2021 | Yang et al. |
| 2021/0130347 | A1 | 5/2021 | Fan et al. |
| 2021/0347785 | A1 | 11/2021 | Zhang et al. |
| 2021/0393759 | A1 | 12/2021 | Li et al. |
| 2023/0044941 | A1 | 2/2023 | Fan et al. |

FOREIGN PATENT DOCUMENTS

| | | |
|---|---|---|
| CN | 108395443 A | 8/2018 |
| CN | 108863963 A | 11/2018 |
| CN | 109336857 A | 2/2019 |
| CN | 109438263 A | 3/2019 |

(Continued)

OTHER PUBLICATIONS

International Search Report and Written Opinion dated Sep. 14, 2020 corresponding to PCT/US2020/032904 filed May 14, 2020; 10 pages.
International Search Report dated Feb. 9, 2021 corresponding to PCT/US2020/055669 filed Oct. 15, 2020; 12 pages.
International Search Report dated Feb. 9, 2021 corresponding to PCT/US2020/055672 filed Oct. 15, 2020; 11 pages.
International Search Report dated Feb. 12, 2021 corresponding to PCT/US2020/038586 filed Jun. 19, 2020; 11 pages.
International Search Report dated Oct. 4, 2021 corresponding to PCT/US2021/038339 filed Jun. 22, 2021; 8 pages.

(Continued)

*Primary Examiner* — Brian E McDowell
(74) *Attorney, Agent, or Firm* — Amy C. Madl

(57) ABSTRACT

Compounds are provided that are useful as immunomodulators. The compounds have the Formula (I)

(I)

including stereoisomers and pharmaceutically acceptable salts thereof, wherein $R^{2a}$, $R^{2b}$, $R^3$, $R^{3a}$, $R^4$, $R^6$, $R^7$, $R^8$, A, Z, $X^1$ and n are as defined herein. Methods associated with preparation and use of such compounds, as well as pharmaceutical compositions comprising such compounds, are also disclosed.

28 Claims, No Drawings

(56) References Cited

FOREIGN PATENT DOCUMENTS

| | | |
|---|---|---|
| CN | 109503546 A | 3/2019 |
| CN | 109665968 A | 4/2019 |
| CN | 109721527 A | 5/2019 |
| CN | 109776377 A | 5/2019 |
| CN | 109776445 A | 5/2019 |
| CN | 106674136 B | 7/2019 |
| CN | 110128415 A | 8/2019 |
| CN | 110200959 A | 9/2019 |
| EP | 3 733 659 A1 | 11/2020 |
| WO | 2007/126957 A2 | 11/2007 |
| WO | 2007/126957 A3 | 11/2007 |
| WO | 2008/008059 A1 | 1/2008 |
| WO | 2015/033299 A1 | 3/2015 |
| WO | 2015/033301 A1 | 3/2015 |
| WO | 2015/034820 A1 | 3/2015 |
| WO | 2015/160641 A2 | 10/2015 |
| WO | 2015/160641 A3 | 10/2015 |
| WO | 2017/066227 A1 | 4/2017 |
| WO | 2017/070089 A1 | 4/2017 |
| WO | 2017/106634 A1 | 6/2017 |
| WO | 2017/112730 A1 | 6/2017 |
| WO | 2017/118762 A1 | 7/2017 |
| WO | 2017/192961 A1 | 11/2017 |
| WO | 2017/202273 A1 | 11/2017 |
| WO | 2017/202274 A1 | 11/2017 |
| WO | 2017/202275 A1 | 11/2017 |
| WO | 2017/202276 A1 | 11/2017 |
| WO | 2017/205464 A1 | 11/2017 |
| WO | 2017/222976 A1 | 12/2017 |
| WO | 2018/005374 A1 | 1/2018 |
| WO | 2018/006795 A1 | 1/2018 |
| WO | 2018/009505 A1 | 1/2018 |
| WO | 2018/013789 A1 | 1/2018 |
| WO | 2018/044783 A1 | 3/2018 |
| WO | 2018/044963 A1 | 3/2018 |
| WO | 2018/045142 A1 | 3/2018 |
| WO | 2018/118848 A1 | 6/2018 |
| WO | 2018/119221 A1 | 6/2018 |
| WO | 2018/119224 A1 | 6/2018 |
| WO | 2018/119236 A1 | 6/2018 |
| WO | 2018/119263 A1 | 6/2018 |
| WO | 2018/119266 A1 | 6/2018 |
| WO | 2018/119286 A1 | 6/2018 |
| WO | 2018/121560 A1 | 7/2018 |
| WO | 2018/183171 A1 | 10/2018 |
| WO | 2018/195321 A1 | 10/2018 |
| WO | 2018/196768 A1 | 11/2018 |
| WO | 2019/034172 A1 | 2/2019 |
| WO | 2019/070643 A1 | 4/2019 |
| WO | 2019/076343 A1 | 4/2019 |
| WO | 2019/087214 A1 | 5/2019 |
| WO | 2019/120297 A1 | 6/2019 |
| WO | 2019/128918 A1 | 7/2019 |
| WO | 2019/147662 A1 | 8/2019 |
| WO | 2019/149183 A1 | 8/2019 |
| WO | 2019/160882 A1 | 8/2019 |
| WO | 2019/169123 A1 | 9/2019 |
| WO | 2019/174533 A1 | 9/2019 |
| WO | 2019/175897 A1 | 9/2019 |
| WO | 2019/191707 A1 | 10/2019 |
| WO | 2019/192506 A1 | 10/2019 |
| WO | 2019/204609 A1 | 10/2019 |
| WO | 2019/217821 A1 | 11/2019 |
| WO | 2020/011209 A1 | 1/2020 |
| WO | 2020/011243 A1 | 1/2020 |
| WO | 2020/014643 A1 | 1/2020 |
| WO | 2020/015716 A1 | 1/2020 |
| WO | 2020/015717 A1 | 1/2020 |
| WO | 2020/025030 A1 | 2/2020 |

OTHER PUBLICATIONS

Extended European Search Report dated Nov. 30, 2022 corresponding to EP 20805234.0 filed May 14, 2020; 8 pages.
Wang, Tianyu et al., "Development of Inhibitors of the Programmed Cell Death-1/Programmed Cell Death-Ligand 1 Signaling Pathway," *J. Med. Chem.* (2019) 62:1715-1730.

HETEROARYL-BIPHENYL AMIDES FOR THE TREATMENT OF PD-L1 DISEASES

CROSS-REFERENCES TO RELATED APPLICATIONS

This application claims the benefit of priority under 35 U.S.C § 119(e) to U.S. Provisional Application Ser. No. 62/915,779 filed Oct. 16, 2019; 63/042,796 filed Jun. 23, 2020; and 63/057,460 filed Jul. 28, 2020, the disclosures of each are incorporated herein by reference in their entirety.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE DISCLOSURE

Programmed cell death protein-1 (PD-1) is a member of the CD28 superfamily that delivers negative signals upon interaction with its two ligands, PD-L1 or PD-L2. PD-1 and its ligands are broadly expressed and exert a wide range of immunoregulatory roles in T cell activation and tolerance. PD-1 and its ligands are involved in attenuating infectious immunity and tumor immunity, and facilitating chronic infection and tumor progression.

Modulation of the PD-1 pathway has therapeutic potential in various human diseases (Hyun-Tak Jin et al., *Curr Top Microbiol Immunol.* (2011); 350:17-37). Blockade of the PD-1 pathway has become an attractive target in cancer therapy. Therapeutic antibodies that block the programmed cell death protein-1 (PD-1) immune checkpoint pathway prevent T-cell down regulation and promote immune responses against cancer. Several PD-1 pathway inhibitors have shown robust activity in various phases of clinical trials (R D Harvey, *Clinical Pharmacology and Therapeutics* (2014); 96(2), 214-223).

Agents that block the interaction of PD-L1 with either PD-1 or CD80 are desired. Some antibodies have been developed and commercialized. A few patent applications disclosing non-peptidic small molecules have been published (WO 2015/160641, WO 2015/034820, and WO 2017/066227 and WO2018/009505 from BMS; WO 2015/033299 and WO 2015/033301 from Aurigene; WO 2017/070089, US 2017/0145025, WO 2017/106634, US2017/0174679, WO2017/192961, WO2017/222976, WO2017/205464, WO2017/112730, WO2017/041899 and WO2018/013789 from Incyte, WO2018/006795 from Maxinovel and WO2018/005374 from us, ChemoCentryx). However there is still a need for alternative compounds such as small molecules as inhibitors of PD-L1, and which may have advantageous characteristics in term of oral administration, stability, bioavailability, therapeutic index, and toxicity.

BRIEF SUMMARY OF THE DISCLOSURE

In one aspect, provided herein are compounds having formula (I):

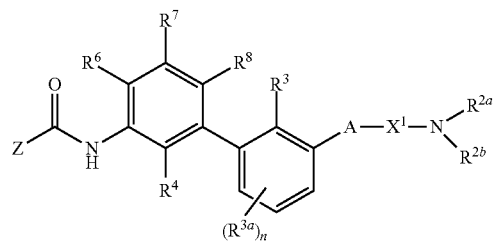

or a pharmaceutically acceptable salt, prodrug or bioisostere thereof, wherein A, Z, $X^1$, $R^{2a}$, $R^{2b}$, $R^3$, $R^{3a}$, $R^4$, $R^6$, $R^7$, $R^8$, and the subscript n are as defined herein.

In addition to the compounds provided herein, the present disclosure further provides pharmaceutical compositions containing one or more of these compounds, as well as methods associated with preparation and use of such compounds. In some embodiments, the compounds are used in therapeutic methods to treat diseases associated with the PD-1/PD-L1 pathway.

BRIEF DESCRIPTION OF THE DRAWINGS

NOT APPLICABLE

DETAILED DESCRIPTION OF THE DISCLOSURE

Abbreviation and Definitions

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The term "alkyl", by itself or as part of another substituent, means, unless otherwise stated, a straight or branched chain hydrocarbon group, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of alkenyl groups include vinyl, 2-propenyl, crotyl, 2-isopentenyl, 2-(butadienyl), 2,4-pentadienyl and 3-(1,4-pentadienyl). Examples of alkynyl groups include ethynyl, 1- and 3-propynyl, 3-butynyl, and the higher homologs and isomers. The term "cycloalkyl" refers to hydrocarbon rings having the indicated number of ring atoms (e.g., $C_{3-6}$ cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc. The bicyclic or polycyclic rings may be fused, bridged, spiro or a combination thereof. The term "heterocycloalkyl" or "heterocyclyl" refers to a cycloalkyl group that contain from one to five heteroatoms selected from N, O, and S, wherein the nitrogen and sulfur atoms are optionally oxidized, and the nitrogen atom(s) are optionally quaternized. The heterocycloalkyl may be a monocyclic, a bicyclic or a polycyclic ring system. The bicyclic or polycyclic rings may be fused, bridged, spiro or a combination thereof. It is understood that the recitation for $C_{4-12}$ heterocyclyl, refers to a group having from 4 to 12 ring members where at least one of the ring members is a heteroatom. Non limiting examples of heterocycloalkyl groups include pyrrolidine, imidazolidine, pyrazolidine, butyrolactam, valerolactam, imidazolidinone, tetrazolone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, quinuclidine, and the like. A heterocycloalkyl group can be attached to the remainder of the molecule through a ring carbon or a heteroatom.

The term "alkylene" by itself or as part of another substituent means a divalent group derived from an alkane, as exemplified by —CH$_2$CH$_2$CH$_2$CH$_2$—. An alkylene group can be linear or branched. An examples of the latter are —CH$_2$C(CH$_3$)$_2$CH$_2$—, —CH$_2$C(CH$_3$)$_2$— or —CH(CH$_3$)CH$_2$CH$_2$—. Typically, an alkyl (or alkylene) group will have from 1 to 12 carbon atoms, with those groups having 8 or fewer carbon atoms being preferred in the present disclosure. Similarly, "alkenylene" and "alkynylene" refer to the unsaturated forms of "alkylene" having double or triple bonds, respectively.

The term "heteroalkyl," by itself or in combination with another term, means, unless otherwise stated, a stable straight or branched chain, or cyclic hydrocarbon group, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$,—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the terms "heteroalkenyl" and "heteroalkynyl" by itself or in combination with another term, means, unless otherwise stated, an alkenyl group or alkynyl group, respectively, that contains the stated number of carbons and having from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group.

The term "heteroalkylene" by itself or as part of another substituent means a divalent group, saturated or unsaturated or polyunsaturated, derived from heteroalkyl, as exemplified by —CH$_2$—CH$_2$—S—CH$_2$CH$_2$— and —CH$_2$—S—CH$_2$—CH$_2$—NH—CH$_2$—, —O—CH$_2$—CH=CH—, —CH$_2$—CH=C(H)CH$_2$—O—CH$_2$— and —S—CH$_2$—C≡C—. For heteroalkylene groups, heteroatoms can also occupy either or both of the chain termini (e.g., alkyleneoxy, alkylenedioxy, alkyleneamino, alkylenediamino, and the like).

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as —NR$^a$R$^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is meant to include trifluoromethyl, 2,2,2-trifluoroethyl, 4-chlorobutyl, 3-bromopropyl, and the like.

The term "hydroxyalkyl" or "alkyl-OH" refers to an alkyl group, as defined above, where at least one (and up to three) of the hydrogen atoms is replaced with a hydroxy group. As for the alkyl group, hydroxyalkyl groups can have any suitable number of carbon atoms, such as $C_{1-6}$. Exemplary hydroxyalkyl groups include, but are not limited to, hydroxymethyl, hydroxyethyl (where the hydroxy is in the 1- or 2-position), hydroxypropyl (where the hydroxy is in the 1-, 2- or 3-position), and 2,3-dihydroxypropyl.

The term "$C_{1-3}$ alkyl-guanidinyl" refers to a $C_{1-3}$ alkyl group, as defined above, where at least one of the hydrogen atoms is replaced with a guanidinyl group (—NHC(NH)NH$_2$).

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. It is understood that the recitation for $C_{5-10}$ heteroaryl, refers to a heteroaryl moiety having from 5 to 10 ring members where at least one of the ring members is a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below.

The term "carbocyclic ring," "carbocyclic" or "carbocyclyl" refers to cyclic moieties with only carbon atoms as ring vertices. Carbocyclic ring moieties are saturated or unsaturated and can be aromatic. Generally, carbocyclic moieties have from 3 to 10 ring members. Carbocyclic moieties with multiple ring structure (e.g. bicyclic) can include a cycloalkyl ring fused to an aromatic ring (e.g. 1,2,3,4-tetrahydronaphthalene). Thus, carbocyclic rings include cyclopentyl, cyclohexenyl, naphthyl, and 1,2,3,4-tetrahydronaphthyl. The term "heterocyclic ring" refers to both "heterocycloalkyl" and "heteroaryl" moieties. Thus, heterocyclic rings are saturated or unsaturated and can be aromatic. Generally, heterocyclic rings are 4 to 10 ring members and include piperidinyl, tetrazinyl, pyrazolyl and indolyl.

When any of the above terms (e.g., "alkyl," "aryl" and "heteroaryl") are referred to as 'substituted' without further notation on the substituents, the substituted forms of the indicated group will be as provided below.

Substituents for the alkyl groups (including those groups often referred to as alkylene, alkenyl, alkynyl and cycloalkyl) can be a variety of groups selected from: -halogen, —OR', —NR'R", —SR', —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN and —NO$_2$ in a number ranging from zero to (2 m'+1), where m' is the total number of carbon atoms in such group. R', R" and R'" each independently refer to hydrogen, unsubstituted C$_{1-8}$ alkyl, unsubstituted heteroalkyl, unsubstituted aryl, aryl substituted with 1-3 halogens, unsubstituted C$_{1-8}$ alkyl, C$_{1-8}$ alkoxy or C$_{1-8}$ thioalkoxy groups, or unsubstituted aryl-C$_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl. The term "acyl" as used by itself or as part of another group refers to an alkyl group wherein two substitutents on the carbon that is closest to the point of attachment for the group is replaced with the substituent =O (e.g., —C(O)CH$_3$, —C(O)CH$_2$CH$_2$OR' and the like).

Similarly, substituents for the aryl and heteroaryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —N$_3$, perfluoro(C$_1$-C$_4$)alkoxy, and perfluoro(C$_1$-C$_4$)alkyl, in a number ranging from zero to the total number of open valences on the aromatic ring system; and where R', R" and R'" are independently selected from hydrogen, C$_{1-8}$ alkyl, C$_{3-6}$ cycloalkyl, C$_{2-8}$ alkenyl, C$_{2-8}$ alkynyl, unsubstituted aryl and heteroaryl, (unsubstituted aryl)-C$_{1-4}$ alkyl, and unsubstituted aryloxy-C$_{1-4}$ alkyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted C$_{1-6}$ alkyl.

As used herein, the term "heteroatom" is meant to include oxygen (O), nitrogen (N), sulfur (S) and silicon (Si).

The disclosure herein further relates to prodrugs and bioisosteres thereof. Suitable bioisosteres, for example, will include carboxylate replacements (phosphonic acids, phosphinic acids, sulfonic acids, sulfinic acids, and acidic heterocyclic groups such as tetrazoles). Suitable prodrugs will include those conventional groups known to hydrolyze and/or oxidize under physiological conditions to provide a compound of Formula I.

The terms "patient" and "subject" include primates (especially humans), domesticated companion animals (such as dogs, cats, horses, and the like) and livestock (such as cattle, pigs, sheep, and the like).

As used herein, the term "treating" or "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to reduce the severity and/or duration of symptoms).

The term "pharmaceutically acceptable salts" is meant to include salts of the active compounds which are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

Certain compounds of the present disclosure can exist in unsolvated forms as well as solvated forms, including hydrated forms. In general, the solvated forms are equivalent to unsolvated forms and are intended to be encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. When a stereochemical depiction is shown, it is meant to refer to the compound in which one of the isomers is present and substantially free of the other isomer. 'Substantially free of' another isomer indicates at least an 80/20 ratio of the two isomers, more preferably 90/10, or 95/5 or more. In some embodiments, one of the isomers will be present in an amount of at least 99%.

The compounds of the present disclosure may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present disclosure, whether radioactive or not, are intended to be encompassed within the scope of the present disclosure. For example, the compounds may be prepared such that any number of hydrogen atoms are replaced with a deuterium ($^2$H) isotope. The compounds of the present disclosure may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere within this application. For instance, isotopic variants of the compounds of the disclosure may find additional utility, including but not limited to, as diagnostic and/or imaging reagents, or as cytotoxic/radiotoxic therapeutic agents. Additionally, isotopic variants of the compounds of the disclosure can have altered pharmacokinetic and pharmacodynamic characteristics which can contribute to enhanced safety, tolerability or efficacy during treatment. All isotopic variations of the compounds of the present disclosure, whether radioactive or not, are intended to be encompassed within the scope of the present disclosure.

Compounds

In one aspect, the present disclosure provides compounds having formula (I):

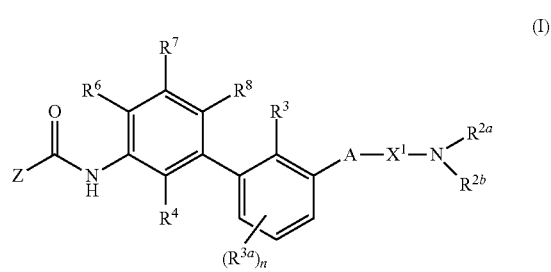

or a pharmaceutically acceptable salt, prodrug or bioisostere thereof, wherein:

A is a 5- to 10-membered heteroaryl group which is unsubstituted or substituted with from one to five members independently selected from the group consisting of halogen, $C_{1-3}$ alkyl, $C_{1-3}$ haloalkyl, $C_{1-3}$ alkoxy, $C_{1-3}$ haloalkoxy, OH, and CN;

$X^1$ is $C_{1-3}$ alkylene, which is unsubstituted or substituted with one or two members independently selected from the group consisting of $C_{1-2}$ alkyl and $CO_2H$;

$R^{2a}$ and $R^{2b}$ are each independently selected from the group consisting of H, $C_{1-8}$ alkyl, $C_{1-8}$ haloalkyl, —Y, —$X^2$—$CO_2R^a$, —$X^2$—$OR^a$, —$X^2$—$NR^aR^b$, —$X^2$—$C(O)NR^aR^b$, —$X^2$—$SO_2R^a$, —$X^2$—$SO_2NR^aR^b$, —$X^2$—$SO_3R^a$ and —$X^2$—Y wherein each $X^2$ is $C_{1-6}$ alkylene and any $C_{1-8}$ alkyl or $C_{1-6}$ alkylene, is unsubstituted or substituted with one or two members independently selected from the group consisting of OH, $SO_2NH_2$, $C(O)NH_2$, $C(O)NHOH$, $PO_3H_2$, $CO_2C_{1-8}$ alkyl and $CO_2H$, and each Y is selected from the group consisting of $C_{3-6}$ cycloalkyl, $C_{4-8}$ heterocyclyl and 5- to 6-membered heteroaryl, each of which is unsubstituted or substituted with one to four substituents independently selected from the group consisting of oxo, OH, $C_{1-4}$ alkyl, $C_{1-4}$ haloalkyl, $C_{1-4}$ hydroxyalkyl, $C_{1-4}$ alkoxy, $C_{1-4}$ haloalkoxy, $C_{1-4}$ hydroxyalkoxy, $SO_2NH_2$, $C(O)NH_2$, $C(O)NHOH$, $PO_3H_2$, $CO_2C_{1-8}$ alkyl, $SO_3H$ and $CO_2H$;

or $R^{2a}$ and $R^{2b}$ are combined to form a 4- to 9-membered ring or spirocyclic ring, having from zero to two additional heteroatom ring vertices selected from O, N or S; wherein the ring formed by combining $R^{2a}$ and $R^{2b}$, is unsubstituted or substituted with 1 to 4 substituents independently selected from the group consisting of oxo, $C_{1-8}$ alkyl, $C_{1-8}$ haloalkyl, $C_{1-8}$ hydroxyalkyl, —$X^3$—$CO_2R^a$, —$X^3$—$OR^a$, —$X^3$—$NR^aR^b$, —$X^3$—$C(O)NR^aR^b$, —$X^3$—$SO_2R^a$, —$X^3$—$SO_2NR^aR^b$, —$X^3$—$N(R^b)SO_2R^a$, and —$X^3$—$SO_3R^a$; wherein $X^3$ is a bond or $C_{1-6}$ alkylene;

$R^3$ and $R^4$ are each independently selected from the group consisting of H, F, Cl, CN, $CH_3$, $OCH_3$, $CH_2CH_3$ and $CF_3$;

the subscript n is 0, 1, 2 or 3;
each $R^{3a}$ is independently selected from the group consisting of H, F, Cl, $C_{1-3}$ alkyl, $C_{1-3}$ alkoxy, $C_{1-3}$ haloalkyl, $C_{1-3}$ haloalkoxy, $C_{2-3}$ alkenyl and CN;
$R^6$, $R^7$ and $R^8$ are each independently selected from the group consisting of H, F, Cl, CN, $CH_3$, $OCH_3$, $CH_2CH_3$ and $CF_3$;
Z is selected from the group consisting of:
  i) a monocyclic, bicyclic, or spirocyclic non-aromatic heterocyclic ring, optionally substituted with one or two oxo groups and optionally substituted with up to four $R^a$ and/or $R^b$; and
  ii) a monocyclic 5- or 6-membered heteroaryl ring, optionally substituted with one to three $R^c$;
each $R^a$ is independently selected from the group consisting of H, $C_{1-6}$ alkyl, $C_{3-6}$ cycloalkyl, $C_{1-6}$ haloalkyl, $C_{1-6}$ hydroxyalkyl, $C_{1-6}$ alkylene-$CO_2H$, and $C_{1-6}$ alkylene-$SO_3H$;
each $R^b$ is independently selected from the group consisting of H, $C_{1-6}$ alkyl, $C_{3-6}$ cycloalkyl, $C_{1-6}$ haloalkyl, $C_{1-6}$ hydroxyalkyl, $C_{1-6}$ alkylene-$CO_2H$, and $C_{1-6}$ alkylene-$SO_3H$, each of which is unsubstituted or substituted with one or two members independently selected from OH, $SO_2NH_2$, $C(O)NH_2$, $C(O)NHOH$, $PO_3H_2$, $CO_2C_{1-8}$ alkyl and $CO_2H$;
and $R^a$ and $R^b$, when attached to the same nitrogen atom, are optionally combined to form a 4- to 8-membered ring or spirocyclic ring, which is unsubstituted or substituted with halogen, OH, $SO_2NH_2$, $C(O)NH_2$, $C(O)NHOH$, $PO_3H_2$, $CO_2C_{1-8}$ alkyl or $CO_2H$;
each $R^c$ is independently selected from the group consisting of H, halogen, CN, $C_{1-6}$ alkyl, $C_{1-6}$ haloalkyl, —$Y^1$, —$X^4$—$CO_2R^a$, —O—$X^4$—$CO_2R^a$, —$X^4$—$OR^a$, —$X^4$—$NR^aR^b$, —$X^4$—$C(O)NR^aR^b$, —O—$X^4$—$C(O)NR^aR^b$, —$X^4$—$SO_2R^a$, —$X^4$—$SO_2NR^aR^b$, —$X^4$—$SO_3R^a$, and —$N(R^a)$—$X^4$—$CO_2R^a$, wherein each $X^4$ is a bond or $C_{1-6}$ alkylene, and each $Y^1$ is selected from the group consisting of $C_{3-6}$ cycloalkyl and $C_{4-8}$ heterocyclyl; and optionally two $R^c$ on adjacent ring vertices are combined to form a fused 5- or 6-membered heterocyclic ring.

In one group of embodiments, the compounds of Formula (I) are those wherein A is a 5- or 6-membered heteroaryl group which is unsubstituted or substituted with from one to three members independently selected from the group consisting of halogen, $C_{1-3}$ alkyl, $C_{1-3}$ haloalkyl, $C_{1-3}$ alkoxy, OH, and CN. In one group of embodiments, the compounds of Formula (I) are those wherein A is a 5- or 6-membered heteroaryl group which is unsubstituted or substituted with from one to three members independently selected from the group consisting of halogen, $C_{1-3}$ alkyl, $C_{1-3}$ haloalkyl, $C_{1-3}$ alkoxy and CN.

In one group of embodiments, the compounds of Formula (I) are those wherein A is a 6-membered heteroaryl group which is unsubstituted or substituted with from one to three members independently selected from the group consisting of halogen, $C_{1-3}$ alkyl, $C_{1-3}$ haloalkyl, $C_{1-3}$ alkoxy, OH, and CN. In one group of embodiments, the compounds of Formula (I) are those wherein A is a 6-membered heteroaryl group which is unsubstituted or substituted with from one to three members independently selected from the group consisting of halogen, $C_{1-3}$ alkyl, $C_{1-3}$ haloalkyl, $C_{1-3}$ alkoxy and CN.

In one group of embodiments, the compounds of Formula (I) are those wherein A is a 6-membered heteroaryl selected from the group consisting of pyridine, pyrimidine, pyrazine and 1,2,4-triazine, each of which is unsubstituted or substituted with one or two members independently selected from the group consisting of $CF_3$, OH, Et, CN, $OCH_3$ and F. In one group of embodiments, the compounds of Formula (I) are those wherein A is a 6-membered heteroaryl selected from the group consisting of pyridine, pyrimidine, pyrazine and 1,2,4-triazine, each of which is unsubstituted or substituted with one or two members independently selected from the group consisting of $OCH_3$ and F.

In one group of embodiments, the compounds of Formula (I) are those wherein A is unsubstituted or substituted with one or two members independently selected from the group consisting of $CF_3$, OH, Et, CN, $OCH_3$ and F. In one group of embodiments, the compounds of Formula (I) are those wherein A is unsubstituted or substituted with one or two members independently selected from the group consisting of $OCH_3$ and F.

In some embodiments, the present disclosure provides compounds of Formula (I) represented by Formula (Ia):

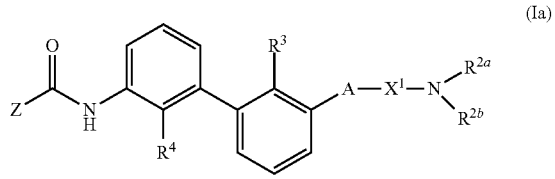

wherein the groups $R^{2a}$, $R^{2b}$, $R^3$, $R^4$, A, $X^1$ and Z have the meanings provided for Formula (I).

In some embodiments, the present disclosure provides compounds of Formula (I) represented by Formula (Ib):

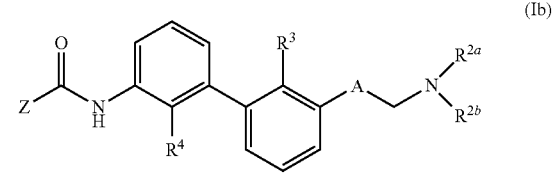

wherein the groups $R^{2a}$, $R^{2b}$, $R^3$, $R^4$, A and Z have the meanings provided for Formula (I).

In selected embodiments, including any of those noted above with respect to the compounds of Formulae (I), (Ia), or (Ib), further embodiments are those wherein Z is a 5- or 6-membered non-aromatic heterocyclic ring, optionally substituted with one or two oxo groups and optionally substituted with $R^a$ and/or $R^b$.

In some selected embodiments, the compounds of Formulae (I), (Ia), or (Ib), are those compounds wherein Z is a non-aromatic heterocyclic ring having a formula selected from the group consisting of:

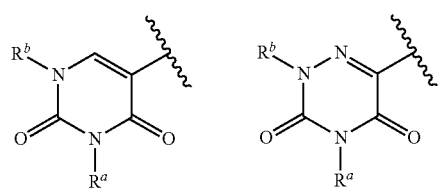

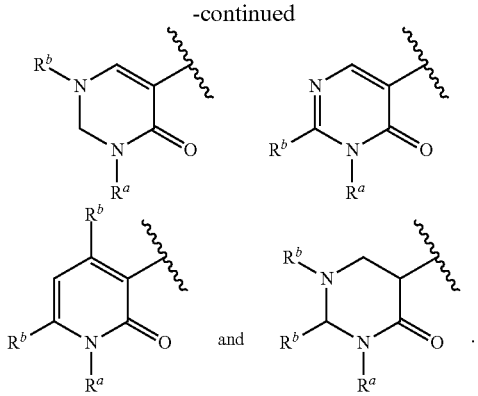

In some selected embodiments, the compounds of Formulae (I), (Ia), or (Ib), are those compounds wherein Z is a non-aromatic heterocyclic ring selected from the group consisting of piperidinyl, morpholinyl, tetrahydropyranyl, and tetrahydrofuranyl, each of which is optionally substituted with up to four $R^a$ and/or $R^b$.

In some selected embodiments, the compounds of Formulae (I), (Ia), or (Ib), are those compounds wherein Z is a 5- or 6-membered heteroaryl ring, optionally substituted with one to three $R^c$; and said heteroaryl ring is selected from the group consisting of pyridinyl, pyrimidinyl, pyrazinyl, oxazolyl, thiazolyl, and pyrazolyl.

In some selected embodiments, the compounds of Formulae (I), (Ia), or (Ib), are those compounds wherein Z is a monocyclic 5- or 6-membered heteroaryl ring, optionally substituted with one to three $R^c$; and said heterocyclic ring is selected from the group consisting of pyridinyl, pyrimidinyl and pyrazinyl.

In selected embodiments, including any of those noted above with respect to the compounds of Formulae (I), (Ia), or (Ib), further embodiments are those wherein the group A is a 5- or 6-membered heteroaryl group and is unsubstituted or substituted with one or two members independently selected from $OCH_3$ and F.

In selected embodiments, including any of those noted above with respect to the compounds of Formulae (I), (Ia), or (Ib), further embodiments are those wherein $R^{2a}$ and $R^{2b}$ are each H.

In selected embodiments, including any of those noted above with respect to the compounds of Formulae (I), (Ia), or (Ib), further embodiments are those wherein $R^{2a}$ and $R^{2b}$ are combined to form a 4- to 9-membered ring or spirocyclic ring, optionally having one or two additional ring vertices selected from O, N or S; wherein said ring or spirocyclic ring is substituted with 0 to 4 substituents independently selected from the group consisting of oxo, $C_{1-8}$ alkyl, $C_{1-8}$ haloalkyl, $C_{1-8}$ hydroxyalkyl, —$X^2$—$CO_2R^a$, —$X^2$—$OR^a$, —$X^2$—$NR^aR^b$, —$X^2$—$C(O)NR^aR^b$, —$X^2$—$SO_2R^a$, —$X^2$—$SO_2NR^aR^b$, and —$X^2$—$SO_3R^a$; wherein $X^2$ is a bond or $C_{1-6}$ alkylene.

In selected embodiments, including any of those noted above with respect to the compounds of Formulae (I), (Ia), or (Ib), further embodiments are those wherein —N($R^{2a}$)($R^{2b}$) is selected from the group consisting of:

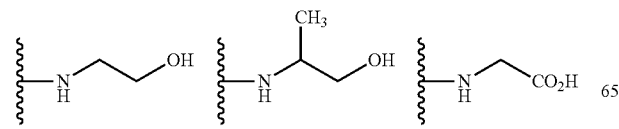

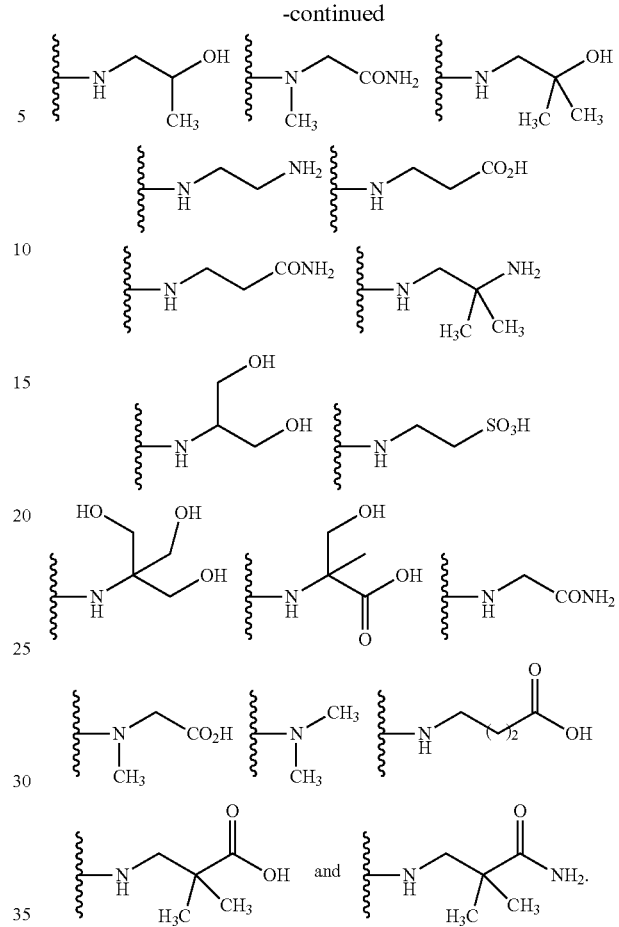

In selected embodiments, including any of those noted above with respect to the compounds of Formulae (I), (Ia), or (Ib), further embodiments are those wherein —N($R^{2a}$)($R^{2b}$) is selected from the group consisting of:

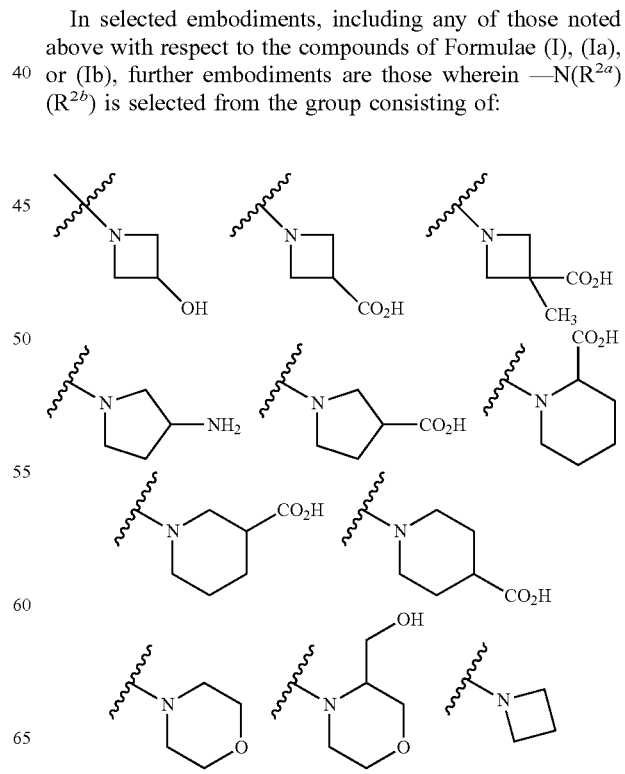

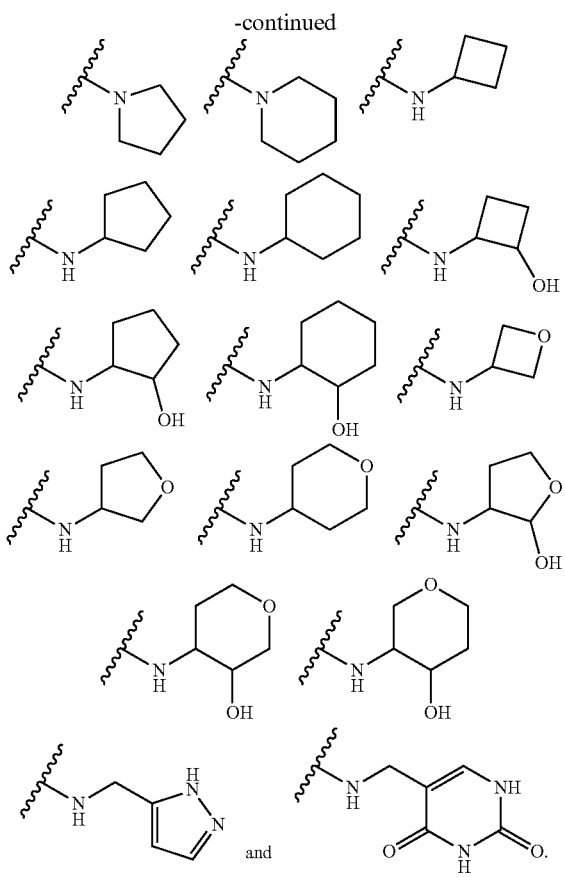

In selected embodiments, including any of those noted above with respect to the compounds of Formulae (I), (Ia), or (Ib), further embodiments are those wherein —N(R$^{2a}$)(R$^{2b}$) is selected from the group consisting of:

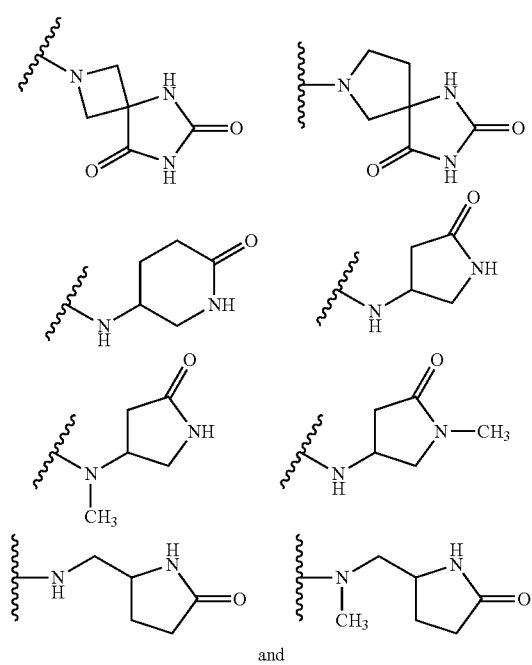

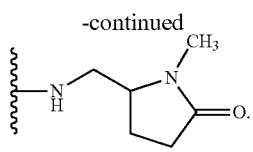

In selected embodiments, including any of those noted above with respect to the compounds of Formulae (I), (Ia), or (Ib), further embodiments are those wherein R$^{2a}$ is H or C$_{1-8}$ alkyl; and R$^{2b}$ is —Y or —X$^2$—Y.

In selected embodiments, including any of those noted above with respect to the compounds of Formulae (I), (Ia), or (Ib), further embodiments are those wherein R$^{2a}$ is H or C$_{1-8}$ alkyl; R$^{2b}$ is —Y or —X$^2$—Y; and Y is selected from the group consisting of C$_{3-6}$ cycloalkyl and C$_{4-8}$ heterocyclyl, each of which is optionally further substituted with one to four substituents independently selected from the group consisting of oxo, OH, C$_{1-4}$ alkyl, C$_{1-4}$ haloalkyl, C$_{1-4}$ hydroxyalkyl, C$_{1-4}$ alkoxy, C$_{1-4}$ haloalkoxy, C$_{1-4}$ hydroxyalkoxy, SO$_2$NH$_2$, C(O)NH$_2$, C(O)NHOH, PO$_3$H$_2$, CO$_2$C$_{1-8}$ alkyl, and CO$_2$H.

In selected embodiments, including any of those noted above with respect to the compounds of Formulae (I), (Ia), or (Ib), further embodiments are those wherein R$^3$ and R$^4$ are are each independently selected from the group consisting of F, Cl, CN, CH$_3$, OCH$_3$, CH$_2$CH$_3$ and CF$_3$. In selected embodiments, including any of those noted above with respect to the compounds of Formulae (I), (Ia), or (Ib), further embodiments are those wherein R$^3$ and R$^4$ are are each independently selected from the group consisting of H, F, Cl, CN, CH$_3$, and CF$_3$.

In selected embodiments, including any of those noted above with respect to the compounds of Formulae (I), (Ia), or (Ib), further embodiments are those wherein the compound is selected from Table 1.

In selected embodiments, including any of those noted above with respect to the compounds of Formulae (I), (Ia), or (Ib), further embodiments are those wherein the compound is selected from Table 1, having ++ or +++ activity.

In selected embodiments, including any of those noted above with respect to the compounds of Formulae (I), (Ia), or (Ib), further embodiments are those wherein the compound is selected from Table 1, having +++ activity.

In addition to the compounds provided above, pharmaceutically acceptable salts of those compounds are also provided. In some embodiments, the pharmaceutically acceptable salts are selected from ammonium, calcium, magnesium, potassium, sodium, zinc, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, procaine, purines, theobromine, triethylamine, trimethylamine, tripropylamine, tromethamine, hydrochloric, carbonic, monohydrogencarbonic, phosphoric, monohydrogenphosphoric, dihydrogenphosphoric, acetic, propionic, isobutyric, malonic, benzoic, succinic, suberic, fumaric, mandelic, phthalic, benzenesulfonic, p-tolylsulfonic, citric, tartaric, methanesulfonic, arginate, glucuronic acid and galactunoric acids. In some embodiments, the pharmaceutically acceptable salts are selected from ammonium, calcium, magnesium, potassium, sodium, hydrochloric, carbonic, monohydrogencarbonic, phosphoric, monohydrogenphosphoric, dihydrogenphosphoric, acetic, propionic, isobutyric, malonic, benzoic, succinic, suberic, fumaric, mandelic, phthalic, benzenesulfonic, p-tolylsulfonic, citric, tartaric, methanesulfonic, arginate, glucuronic acid and galactunoric acids. In some embodiments, the pharmaceutically acceptable salts are sodium or hydrochloric.

In addition to salt forms, the present disclosure provides compounds which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

An ester may be used as a prodrug for the corresponding carboxylic acid. A $C_{1-10}$ alkyl ester or a $C_{1-10}$ haloalkyl ester may be used as a prodrug for the corresponding carboxylic acid. The following esters may be used: tert-butyl ester, methyl ester, ethyl ester, isopropyl ester.

METHODS OF PREPARATION

In addition to the methods described in the Examples below, general methods for the preparation of compounds of formula (I) are provided in Schemes 1 and 2.

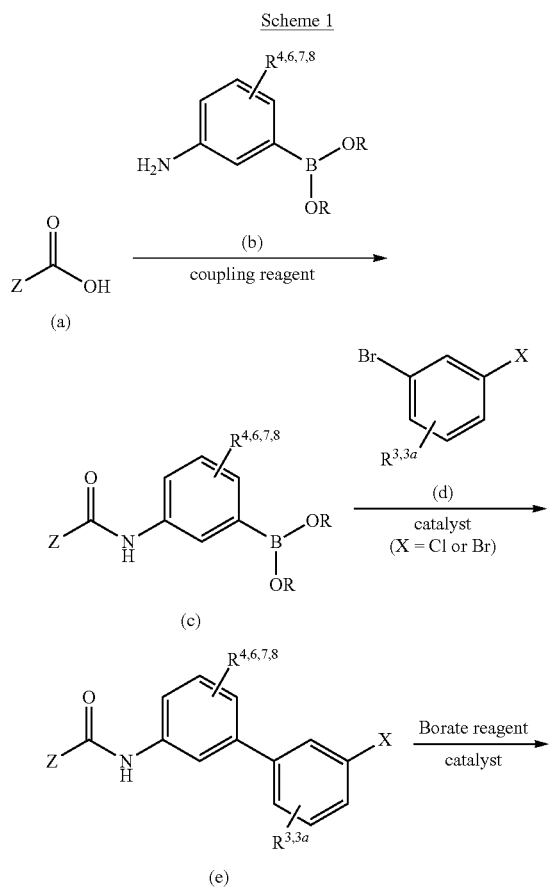

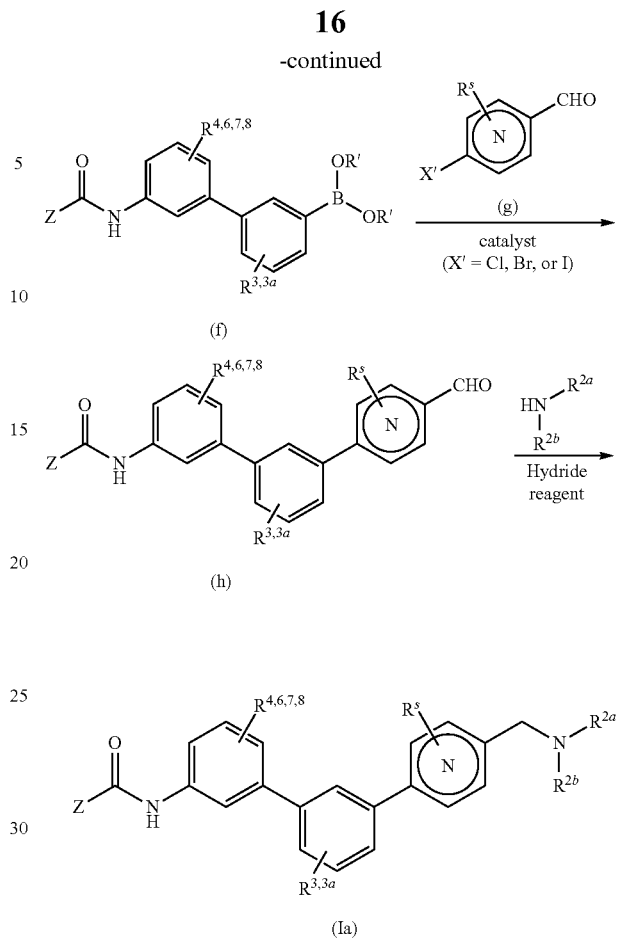

Scheme 1 illustrates a general method for the preparation of compounds having formula (I), wherein A is a six-membered nitrogen containing heteroaryl ring (e.g., pyridyl, pyrimidinyl), and $X^1$ is $CH_2$. In the above scheme, $R^s$ represents one or more substituents on the heteroaryl ring.

Amide formation between a carboxylic acid (a) and a boronate-aniline compound (b) proceeds smoothly in the presence of a coupling reagent to provide (c). Suzuki-type coupling of (c) with (d) in the presence of a catalyst then provides the biphenyl compound (e). Compound (e) can then be converted a boronate (f), followed by a second Suzuki-type coupling (with the halo-heteroaryl compound (g)) to afford the triaryl aldehyde (h). Reductive amination of the aldehyde with $HNR^{2a}R^{2b}$ can then provide compounds of formula (Ia).

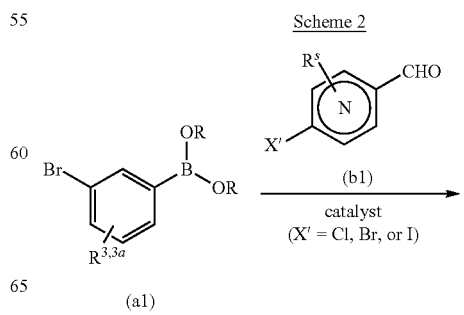

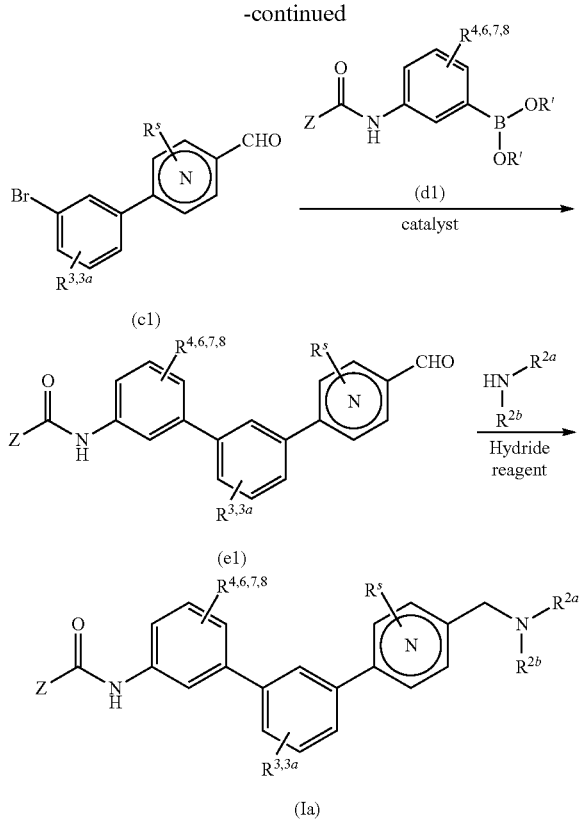

In another Suzuki-coupling based approach, a boronate compound (a1) can be combined with aldehyde (b1) to form the aryl-heteroaryl adduct (c1), which when subjected to a second Suzuki-type coupling with (d1), provides the triaryl aldehyde (e1). As in Scheme 1, reductive amination of the aldehyde with $HNR^{2a}R^{2b}$ can then provide compounds of formula (Ia).

Pharmaceutical Compositions

In addition to the compounds provided herein, compositions of those compounds will typically contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

In another embodiment, a pharmaceutical composition comprising a compound of the present disclosure including a compound of Formulae (I), (Ia), or (Ib), or a pharmaceutically acceptable salt thereof, and a pharmaceutically acceptable excipient, is provided.

In some embodiments, the pharmaceutical composition further comprises one or more additional therapeutic agents. In some embodiments, the one or more additional therapeutic agent is selected from the group consisting of an antimicrobial agent, an antiviral agent, a cytotoxic agent, a gene expression modulatory agent, a chemotherapeutic agent, an anti-cancer agent, an anti-angiogenic agent, an immunotherapeutic agent, an anti-hormonal agent, an anti-fibrotic agent, radiotherapy, a radiotherapeutic agent, an anti-neoplastic agent, and an anti-proliferation agent. In some embodiments, the one or more additional therapeutic agent is an antagonist of a chemokine and/or chemoattractant receptor, which includes but is not limited to, CCR1, CCR2, CCR3, CCR4, CCR5, CCR6, CCR7, CCR8, CCR9, CCR10, CCR11, CCR12, CXCR1, CXCR2, CXCR3, CXCR4, CXCR5, CXCR6, CXCR7, C3aR, and/or C5aR. Chemokine and/or chemoattractant receptor antagonists are known in the art and described in, for example, WO2007/002667, WO2007/002293, WO/2003/105853, WO/2007/022257, WO/2007/059108, WO/2007/044804, WO2007/115232, WO2007/115231, WO2008/147815, WO2010/030815, WO2010/075257, WO2011/163640, WO2010/054006, WO2010/051561, WO2011/035332, WO2013/082490, WO2013/082429, WO2014/085490, WO2014/100735, WO2014/089495, WO2015/084842, WO2016/187393, WO2017/127409, WO 2017/087607, WO2017/087610, WO2017/176620, WO2018/222598, WO2018/222601, WO2013/130811, WO2006/076644, WO2008/008431, WO2009/038847, WO2008/008375, WO2008/008374, WO2008/010934, WO2009/009740, WO2005/112925, WO2005/112916, WO2005/113513, WO2004/085384, WO2004/046092. Chemokine and/or chemoattractant receptor antagonists also include CCX354, CCX9588, CCX140, CCX872, CCX598, CCX6239, CCX9664, CCX2553, CCX3587, CCX3624, CCX 2991, CCX282, CCX025, CCX507, CCX430, CCX765, CCX224, CCX662, CCX650, CCX832, CCX168, CCX168-M1, CCX3022 and/or CCX3384.

The pharmaceutical compositions for the administration of the compounds of this disclosure may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self-emulsifications as described in U.S. Patent Application 2002-0012680, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, polyethylene glycol (PEG) of various average sizes (e.g., PEG400, PEG4000) and certain surfactants such as cremophor or solutol, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono- or di-glycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the disclosure may also be in the form of oil-in-water emulsions. The oily phase may be a vegetable oil, for example olive oil or *arachis* oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present disclosure may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present disclosure are employed. As used herein, topical application is also meant to include the use of mouth washes and gargles.

The compounds of this disclosure may also be coupled with a carrier that is a suitable polymer for targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the compounds of the disclosure may be coupled to a carrier that is a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like. In one embodiment of the disclosure, the compound of the disclosure is coupled to a polymer or semipermeable polymer matrix that is formed as a stent or stent-graft device.

Methods of Treating Diseases and Disorders

The compounds of the disclosure may be used as immunomodulators. The compounds of the disclosure may be used as agonists, antagonists, partial agonists, inverse agonists, inhibitors of PD-1 and/or PD-L1 in a variety of contexts, both in vitro and in vivo. In some embodiments, the compounds of the disclosure may be used as inhibitors of the PD-1/PD-L1 protein protein interaction. In some embodiments, the compounds of the disclosure may be used as inhibitors of PD-L1. In some embodiments, the compounds of the disclosure may be used as inhibitors of the CD80/PD-L1 protein protein interaction. In some embodiments, the compounds of the disclosure may be used to inhibit the interaction between PD-1 and PD-L1 and/or PD-1 and CD80 and/or PD-1 and PD-L2 in vitro or in vivo. In some embodiments, the compounds of the disclosure may be used to inhibit VISTA and/or TIM-3. In some embodiments, the compounds of the disclosure may be inhibitors of the PD-1/PD-L1 protein protein interaction and inhibitors of VISTA and/or TIM-3. In some embodiments, in addition to being inhibitors of the PD-1/PD-L1 protein protein interaction, the compounds of the disclosure may be inhibitors of CTLA-4 and/or BTLA and/or LAG-3 and/or KLRG-1 and/or 2B4 and/or CD160 and/or HVEM and/or CD48 and/or E-cadherin and/or MHC-II and/or galectin-9 and/or CD86 and/or PD-L2 and/or VISTA and/or TIM-3 and/or CD80.

The compounds of the disclosure may be contacted with the receptor they interact with, in aqueous solution and under conditions otherwise suitable for binding of the ligand to the receptor. The receptor may be present in suspension (e.g., in an isolated membrane or cell preparation), in a cultured or isolated cell, or in a tissue or organ.

Preferably, the amount of the compounds of the disclosure contacted with the receptor should be sufficient to inhibit the PD-1/PD-L1 binding in vitro as measured, for example, using an ELISA. The receptor may be present in solution or suspension, in a cultured or isolated cell preparation or within a patient.

In some embodiments, the compounds of the present disclosure are useful for restoring and augmenting T cell activation. In some embodiments, the compounds of the present disclosure are useful for enhancing an immune response in a patient. In some embodiments, the compounds of the present disclosure are useful for treating, preventing, or slowing the progression of diseases or disorders in a variety of therapeutic areas, such as cancer and infectious diseases.

In some embodiments, the compounds of the present disclosure can be used for treating patients suffering from conditions that are responsive to PD-1/PD-L1 protein protein interaction modulation.

In some embodiments, a method of modulating an immune response mediated by the PD-1 signaling pathway in a subject, comprising administering to the subject a therapeutically effective amount of a compound of the present disclosure including a compound of Formulae (I), (Ia), or (Ib), or a pharmaceutically acceptable salt thereof or a composition comprising a compound of Formulae (I), (Ia), or (Ib), or a pharmaceutically acceptable salt thereof, is provided.

In some embodiments, a method of enhancing, stimulating, modulating and/or increasing the immune response in a subject in need thereof, comprising administering to the subject a therapeutically effective amount of a compound of the present disclosure including a compound of Formulae (I), (Ia), or (Ib), or a pharmaceutically effective amount thereof or a composition of a compound of the present disclosure including a compound of Formula (I), (Ia), or (Ib), or a pharmaceutically acceptable salt thereof, is provided.

In some embodiments, a method of inhibiting growth, proliferation, or metastasis of cancer cells in a subject in need thereof, comprising administering to the subject a therapeutically effective amount of a compound of the present disclosure including a compound of Formula (I), (Ia), or (Ib), or a pharmaceutically acceptable salt thereof or a composition of a compound of the present disclosure including a compound of Formula (I), (Ia), or (Ib), or a pharmaceutically acceptable salt thereof, is provided.

In some embodiments, a method of treating a subject in need thereof, comprising administering to the subject a therapeutically effective amount of a compound of the present disclosure including a compound of Formulae (I), (Ia), or (Ib), or a pharmaceutically acceptable salt thereof or a composition of a compound of the present disclosure including a compound of Formulae (I), (Ia), or (Ib), or a pharmaceutically acceptable salt thereof, is provided.

In some embodiments, the subject suffers from a disease or disorder selected from the group consisting of an infectious disease, a bacterial infectious disease, a viral infectious disease a fungal infectious disease, a solid tumor, a hematological malignancy, an immune disorder, an inflammatory disease, and cancer. In some embodiments, the disease or disorder is selected from the group consisting of melanoma, glioblastoma, esophagus tumor, nasopharyngeal carcinoma, uveal melanoma, lymphoma, lymphocytic lymphoma, primary CNS lymphoma, T-cell lymphoma, diffuse large B-cell lymphoma, primary mediastinal large B-cell lymphoma, prostate cancer, castration-resistant prostate cancer, chronic myelocytic leukemia, Kaposi's sarcoma fibrosarcoma, liposarcoma, chondrosarcoma, osteogenic sarcoma, angiosarcoma, lymphangiosarcoma, synovioma, meningioma, leiomyosarcoma, rhabdomyosarcoma, sarcoma of soft tissue, sarcoma, sepsis, biliary tumor, basal cell carcinoma, thymus neoplasm, cancer of the thyroid gland, cancer of the parathyroid gland, uterine cancer, cancer of the adrenal gland, liver infection, Merkel cell carcinoma, nerve tumor, follicle center lymphoma, colon cancer, Hodgkin's disease, non-Hodgkin's lymphoma, leukemia, chronic or acute leukemias including acute myeloid leukemia, chronic myeloid leukemia, acute lymphoblastic leukemia, chronic lymphocytic leukemia, multiple myeloma, ovary tumor, myelodysplastic syndrome, cutaneous or intraocular malignant melanoma, renal cell carcinoma, small-cell lung cancer, lung cancer, mesothelioma, breast cancer, squamous non-small cell lung cancer (SCLC), non-squamous NSCLC, colorectal cancer, ovarian cancer, gastric cancer, hepatocellular carcinoma, pancreatic carcinoma, pancreatic cancer, Pancreatic ductal adenocarcinoma, squamous cell carcinoma of the head and neck, cancer of the head or neck, gastrointestinal tract, stomach cancer, HIV, Hepatitis A, Hepatitis B, Hepatitis C, hepatitis D, herpes viruses, papillomaviruses, influenza, bone cancer, skin cancer, rectal cancer, cancer of the anal region, testicular cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the urethra, cancer of the penis, cancer of the bladder, cancer of the kidney, cancer of the ureter, carcinoma of the renal pelvis, neoplasm of the central nervous system (CNS), tumor angiogenesis, spinal axis tumor, brain stem glioma, pituitary adenoma, epidermoid cancer, abestosis, carcinoma, adenocarcinoma, papillary carcinoma, cystadenocarcinoma, bronchogenic carcinoma, renal cell carcinoma, transitional cell carcinoma, choriocarcinoma, seminoma, embryonal carcinoma, wilm's tumor, pleomorphic adenoma, liver cell papilloma, renal tubular adenoma, cystadenoma, papilloma, adenoma, leiomyoma, rhabdomyoma, hemangioma, lymphangioma, osteoma, chondroma, lipoma and fibroma.

In some embodiments, a therapeutically effective amount of one or more additional therapeutic agents is further administered to the subject. In some embodiments, the one or more additional therapeutic agents is selected from the group consisting of an antimicrobial agent, an antiviral agent, a cytotoxic agent, a gene expression modulatory agent, a chemotherapeutic agent, an anti-cancer agent, an anti-angiogenic agent, an immunotherapeutic agent, an anti-hormonal agent, an anti-fibrotic agent, radiotherapy, a radiotherapeutic agent, an anti-neoplastic agent, and an anti-proliferation agent. In some embodiments, the one or more additional therapeutic agent is an antagonist of a chemokine and/or chemoattractant receptor, which includes but is not limited to, CCR1, CCR2, CCR3, CCR4, CCR5, CCR6, CCR7, CCR8, CCR9, CCR10, CCR11, CCR12, CXCR1, CXCR2, CXCR3, CXCR4, CXCR5, CXCR6, CXCR7, C3aR, and/or C5aR. Chemokine and/or chemoattractant receptor antagonists are known in the art and described in, for example, WO2007/002667, WO2007/002293, WO/2003/105853, WO/2007/022257, WO/2007/059108, WO/2007/044804, WO2007/115232, WO2007/115231, WO2008/147815, WO2010/030815, WO2010/075257, WO2011/163640, WO2010/054006, WO2010/051561, WO2011/035332, WO2013/082490, WO2013/082429, WO2014/085490, WO2014/100735, WO2014/089495, WO2015/084842, WO2016/187393, WO2017/127409, WO 2017/087607, WO2017/087610, WO2017/176620, WO2018/222598, WO2018/222601, WO2013/130811, WO2006/076644, WO2008/008431, WO2009/038847, WO2008/008375, WO2008/008374, WO2008/010934, WO2009/009740, WO2005/112925, WO2005/112916, WO2005/113513, WO2004/085384, WO2004/046092. Chemokine and/or chemoattractant receptor antagonists also include CCX354, CCX9588, CCX140, CCX872, CCX598, CCX6239, CCX9664, CCX2553, CCX3587, CCX3624, CCX 2991, CCX282, CCX025, CCX507, CCX430, CCX765, CCX224, CCX662, CCX650, CCX832, CCX168, CCX168-M1, CCX3022 and/or CCX3384.

In some embodiments, the compounds of the present disclosure may be used to inhibit an infectious disease. The infectious disease includes but is not limited to HIV, Influenza, Herpes, Giardia, Malaria, Leishmania, the pathogenic infection by the virus Hepatitis (A, B, and C), herpes virus (e.g., VZV, HSV-I, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus, pathogenic infection by the bacteria *chlamydia*, rickettsial bacteria, mycobacteria, staphylococci, streptococci, pneumonococci, meningococci and conococci, *klebsiella, proteus, serratia, pseudomonas, E. coli, legionella*, diphtheria, *salmonella*, bacilli, cholera, tetanus, botulism, anthrax, plague, leptospirosis, and Lyme's disease bacteria, pathogenic infection by the fungi *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum*, and pathogenic infection by the parasites *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi, Nippostrongylus brasiliensis*.

In some embodiments, the compounds of the present disclosure may be used to inhibit HIV infection, delay AIDS progression, deplete HIV viral reservoir or decrease the severity of symptoms or HIV infection and AIDS.

The compounds of the present disclosure may be used for the treatment of cancers and precancerous conditions in a subject.

Treatment methods provided herein include, in general, administration to a patient an effective amount of one or more compounds provided herein. Suitable patients include those patients suffering from or susceptible to (i.e., prophylactic treatment) a disorder or disease identified herein. Typical patients for treatment as described herein include mammals, particularly primates, especially humans. Other suitable patients include domesticated companion animals such as a dog, cat, horse, and the like, or a livestock animal such as cattle, pig, sheep and the like.

In general, treatment methods provided herein comprise administering to a patient an effective amount of a compound one or more compounds provided herein. In a preferred embodiment, the compound(s) of the disclosure are preferably administered to a patient (e.g., a human) intravenously, orally or topically. The effective amount may be an amount sufficient to modulate the PD-1/PD-L1 interaction and/or an amount sufficient to reduce or alleviate the symptoms presented by the patient. Preferably, the amount administered is sufficient to yield a plasma concentration of the compound (or its active metabolite, if the compound is a pro-drug) high enough to sufficiently modulate the PD-1/PD-L1 interaction. Treatment regimens may vary depending on the compound used and the particular condition to be treated; for treatment of most disorders, a frequency of administration of 4 times daily or less is preferred. In general, a dosage regimen of 2 times daily is more preferred, with once a day dosing particularly preferred. It will be understood, however, that the specific dose level and treatment regimen for any particular patient will depend upon a variety of factors including the activity of the specific compound employed, the age, body weight, general health, sex, diet, time of administration, route of administration, rate of excretion, drug combination (i.e., other drugs being administered to the patient) and the severity of the particular disease undergoing therapy, as well as the judgment of the prescribing medical practitioner. In general, the use of the minimum dose sufficient to provide effective therapy is preferred. Patients may generally be monitored for therapeutic effectiveness using medical or veterinary criteria suitable for the condition being treated or prevented.

Combinations

A concomitant medicine comprising the compounds of the present disclosure and other drug may be administered as a combination preparation in which both components are contained in a single formulation, or administered as separate formulations. The administration by separate formulations includes simultaneous administration and administration with some time intervals. In the case of the administration with some time intervals, the compound of the present disclosure can be administered first, followed by another drug or another drug can be administered first, followed by the compound of the present disclosure. The administration method of the respective drugs may be the same or different.

The dosage of the other drug can be properly selected, based on a dosage that has been clinically used. The compounding ratio of the compound of the present disclosure and the other drug can be properly selected according to age and weight of a subject to be administered, administration method, administration time, disorder to be treated, symptom and combination thereof. For example, the other drug may be used in an amount of 0.01 to 100 parts by mass, based on 1 part by mass of the compound of the present disclosure. The other drug may be a combination of two or more kind of arbitrary drugs in a proper proportion.

The compounds described herein may be used or combined with one or more therapeutic agent such as an antimicrobial agent, an antiviral agent, a cytotoxic agent, a gene expression modulatory agent, a chemotherapeutic agent, an anti-cancer agent, an anti-angiogenic agent, an immunotherapeutic agent, an anti-hormonal agent, an anti-fibrotic agent, radiotherapy, a radiotherapeutic agent, an anti-neoplastic agent, and an anti-proliferation agent. These therapeutic agents may be in the forms of compounds, antibodies, polypeptides, or polynucleotides.

The compounds described herein may be used or combined with one or more of a therapeutic antibody, a bispecific antibody and "antibody-like" therapeutic protein (such as DARTs®, Duobodies®, Bites®, XmAbs®, TandAbs®, Fab derivatives), an antibody-drug conjugate (ADC), a virus, an oncolytic virus, gene modifiers or editors such as CRISPR (including CRISPR Cas9), zinc finger nucleases or synthetic nucleases (TALENs), a CAR (chimeric antigen receptor) T-cell immunotherapeutic agent, or any combination thereof.

Examples of chemotherapeutics include an alkylation agent, nitrosourea agent, antimetabolite, anticancer antibiotics, vegetable-origin alkaloid, topoisomerase inhibitor, hormone drug, hormone antagonist, aromatase inhibitor, P-glycoprotein inhibitor, platinum complex derivative, other immunotherapeutic drugs and other anticancer drugs.

The compounds described herein may be used or combined with a cancer treatment adjunct, such as a leucopenia (neutropenia) treatment drug, thrombocytopenia treatment drug, antiemetic and cancer pain intervention drug, concomitantly or in a mixture form.

The compounds described herein may be used or combined with a kinase inhibitor.

In one embodiment, the compounds of the present disclosure can be used with other immunomodulators and/or a potentiating agent concomitantly or in a mixture form. Examples of the immunomodulator include various cytokines, vaccines and adjuvants. Examples of these cytokines, vaccines and adjuvants that stimulates immune responses include but not limited to GM-CSF, M-CSF, G-CSF, interferon-a, beta, or gamma, IL-1, IL-2, IL-3, IL-12, Poly (I:C) and CPG. The potentiating agents include cyclophosphamide and analogs of cyclophosphamide, anti-TGF and imatinib (Gleevac), a mitosis inhibitor, such as paclitaxel, Sunitinib (Sutent) or other antiangiogenic agents, an aromatase inhibitor, such as letrozole, an A2a adenosine receptor (A2AR) antagonist, an angiogenesis inhibitor, anthracyclines, oxaliplatin, doxorubicin, TLR4 antagonists, and IL-18 antagonists.

In some embodiments, the compounds described herein may be used or combined with one or more modulator of CCR1, CCR2, CCR3, CCR4, CCR5, CCR6, CCR7, CCR8, CCR9, CCR10, CCR11, CXCR1, CXCR2, CXCR3, CXCR4, CXCR5, CXCR6, CXCR7, ChemR23, C5aR, C5a, and C5. In some embodiments, the modulator is an antagonist.

In some embodiments, the compounds described herein may be used or combined with one or more chemokine and/or chemoattractant receptor antagonists described in, for example, WO2007/002667, WO2007/002293, WO/2003/105853, WO/2007/022257, WO/2007/059108, WO/2007/044804, WO2007/115232, WO2007/115231, WO2008/147815, WO2010/030815, WO2010/075257, WO2011/163640, WO2010/054006, WO2010/051561, WO2011/035332, WO2013/082490, WO2013/082429, WO2014/085490, WO2014/100735, WO2014/089495, WO2015/084842, WO2016/187393, WO2017/127409, WO 2017/087607, WO2017/087610, WO2017/176620, WO2018/222598, WO2018/222601, WO2013/130811, WO2006/076644, WO2008/008431, WO2009/038847, WO2008/008375, WO2008/008374, WO2008/010934, WO2009/009740, WO2005/112925, WO2005/112916, WO2005/113513, WO2004/085384, WO2004/046092. Chemokine and/or chemoattractant receptor antagonists useful in the present disclosure also include CCX354, CCX9588, CCX140, CCX872, CCX598, CCX6239, CCX9664, CCX2553, CCX3587, CCX3624, CCX 2991, CCX282, CCX025, CCX507, CCX430, CCX765, CCX224, CCX662, CCX650, CCX832, CCX168, CCX168-M1, CCX3022 and/or CCX3384.

Dosage

Dosage levels of the order of from about 0.1 mg to about 140 mg per kilogram of body weight per day are useful in the treatment or preventions of conditions involving the PD-1/PD-L1 interaction (about 0.5 mg to about 7 g per human patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. For compounds administered orally, transdermally, intravenously, or subcutaneously, it is preferred that sufficient amount of the compound be administered to achieve a serum concentration of 5 ng (nanograms)/mL-10 μg (micrograms)/mL serum, more preferably sufficient compound to achieve a serum concentration of 20 ng-1 μg/ml serum should be administered, most preferably sufficient compound to achieve a serum concentration of 50 ng/ml-200 ng/ml serum should be administered. For direct injection into the synovium (for the treatment of arthritis) sufficient compounds should be administered to achieve a local concentration of approximately 1 micromolar.

Frequency of dosage may also vary depending on the compound used and the particular disease treated. However, for treatment of most disorders, a dosage regimen of 4 times daily, three times daily, or less is preferred, with a dosage regimen of once daily or 2 times daily being particularly preferred. It will be understood, however, that the specific dose level for any particular patient will depend upon a variety of factors including the activity of the specific compound employed, the age, body weight, general health, sex, diet, time of administration, route of administration, and rate of excretion, drug combination (i.e., other drugs being administered to the patient), the severity of the particular disease undergoing therapy, and other factors, including the judgment of the prescribing medical practitioner.

In another aspect of the disclosure, the compounds of the disclosure can be used in a variety of non-pharmaceutical in vitro and in vivo application. The compounds of the disclosure may also be used as positive controls in assays for PD-1/PD-L1 interaction activity, i.e., as standards for determining the ability of a candidate agent to bind to PD-1 and/or PD-L1, or as radiotracers for positron emission tomography (PET) imaging or for single photon emission computerized tomography (SPECT).

Also within the scope of the present disclosure are kits comprising a compound of the present disclosure or pharmaceutically acceptable salts thereof and instructions for use. The kit can further contain at least one additional reagent. Kits typically include a label indicating the intended use of the contents of the kit. The term label includes any writing, or recorded material supplied on or with the kit, or which otherwise accompanies the kit.

EXAMPLES

The following Examples illustrate various methods of making compounds of this disclosure including compounds of Formulae (I), (Ia) or (Ib). The following examples are offered to illustrate, but not to limit the claimed disclosure.

Reagents and solvents used below can be obtained from commercial sources such as Aldrich Chemical Co. (Milwaukee, Wis., USA). $^1$H-NMR spectra were recorded on a Varian Mercury 400 MHz NMR spectrometer. Significant peaks are provided relative to TMS and are tabulated in the order: multiplicity (s, singlet; d, doublet; t, triplet; q, quartet; m, multiplet) and number of protons. Mass spectrometry results are reported as the ratio of mass over charge. In the examples, a single m/z value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP1100 HPLC for sample delivery. Normally the analyte was dissolved in methanol or CH$_3$CN at 0.1 mg/mL and 1 microliter was infused with the delivery solvent into the mass spectrometer, which scanned from 100 to 1000 Daltons. All compounds could be analyzed in the positive or negative ESI mode, using acetonitrile/water with 1% formic acid as the delivery solvent.

The following abbreviations are used in the Examples and throughout the description of the disclosure: TLC means Thin layer chromatography.

Compounds within the scope of this disclosure can be synthesized as described below, using a variety of reactions known to the skilled artisan. One skilled in the art will also recognize that alternative methods may be employed to synthesize the target compounds of this disclosure, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are claimed unless a specific enantiomer is specified.

The detailed description of the experimental procedures used to synthesize key compounds in this text lead to molecules that are described by the physical data identifying them as well as by the structural depictions associated with them.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Example 1: N-(2'-chloro-3'-(5-((((3R,4R)-3-hydroxytetrahydro-2H-pyran-4-yl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide

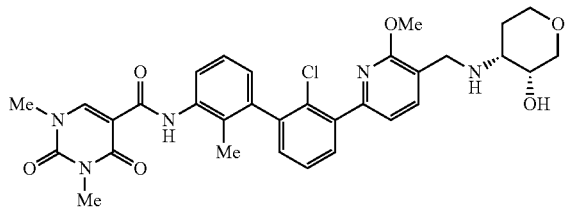 [SMILES: COc1nc(-c2cccc(-c3cccc(NC(=O)c4cn(C)c(=O)n(C)c4=O)c3C)c2Cl)ccc1CN[C@@H]1CCOC[C@@H]1O]

Step a: To a mixture of 1,3-dimethyl-N-(2-methyl-3-(4,4,5,5-tetramethyl-1,3,2-dioxaborolan-2-yl)phenyl)-2,4-dioxo-1,2,3,4-tetrahydropyrimidine-5-carboxamide (3.6 g, 9.0 mmol), 1,3-dibromo-2-chlorobenzene (6.9 g, 25.5 mmol), and K$_2$CO$_3$ (3.8 g, 27.5 mmol) in p-dioxane (40 mL) and DI H$_2$O (6 mL) was added Pd(dppf)Cl$_2$ complex with dichloromethane (912 mg, 1.12 mmol). The reaction mixture was degassed and stirred under N$_2$ at 90° C. for 2 h. The contents were diluted with EtOAc, filtered through Celite, washed with brine and dried over MgSO$_4$. The solvent was removed under reduced pressure and the residue was purified by silica gel flash chromatography to give N-(3'-bromo-2'-chloro-2-methyl-[1,1'-biphenyl]-3-yl)-1,3-dimethyl-2,4-dioxo-1,2,3,4-tetrahydropyrimidine-5-carboxamide. MS: (ES) m/z calculated for C$_{20}$H$_{18}$BrClN$_3$O$_3$ [M+H]$^+$ 462.0. found 462.0.

Step b: To a mixture of N-(3'-bromo-2'-chloro-2-methyl-[1,1'-biphenyl]-3-yl)-1,3-dimethyl-2,4-dioxo-1,2,3,4-tetrahydropyrimidine-5-carboxamide (1.4 g, 3.03 mmol), pinacol diborane (1.0 g, 3.94 mmol), and KOAc (1.2 g, 10.2 mmol) in p-dioxane (18 mL) was added Pd(dppf)Cl$_2$ complex with dichloromethane (350 mg, 0.43 mmol). The reaction mixture was degassed (N$_2$) and stirred under N$_2$ at 90° C. for 3 h. The contents were diluted with EtOAc, filtered through Celite, washed with brine and dried over MgSO$_4$. The solvent was removed under reduced pressure and the residue was purified by silica gel flash chromatography to give N-(2'-chloro-2-methyl-3'-(4,4,5,5-tetramethyl-1,3,2-dioxaborolan-2-yl)-[1,1'-biphenyl]-3-yl)-1,3-dimethyl-2,4-dioxo-1,2,3,4-tetrahydropyrimidine-5-carboxamide. MS: (ES) m/z calculated for C$_{26}$H$_{30}$BClN$_3$O$_5$ [M+H]$^+$ 510.2. found 510.1.

Step c: To a mixture of N-(2'-chloro-2-methyl-3'-(4,4,5,5-tetramethyl-1,3,2-dioxaborolan-2-yl)-[1,1'-biphenyl]-3-yl)-1,3-dimethyl-2,4-dioxo-1,2,3,4-tetrahydropyrimidine-5-carboxamide (400 mg, 0.78 mmol), 6-chloro-2-methoxynicotinaldehyde (200 mg, 1.17 mmol), and K$_2$CO$_3$ (350 mg, 2.53 mmol) in p-dioxane (10 mL) and DI H$_2$O (2 mL) was added Pd(dppf)Cl$_2$ complex with dichloromethane (70 mg, 0.086 mmol). The reaction mixture was degassed and stirred under N$_2$ at 95° C. for 2 h. The contents were diluted with EtOAc, filtered through Celite, washed with brine and dried over MgSO$_4$. The solvent was removed under reduced pressure and the residue was purified by silica gel flash chromatography to give N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide. MS: (ES) m/z calculated for C$_{27}$H$_{24}$ClN$_4$O$_5$ [M+H]$^+$ 519.1. found 519.1.

Step d: To a stirred solution of N-(2'-chloro-3'-(5-formyl-6-methoxypyridin-2-yl)-2-methyl-[1,1'-biphenyl]-3-yl)-1,3- dimethyl-2,4-dioxo-1,2,3,4-tetrahydropyrimidine-5-carboxamide (40 mg, 0.077 mmol) and (3R,4R)-4-aminotetrahydro-2H-pyran-3-ol hydrochloride (24 mg, 0.154 mmol) in dichloroethane (2 mL) and ethanol (1 mL) was added triethylamine (2 drops) followed by acetic acid (2 drops). The reaction mixture was stirred at 70° C. for 1 hr, then cooled to 0° C. and NaBH$_3$CN (10 mg, 0.154 mmol) was added slowly. The contents were stirred at 0° C. for 10 min, filtered and then purified by preparative HPLC to give N-(2'-chloro-3'-(5-((((3R,4R)-3-hydroxytetrahydro-2H-pyran-4-yl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.18 (s, 1H), 8.63 (s, 1H), 8.13-8.06 (m, 1H), 7.88 (d, J=7.6 Hz, 1H), 7.61 (dd, J=7.6, 1.7 Hz, 1H), 7.49 (t, J=7.6 Hz, 1H), 7.39-7.25 (m, 3H), 7.00 (d, J=7.7 Hz, 1H), 4.35 (d, J=13.3 Hz, 1H), 4.24 (d, J=13.2 Hz, 1H), 4.11-3.93 (m, 6H), 3.61-3.36 (m, 10H), 2.13 (s, 4H), 1.87 (d, J=12.4 Hz, 1H). MS: (ES) m/z calculated for C$_{32}$H$_{34}$ClN$_5$O$_6$ [M+H]$^+$ 620.2. found 620.2.

Example 2: (S)—N-(2'-chloro-3'-(6-methoxy-5-(((5-oxopyrrolidin-3-yl)amino)methyl)pyridin-2-yl)-2-methyl-[1,1'-biphenyl]-3-yl)-1,3-dimethyl-2,4-dioxo-1,2,3,4-tetrahydropyrimidine-5-carboxamide

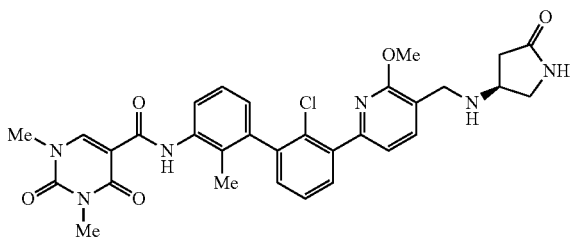 [SMILES: COc1nc(-c2cccc(-c3cccc(NC(=O)c4cn(C)c(=O)n(C)c4=O)c3C)c2Cl)ccc1CN[C@@H]1CNC(=O)C1]

The title compound was prepared from N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide and (4S)-4-aminopyrrolidin-2-one hydrochloride using a procedure similar to step d in Example 1. The product was purified by preparative HPLC to give the desired product (S)—N-(2'-chloro-3'-(6-methoxy-5-(((5-oxopyrrolidin-3-yl)amino)methyl)pyridin-2-yl)-2-methyl-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.17 (s, 1H), 8.63 (s, 1H), 8.11 (t, J=7.5 Hz, 1H), 7.89 (d, J=7.6 Hz, 1H), 7.61 (dd, J=7.7, 1.6 Hz, 1H), 7.49 (t, J=7.6 Hz, 1H), 7.40-7.25 (m, 3H), 7.04-6.97 (m, 1H), 4.32 (s, 2H), 4.24 (tt, J=8.3, 4.2 Hz, 1H), 4.10 (d, J=0.8 Hz, 3H), 3.87 (dd, J=11.7, 7.6 Hz, 1H), 3.63-3.53 (m, 4H), 3.39 (s, 3H), 3.31 (p, J=1.6 Hz, 11H), 2.90 (dd, J=17.8, 8.8 Hz, 1H), 2.57 (dd, J=17.8, 4.7 Hz, 1H), 2.13 (s, 3H). MS: (ES) m/z calculated for C$_{31}$H$_{31}$ClN$_6$O$_5$ [M+H]$^+$ 603.2. found 603.2.

Example 3: (S)—N-(2'-chloro-3'-(6-methoxy-5-((((5-oxopyrrolidin-2-yl)methyl)amino)methyl)pyridin-2-yl)-2-methyl-[1,1'-biphenyl]-3-yl)-1,3-dimethyl-2,4-dioxo-1,2,3,4-tetrahydropyrimidine-5-carboxamide

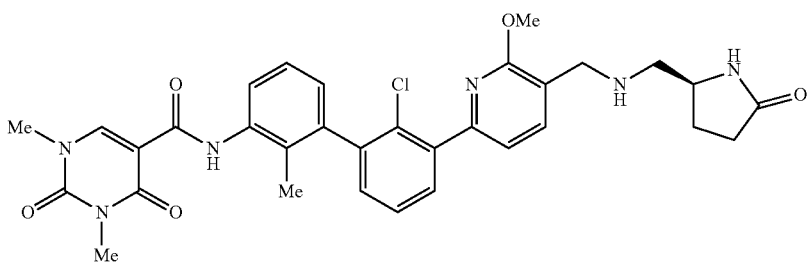 [SMILES: COc1nc(-c2cccc(-c3cccc(NC(=O)c4cn(C)c(=O)n(C)c4=O)c3C)c2Cl)ccc1CNC[C@@H]1CCC(=O)N1]

The title compound was prepared from N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide and (S)-5-aminomethylpyrrolidin-2-one hydrochloride using a procedure similar to step d in Example 1. The product was purified by preparative HPLC to give the desired product (S)—N-(2'-chloro-3'-(6-methoxy-5-((((5-oxopyrrolidin-2-yl)methyl)amino)methyl)pyridin-2-yl)-2-methyl-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 8.63 (d, J=1.1 Hz, 1H), 8.12 (dd, J=7.9, 1.3 Hz, 1H), 7.88 (d, J=7.6 Hz, 1H), 7.61 (d, J=7.7 Hz, 1H), 7.50 (dd, J=7.6, 7.6 Hz, 1H), 7.41-7.25 (m, 3H), 7.00 (d, J=7.5 Hz, 1H), 4.34 (d, J=2.0 Hz, 2H), 4.13-4.00 (m, 4H), 3.55 (d, J=1.0 Hz, 3H), 3.39 (d, J=1.0 Hz, 3H), 3.34-3.22 (m, 2H), 2.49-2.32 (m, 3H), 2.13 (s, 3H), 1.92 (q, J=7.5 Hz, 1H). MS: (ES) m/z calculated for C$_{32}$H$_{33}$ClN$_6$O$_5$ [M+H]$^+$ 617.2. found 617.2.

Example 4: N-(2,2'-dichloro-3'-(5-((((3R,4R)-3-hydroxytetrahydro-2H-pyran-4-yl)amino)methyl)-6-methoxypyrazin-2-yl)-[1,1'-biphenyl]-3-yl)-1,3-dimethyl-2,4-dioxo-1,2,3,4-tetrahydropyrimidine-5-carboxamide

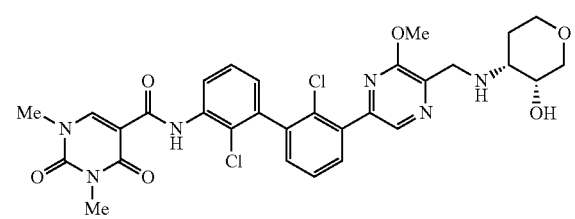 [SMILES: COc1nc(-c2cccc(-c3cccc(NC(=O)c4cn(C)c(=O)n(C)c4=O)c3Cl)c2Cl)cnc1CN[C@@H]1CCOC[C@@H]1O]

The compound was prepared from N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide and (3R,4R)-4-aminotetrahydro-2H-pyran-3-ol hydrochloride using a procedure similar to step d in Example 1. The product was purified by preparative HPLC to give the desired product N-(2,2'-dichloro-3'-(5-((((3R,4R)-3-hydroxytetrahydro-2H-pyran-4-yl)amino)methyl)-6-methoxypyrazin-2-yl)-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.70 (s, 1H), 8.67 (s, 1H), 8.56 (d, J=6.9 Hz, 2H), 7.77-7.67 (m, 1H), 7.57 (t, J=7.9 Hz, 1H), 7.43 (d, J=20.5 Hz, 2H), 7.12 (d, J=8.8 Hz, 1H), 4.49 (s, 2H), 4.13 (s, 3H), 4.10-3.95 (m, 3H), 3.64-3.53 (m, 5H), 3.52-3.42 (m, 1H), 3.39 (s, 3H), 2.23-2.09 (m, 1H), 1.97-1.88 (m, 1H). MS: (ES) m/z calculated for C$_{30}$H$_{30}$Cl$_2$N$_6$O$_6$ [M+H]$^+$ 641.2. found 641.1.

Example 5: N-(2,2'-dichloro-3'-(5-((((3S,4S)-3-hydroxytetrahydro-2H-pyran-4-yl)amino)methyl)-6-methoxypyrazin-2-yl)-[1,1'-biphenyl]-3-yl)-1,3-dimethyl-2,4-dioxo-1,2,3,4-tetrahydropyrimidine-5-carboxamide

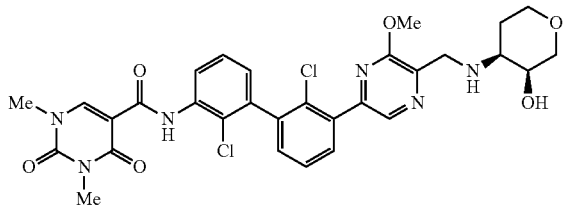

The title compound was prepared from N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide and (3S,4S)-4-aminotetrahydro-2H-pyran-3-ol hydrochloride using a procedure similar to step d in Example 1. The product was purified by preparative HPLC to give the desired product N-(2,2'-dichloro-3'-(5-((((3S,4S)-3-hydroxytetrahydro-2H-pyran-4-yl)amino)methyl)-6-methoxypyrazin-2-yl)-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.71 (s, 1H), 8.67 (s, 1H), 8.56 (d, J=6.9 Hz, 2H), 7.73-7.71 (m, 1H), 7.57 (t, J=7.9 Hz, 1H), 7.46-7.41 (m, 2H), 7.12 (d, J=8.8 Hz, 1H), 4.49 (s, 2H), 4.13 (s, 3H), 4.10-3.96 (m, 3H), 3.62-3.56 (m, 5H), 3.50-3.47 (m, 1H), 3.39 (s, 3H), 2.20-2.14 (m, 1H), 1.97-1.91 (m, 1H). MS: (ES) m/z calculated for C$_{30}$H$_{30}$Cl$_2$N$_6$O$_6$ [M+H]$^+$ 641.2. found 641.0.

Example 6: (S)—N-(2,2'-dichloro-3'-(6-methoxy-5-(((((5-oxopyrrolidin-2-yl)methyl)amino)methyl)pyrazin-2-yl)-[1,1'-biphenyl]-3-yl)-1,3-dimethyl-2,4-dioxo-1,2,3,4-tetrahydropyrimidine-5-carboxamide The title compound was prepared from N-(2,2'-dichloro-3'-(5-formyl-6-methoxypyrazin-2-yl)-[1,1'-biphenyl]-3-yl)-1,3-dimethyl-2,4-dioxo-1,2,3,4-tetrahydropyrimidine-5-carboxamide and (S)-5-aminomethylpyrrolidin-2-one hydrochloride using a procedure similar to step d in Example 1. The product was purified by preparative HPLC to give the desired product (S)—N-(2,2'-dichloro-3'-(6-methoxy-5-((((5-oxopyrrolidin-2-yl)methyl)amino)methyl)pyrazin-2-yl)-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 8.67 (s, 1H), 8.59-8.52 (m, 2H), 7.71 (dd, J=7.6, 1.5 Hz, 1H), 7.57 (dd, J=7.7, 7.7 Hz, 1H), 7.48-7.37 (m, 2H), 7.11 (d, J=7.5 Hz, 1H), 4.53 (d, J=3.8 Hz, 2H), 4.13 (d, J=1.1 Hz, 4H), 3.56 (d, J=1.1 Hz, 3H), 3.41-3.29 (m, 6H), 2.50-2.34 (m, 3H), 1.97 (q, J=10.0 Hz, 1H). MS: (ES) m/z calculated for C$_{30}$H$_{29}$Cl$_2$N$_7$O$_5$ [M+H]$^+$ 638.1, found 638.0.

Example 7: (S)—N-(2,2'-dichloro-3'-(6-methoxy-5-(((5-oxopyrrolidin-3-yl)amino)methyl)pyrazin-2-yl)-[1,1'-biphenyl]-3-yl)-1,3-dimethyl-2,4-dioxo-1,2,3,4-tetrahydropyrimidine-5-carboxamide

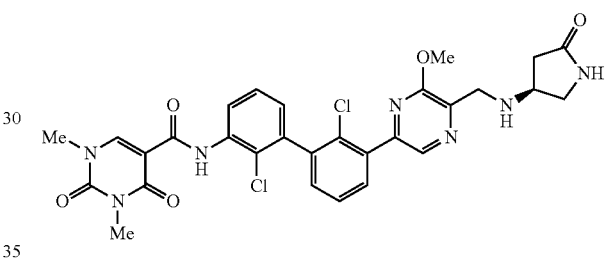

The title compound was prepared from N-(2,2'-dichloro-3'-(5-formyl-6-methoxypyrazin-2-yl)-[1,1'-biphenyl]-3-yl)-1,3-dimethyl-2,4-dioxo-1,2,3,4-tetrahydropyrimidine-5-carboxamide and (S)-4-aminopyrrolidin-2-one hydrochloride using a procedure similar to step d in Example 1. The product was purified by preparative HPLC to give the desired product (S)—N-(2,2'-dichloro-3'-(6-methoxy-5-(((5-oxopyrrolidin-3-yl)amino)methyl)pyrazin-2-yl)-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.70 (s, 1H), 8.67 (s, 1H), 8.55 (d, J=9.1 Hz, 2H), 7.72 (d, J=8.2 Hz, 1H), 7.57 (d, J=14.8 Hz, 1H), 7.46-7.41 (m, 2H), 7.11 (d, J=7.8 Hz, 1H), 4.53 (s, 2H), 4.37-4.28 (m, 1H), 4.14 (s, 3H), 3.94-3.86 (m, 1H), 3.69-3.60 (m, 1H), 3.56 (s, 3H), 3.39 (s, 3H), 2.96-2.86 (m, 1H), 2.65 (dd, J=18.5, 6.6 Hz, 1H). MS: (ES) m/z calculated for C$_{29}$H$_{27}$Cl$_2$N$_7$O$_5$ [M+H]$^+$ 624.2. found 624.0.

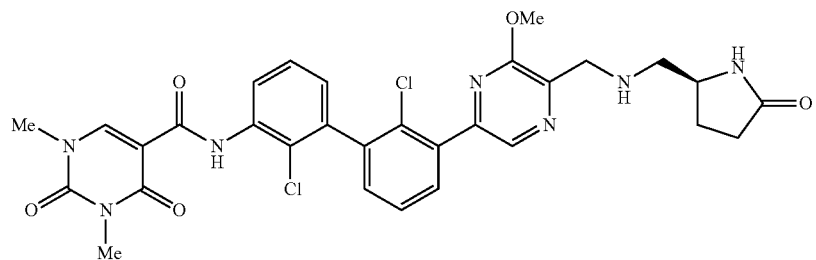 [SMILES: COc1nc(-c2cccc(-c3cccc(NC(=O)c4cn(C)c(=O)n(C)c4=O)c3Cl)c2Cl)cnc1CNC[C@@H]1CCC(=O)N1]

Example 8: (R)—N-(2,2'-dichloro-3'-(6-methoxy-5-(((6-oxopiperidin-3-yl)amino)methyl)pyrazin-2-yl)-[1,1'-biphenyl]-3-yl)-1,3-dimethyl-2,4-dioxo-1,2,3,4-tetrahydropyrimidine-5-carboxamide

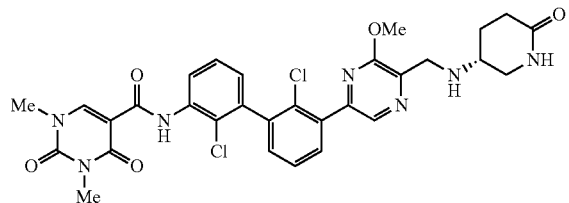 [SMILES: COc1nc(-c2cccc(-c3cccc(NC(=O)c4cn(C)c(=O)n(C)c4=O)c3Cl)c2Cl)cnc1CN[C@@H]1CCC(=O)NC1]

The title compound was prepared from N-(2,2'-dichloro-3'-(5-formyl-6-methoxypyrazin-2-yl)-[1,1'-biphenyl]-3-yl)-1,3-dimethyl-2,4-dioxo-1,2,3,4-tetrahydropyrimidine-5-carboxamide and (R)-5-aminopiperidin-2-one hydrochloride using a procedure similar to step d in Example 1. The product was purified by preparative HPLC to give the desired product (R)—N-(2,2'-dichloro-3'-(6-methoxy-5-(((6-oxopiperidin-3-yl)amino)methyl)pyrazin-2-yl)-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.70 (s, 1H), 8.67 (s, 1H), 8.56 (d, J=3.3 Hz, 2H), 7.72 (d, J=7.7 Hz, 1H), 7.57 (t, J=7.9 Hz, 1H), 7.46-7.40 (m, 2H), 7.11 (d, J=8.6 Hz, 1H), 4.65-4.49 (m, 2H), 4.14 (s, 3H), 3.88-3.73 (m, 2H), 3.56 (s, 3H), 3.55-3.48 (m, 1H), 3.39 (s, 3H), 2.55-2.49 (m, 2H), 2.45-2.38 (m, 1H), 2.18-2.08 (m, 1H). MS: (ES) m/z calculated for C$_{29}$H$_{27}$Cl$_2$N$_7$O$_5$ [M+H]$^+$ 638.2, found 638.0.

Example 9: (S)—N-(2'-chloro-3'-(6-ethoxy-5-((((5-oxopyrrolidin-2-yl)methyl)amino)methyl)pyridin-2-yl)-2-methyl-[1,1'-biphenyl]-3-yl)-1,3-dimethyl-2,4-dioxo-1,2,3,4-tetrahydropyrimidine-5-carboxamide

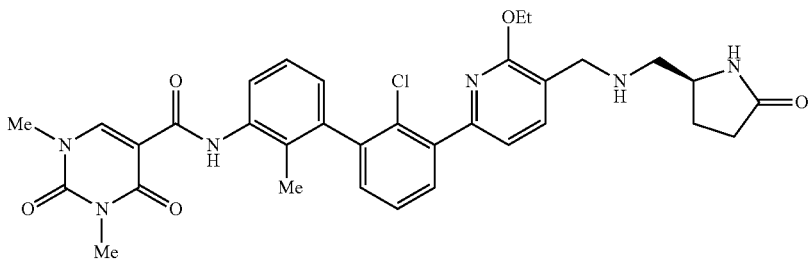 [SMILES: CCOc1nc(-c2cccc(-c3cccc(NC(=O)c4cn(C)c(=O)n(C)c4=O)c3C)c2Cl)ccc1CNC[C@@H]1CCC(=O)N1]

The compound was prepared from N-(2'-chloro-3'-(6-ethoxy-5-formylpyridin-2-yl)-2-methyl-[1,1'-biphenyl]-3-yl)-1,3-dimethyl-2,4-dioxo-1,2,3,4-tetrahydropyrimidine-5-carboxamide and (S)-(5-oxopyrrolidin-2-yl)methanamine hydrochloride using a procedure similar to step d in Example 1. The crude product was purified by preparative HPLC to give the desired product (S)—N-(2'-chloro-3'-(6-ethoxy-5-((((5-oxopyrrolidin-2-yl)methyl)amino)methyl)pyridin-2-yl)-2-methyl-[1,1'-biphenyl]-3-yl)-1,3-dimethyl-2,4-dioxo-1,2,3,4-tetrahydropyrimidine-5-carboxamide. H NMR (400 MHz, CDCl$_3$) δ 10.93 (d, J=5.0 Hz, 1H), 8.55 (d, J=7.4 Hz, 1H), 8.18 (dd, J=8.1, 4.2 Hz, 1H), 8.02 (s, 1H), 7.80-7.70 (m, 1H), 7.61-7.52 (m, 1H), 7.40 (dd, J=7.6, 7.6 Hz, 1H), 7.29 (td, J=6.8, 5.6, 2.8 Hz, 3H), 7.02 (d, J=7.6 Hz, 1H), 4.51 (d, J=7.9 Hz, 2H), 4.21 (d, J=33.5 Hz, 3H), 3.58 (d, J=2.1 Hz, 3H), 3.44 (s, 3H), 3.20-3.00 (m, 2H), 2.34 (s, 4H), 2.16 (d, J=1.4 Hz, 3H), 1.73 (s, 1H), 1.40 (t, J=7.0 Hz, 3H). MS: (ES) m/z calculated for C$_{33}$H$_{36}$ClN$_6$O$_5$ [M+H]$^+$ 631.2. found 631.2.

Example 10: N-(2,2'-dichloro-3'-(6-methoxy-5-((6-oxo-2,5-diazaspiro[3.4]octan-2-yl)methyl)pyrazin-2-yl)-[1,1'-biphenyl]-3-yl)-1,3-dimethyl-2,4-dioxo-1,2,3,4-tetrahydropyrimidine-5-carboxamide

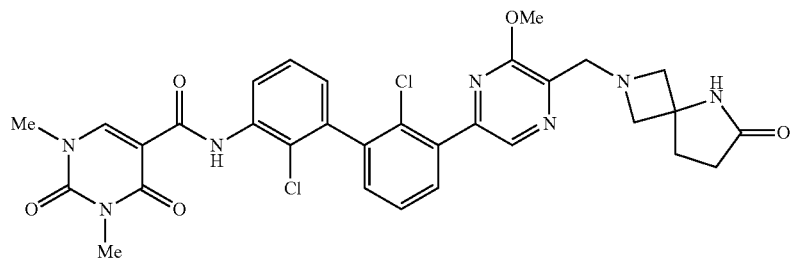 [SMILES: COc1nc(-c2cccc(-c3cccc(NC(=O)c4cn(C)c(=O)n(C)c4=O)c3Cl)c2Cl)cnc1CN1CC2(CCC(=O)N2)C1]

The compound was prepared from N-(2,2'-dichloro-3'-(5-formyl-6-methoxypyrazin-2-yl)-[1,1'-biphenyl]-3-yl)-1,3-dimethyl-2,4-dioxo-1,2,3,4-tetrahydropyrimidine-5-carboxamide and 2,5-diazaspiro[3.4]octan-6-one hydrochloride using a procedure similar to step d in Example 1. The crude product was purified by preparative HPLC to give the desired product N-(2,2'-dichloro-3'-(6-methoxy-5-((6-oxo-2,5-diazaspiro[3.4]octan-2-yl)methyl)pyrazin-2-yl)-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.70 (s, 1H), 8.67 (d, J=1.2 Hz, 1H), 8.58-8.48 (m, 2H), 7.70 (d, J=7.9 Hz, 1H), 7.56 (dd, J=7.6, 7.6 Hz, 1H), 7.47-7.37 (m, 2H), 7.14-7.07 (m, 1H), 4.75 (s, 2H), 4.63 (s, 1H), 4.34 (s, 1H), 4.12 (d, J=1.1 Hz, 3H), 3.56 (d, J=1.3 Hz, 3H), 3.39 (d, J=1.1 Hz, 3H), 3.35-3.29 (m, 3H), 2.57 (t, J=7.8 Hz, 2H), 2.43 (d, J=7.9 Hz, 2H). MS: (ES) m/z calculated for C$_{31}$H$_{30}$Cl$_2$N$_7$O$_5$ [M+H]$^+$ 650.2. found 650.0.

Example 11: N-(2,2'-dichloro-3'-(5-((3-hydroxyazetidin-1-yl)methyl)-6-methoxypyrazin-2-yl)-[1,1'-biphenyl]-3-yl)-1,3-dimethyl-2,4-dioxo-1,2,3,4-tetrahydropyrimidine-5-carboxamide

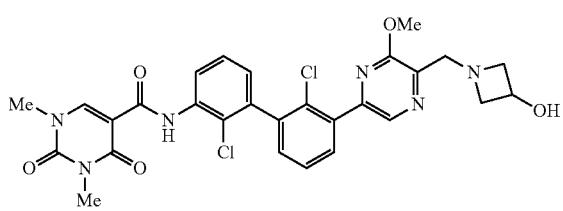 [SMILES: COc1nc(-c2cccc(-c3cccc(NC(=O)c4cn(C)c(=O)n(C)c4=O)c3Cl)c2Cl)cnc1CN1CC(O)C1]

The compound was prepared from N-(2,2'-dichloro-3'-(5-formyl-6-methoxypyrazin-2-yl)-[1,1'-biphenyl]-3-yl)-1,3-dimethyl-2,4-dioxo-1,2,3,4-tetrahydropyrimidine-5-carboxamide and azetidin-3-ol using a procedure similar to step d in Example 1. The crude product was purified by preparative HPLC to give N-(2,2'-dichloro-3'-(5-((3-hydroxyazetidin-1-yl)methyl)-6-methoxypyrazin-2-yl)-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.71 (s, 1H), 8.67 (s, 1H), 8.56-8.50 (m, 2H), 7.70 (d, J=7.5 Hz, 1H), 7.56 (dd, J=7.7, 7.7 Hz, 1H), 7.47-7.40 (m, 2H), 7.11 (dd, J=7.6, 1.4 Hz, 1H), 4.81-4.63 (m, 3H), 4.42-4.27 (m, 2H), 4.12 (m, 5H), 4.06-4.03 (m, 1H), 3.56 (s, 3H), 3.35 (m, 3H). MS: (ES) m/z calculated for C$_{28}$H$_{27}$Cl$_2$N$_6$O$_5$ [M+H]$^+$ 597.1. found 597.0.

Example 12: N-(2,2'-dichloro-3'-(5-((3-hydroxyazetidin-1-yl)methyl)-6-methoxypyridin-2-yl)-[1,1'-biphenyl]-3-yl)-1,3-dimethyl-2,4-dioxo-1,2,3,4-tetrahydropyrimidine-5-carboxamide

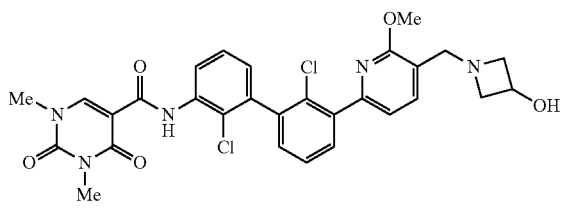 [SMILES: COc1nc(-c2cccc(-c3cccc(NC(=O)c4cn(C)c(=O)n(C)c4=O)c3Cl)c2Cl)ccc1CN1CC(O)C1]

The compound was prepared from N-(2,2'-dichloro-3'-(5-formyl-6-methoxypyridin-2-yl)-[1,1'-biphenyl]-3-yl)-1,3-dimethyl-2,4-dioxo-1,2,3,4-tetrahydropyrimidine-5-carboxamide and azetidin-3-ol using a procedure similar to step d in Example 1. The crude product was purified by preparative HPLC to give N-(2,2'-dichloro-3'-(5-((3-hydroxyazetidin-1-yl)methyl)-6-methoxypyridin-2-yl)-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.67 (s, 1H), 8.65 (s, 1H), 8.53 (d, J=7.9 Hz, 1H), 7.93-7.86 (m, 1H), 7.66-7.60 (m, 1H), 7.47 (d, J=7.4 Hz, 1H), 7.42-7.36 (m, 3H), 7.09 (d, J=7.1 Hz, 1H), 4.76 (s, 1H), 4.62-4.41 (m, 4H), 4.09-4.02 (m, 5H), 3.54 (s, 3H), 3.37 (s, 3H). MS: (ES) m/z calculated for C$_{29}$H$_{28}$Cl$_2$N$_5$O$_5$ [M+H]$^+$ 596.1, found 596.2.

Example 13: N-(2,2'-dichloro-3'-(5-((((3R,4R)-3-hydroxytetrahydro-2H-pyran-4-yl)amino)methyl)-4-methoxypyrimidin-2-yl)-[1,1'-biphenyl]-3-yl)-1,3-dimethyl-2,4-dioxo-1,2,3,4-tetrahydropyrimidine-5-carboxamide

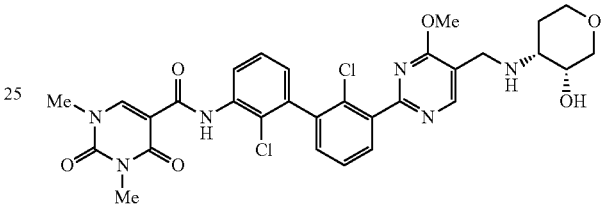

Step a: To a mixture of N-(2,2'-dichloro-3'-(4,4,5,5-tetramethyl-1,3,2-dioxaborolan-2-yl)-[1,1'-biphenyl]-3-yl)-1,3-dimethyl-2,4-dioxo-1,2,3,4-tetrahydropyrimidine-5-carboxamide (1.0 g, 1.9 mmol), 2-chloro-4-methoxypyrimidine-5-carbaldehyde (400 mg, 2.3 mmol), 2 M K$_2$CO$_3$ (3 mL, 6 mmol) in p-dioxane (20 mL) was added Pd(PPh$_3$)$_4$ (260 mg, 0.22 mmol). The reaction mixture was degassed for 5 min and stirred at 80° C. for 2 h. Dioxane was removed from the reaction mixture under reduced pressure and the residue was taken up in a mixture of chloroform and water. The contents were filtered and the filtrate was evaporated and dried to afford N-(2,2'-dichloro-3'-(5-formyl-4-methoxypyrimidin-2-yl)-[1,1'-biphenyl]-3-yl)-1,3-dimethyl-2,4-dioxo-1,2,3,4-tetrahydropyrimidine-5-carboxamide. MS: (ES) m/z calculated for C$_{25}$H$_{20}$Cl$_2$N$_2$O$_5$ [M+H]$^+$ 540.0. found 540.1.

Step b: To a stirred suspension of N-(2,2'-dichloro-3'-(5-formyl-4-methoxypyrimidin-2-yl)-[1,1'-biphenyl]-3-yl)-1,3-dimethyl-2,4-dioxo-1,2,3,4-tetrahydropyrimidine-5-carboxamide (39 mg, 0.07 mmol) and (3R,4R)-aminooxan-3-ol hydrochloride (47 mg, 0.3 mmol) in 20% (v/v) MeOH in DCM was added Et$_3$N (43 µL, 0.31 mmol). After stirring for 5 min, Na(OAc)$_3$BH (78 mg, 0.37 mmol) was added to the reaction mixture. An additional portion of Na(OAc)$_3$BH (82 mg, 0.39 mmol) was added and the contents were stirred for an additional 15 h. The solvent was removed in vacuo and the residue was dissolved in a mixture of p-dioxane, DMSO, TFA, and water then filtered. The crude residue was purified by preparative HPLC to give N-(2,2'-dichloro-3'-(5-((((3R,4R)-3-hydroxytetrahydro-2H-pyran-4-yl)amino)methyl)-4-methoxypyrimidin-2-yl)-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.69 (s, 1H), 8.70 (s, 1H), 8.66 (s, 1H), 8.54 (d, J=8.4 Hz, 1H), 7.78 (d, J=8.0 Hz, 1H), 7.55 (dd, J=7.6, 7.6 Hz, 1H), 7.48-7.38 (m, 2H), 7.10 (d, J=7.6 Hz, 1H), 4.41-3.23 (m, 2H), 4.17 (s, 3H), 4.08-3.96 (m, 3H), 3.62-3.52 (m, 5H), 3.52-3.43 (m, 1H), 3.38 (s, 3H), 2.18-2.05 (m, 1H), 1.87 (d, J=7.6 Hz, 12.4 Hz, 1H). MS: (ES) m/z calculated for C$_{30}$H$_{31}$Cl$_2$N$_6$O$_6$ [M+H]$^+$ 641.2. found 641.0.

Example 14: (S)—N-(2,2'-dichloro-3'-(6-methoxy-5-((((5-oxopyrrolidin-2-yl)methyl)amino)methyl)pyridin-2-yl)-[1,1'-biphenyl]-3-yl)-1,3-dimethyl-2,4-dioxo-1,2,3,4-tetrahydropyrimidine-5-carboxamide

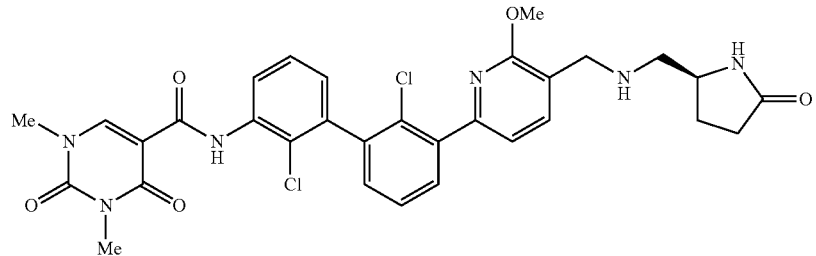 [SMILES: COc1nc(-c2cccc(-c3cccc(NC(=O)c4cn(C)c(=O)n(C)c4=O)c3Cl)c2Cl)ccc1CNC[C@@H]1CCC(=O)N1]

The compound was prepared from N-(2,2'-dichloro-3'-(5-formyl-6-methoxypyridin-2-yl)-[1,1'-biphenyl]-3-yl)-1,3-dimethyl-2,4-dioxo-1,2,3,4-tetrahydropyrimidine-5-carboxamide and (S)-5-(aminomethyl)pyrrolidin-2-one hydrochloride using a procedure similar to step d in Example 1. The crude product was purified by preparative HPLC to give (S)—N-(2,2'-dichloro-3'-(6-methoxy-5-((((5-oxopyrrolidin-2-yl)methyl)amino)methyl)pyridin-2-yl)-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.69 (s, 1H), 8.66 (s, 1H), 8.54 (d, J=8.3 Hz, 1H), 7.93-7.85 (m, 1H), 7.65 (dd, J=7.8, 1.8 Hz, 1H), 7.51 (dd, J=7.7, 7.7 Hz, 1H), 7.45-7.35 (m, 3H), 7.10 (d, J=7.6 Hz, 1H), 4.34 (s, 2H), 4.14-4.01 (m, 4H), 3.56 (d, J=1.6 Hz, 3H), 3.39 (d, J=1.8 Hz, 3H), 3.30-3.20 (m, 3H), 2.40 (dd, J=11.8, 11.1 Hz, 2H), 2.03 (d, J=1.7 Hz, 1H), 1.92 (d, J=6.9 Hz, 1H). MS: (ES) m/z calculated for C$_{31}$H$_{31}$Cl$_2$N$_6$O$_5$ [M+H]$^+$ 637.2. found 637.2.

Example 15: N-(2,2'-dichloro-3'-(5-((((3R,4R)-3-hydroxytetrahydro-2H-pyran-4-yl)amino)methyl)-6-methoxypyridin-2-yl)-[1,1'-biphenyl]-3-yl)-1,3-dimethyl-2,4-dioxo-1,2,3,4-tetrahydropyrimidine-5-carboxamide

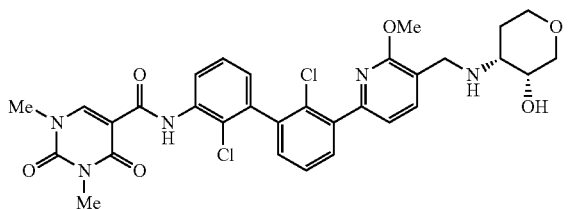 [SMILES: COc1nc(-c2cccc(-c3cccc(NC(=O)c4cn(C)c(=O)n(C)c4=O)c3Cl)c2Cl)ccc1CN[C@@H]1CCOC[C@@H]1O]

The compound was prepared from N-(2,2'-dichloro-3'-(5-formyl-6-methoxypyridin-2-yl)-[1,1'-biphenyl]-3-yl)-1,3-dimethyl-2,4-dioxo-1,2,3,4-tetrahydropyrimidine-5-carboxamide and (3R,4R)-4-aminotetrahydro-2H-pyran-3-ol hydrochloride using a procedure similar to step d in Example 1. The crude product was purified by preparative HPLC to give N-(2,2'-dichloro-3'-(5-((((3R,4R)-3-hydroxytetrahydro-2H-pyran-4-yl)amino)methyl)-6-methoxypyridin-2-yl)-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.69 (s, 1H), 8.67 (s, 1H), 8.53 (d, J=8.3 Hz, 1H), 7.88 (d, J=7.7 Hz, 1H), 7.69-7.62 (m, 1H), 7.51 (dd, J=7.7, 7.7 Hz, 1H), 7.45-7.33 (m, 3H), 7.13-7.06 (m, 1H), 4.35 (d, J=13.2 Hz, 1H), 4.24 (d, J=13.2 Hz, 1H), 4.12-3.93 (m, 6H), 3.62-3.42 (m, 6H), 3.39 (s, 3H), 2.18-2.07 (m, 1H), 2.03 (d, J=1.6 Hz, 2H), 1.87 (d, J=12.7 Hz, 1H). MS: (ES) m/z calculated for C$_{31}$H$_{32}$Cl$_2$N$_5$O$_6$ [M+H]$^+$ 640.2. found 640.5.

Example 16: (S)—N-(2,2'-dichloro-3'-(6-methoxy-5-((((5-oxopyrrolidin-2-yl)methyl)amino)methyl)pyridin-2-yl)-[1,1'-biphenyl]-3-yl)-2,4-dimethyl-3,5-dioxo-2,3,4,5-tetrahydro-1,2,4-triazine-6-carboxamide

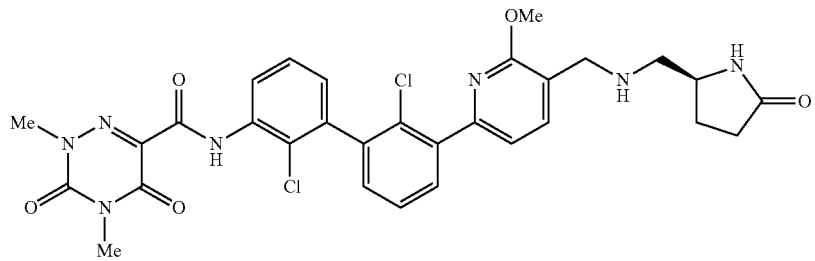 [SMILES: COc1nc(-c2cccc(-c3cccc(NC(=O)c4nn(C)c(=O)n(C)c4=O)c3Cl)c2Cl)ccc1CNC[C@@H]1CCC(=O)N1]

Step a: To a mixture of 2,4-dimethyl-3,5-dioxo-2,3,4,5-tetrahydro-1,2,4-triazine-6-carboxylic acid (200 mg, 1.1 mmol), 2-chloro-3-(4,4,5,5-tetramethyl-1,3,2-dioxaborolan-2-yl)aniline (350 mg, 1.4 mmol) and N,N-diisopropylethylamine (0.35 mL, 2.0 mmol) in DMF (3 mL) was added (1-[bis(dimethylamino)methylene]-1H-1,2,3-triazolo[4,5-b]pyridinium 3-oxide hexafluorophosphate (600 mg, 1.6 mmol). The mixture was heated at 60° C. for 1.5 h, cooled to room temperature, and added to water. The resulting precipitate was collected by filtration and dried in vacuo to give N-(2-chloro-3-(4,4,5,5-tetramethyl-1,3,2-dioxaborolan-2-yl)phenyl)-2,4-dimethyl-3,5-dioxo-2,3,4,5-tetrahydro-1,2,4-triazine-6-carboxamide. $^1$H NMR (400 MHz, DMSO-$d_6$) δ 11.34 (s, 1H), 8.47 (d, J=8.0 Hz, 1H), 7.44-7.38 (m, 2H), 3.68 (s, 3H), 3.25 (s, 3H), 1.32 (s, 12H).

Step b: To a mixture of N-(2-chloro-3-(4,4,5,5-tetramethyl-1,3,2-dioxaborolan-2-yl)phenyl)-2,4-dimethyl-3,5-dioxo-2,3,4,5-tetrahydro-1,2,4-triazine-6-carboxamide (100 mg, 0.24 mmol), 6-(3-bromo-2-chlorophenyl)-2-methoxynicotinaldehyde (70 mg, 0.21 mmol), and 2 M K$_2$CO$_3$ (1 mL, 2 mmol) in dioxane (4 mL) was added Pd(dppf)Cl$_2$ complex with DCM (39 mg, 0.05 mmol). The reaction mixture was degassed and stirred under N$_2$ at 90° C. for 1 h. The contents were diluted with EtOAc and water, the organic phase was collected and the solvent was removed under reduced pressure. The resultant residue was purified by silica gel flash chromatography to give N-(2,2'-dichloro-3'-(5-formyl-6-methoxypyridin-2-yl)-[1,1'-biphenyl]-3-yl)-2,4-dimethyl-3,5-dioxo-2,3,4,5-tetrahydro-1,2,4-triazine-6-carboxamide. MS: (ES) m/z calculated for C$_{25}$H$_{20}$Cl$_2$N$_5$O$_5$ [M+H]$^+$ 640.1. found 639.7.

Step c: To a mixture of N-(2,2'-dichloro-3'-(5-formyl-6-methoxypyridin-2-yl)-[1,1'-biphenyl]-3-yl)-2,4-dimethyl-3,5-dioxo-2,3,4,5-tetrahydro-1,2,4-triazine-6-carboxamide (94 mg, 0.17 mmol) and (S)-5-aminomethylpyrrolidin-2-one hydrochloride (51 mg, 0.34 mmol) in 20% (v/v) MeOH in DCM was added Et$_3$N (47 μL, 0.34 mmol). The mixture stirred at room temperature for 10 min, and Na(OAc)$_3$BH (116 mg, 0.55 mmol) was added. After stirring for 25 min, the solvent was removed in vacuo and the residue was dissolved in dioxane, MeCN, water and TFA and then filtered. The crude material was purified by preparative HPLC to give (S)—N-(2,2'-dichloro-3'-(6-methoxy-5-((((5-oxopyrrolidin-2-yl)methyl)amino)methyl)pyridin-2-yl)-[1,1'-biphenyl]-3-yl)-2,4-dimethyl-3,5-dioxo-2,3,4,5-tetrahydro-1,2,4-triazine-6-carboxamide. $^1$H NMR (400 MHz, CD$_3$OD) δ 11.68 (s, 1H), 8.58 (d, J=8.4 Hz, 1H), 7.89 (d, J=7.6 Hz, 1H), 7.66 (d, J=7.6 Hz, 1H), 7.52 (dd, J=8.0, 8.0 Hz, 1H), 7.46 (dd, J=8.0, 8.0 Hz, 1H), 7.42-7.36 (m, 2H), 7.17 (d, J=8.0 Hz, 1H), 4.34 (s, 2H), 4.11 (s, 3H), 4.09-4.02 (m, 1H), 3.79 (s, 3H), 3.39 (s, 3H), 3.28-3.22 (m, 2H), 2.48-2.34 (m, 3H), 1.97-1.87 (m, 1H). MS: (ES) m/z calculated for C$_{30}$H$_{30}$Cl$_2$N$_7$O$_5$ [M+H]$^+$ 638.2. found 638.5.

Example 17: (S)—N-(2-chloro-2'-fluoro-3'-(6-methoxy-5-((((5-oxopyrrolidin-2-yl)methyl)amino)methyl)pyridin-2-yl)-[1,1'-biphenyl]-3-yl)-1,3-dimethyl-2,4-dioxo-1,2,3,4-tetrahydropyrimidine-5-carboxamide

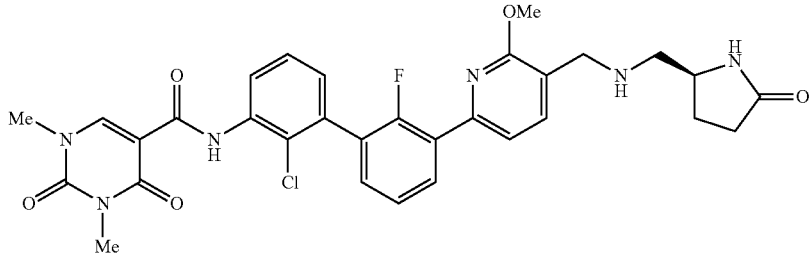 [SMILES: COc1nc(-c2cccc(-c3cccc(NC(=O)c4cn(C)c(=O)n(C)c4=O)c3Cl)c2F)ccc1CNC[C@@H]1CCC(=O)N1]

The compound was prepared from N-(2-chloro-2'-fluoro-3'-(5-formyl-6-methoxypyridin-2-yl)-[1,1'-biphenyl]-3-yl)-1,3-dimethyl-2,4-dioxo-1,2,3,4-tetrahydropyrimidine-5-carboxamide and (S)-5-aminomethylpyrrolidin-2-one hydrochloride using a procedure similar to step d in Example 1. The crude product was purified by preparative HPLC to give (S)—N-(2-chloro-2'-fluoro-3'-(6-methoxy-5-((((5-oxopyrrolidin-2-yl)methyl)amino)methyl)pyridin-2-yl)-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.71 (s, 1H), 8.67 (s, 1H), 8.56 (d, J=8.4 Hz, 1H), 8.22-8.14 (m, 1H), 7.87 (d, J=7.6 Hz, 1H), 7.57 (d, J=7.6 Hz, 1H), 7.46-7.39 (m, 3H), 7.18 (d, J=7.6 Hz, 1H), 4.34 (s, 2H), 4.17 (s, 3H), 4.09-4.00 (m, 1H), 3.56 (s, 3H), 3.39 (s, 3H), 3.28-3.20 (m, 2H), 2.52-2.28 (m, 3H), 1.99-1.90 (m, 1H). MS: (ES) m/z calculated for C$_{31}$H$_{31}$ClFN$_6$O$_5$ [M+H]$^+$ 621.2. found 621.5.

Example 18: (S)—N-(2,2'-dichloro-3'-(6-methoxy-5-((((5-oxopyrrolidin-2-yl)methyl)amino)methyl)pyridin-2-yl)-[1,1'-biphenyl]-3-yl)-1-methyl-6-oxo-1,6-dihydropyrimidine-5-carboxamide

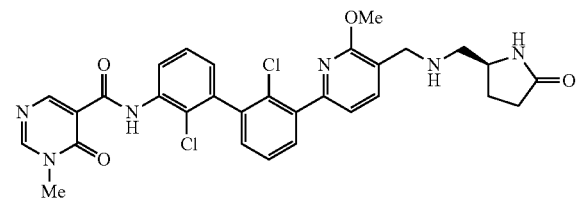 [SMILES: COc1nc(-c2cccc(-c3cccc(NC(=O)c4cncn(C)c4=O)c3Cl)c2Cl)ccc1CNC[C@@H]1CCC(=O)N1]

The compound was prepared from N-(2,2'-dichloro-3'-(5-formyl-6-methoxypyridin-2-yl)-[1,1'-biphenyl]-3-yl)-1-methyl-6-oxo-1,6-dihydropyrimidine-5-carboxamide and (S)-5-(aminomethyl)pyrrolidin-2-one hydrochloride using a procedure similar to step d in Example 1. The crude product was purified by preparative HPLC to give (S)—N-(2,2'-dichloro-3'-(6-methoxy-5-((((5-oxopyrrolidin-2-yl)methyl)amino)methyl)pyridin-2-yl)-[1,1'-biphenyl]-3-yl)-1-methyl-6-oxo-1,6-dihydropyrimidine-5-carboxamide. $^1$H NMR (400 MHz, CD$_3$OD) δ 11.94-11.89 (m, 1H), 8.94 (d, J=1.1 Hz, 1H), 8.67 (s, 1H), 8.62-8.55 (m, 1H), 7.92-7.85 (m, 1H), 7.66 (dd, J=7.8, 1.9 Hz, 1H), 7.56-7.35 (m, 4H), 7.13 (d, J=7.6 Hz, 1H), 4.34 (s, 2H), 4.13-3.99 (m, 4H), 3.65 (d, J=1.3 Hz, 3H), 3.29 (d, J=19.8 Hz, 3H), 2.49-2.32 (m, 3H), 1.92 (m, 1H). MS: (ES) m/z calculated for $C_{30}H_{29}Cl_2N_6O_4$ [M+H]$^+$ 607.2. found 607.1.

Example 19: N-(2'-chloro-3'-(5-(((2-hydroxyethyl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide

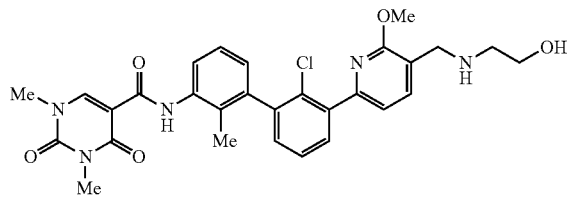 [SMILES: COc1nc(-c2cccc(-c3cccc(NC(=O)c4cn(C)c(=O)n(C)c4=O)c3C)c2Cl)ccc1CNCCO]

A mixture of N-(2,2'-dichloro-3'-(5-formyl-6-methoxypyridin-2-yl)-[1,1'-biphenyl]-3-yl)-1,3-dimethyl-2,4-dioxo-1,2,3,4-tetrahydropyrimidine-5-carboxamide (50 mg, 0.096 mmol), 2-aminoethan-1-ol (40 mg, 0.65 mmol) and AcOH (50 mg, 0.83 mmol) in DCM (2 mL) was stirred at room temperature for 1 h. To the mixture was added NaBH(OAc)$_3$ (61 mg, 0.29 mmol). After 2 h, the reaction was quenched with sat. aq. NaHCO$_3$ and extracted with DCM. The organic layer was separated, concentrated in vacuo and purified by preparative HPLC to give N-(2'-chloro-3'-(5-(((2-hydroxy-2-methylpropyl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.16 (s, 1H), 8.62 (s, 1H), 8.10 (dd, J=6.8, 6.8 Hz, 1H), 7.87 (d, J=7.6 Hz, 1H), 7.61 (dd, J=7.6, 1.6 Hz, 1H), 7.49 (dd, J=7.6, 7.6 Hz, 1H), 7.36-7.33 (m, 2H), 7.29 (dd, J=7.8, 7.8 Hz, 1H), 6.99 (d, J=7.2 Hz, 1H), 4.31 (s, 2H), 4.09 (s, 3H), 3.86 (m, 2H), 3.54 (s, 3H), 3.37 (s, 3H), 3.20 (d, J=4.8, 4.8 Hz, 2H), 2.13 (s, 3H). MS: (ES) m/z calculated for $C_{29}H_{31}ClN_5O_5$ [M+H]$^+$ 564.2. found 564.5.

Example 20: N-(2'-chloro-3'-(5-(((2-hydroxy-2-methylpropyl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide

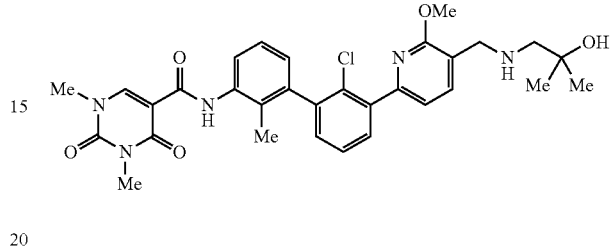

A mixture of N-(2,2'-dichloro-3'-(5-formyl-6-methoxypyridin-2-yl)-[1,1'-biphenyl]-3-yl)-1,3-dimethyl-2,4-dioxo-1,2,3,4-tetrahydropyrimidine-5-carboxamide (50 mg, 0.096 mmol), 1-amino-2-methylpropan-2-ol (50 mg, 0.56 mmol) and AcOH (50 mg, 0.83 mmol) in DCM (2 mL) was stirred at room temperature for 1 h. To the mixture was added NaBH(OAc)$_3$ (70 mg, 0.33 mmol). After 1 h, the reaction was quenched with sat. aq. NaHCO$_3$ and extracted with DCM. The organic layer was separated, concentrated in vacuo and purified by preparative HPLC to give N-(2'-chloro-3'-(5-(((2-hydroxy-2-methylpropyl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.16 (s, 1H), 8.61 (s, 1H), 8.12 (dd, J=6.8, 6.8 Hz, 1H), 7.87 (d, J=7.6 Hz, 1H), 7.62 (dd, J=8.0, 1.6 Hz, 1H), 7.49 (dd, J=7.6, 7.6 Hz, 1H), 7.37-7.33 (m, 2H), 7.30 (dd, J=7.8, 7.8 Hz, 2H), 6.99 (d, J=7.6 Hz, 1H), 4.33 (s, 2H), 4.09 (s, 3H), 3.53 (s, 3H), 3.36 (s, 3H), 3.02 (s, 2H), 2.13 (s, 3H), 1.30 (s, 6H). MS: (ES) m/z calculated for $C_{31}H_{35}ClN_5O_5$ [M+H]$^+$ 592.2. found 592.5.

Example 21: 1-((6-(2-chloro-3'-(1,3-dimethyl-2,4-dioxo-1,2,3,4-tetrahydropyrimidine-5-carboxamido)-2'-methyl-[1,1'-biphenyl]-3-yl)-2-methoxypyridin-3-yl)methyl)-3-methylazetidine-3-carboxylic Acid

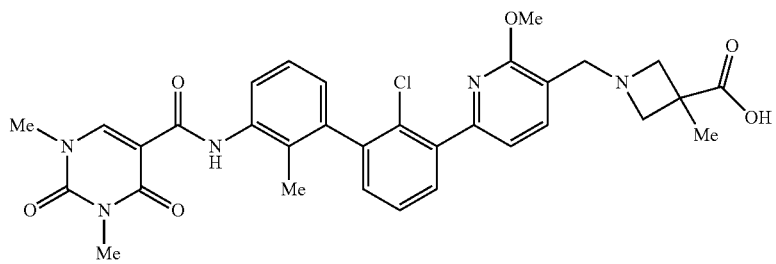 [SMILES: COc1nc(-c2cccc(-c3cccc(NC(=O)c4cn(C)c(=O)n(C)c4=O)c3C)c2Cl)ccc1CN1CC(C)(C(=O)O)C1]

A mixture of N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide (50 mg, 0.096 mmol), 3-methylazetidine-3-carboxylic acid (30 mg, 0.26 mmol) and AcOH (30 mg, 0.50 mmol) in DMF (1 mL) was stirred at room temperature for 1.5 h. To the mixture was added NaBH(OAc)₃ (70 mg, 0.33 mmol). After stirring for 30 min at 0° C. the reaction was quenched with 2 drops of water. The crude material was purified by preparative HPLC to give 1-((6-(2-chloro-3'-(1,3-dimethyl-2,4-dioxo-1,2,3,4-tetrahydropyrimidine-5-carboxamido)-2'-methyl-[1,1'-biphenyl]-3-yl)-2-methoxypyridin-3-yl)methyl)-3-methylazetidine-3-carboxylic acid. ¹H NMR (400 MHz, CD₃OD) δ 11.16 (s, 1H), 8.60 (s, 1H), 8.12 (dd, J=7.0, 7.0 Hz, 1H), 7.87 (d, J=7.6 Hz, 1H), 7.61 (dd, J=8.0, 1.6 Hz, 1H), 7.48 (dd, J=7.6, 7.6 Hz, 1H), 7.37-7.32 (m, 2H), 7.30 (dd, J=7.8, 7.8 Hz, 1H), 6.99 (d, J=7.6 Hz, 1H), 4.56-4.50 (m, 2H), 4.50 (s, 2H), 4.13 (d, J=10.4 Hz, 2H), 4.07 (s, 3H), 3.53 (s, 3H), 3.36 (s, 3H), 3.12 (s, 3H), 1.61 (s, 3H). MS: (ES) m/z calculated for C₃₂H₃₃ClN₅O₆ [M+H]⁺ 618.2. found 618.6.

Example 22: N-(2'-chloro-3'-(5-(((2-hydroxyethyl)(methyl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide

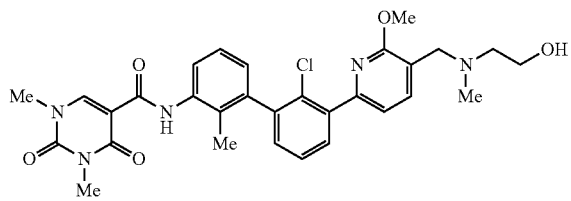 [SMILES: COc1nc(-c2cccc(-c3cccc(NC(=O)c4cn(C)c(=O)n(C)c4=O)c3C)c2Cl)ccc1CN(C)CCO]

A mixture of N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide (50 mg, 0.096 mmol), 2-(methylamino)ethan-1-ol (40 mg, 0.53 mmol) and AcOH (30 mg, 0.50 mmol) in DCM (2 mL) and EtOH (1 mL) was heated at 60° C. for 0.5 h. The mixture was cooled to 0° C. and NaBH₃CN (25 mg, 0.40 mmol) was added. After stirring for 30 min at 0° C. the reaction was quenched with 1 drop of water. The crude material was purified by preparative HPLC to give N-(2'-chloro-3'-(5-(((2-hydroxyethyl)(methyl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide. ¹H NMR (400 MHz, CD₃OD) δ 11.14 (s, 1H), 8.58 (s, 1H), 8.13 (dd, J=7.0, 7.0 Hz, 1H), 7.92 (d, J=7.6 Hz, 1H), 7.63 (dd, J=7.6, 2.0 Hz, 1H), 7.49 (dd, J=7.6, 7.6 Hz, 1H), 7.38 (d, J=7.6 Hz, 1H), 7.34 (dd, J=7.2, 1.6 Hz, 1H), 7.27 (dd, J=7.8, 7.8 Hz, 1H), 6.98 (d, J=6.8 Hz, 1H), 4.60 (d, J=13.2 Hz, 1H), 4.31 (d, J=13.2 Hz, 1H), 4.08 (s, 3H), 3.97-3.90 (m, 2H), 3.51 (s, 3H), 3.42-3.34 (m, 2H), 3.33 (s, 3H), 2.91 (s, 3H), 2.12 (s, 3H). MS. (ES) m/z calculated for C₃H₃₃ClN₅O₅ [M+H]⁺ 578.2. found 578.5.

Example 23: N-(2'-chloro-3'-(5-(((3-hydroxy-2,2-dimethylpropyl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide

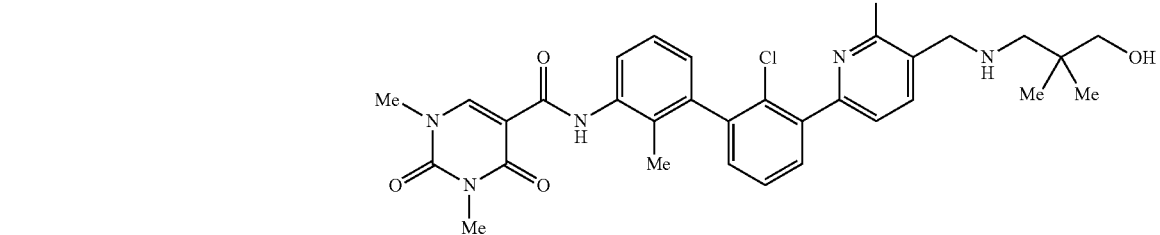

The compound was prepared from N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide and 3-amino-2,2-dimethylpropan-1-ol using a procedure similar to Example 1. The crude product was purified by preparative HPLC to give N-(2'-chloro-3'-(5-(((3-hydroxy-2,2-dimethylpropyl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide. ¹H NMR (400 MHz, CDCl₃) δ 10.89 (s, 1H), 8.53 (s, 1H), 8.22 (d, J=7.4 Hz, 1H), 7.63 (dd, J=7.6, 1.8 Hz, 1H), 7.56 (d, J=7.4 Hz, 1H), 7.40 (dd, J=7.6, 7.6 Hz, 1H), 7.35-7.22 (m, 3H), 7.03 (dd, J=7.6, 1.2 Hz, 1H), 4.02 (s, 3H), 3.80 (s, 2H), 3.58 (s, 3H), 3.52 (s, 2H), 3.44 (s, 3H), 2.65 (s, 2H), 2.19 (s, 3H), 0.94 (s, 6H). MS: (ES) m/z calculated for C₃₂H₃₇ClN₅O₅ [M+H]⁺ 606.2. found 606.6.

Example 24: (R)—N-(2'-chloro-3'-(5-((3-hydroxy-3-methylpyrrolidin-1-yl)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide

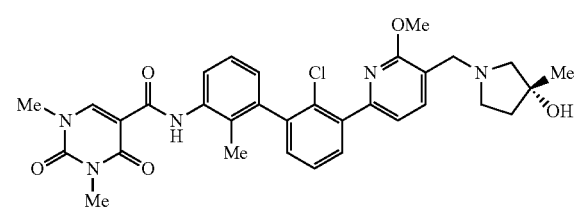 [SMILES: COc1nc(-c2cccc(-c3cccc(NC(=O)c4cn(C)c(=O)n(C)c4=O)c3C)c2Cl)ccc1CN1CC[C@@](C)(O)C1]

The compound was prepared from N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide and (3R)-3-methylpyrrolidin-3-ol hydrochloride using a procedure similar to step d in Example 1. The crude product was purified by silica gel flash chromatography to give (R)—N-(2'-chloro-3'-(5-((3-hydroxy-3-methylpyrrolidin-1-yl)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide. ¹H NMR (400 MHz, CD₃OD) δ 8.62 (s, 1H), 8.12 (d, J=8.0 Hz, 1H), 7.79 (d, J=7.2 Hz, 1H), 7.66 (dd, J=8.0, 2.0 Hz, 1H), 7.46 (dd, J=7.6, 7.6 Hz, 1H), 7.33-7.24 (m, 3H), 7.00 (d, J=8.0 Hz, 1H), 4.01 (s, 3H), 3.89-3.80 (m, 2H), 3.54 (s, 3H), 3.38 (s, 3H), 3.09-3.00 (m, 1H), 2.88-2.69 (m, 3H), 2.14 (s, 3H), 1.96-1.89 (m, 2H), 1.37 (s, 3H). MS: (ES) m/z calculated for C₃₂H₃₅ClN₅O₅ [M+H]⁺ 604.2. found 604.5.

Example 25: N-(2'-chloro-3'-(5-((4-hydroxypiperidin-1-yl)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide

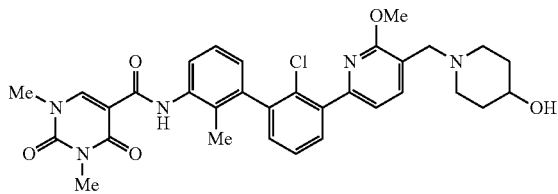 [SMILES: COc1nc(-c2cccc(-c3cccc(NC(=O)c4cn(C)c(=O)n(C)c4=O)c3C)c2Cl)ccc1CN1CCC(O)CC1]

The compound was prepared from N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide and piperidin-4-ol hydrochloride using a procedure similar to step d in Example 1. The crude product was purified by preparative HPLC to give N-(2'-chloro-3'-(5-((4-hydroxypiperidin-1-yl)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide. ¹H NMR (400 MHz, DMSO-d₆) δ 11.08 (s, 1H), 8.77 (s, 1H), 8.27-8.25 (m, 1H), 7.74 (d, J=7.5 Hz, 1H), 7.65 (dd, J=7.6, 1.7 Hz, 1H), 7.52 (dd, J=7.6, 7.6 Hz, 1H), 7.37-7.28 (m, 3H), 7.00-6.98 (m, 1H), 4.57 (s, 1H), 3.90 (s, 3H), 3.50-3.45 (m, 6H), 3.27 (s, 3H), 2.73-2.69 (m, 2H), 2.14-2.09 (m, 5H), 1.74-1.70 (m, 2H), 1.47-1.37 (m, 2H). MS: (ES) m/z calculated for C₃₂H₃₅ClN₅O₅ [M+H]⁺ 604.2. found 604.5.

Example 26: (R)—N-(2'-chloro-3'-(5-(((2,3-dihydroxypropyl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide The compound was prepared from N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide and (R)-3-amino-1,2-propanediol using a procedure similar to step d in Example 1. The crude product was purified by silica gel flash chromatography to give (R)—N-(2'-chloro-3'-(5-(((2,3-dihydroxypropyl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide. ¹H NMR (400 MHz, CD₃OD) δ 8.62 (s, 1H), 8.11 (d, J=8.0 Hz, 1H), 7.73 (d, J=7.2 Hz, 1H), 7.60 (dd, J=7.2, 1.6 Hz, 1H), 7.46 (dd, J=8.0, 8.0 Hz, 1H), 7.33-7.22 (m, 3H), 7.00 (d, J=8.0 Hz, 1H), 4.03 (s, 3H), 3.96-3.83 (m, 2H), 3.83-3.76 (m, 1H), 3.55 (s, 3H), 3.54-3.50 (m, 2H), 3.38 (s, 3H), 2.86-2.79 (m, 1H), 2.72-2.65 (m, 1H), 2.14 (s, 3H). MS: (ES) m/z calculated for C₃₀H₃₃ClN₅O₆ [M+H]⁺ 594.2. found 594.3.

Example 27: N-(2'-chloro-3'-(5-((((3S,4S)-3-hydroxytetrahydro-2H-pyran-4-yl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide

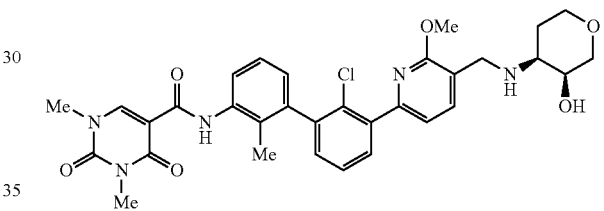

The compound was prepared from N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide and (3S,4S)-4-aminotetrahydro-2H-pyran-3-ol hydrochloride using a procedure similar to step d in Example 1. The crude product was purified by preparative HPLC to give N-(2'-chloro-3'-(5-((((3S,4S)-3-hydroxytetrahydro-2H-pyran-4-yl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide. ¹H NMR (400 MHz, CD₃OD) δ 11.07 (s, 1H), 8.77 (s, 1H), 8.27-8.25 (m, 1H), 7.85 (d, J=7.5 Hz, 1H), 7.63 (dd, J=7.7, 1.8 Hz, 1H), 7.52 (dd, J=7.6, 7.6 Hz, 1H), 7.37-7.27 (m, 3H), 6.99 (dd, J=7.7, 1.4 Hz, 1H), 4.66 (s, 1H), 3.92 (s, 3H), 3.79-3.61 (m, 5H), 3.55 (s, 3H), 3.49 (s, 3H), 3.25 (s, 3H), 2.73 (d, J=9.0

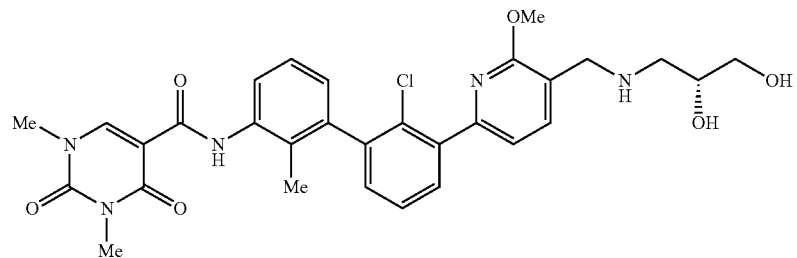

Hz, 1H), 2.09 (s, 3H), 1.73-1.65 (m, 1H), 1.58-1.50 (m, 1H). MS: (ES) m/z calculated for $C_{32}H_{34}ClN_5O_6$ [M+H]$^+$ 620.2. found 620.2.

Example 28: N-(3'-(5-(((3-amino-2,2-dimethyl-3-oxopropyl)amino)methyl)-6-methoxypyridin-2-yl)-2'-chloro-2-methyl-[1,1'-biphenyl]-3-yl)-1,3-dimethyl-2,4-dioxo-1,2,3,4-tetrahydropyrimidine-5-carboxamide

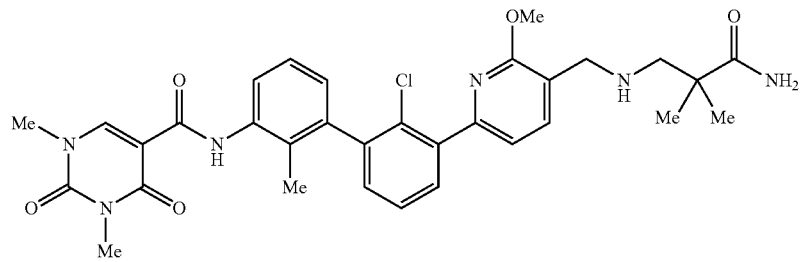 [SMILES: COc1nc(-c2cccc(-c3cccc(NC(=O)c4cn(C)c(=O)n(C)c4=O)c3C)c2Cl)ccc1CNCC(C)(C)C(N)=O]

The compound was prepared from N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide and 3-amino-2,2-dimethylpropanamide using a procedure similar to step d in Example 1. The crude product was purified by preparative HPLC to give N-(3'-(5-(((3-amino-2,2-dimethyl-3-oxopropyl)amino)methyl)-6-methoxypyridin-2-yl)-2'-chloro-2-methyl-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 8.63 (s, 1H), 8.13-8.10 (m, 1H), 7.86 (d, J=7.5 Hz, 1H), 7.63 (dd, J=7.7, 1.7 Hz, 1H), 7.50 (dd, J=7.6, 7.6 Hz, 1H), 7.36-7.28 (m, 3H), 7.02-7.00 (m, 1H), 4.28 (s, 2H), 4.12 (s, 3H), 3.55 (s, 3H), 3.39 (s, 3H), 3.14 (s, 2H), 2.14 (s, 3H), 1.35 (s, 6H). MS: (ES) m/z calculated for $C_{32}H_{36}ClN_6O_5$ [M+H]$^+$ 619.2. found 619.5.

Example 29: N-(2,2'-dichloro-3'-(5-(((2-hydroxyethyl)amino)methyl)-6-methoxypyridin-2-yl)-[1,1'-biphenyl]-3-yl)-1,3-dimethyl-2,4-dioxo-1,2,3,4-tetrahydropyrimidine-5-carboxamide

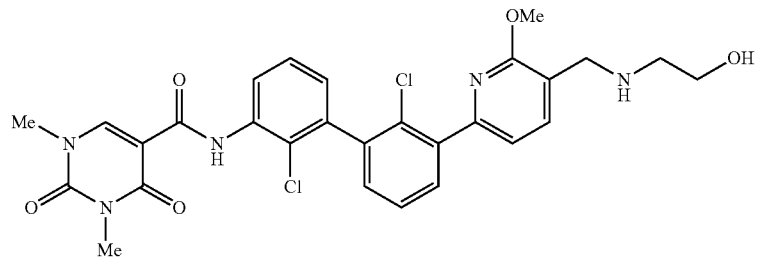 [SMILES: COc1nc(-c2cccc(-c3cccc(NC(=O)c4cn(C)c(=O)n(C)c4=O)c3Cl)c2Cl)ccc1CNCCO]

A mixture of N-(2,2'-dichloro-3'-(5-formyl-6-methoxypyridin-2-yl)-[1,1'-biphenyl]-3-yl)-1,3-dimethyl-2,4-dioxo-1,2,3,4-tetrahydropyrimidine-5-carboxamide (42 mg, 0.078 mmol), 2-aminoethan-1-ol (15 mg, 0.25 mmol) and AcOH (32 mg, 0.53 mmol) in DCM (1.5 mL) and EtOH (0.75 mL) was heated at 60° C. for 0.5 h. The mixture was cooled to 0° C. and NaBH$_3$CN (25 mg, 0.40 mmol) was added. After stirring for 15 min at 0° C. the reaction was quenched with 1 drop of water. The crude material was purified by preparative HPLC to give N-(2,2'-dichloro-3'-(5-(((2-hydroxyethyl)amino)methyl)-6-methoxypyridin-2-yl)-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.66 (s, 1H), 8.63 (s, 1H), 8.60-8.50 (m, 1H), 7.87 (d, J=8.0 Hz, 1H), 7.65 (dd, J=7.6, 1.6 Hz, 1H), 7.50 (dd, J=7.6, 7.6 Hz, 1H), 7.42-7.33 (m, 3H), 7.09 (dd, J=7.6, 1.6 Hz, 1H), 4.31 (s, 2H), 4.09 (s, 3H), 3.85 (t, J=5.2 Hz, 2H), 3.53 (s, 3H), 3.36 (s, 3H), 3.20 (t, J=5.2 Hz, 2H). MS: (ES) m/z calculated for $C_{28}H_{28}Cl_2N_5O_5$ [M+H]$^+$ 584.1. found 584.4.

Example 30: N-(2'-chloro-3'-(5-((3-hydroxy-3-methylazetidin-1-yl)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide

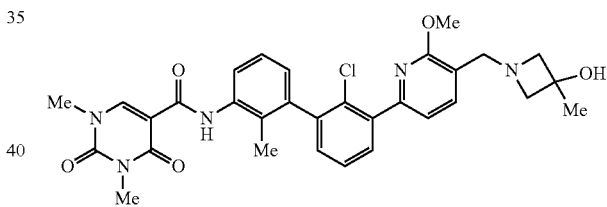

The compound was prepared from N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide and 3-methylazetidin-3-ol hydrochloride using a procedure similar to step d in Example 1. The crude product was purified by preparative HPLC to give N-(2'-chloro-3'-(5-((3-hydroxy-3-methylazetidin-1-yl)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide. $^1$H NMR (400 MHz, CDCl$_3$) δ 10.89 (s, 1H), 8.53 (s, 1H), 8.25-8.18 (m, 1H), 7.62 (dd, J=7.7, 1.9 Hz, 2H), 7.43-7.21 (m, 4H), 7.03 (d, J=7.7 Hz, 1H), 4.00 (s, 3H), 3.70 (s, 2H), 3.58 (s, 3H), 3.44 (m, 5H), 3.19 (d, J=7.8 Hz, 2H), 2.18 (s, 3H), 1.54 (s, 3H). MS: (ES) m/z calculated for $C_{31}H_{33}ClN_5O_5$ [M+H]$^+$ 590.2. found 590.5.

Example 31: N-(2'-chloro-3'-(5-((isopropylamino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide

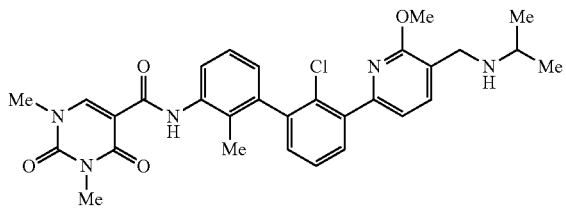 [SMILES: COc1nc(-c2cccc(-c3cccc(NC(=O)c4cn(C)c(=O)n(C)c4=O)c3C)c2Cl)ccc1CNC(C)C]

The compound was prepared from N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide and isopropylamine hydrochloride using a procedure similar to step d in Example 1. The crude product was purified by preparative HPLC to give N-(2'-chloro-3'-(5-((isopropylamino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 8.64 (s, 1H), 8.13-8.11 (m, 1H), 7.85 (d, J=7.5 Hz, 1H), 7.61 (dd, J=7.7, 1.7 Hz, 1H), 7.49 (dd, J=7.6, 7.6 Hz, 1H), 7.36-7.28 (m, 3H), 7.01 (dd, J=7.6, 1.2 Hz, 1H), 4.16 (s, 2H), 4.08 (s, 3H), 3.56 (s, 3H), 3.39 (s, 3H), 3.38-3.33 (m, 1H), 2.14 (s, 3H), 1.37 (d, J=6.5 Hz, 6H). MS: (ES) m/z calculated for $C_{30}H_{33}ClN_5O_4$ [M+H]$^+$ 562.2. found 562.5.

Example 32: N-(2,2'-dichloro-3'-(5-(((3-hydroxypropyl)amino)methyl)-6-methoxypyridin-2-yl)-[1,1'-biphenyl]-3-yl)-1,3-dimethyl-2,4-dioxo-1,2,3,4-tetrahydropyrimidine-5-carboxamide

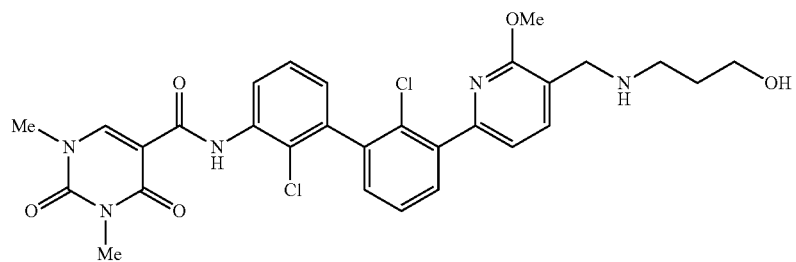 [SMILES: COc1nc(-c2cccc(-c3cccc(NC(=O)c4cn(C)c(=O)n(C)c4=O)c3Cl)c2Cl)ccc1CNCCCO]

A mixture of N-(2,2'-dichloro-3'-(5-formyl-6-methoxypyridin-2-yl)-[1,1'-biphenyl]-3-yl)-1,3-dimethyl-2,4-dioxo-1,2,3,4-tetrahydropyrimidine-5-carboxamide (42 mg, 0.078 mmol), 1-(aminomethyl)cyclopropan-1-ol (40 mg, 0.46 mmol) and AcOH (32 mg, 0.53 mmol) in DCM (1.5 mL) and EtOH (0.5 mL) was heated at 60° C. for 0.5 h. The contents were cooled to 0° C. and NaBH$_3$CN (25 mg, 0.40 mmol) was added. After stirring for 5 min at 0° C. the reaction was quenched with 1 drop of water. The crude material was purified by preparative HPLC to give N-(2,2'-dichloro-3'-(5-(((3-hydroxypropyl)amino)methyl)-6-methoxypyridin-2-yl)-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.66 (s, 1H), 8.63 (s, 1H), 8.55-8.50 (m, 1H), 7.86 (d, J=7.6 Hz, 1H), 7.65 (dd, J=7.6, 2.0 Hz, 1H), 7.50 (dd, J=7.6, 7.6 Hz, 1H), 7.42-7.33 (m, 3H), 7.08 (dd, J=8.0, 1.6 Hz, 1H), 4.27 (s, 2H), 4.08 (s, 3H), 3.74 (t, J=5.8 Hz, 2H), 3.52 (s, 3H), 3.35 (s, 3H), 3.26 (t, J=6.8 Hz, 2H), 1.95 (m, 2H). MS: (ES) m/z calculated for $C_{29}H_3Cl_2N_5O_5$ [M+H]$^+$ 598.2, found 598.2.

Example 33: N-(2,2'-dichloro-3'-(5-((((1-hydroxycyclopropyl)methyl)amino)methyl)-6-methoxypyridin-2-yl)-[1,1'-biphenyl]-3-yl)-1,3-dimethyl-2,4-dioxo-1,2,3,4-tetrahydropyrimidine-5-carboxamide

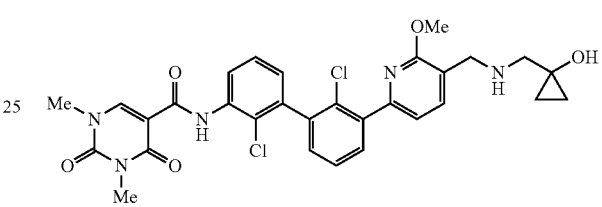

A mixture of N-(2,2'-dichloro-3'-(5-formyl-6-methoxypyridin-2-yl)-[1,1'-biphenyl]-3-yl)-1,3-dimethyl-2,4-dioxo-1,2,3,4-tetrahydropyrimidine-5-carboxamide (42 mg, 0.078 mmol), 1-(aminomethyl)cyclopropan-1-ol (40 mg, 0.46 mmol) and AcOH (32 mg, 0.53 mmol) in DCM (1.5 mL) and EtOH (0.5 mL) was heated at 60° C. for 0.5 h. The contents were cooled to 0° C. and NaBH$_3$CN (25 mg, 0.40 mmol) was added. After stirring for 5 min at 0° C. the reaction was quenched with 1 drop of water. The crude material was purified by preparative HPLC to give N-(2,2'-dichloro-3'-(5-((((1-hydroxycyclopropyl)methyl)amino)methyl)-6-methoxypyridin-2-yl)-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.67 (s, 1H), 8.65 (s, 1H), 8.56-8.51 (m, 1H), 7.87 (d, J=7.6 Hz, 1H), 7.65 (dd, J=7.6, 2.0 Hz, 1H), 7.51 (dd, J=7.6, 7.6 Hz, 1H), 7.43-7.35 (m, 3H), 7.10 (dd, J=7.6, 1.6 Hz, 1H), 4.37 (s, 2H), 4.10 (s, 3H), 3.55 (s, 3H), 3.38 (s, 3H), 3.19 (s, 2H), 0.91 (t, J=6.4 Hz, 2H), 0.73 (d, J=6.2 Hz, 2H). MS: (ES) m/z calculated for $C_{30}H_{30}Cl_2N_5O_5$ [M+H]$^+$ 610.2. found 610.1.

Example 34: (S)—N-(2,2'-dichloro-3'-(5-(((2-hydroxypropyl)amino)methyl)-6-methoxypyridin-2-yl)-[1,1'-biphenyl]-3-yl)-1,3-dimethyl-2,4-dioxo-1,2,3,4-tetrahydropyrimidine-5-carboxamide

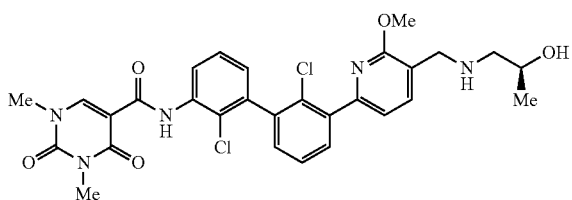 [SMILES: COc1nc(-c2cccc(-c3cccc(NC(=O)c4cn(C)c(=O)n(C)c4=O)c3Cl)c2Cl)ccc1CNC[C@H](C)O]

A mixture of N-(2,2'-dichloro-3'-(5-formyl-6-methoxypyridin-2-yl)-[1,1'-biphenyl]-3-yl)-1,3-dimethyl-2,4-dioxo-1,2,3,4-tetrahydropyrimidine-5-carboxamide (45 mg, 0.083 mmol), (S)-1-aminopropan-2-ol (30 mg, 0.40 mmol) and AcOH (27 mg, 0.45 mmol) in DCM (1.5 mL) and EtOH (0.5 mL) was heated at 60° C. for 0.5 h. The contents were cooled to 0° C. and NaBH$_3$CN (20 mg, 0.32 mmol) was added. After stirring for 5 min at 0° C. the reaction was quenched with 1 drop of water. The crude material was purified by preparative HPLC to give (S)—N-(2,2'-dichloro-3'-(5-(((2-hydroxypropyl)amino)methyl)-6-methoxypyridin-2-yl)-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) 11.68 (s, 1H), 8.65 (s, 1H), 8.53 (dd, J=8.8, 1.8 Hz, 1H), 7.87 (d, J=7.6 Hz, 1H), 7.65 (dd, J=7.6, 1.6 Hz, 1H), 7.51 (dd, J=7.6, 7.6 Hz, 1H), 7.43-7.34 (m, 3H), 7.10 (dd, J=7.2, 1.6 Hz, 1H), 4.30 (s, 2H), 4.09 (s, 3H), 4.12-4.04 (m, 1H), 3.55 (s, 3H), 3.38 (s, 3H), 3.13 (dd, J=12.8, 2.8 Hz, 1H), 2.94-2.87 (m, 1H), 1.24 (d, J=6.4 Hz, 3H). MS: (ES) m/z calculated for C$_{29}$H$_{30}$Cl$_2$N$_5$O$_5$ [M+H]$^+$ 598.2. found 598.5.

Example 35: (R)—N-(2,2'-dichloro-3'-(5-(((2-hydroxypropyl)amino)methyl)-6-methoxypyridin-2-yl)-[1,1'-biphenyl]-3-yl)-1,3-dimethyl-2,4-dioxo-1,2,3,4-tetrahydropyrimidine-5-carboxamide

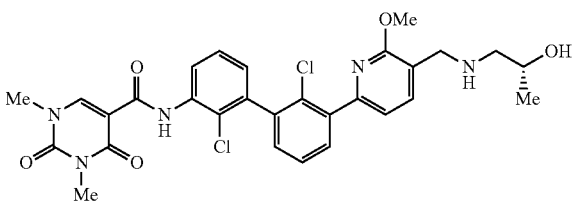 [SMILES: COc1nc(-c2cccc(-c3cccc(NC(=O)c4cn(C)c(=O)n(C)c4=O)c3Cl)c2Cl)ccc1CNC[C@@H](C)O]

A mixture of N-(2,2'-dichloro-3'-(5-formyl-6-methoxypyridin-2-yl)-[1,1'-biphenyl]-3-yl)-1,3-dimethyl-2,4-dioxo-1,2,3,4-tetrahydropyrimidine-5-carboxamide (42 mg, 0.078 mmol), (R)-1-aminopropan-2-ol (20 mg, 0.27 mmol) and AcOH (27 mg, 0.45 mmol) in DCM (1.5 mL) and EtOH (0.5 mL) was heated at 60° C. for 0.5 h. The contents were cooled to 0° C. and NaBH$_3$CN (20 mg, 0.32 mmol) was added. After stirring for 5 min at 0° C. the reaction was quenched with 1 drop of water. The crude material was purified by preparative HPLC to give (R)—N-(2,2'-dichloro-3'-(5-(((2-hydroxypropyl)amino)methyl)-6-methoxypyridin-2-yl)-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.67 (s, 1H), 8.63 (s, 1H), 8.52 (dd, J=8.4, 1.6 Hz, 1H), 7.86 (d, J=7.6 Hz, 1H), 7.65 (dd, J=7.6, 2.0 Hz, 1H), 7.50 (dd, J=7.6, 7.6 Hz, 1H), 7.42-7.34 (m, 3H), 7.09 (dd, J=8.0, 1.6 Hz, 1H), 4.30 (s, 2H), 4.09 (s, 3H), 4.12-4.04 (m, 1H), 3.53 (s, 3H), 3.36 (s, 3H), 3.11 (dd, J=12.4, 3.2 Hz, 1H), 2.95-2.87 (m, 1H), 1.24 (d, J=6.4 Hz, 3H). MS: (ES) m/z calculated for C$_{29}$H$_{30}$Cl$_2$N$_5$O$_5$ [M+H]$^+$ 598.2. found 598.5.

Example 36: N-(2'-chloro-3'-(6-methoxy-5-((methylamino)methyl)pyridin-2-yl)-2-methyl-[1,1'-biphenyl]-3-yl)-1,3-dimethyl-2,4-dioxo-1,2,3,4-tetrahydropyrimidine-5-carboxamide

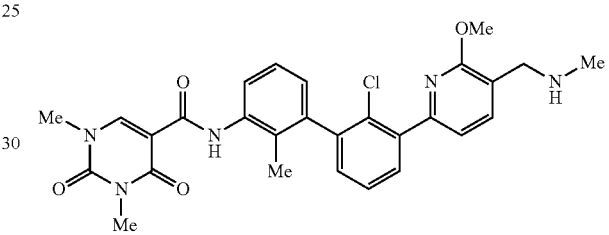

The compound was prepared from N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide and methylamine hydrochloride using a procedure similar to step d in Example 1. The crude product was purified by preparative HPLC to give N-(2'-chloro-3'-(6-methoxy-5-((methylamino)methyl)pyridin-2-yl)-2-methyl-[1,1'-biphenyl]-3-yl)-1,3-dimethyl-2,4-dioxo-1,2,3,4-tetrahydropyrimidine-5-carboxamide. $^1$H NMR (400 MHz, DMSO-d$_6$) δ 11.08 (s, 1H), 8.77 (s, 1H), 8.27-8.25 (m, 1H), 7.79 (d, J=7.5 Hz, 1H), 7.64 (dd, J=7.7, 1.7 Hz, 1H), 7.52 (dd, J=7.6, 7.6 Hz, 1H), 7.37-7.28 (m, 3H), 6.99 (dd, J=7.6, 1.2 Hz, 1H), 3.92 (s, 3H), 3.71 (s, 2H), 3.50 (s, 3H), 3.27 (s, 3H), 3.20 (s, 1H), 2.36 (s, 3H), 2.09 (s, 3H). MS: (ES) m/z calculated for C$_{28}$H$_{29}$ClN$_5$O$_4$ [M+H]$^+$ 534.2. found 534.1.

Example 37: (R)—N-(2,2'-dichloro-3'-(5-(((2,3-dihydroxypropyl)amino)methyl)-6-methoxypyridin-2-yl)-[1,1'-biphenyl]-3-yl)-1,3-dimethyl-2,4-dioxo-1,2,3,4-tetrahydropyrimidine-5-carboxamide

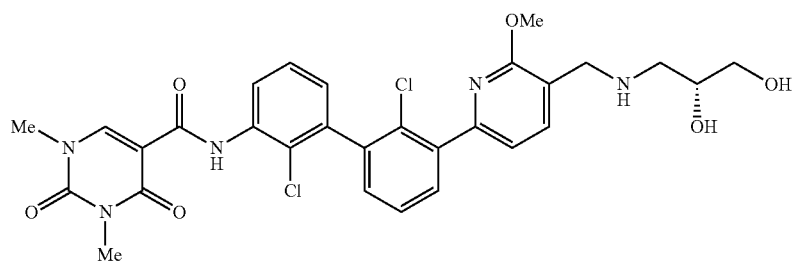 [SMILES: COc1nc(-c2cccc(-c3cccc(NC(=O)c4cn(C)c(=O)n(C)c4=O)c3Cl)c2Cl)ccc1CNC[C@@H](O)CO]

The compound was prepared from N-(2'-chloro-3'-(5-formyl-6-methoxypyridin-2-yl)-2-chloro-[1,1'-biphenyl]-3-yl)-1,3-dimethyl-2,4-dioxo-1,2,3,4-tetrahydropyrimidine-5-carboxamide and (R)-3-amino-1,2-propanediol using a procedure similar to step d in Example 1. The crude product was purified by preparative HPLC to give (R)—N-(2,2'-dichloro-3'-(5-(((2,3-dihydroxypropyl)amino)methyl)-6-methoxypyridin-2-yl)-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.69 (s, 1H), 8.66 (s, 1H), 8.53 (dd, J=8.4, 1.6 Hz, 1H), 7.87 (d, J=7.6 Hz, 1H), 7.66 (dd, J=7.6, 1.6 Hz, 1H), 7.51 (dd, J=8.0, 8.0 Hz, 1H), 7.43-7.34 (m, 3H), 7.10 (dd, J=7.6, 1.6 Hz, 1H), 4.32 (s, 2H), 4.09 (s, 3H), 3.99-3.92 (m, 1H), 3.67-3.56 (m, 2H), 3.55 (s, 3H), 3.38 (s, 3H), 3.29-3.22 (m, 1H), 3.15-3.07 (m, 1H). MS: (ES) m/z calculated for C$_{29}$H$_3$Cl$_2$N$_5$O$_6$ [M+H]$^+$ 614.2, found 614.5.

Example 38: (S)—N-(2'-chloro-3'-(5-(((2-hydroxypropyl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide

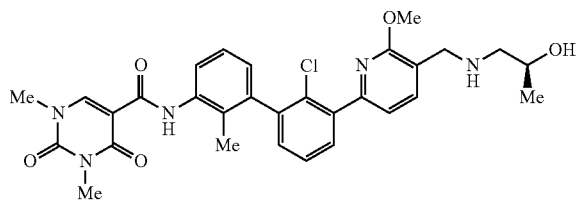 [SMILES: COc1nc(-c2cccc(-c3cccc(NC(=O)c4cn(C)c(=O)n(C)c4=O)c3C)c2Cl)ccc1CNC[C@H](C)O]

A mixture of N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide (45 mg, 0.086 mmol), (S)-1-aminopropan-2-ol (20 mg, 0.27 mmol) and HOAc (27 mg, 0.45 mmol) in DCM (1.5 mL) and EtOH (0.5 mL) was heated at 60° C. for 0.5 h. The contents were cooled to 0° C. and NaBH$_3$CN (20 mg, 0.32 mmol) was added. After stirring for 10 min at 0° C. the reaction was quenched with 1 drop of water. The crude material was purified by preparative HPLC to give (S)—N-(2'-chloro-3'-(5-(((2-hydroxypropyl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.16 (s, 1H), 8.61 (s, 1H), 8.11 (dd, J=6.8, 6.8 Hz, 1H), 7.86 (d, J=7.6 Hz, 1H), 7.61 (dd, J=7.6, 2.0 Hz, 1H), 7.49 (dd, J=7.6, 7.6 Hz, 1H), 7.34 (dd, J=7.2, 1.6 Hz, 2H), 7.28 (t, J=8.0 Hz, 1H), 7.00 (d, J=7.2 Hz, 1H), 4.30 (s, 2H), 4.08 (s, 3H), 4.12-4.04 (m, 1H), 3.54 (s, 3H), 3.37 (s, 3H), 3.13 (dd, J=13.2, 3.2 Hz, 1H), 2.94-2.87 (m, 1H), 2.13 (s, 3H), 1.24 (d, J=6.4 Hz, 3H). MS: (ES) m/z calculated for C$_{30}$H$_{33}$ClN$_5$O$_5$ [M+H]$^+$ 578.2, found 578.5.

Example 39: (R)—N-(2'-chloro-3'-(5-(((2-hydroxypropyl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide

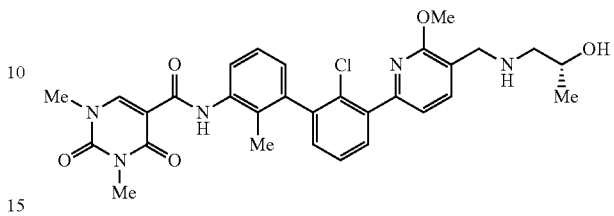

A mixture of N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide (45 mg, 0.086 mmol), (R)-1-aminopropan-2-ol (20 mg, 0.27 mmol) and AcOH (27 mg, 0.45 mmol) in DCM (1.5 mL) and EtOH (0.5 mL) was heated at 60° C. for 0.5 h. The contents were cooled to 0° C. and NaBH$_3$CN (20 mg, 0.32 mmol) was added. After stirring for 10 min at 0° C. the reaction was quenched with 1 drop of water. The crude material was purified by preparative HPLC to give (R)—N-(2'-chloro-3'-(5-(((2-hydroxypropyl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.16 (s, 1H), 8.61 (s, 1H), 8.11 (dd, J=6.8, 6.8 Hz, 1H), 7.86 (d, J=7.6 Hz, 1H), 7.61 (dd, J=8.0, 2.0 Hz, 1H), 7.49 (dd, J=7.6, 7.6 Hz, 1H), 7.34 (dd, J=7.2, 1.6 Hz, 2H), 7.29 (dd, J=7.8, 7.8 Hz, 1H), 7.00 (d, J=7.2 Hz, 1H), 4.30 (s, 2H), 4.08 (s, 3H), 4.12-4.04 (m, 1H), 3.53 (s, 3H), 3.37 (s, 3H), 3.13 (dd, J=12.4, 3.2 Hz, 1H), 2.94-2.87 (m, 1H), 2.15 (s, 3H), 1.24 (d, J=6.4 Hz, 3H). MS: (ES) m/z calculated for C$_{30}$H$_{33}$ClN$_5$O$_5$ [M+H]$^+$ 578.2. found 578.5.

Example 40: (R)—N-(2,2'-dichloro-3'-(5-((3-hydroxy-3-methylpyrrolidin-1-yl)methyl)-6-methoxypyridin-2-yl)-[1,1'-biphenyl]-3-yl)-1,3-dimethyl-2,4-dioxo-1,2,3,4-tetrahydropyrimidine-5-carboxamide

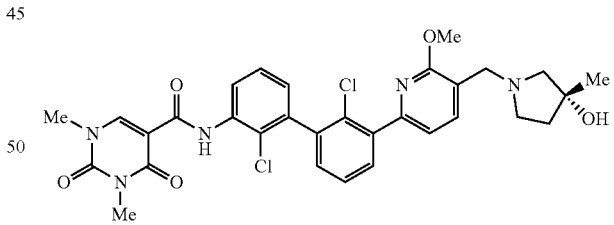

The compound was prepared from N-(2'-chloro-3'-(5-formyl-6-methoxypyridin-2-yl)-2-chloro-[1,1'-biphenyl]-3-yl)-1,3-dimethyl-2,4-dioxo-1,2,3,4-tetrahydropyrimidine-5-carboxamide and (3R)-3-methylpyrrolidin-3-ol hydrochloride using a procedure similar to step d in Example 1. The crude product was purified by silica gel flash chromatography to give (R)—N-(2,2'-dichloro-3'-(5-((3-hydroxy-3-methylpyrrolidin-1-yl)methyl)-6-methoxypyridin-2-yl)-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 8.66 (s, 1H), 8.54 (dd, J=8.4, 1.5 Hz, 1H), 7.89 (d, J=7.6 Hz, 1H), 7.66 (dd, J=7.6, 1.6 Hz, 1H), 7.51 (dd, J=7.6, 7.6 Hz, 1H), 7.44-7.35 (m, 3H), 7.10 (dd, J=7.6, 1.3

Hz, 1H), 4.36 (s, 2H), 4.08 (s, 3H), 3.66-3.53 (m, 1H), 3.55 (s, 3H), 3.47-3.36 (s, 1H), 3.38 (s, 3H), 3.27-3.11 (m, 2H), 2.14-2.03 (m, 2H), 1.43 (s, 3H). MS: (ES) m/z calculated for $C_{31}H_{32}Cl_2N_5O_5$ [M+H]$^+$ 624.2. found 624.5.

Example 41: N-(2'-chloro-3'-(5-(((3-hydroxy-3-methylbutyl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide

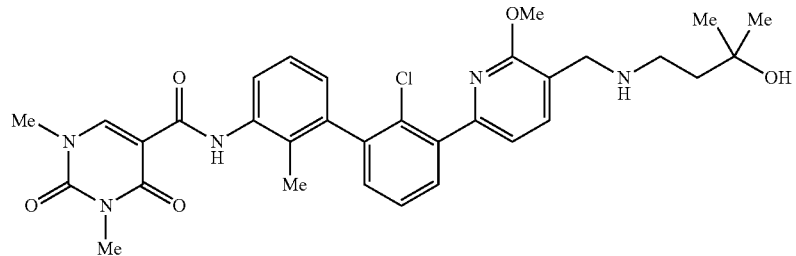 [SMILES: COc1nc(-c2cccc(-c3cccc(NC(=O)c4cn(C)c(=O)n(C)c4=O)c3C)c2Cl)ccc1CNCCC(C)(C)O]

A mixture of N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide (50 mg, 0.096 mmol), 4-amino-2-methylbutan-2-ol (20 mg, 0.19 mmol) and AcOH (22 mg, 0.37 mmol) in DCM (1.5 mL) and EtOH (0.5 mL) was heated at 60° C. for 0.5 h. The contents were cooled to 0° C. and NaBH$_3$CN (25 mg, 0.40 mmol) was added. After stirring for 10 min at 0° C. the reaction was quenched with 1 drop of water. The crude material was purified by preparative HPLC to give N-(2'-chloro-3'-(5-(((3-hydroxy-3-methylbutyl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.18 (s, 1H), 8.63 (s, 1H), 8.11 (dd, J=7.4, 7.4 Hz, 1H), 7.85 (d, J=7.2 Hz, 1H), 7.60 (dd, J=7.6, 1.6 Hz, 1H), 7.49 (dd, J=7.6, 7.6 Hz, 1H), 7.36-7.33 (m, 2H), 7.29 (dd, J=8.2, 8.2 Hz, 1H), 7.00 (d, J=8.0 Hz, 1H), 4.26 (s, 2H), 4.08 (s, 3H), 3.55 (s, 3H), 3.38 (s, 3H), 3.26 (t, J=6.8 Hz, 2H), 2.13 (s, 3H), 1.85 (t, J=6.8 Hz, 2H), 1.27 (s, 6H). MS: (ES) m/z calculated for $C_{32}H_{37}ClN_5O_5$ [M+H]$^+$ 606.2. found 606.6.

Example 42: N-(2'-chloro-3'-(5-((((1-hydroxycyclopropyl)methyl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide

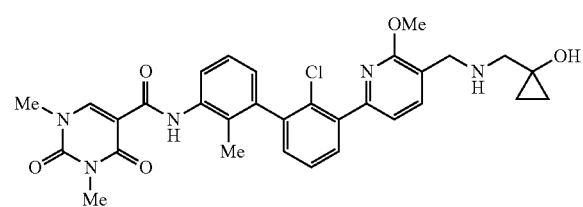 [SMILES: COc1nc(-c2cccc(-c3cccc(NC(=O)c4cn(C)c(=O)n(C)c4=O)c3C)c2Cl)ccc1CNCC1(O)CC1]

A mixture of N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide (45 mg, 0.086 mmol), 1-(aminomethyl)cyclopropan-1-ol (25 mg, 0.29 mmol) and AcOH (22 mg, 0.37 mmol) in DCM (1.5 mL) and EtOH (0.5 mL) was heated at 60° C. for 0.5 h. The contents were cooled to 0° C. and NaBH$_3$CN (25 mg, 0.40 mmol) was added. After stirring for 10 min at 0° C. the reaction was quenched with 1 drop of water. The crude material was purified by preparative HPLC to give N-(2'-chloro-3'-(5-((((1-hydroxycyclopropyl)methyl)amino)methyl)-6-methoxypyridin-2-yl)-2-methyl-[1,1'-biphenyl]-3-yl)-2-methyl-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.17 (s, 1H), 8.61 (s, 1H), 8.11 (dd, J=6.8, 6.8 Hz, 1H), 7.87 (d, J=8.0 Hz, 1H), 7.61 (dd, J=8.0, 1.2 Hz, 1H), 7.49 (dd, J=7.6, 7.6 Hz, 1H), 7.36-7.33 (m, 2H), 7.29 (dd, J=8.0, 8.0 Hz, 1H), 6.99 (d, J=7.6 Hz, 1H), 4.37 (s, 2H), 4.09 (s, 3H), 3.54 (s, 3H), 3.38 (s, 3H), 3.20 (s, 2H), 2.13 (s, 3H), 0.91 (dd, J=6.4, 6.4 Hz, 2H), 0.73 (dd, J=6.2, 6.2 Hz, 2H). MS: (ES) m/z calculated for $C_{31}H_{33}ClN_5O_5$ [M+H]$^+$ 590.2, found 590.5.

Example 43: (S)—N-(2'-chloro-3'-(5-(((1-hydroxypropan-2-yl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide

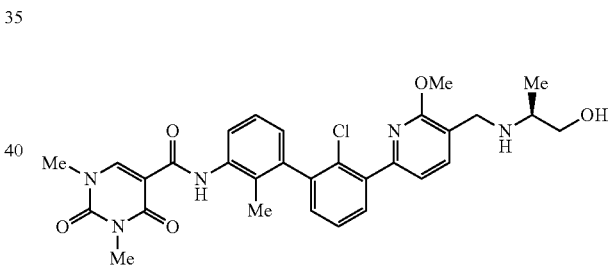

A mixture of N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide (45 mg, 0.086 mmol), L-alaninol (30 mg, 0.40 mmol) and AcOH (27 mg, 0.45 mmol) in DCM (1.5 mL) and EtOH (0.5 mL) was heated at 60° C. for 0.5 h. The contents were cooled to 0° C. and NaBH$_3$CN (30 mg, 0.48 mmol) was added. After stirring for 15 min at 0° C. the reaction was quenched with 1 drop of water. The crude material was purified by preparative to give (S)—N-(2'-chloro-3'-(5-(((1-hydroxypropan-2-yl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.14 (s, 1H), 8.58 (s, 1H), 8.13 (dd, J=7.4, 7.4 Hz, 1H), 7.88 (d, J=7.6 Hz, 1H), 7.60 (dd, J=7.6, 1.6 Hz, 1H), 7.48 (dd, J=7.6, 7.6 Hz, 1H), 7.33 (d, J=8.0 Hz, 2H), 7.27 (dd, J=7.8, 7.8 Hz, 1H), 6.98 (d, J=7.2 Hz, 1H), 4.31 (s, 2H), 4.08 (s, 3H), 3.86 (d, J=12.0, 4.0 Hz, 1H), 3.66-3.60 (m, 1H), 3.51 (s, 3H), 3.44-3.36 (m, 1H), 3.33 (s, 3H), 2.11 (s, 3H), 1.38 (d, J=6.8 Hz, 3H). MS: (ES) m/z calculated for $C_3H_{33}ClN_5O_5$ [M+H]$^+$ 578.2. found 578.5.

Example 44: (R)—N-(2'-chloro-3'-(5-(((1-hydroxy-propan-2-yl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide

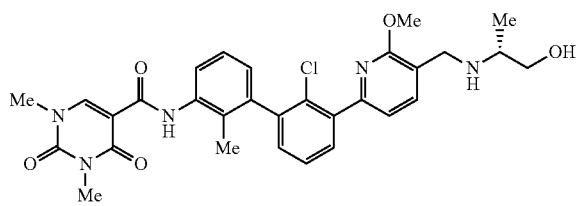 [SMILES: COc1nc(-c2cccc(-c3cccc(NC(=O)c4cn(C)c(=O)n(C)c4=O)c3C)c2Cl)ccc1CN[C@H](C)CO]

A mixture of N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide (45 mg, 0.086 mmol), D-alaninol (30 mg, 0.40 mmol) and AcOH (27 mg, 0.45 mmol) in DCM (1.5 mL) and EtOH (0.5 mL) was heated at 60° C. for 0.5 h. The contents were cooled to 0° C. and NaBH$_3$CN (30 mg, 0.48 mmol) was added. After stirring for 15 min at 0° C. the reaction was quenched with 1 drop of water. The crude material was purified by preparative HPLC to give (R)—N-(2'-chloro-3'-(5-(((1-hydroxypropan-2-yl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.13 (s, 1H), 8.56 (s, 1H), 8.12 (d, J=6.8 Hz, 1H), 7.87 (d, J=7.6 Hz, 1H), 7.60 (dd, J=7.6, 1.6 Hz, 1H), 7.47 (dd, J=7.6, 7.6 Hz, 1H), 7.34-7.31 (m, 2H), 7.26 (dd, J=8.0, 8.0 Hz, 1H), 6.97 (d, J=6.8 Hz, 1H), 4.30 (s, 2H), 4.08 (s, 3H), 3.86 (dd, J=12.0, 4.0 Hz, 1H), 3.66-3.60 (m, 1H), 3.50 (s, 3H), 3.43-3.36 (m, 1H), 3.31 (s, 3H), 2.11 (s, 3H), 1.38 (d, J=7.2 Hz, 3H). MS: (ES) m/z calculated for C$_3$H$_{33}$ClN$_5$O$_5$ [M+H]$^+$ 578.2. found 578.5.

Example 45: N-(2-chloro-2'-fluoro-3'-(5-((((3R,4R)-3-hydroxytetrahydro-2H-pyran-4-yl)amino)methyl)-6-methoxypyridin-2-yl)-[1,1'-biphenyl]-3-yl)-1,3-dimethyl-2,4-dioxo-1,2,3,4-tetrahydropyrimidine-5-carboxamide

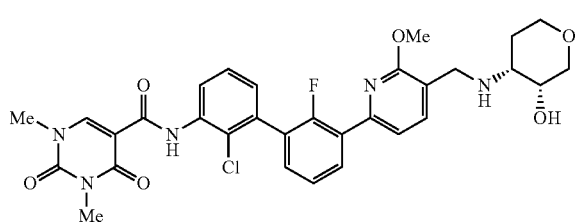

The compound was prepared from N-(2-chloro-2'-fluoro-3'-(5-formyl-6-methoxypyridin-2-yl)-[1,1'-biphenyl]-3-yl)-1,3-dimethyl-2,4-dioxo-1,2,3,4-tetrahydropyrimidine-5-carboxamide and (3R,4R)-4-aminooxan-3-ol hydrochloride using a procedure similar to step d in Example 1. The crude product was purified by preparative HPLC to give N-(2-chloro-2'-fluoro-3'-(5-((((3R,4R)-3-hydroxytetrahydro-2H-pyran-4-yl)amino)methyl)-6-methoxypyridin-2-yl)-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.70 (s, 1H), 8.66 (s, 1H), 8.55 (dd, J=8.4, 1.5 Hz, 1H), 8.20-8.14 (m, 1H), 7.86 (d, J=7.6 Hz, 1H), 7.55 (dd, J=7.6, 1.8 Hz, 1H), 7.45-7.38 (m, 3H), 7.18 (dd, J=7.6, 1.7 Hz, 1H), 4.37-4.21 (m, 2H), 4.15 (s, 3H), 4.07-3.94 (m, 3H), 3.59-3.42 (m, 3H), 3.55 (s, 3H), 3.37 (s, 3H), 2.19-2.05 (m, 1H), 1.91-1.83 (m, 1H). MS: (ES) m/z calculated for C$_{31}$H$_{32}$ClFN$_5$O$_6$ [M+H]$^+$ 624.2. found 624.5.

Example 46: N-(2'-chloro-3'-(5-((((1R,2S)-2-hydroxycyclohexyl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide

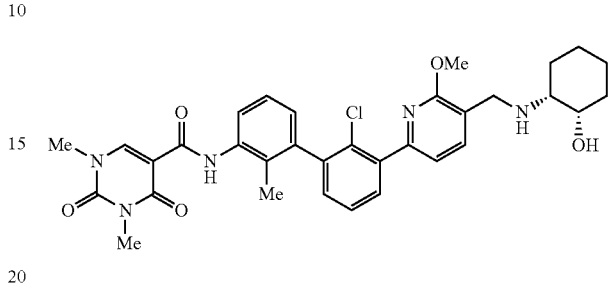

The compound was prepared from N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide and (1S,2R)-2-aminocyclohexan-1-ol hydrochloride using a procedure similar to step d in Example 1. The crude product was purified by preparative HPLC to give N-(2'-chloro-3'-(5-((((1R,2S)-2-hydroxycyclohexyl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide. $^1$H NMR (400 MHz, DMSO-d$_6$) δ 11.07 (s, 1H), 8.77 (s, 1H), 8.26 (dd, J=8.0, 1.2 Hz, 1H), 7.84 (d, J=7.5 Hz, 1H), 7.64 (dd, J=7.7, 1.7 Hz, 1H), 7.52 (dd, J=7.6, 7.6 Hz, 1H), 7.37-7.27 (m, 3H), 6.99 (dd, J=7.7, 1.3 Hz, 1H), 4.40 (s, 1H), 3.91 (s, 3H), 3.81-3.75 (m, 3H), 3.50 (s, 3H), 3.27 (s, 3H), 2.58-2.53 (m, 1H), 2.09 (s, 3H), 1.75-1.67 (m, 1H), 1.63-1.43 (m, 4H), 1.39-1.33 (m, 1H), 1.28-1.16 (m, 2H). MS: (ES) m/z calculated for C$_{33}$H$_{37}$ClN$_5$O$_5$ [M+H]$^+$ 618.2, found 618.2.

Example 47: 1-((5-(2,2'-dichloro-3'-(1,3-dimethyl-2,4-dioxo-1,2,3,4-tetrahydropyrimidine-5-carboxamido)-[1,1'-biphenyl]-3-yl)-3-methoxypyrazin-2-yl)methyl)azetidine-3-carboxylic Acid

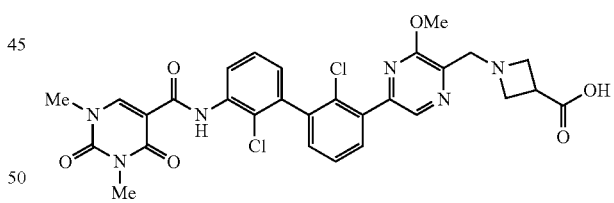

The compound was prepared from N-(2,2'-dichloro-3'-(5-formyl-6-methoxypyrazin-2-yl)-[1,1'-biphenyl]-3-yl)-1,3-dimethyl-2,4-dioxo-1,2,3,4-tetrahydropyrimidine-5-carboxamide and azetidine-3-carboxylic acid hydrochloride using a procedure similar to step d in Example 1. The crude material was purified by preparative HPLC to give the desired product 1-((5-(2,2'-dichloro-3'-(1,3-dimethyl-2,4-dioxo-1,2,3,4-tetrahydropyrimidine-5-carboxamido)-[1,1'-biphenyl]-3-yl)-3-methoxypyrazin-2-yl)methyl)azetidine-3-carboxylic acid. $^1$H NMR (400 MHz, CD$_3$OD) δ 11.70 (s, 1H), 8.67 (s, 1H), 8.56 (d, J=8.1 Hz, 1H), 8.52 (s, 1H), 7.69 (d, J=7.8 Hz, 1H), 7.56 (dd, J=8.0, 8.0 Hz, 1H), 7.46-7.38 (m, 2H), 7.11 (d, J=7.3 Hz, 1H), 4.74 (s, 2H), 4.70-4.55 (bs, 2H), 4.50-4.35 (bs, 2H), 4.12 (s, 3H), 3.78 (bs, 1H), 3.56 (s, 3H), 3.39 (s, 3H). MS: (ES) m/z calculated for C$_{29}$H$_{27}$Cl$_2$N$_6$O$_6$ [M+H]$^+$ 625.1. found 625.0.

Example 48: N-(2,2'-dichloro-3'-(6-methoxy-5-((5-oxo-2,6-diazaspiro[3.4]octan-2-yl)methyl)pyrazin-2-yl)-[1,1'-biphenyl]-3-yl)-1,3-dimethyl-2,4-dioxo-1,2,3,4-tetrahydropyrimidine-5-carboxamide

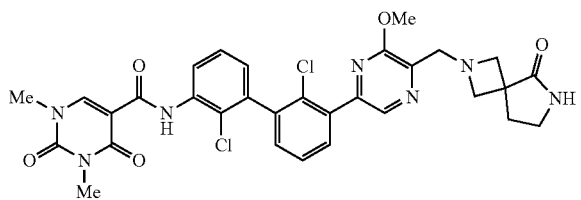 [SMILES: COc1nc(-c2cccc(-c3cccc(NC(=O)c4cn(C)c(=O)n(C)c4=O)c3Cl)c2Cl)cnc1CN1CC2(CCNC2=O)C1]

The compound was prepared from N-(2,2'-dichloro-3'-(5-formyl-6-methoxypyrazin-2-yl)-[1,1'-biphenyl]-3-yl)-1,3-dimethyl-2,4-dioxo-1,2,3,4-tetrahydropyrimidine-5-carboxamide and 2,6-diazaspiro[3.4]octan-5-one tosylate using a procedure similar to step d in Example 1. The crude material was purified by preparative HPLC to give the desired product N-(2,2'-dichloro-3'-(6-methoxy-5-((5-oxo-2,6-diazaspiro[3.4]octan-2-yl)methyl)pyrazin-2-yl)-[1,1'-biphenyl]-3-yl)-1,3-dimethyl-2,4-dioxo-1,2,3,4-tetrahydropyrimidine-5-carboxamide. $^1$H NMR (400 MHz, CD$_3$-OD) δ 11.70 (s, 1H), 8.67 (s, 1H), 8.56 (d, J=8.1 Hz, 1H), 8.53 (s, 1H), 7.70 (d, J=7.8 Hz, 1H), 7.56 (dd, J=8.0, 8.0 Hz, 1H), 7.46-7.38 (m, 2H), 7.11 (d, J=7.3 Hz, 1H), 4.71 (bs, 1H), 4.47 (bs, 1H), 4.33 (s, 2H), 4.12 (s, 3H), 3.56 (s, 3H), 3.47 (m, 1H), 3.36 (s, 3H), 3.41-3.29 (bs, 2H), 3.12 (m, 1H), 2.58 (bs, 2H). MS: (ES) m/z calculated for C$_{31}$H$_{30}$Cl$_2$N$_7$O$_5$ [M+H]$^+$ 650.2, found 650.0.

Example 49: (S)—N-(2'-chloro-3'-(5-((((4,4-dimethyl-5-oxopyrrolidin-2-yl)methyl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide The compound was prepared from N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide and (S)-5-(aminomethyl)-3,3-dimethylpyrrolidin-2-one using a procedure similar to step d in Example 1. The crude product was purified by preparative HPLC to give (S)—N-(2'-chloro-3'-(5-((((4,4-dimethyl-5-oxopyrrolidin-2-yl)methyl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide. $^1$H NMR (400 MHz, CDCl$_3$) δ 10.89 (s, 1H), 8.53 (s, 1H), 8.21 (d, J=7.6 Hz, 1H), 7.66-7.53 (m, 2H), 7.40 (dd, J=7.6, 7.6 Hz, 1H), 7.35-7.22 (m, 3H), 7.06-6.99 (m, 1H), 5.94 (s, 1H), 4.02 (s, 3H), 3.80 (s, 2H), 3.75-3.63 (m, 1H), 3.58 (s, 3H), 3.44 (s, 3H), 2.81 (dd, J=12.0, 4.0 Hz, 1H), 2.51 (dd, J=12.0, 8.9 Hz, 1H), 2.19 (s, 3H), 2.05 (dd, J=12.8, 6.9 Hz, 1H), 1.18 (d, J=5.3 Hz, 6H). MS: (ES) m/z calculated for C$_{34}$H$_{38}$ClN$_6$O$_5$ [M+H]$^+$ 645.2, found 645.6.

Example 50: N-(2'-chloro-3'-(6-methoxy-5-((((2-methyl-5-oxopyrrolidin-2-yl)methyl)amino)methyl)pyridin-2-yl)-2-methyl-[1,1'-biphenyl]-3-yl)-1,3-dimethyl-2,4-dioxo-1,2,3,4-tetrahydropyrimidine-5-carboxamide

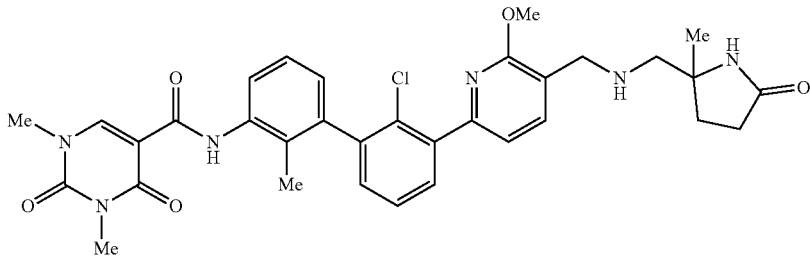

The compound was prepared from N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide and 5-(aminomethyl)-5-methylpyrrolidin-2-one hydrochloride using a procedure similar to step d in Example 1. The crude product was purified by preparative HPLC to give N-(2'-chloro-3'-(6-methoxy-5-((((2-methyl-5-oxopyrrolidin-2-yl)methyl)amino)methyl)pyridin-2-yl)-2-methyl-[1,1'-biphenyl]-3-yl)-1,3-dimethyl-2,4-dioxo-1,2,3,4-tetrahydropyrimidine-5-carboxamide. $^1$H NMR (400 MHz, CDCl$_3$) δ 10.89 (s, 1H), 8.53 (s, 1H), 8.25-8.18 (m, 1H), 7.67-7.54 (m, 2H), 7.40 (dd, J=7.6, 7.6 Hz, 1H), 7.35-7.22 (m, 3H), 7.03 (d, J=7.5 Hz, 1H), 5.72 (s, 1H), 4.02 (s, 3H), 3.88-3.75 (m, 2H), 3.57 (s, 3H), 3.44 (s, 3H), 2.67 (d, J=12.1 Hz, 1H), 2.54 (d, J=12.1 Hz, 1H), 2.48-2.38 (m,

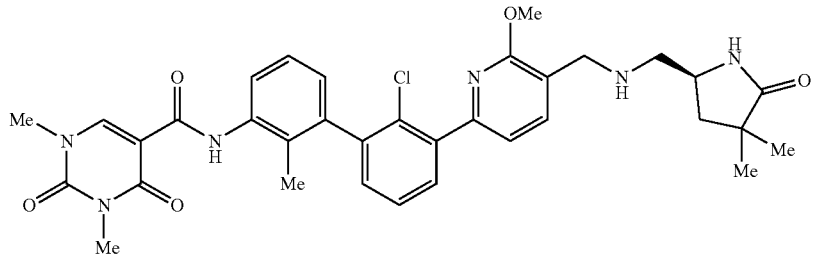 [SMILES: COc1nc(-c2cccc(-c3cccc(NC(=O)c4cn(C)c(=O)n(C)c4=O)c3C)c2Cl)ccc1CNC[C@@H]1CC(C)(C)C(=O)N1]

2H), 2.19 (s, 3H), 2.08 (ddd, J=12.7, 8.9, 7.6 Hz, 1H), 1.85 (ddd, J=12.9, 8.3, 8.3 Hz, 1H), 1.27 (s, 3H). MS: (ES) m/z calculated for $C_{33}H_{36}ClN_6O_5$ [M+H]$^+$ 631.2. found 631.2.

Example 51: N-(2'-chloro-3'-(5-((((3S,4R)-3-hydroxytetrahydro-2H-pyran-4-yl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide

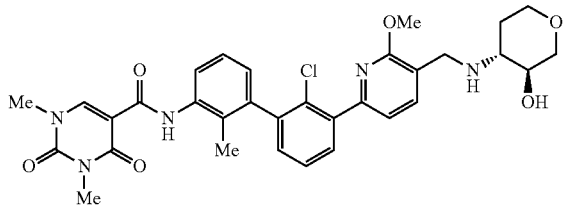 [SMILES: COc1nc(-c2cccc(-c3cccc(NC(=O)c4cn(C)c(=O)n(C)c4=O)c3C)c2Cl)ccc1CN[C@@H]1CCOC[C@H]1O]

The compound was prepared from N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide and (3S,4R)-4-aminotetrahydro-2H-pyran-3-ol hydrochloride using a procedure similar to step d in Example 1. The crude product was purified by preparative HPLC to give N-(2'-chloro-3'-(5-((((3S,4R)-3-hydroxytetrahydro-2H-pyran-4-yl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide. $^1$H NMR (400 MHz, CDCl$_3$) δ 10.89 (s, 1H), 8.52 (s, 1H), 8.22 (d, J=8.0 Hz, 1H), 7.67-7.58 (m, 2H), 7.40 (t, J=7.6 Hz, 1H), 7.35-7.22 (m, 3H), 7.02 (d, J=7.3 Hz, 1H), 4.10-3.92 (m, 4H), 3.75 (d, J=13.7 Hz, 1H), 3.57 (s, 3H), 3.51-3.36 (m, 6H), 3.17 (dd, J=10.9, 9.8 Hz, 1H), 2.63-2.52 (m, 1H), 2.19 (s, 3H), 2.06 (d, J=13.6 Hz, 1H). MS: (ES) m/z calculated for $C_{32}H_{35}ClN_5O_6$ [M+H]$^+$ 620.2. found 620.2.

Example 52: N-(2'-chloro-3'-(5-((((3R,4R)-4-hydroxytetrahydrofuran-3-yl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide

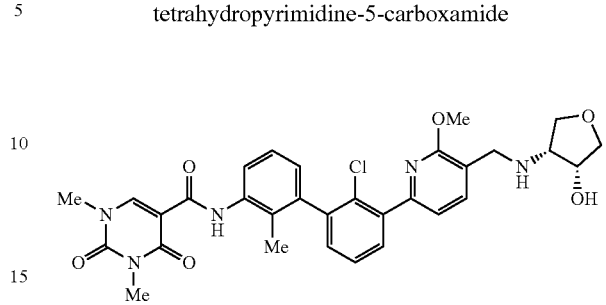

The compound was prepared from N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide and (3R,4R)-4-aminotetrahydrofuran-3-ol hydrochloride using a procedure similar to step d in Example 1. The crude product was purified by preparative HPLC to give N-(2'-chloro-3'-(5-((((3R,4R)-4-hydroxytetrahydrofuran-3-yl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.19 (s, 1H), 8.64 (s, 1H), 8.11 (d, J=8.0 Hz, 1H), 7.89 (d, J=7.6 Hz, 1H), 7.62 (dd, J=7.7, 1.7 Hz, 1H), 7.50 (dd, J=7.6, 7.6 Hz, 1H), 7.37-7.28 (m, 3H), 7.01 (d, J=7.5 Hz, 1H), 4.60-4.58 (m, 1H), 4.41-4.26 (m, 2H), 4.09 (s, 3H), 4.07-4.01 (m, 1H), 3.97-3.83 (m, 4H), 3.55 (s, 3H), 3.39 (s, 3H), 2.14 (s, 3H). MS: (ES) m/z calculated for $C_{31}H_{33}ClN_5O_6$ [M+H]$^+$ 606.2. found 606.5.

Example 53: ((6-(2-chloro-3'-(1,3-dimethyl-2,4-dioxo-1,2,3,4-tetrahydropyrimidine-5-carboxamido)-2'-methyl-[1,1'-biphenyl]-3-yl)-2-methoxypyridin-3-yl)methyl)glycine

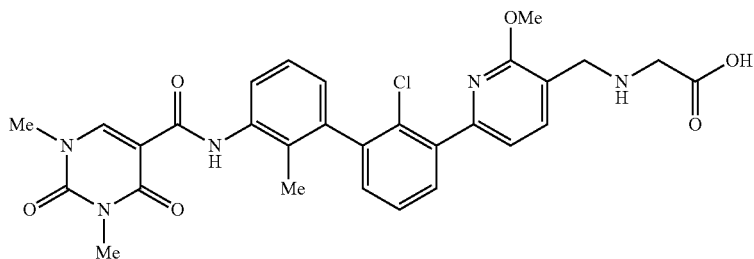 [SMILES: COc1nc(-c2cccc(-c3cccc(NC(=O)c4cn(C)c(=O)n(C)c4=O)c3C)c2Cl)ccc1CNCC(=O)O]

A mixture of N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide (50 mg, 0.096 mmol), glycine (30 mg, 0.04 mmol) and AcOH (75 mg, 1.3 mmol) in DMF (1 mL) was stirred at room temperature for 1.5 h. To the mixture was added NaBH(OAc)$_3$ (70 mg, 0.33 mmol). After stirring 1 h at room temperature the crude material was purified by preparative HPLC to yield ((6-(2-chloro-3'-(1,3-dimethyl-2,4-dioxo-1,2,3,4-tetrahydropyrimidine-5-carboxamido)-2'-methyl-[1,1'-biphenyl]-3-yl)-2-methoxypyridin-3-yl)methyl)glycine. $^1$H NMR (400 MHz, CD$_3$OD) δ 11.18 (s, 1H), 8.63 (s, 1H), 8.11 (dd, J=72, 7.2 Hz, 1H), 7.86 (d, J=7.2 Hz, 1H), 7.62 (dd, J=8.0, 1.6 Hz, 1H), 7.49 (dd, J=7.6, 7.6 Hz, 1H), 7.35 (dd, J=7.6, 2.0 Hz, 2H), 7.29 (dd, J=8.0, 8.0 Hz, 1H), 7.00 (d, J=7.2 Hz, 1H), 4.34 (s, 2H), 4.09 (s, 3H), 3.96 (s, 2H), 3.55 (s, 3H), 3.39 (s, 3H), 2.13 (s, 3H). MS: (ES) m/z calculated $C_{29}H_{29}ClN_5O_6$ [M+H]$^+$ 578.2, found 578.5.

Example 54: (R)—N-(2,2'-dichloro-3'-(6-methoxy-5-((((5-oxopyrrolidin-2-yl)methyl)amino)methyl)pyridin-2-yl)-[1,1'-biphenyl]-3-yl)-1,3-dimethyl-2,4-dioxo-1,2,3,4-tetrahydropyrimidine-5-carboxamide

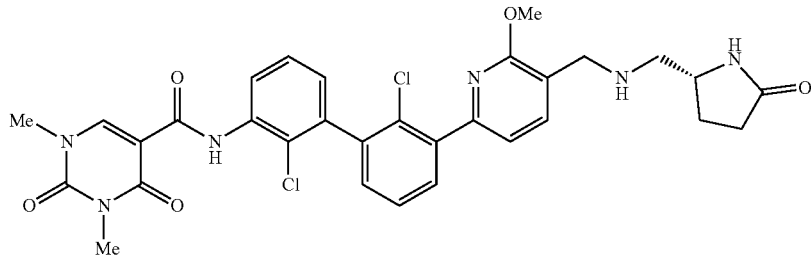 [SMILES: COc1nc(-c2cccc(-c3cccc(NC(=O)c4cn(C)c(=O)n(C)c4=O)c3Cl)c2Cl)ccc1CNC[C@H]1CCC(=O)N1]

The compound was prepared from N-(2,2'-dichloro-3'-(5-formyl-6-methoxypyridin-2-yl)-[1,1'-biphenyl]-3-yl)-1,3-dimethyl-2,4-dioxo-1,2,3,4-tetrahydropyrimidine-5-carboxamide and (R)-5-aminomethylpyrrolidin-2-one hydrochloride using a procedure similar to step d in Example 1. The crude product was purified by silica gel flash chromatography. The material was treated with 1N HCl in Et$_2$O (1 mL) and triturated with MeCN (5 mL) to give (R)—N-(2,2'-dichloro-3'-(6-methoxy-5-((((5-oxopyrrolidin-2-yl)methyl)amino)methyl)pyridin-2-yl)-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.69 (s, 1H), 8.66 (d, J=1.9 Hz, 1H), 8.54 (d, J=8.4 Hz, 1H), 7.92 (d, J=7.6 Hz, 1H), 7.66 (d, J=7.8 Hz, 1H), 7.51 (dd, J=7.7, 7.7 Hz, 1H), 7.45-7.34 (m, 3H), 7.14-7.07 (m, 1H), 4.35 (d, J=2.2 Hz, 2H), 4.14-4.03 (m, 4H), 3.56 (d, J=1.9 Hz, 3H), 3.39 (d, J=1.9 Hz, 3H), 3.26 (d, J=6.1 Hz, 2H), 2.49-2.32 (m, 3H), 1.98-1.88 (m, 1H). MS: (ES) m/z calculated for C$_{31}$H$_{31}$Cl$_2$N$_6$O$_5$ [M+H]$^+$ 637.2. found 637.5.

Example 55: (S)—N-(2,2'-dichloro-3'-(6-ethyl-5-((((5-oxopyrrolidin-2-yl)methyl)amino)methyl)pyrazin-2-yl)-[1,1'-biphenyl]-3-yl)-1,3-dimethyl-2,4-dioxo-1,2,3,4-tetrahydropyrimidine-5-carboxamide

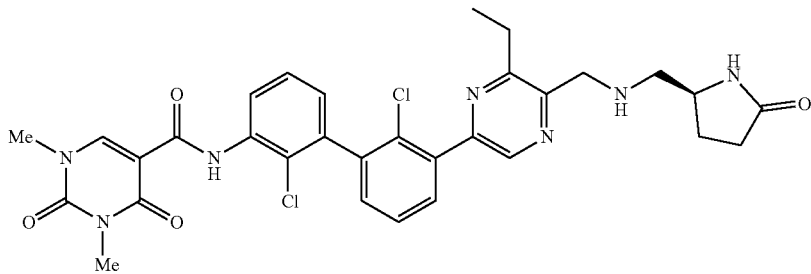 [SMILES: CCc1nc(-c2cccc(-c3cccc(NC(=O)c4cn(C)c(=O)n(C)c4=O)c3Cl)c2Cl)cnc1CNC[C@@H]1CCC(=O)N1]

The compound was prepared from N-(2,2'-dichloro-3'-(6-ethyl-5-formylpyrazin-2-yl)-[1,1'-biphenyl]-3-yl)-1,3-dimethyl-2,4-dioxo-1,2,3,4-tetrahydropyrimidine-5-carboxamide and (S)-5-aminomethylpyrrolidin-2-one hydrochloride using a procedure similar to step d in Example 1. The crude product was purified by silica gel flash chromatography, followed by preparative HPLC to give (S)—N-(2,2'-dichloro-3'-(6-ethyl-5-((((5-oxopyrrolidin-2-yl)methyl)amino)methyl)pyrazin-2-yl)-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.70 (s, 1H), 8.84 (s, 1H), 8.67 (d, J=1.8 Hz, 1H), 8.55 (d, J=8.4 Hz, 1H), 7.73-7.66 (m, 1H), 7.58 (dd, J=7.7, 7.7 Hz, 1H), 7.48-7.38 (m, 2H), 7.12 (d, J=7.8 Hz, 1H), 4.73-4.58 (m, 2H), 4.16-4.09 (m, 1H), 3.56 (d, J=1.6 Hz, 3H), 3.42-3.27 (m, 5H), 2.95 (q, J=7.5 Hz, 2H), 2.50-2.35 (m, 3H), 2.02-1.94 (m, 1H), 1.40 (t, J=7.5 Hz, 3H). MS: (ES) m/z calculated for C$_{31}$H$_{32}$Cl$_2$N$_7$O$_4$ [M+H]$^+$ 636.2. found 636.2.

Example 56: (S)—N-(2'-chloro-3'-(6-methoxy-5-((((5-oxopyrrolidin-2-yl)methyl)amino)methyl)pyridin-2-yl)-2-methyl-[1,1'-biphenyl]-3-yl)-3-methyl-2,4-dioxo-1,2,3,4-tetrahydropyrimidine-5-carboxamide

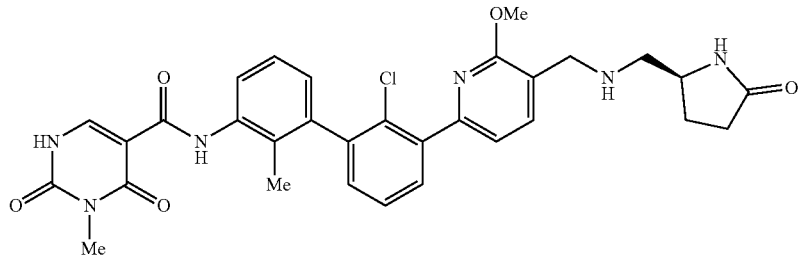 [SMILES: COc1nc(-c2cccc(-c3cccc(NC(=O)c4c[nH]c(=O)n(C)c4=O)c3C)c2Cl)ccc1CNC[C@@H]1CCC(=O)N1]

The compound was prepared from N-(2'-chloro-3'-(5-formyl-6-methoxypyridin-2-yl)-2-methyl-[1,1'-biphenyl]-3-yl)-3-methyl-2,4-dioxo-1,2,3,4-tetrahydropyrimidine-5-carboxamide and (S)-5-aminomethylpyrrolidin-2-one hydrochloride using a procedure similar to step d in Example 1. The crude product was purified by silica gel flash chromatography, followed by preparative HPLC to give (S)—N-(2'-chloro-3'-(6-methoxy-5-((((5-oxopyrrolidin-2-yl)methyl)amino)methyl)pyridin-2-yl)-2-methyl-[1,1'-biphenyl]-3-yl)-3-methyl-2,4-dioxo-1,2,3,4-tetrahydropyrimidine-5-carboxamide. $^1$H NMR (400 MHz, CD$_3$OD) δ 11.17 (s, 1H), 8.42 (s, 1H), 8.10 (d, J=8.2 Hz, 1H), 7.88 (d, J=7.5 Hz, 1H), 7.61 (d, J=7.4 Hz, 1H), 7.50 (dd, J=8.4, 6.9 Hz, 1H), 7.41-7.25 (m, 3H), 7.01 (d, J=7.5 Hz, 1H), 4.38-4.31 (m, 2H), 4.13-4.00 (m, 4H), 3.39-3.22 (m, 5H), 2.49-2.32 (m, 3H), 2.13 (s, 3H), 1.96-1.88 (m, 1H). MS: (ES) m/z calculated for C$_{31}$H$_{32}$ClN$_6$O$_5$ [M+H]$^+$ 603.2. found 603.6.

Example 57: (S)—N-(2'-chloro-3'-(6-ethyl-5-((((5-oxopyrrolidin-2-yl)methyl)amino)methyl)pyridin-2-yl)-2-methyl-[1,1'-biphenyl]-3-yl)-1,3-dimethyl-2,4-dioxo-1,2,3,4-tetrahydropyrimidine-5-carboxamide

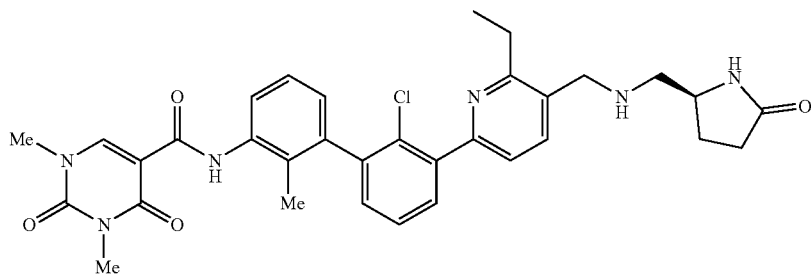

The compound was prepared from N-(2'-chloro-3'-(6-ethyl-5-formylpyridin-2-yl)-2-methyl-[1,1'-biphenyl]-3-yl)-1,3-dimethyl-2,4-dioxo-1,2,3,4-tetrahydropyrimidine-5-carboxamide and (S)-5-aminomethylpyrrolidin-2-one hydrochloride using a procedure similar to step d in Example 1. The crude product was purified by silica gel flash chromatography, followed by preparative HPLC to give (S)—N-(2'-chloro-3'-(6-ethyl-5-((((5-oxopyrrolidin-2-yl)methyl)amino)methyl)pyridin-2-yl)-2-methyl-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.18 (s, 1H), 8.63 (s, 1H), 8.10 (d, J=8.0 Hz, 1H), 8.00 (d, J=8.2 Hz, 1H), 7.65 (d, J=8.0 Hz, 1H), 7.59-7.48 (m, 2H), 7.39 (dd, J=7.1, 2.2 Hz, 1H), 7.29 (dd, J=7.9, 7.9 Hz, 1H), 7.00 (d, J=7.7 Hz, 1H), 4.50-4.42 (m, 2H), 4.09-4.02 (s, 1H), 3.55 (s, 3H), 3.42-3.31 (m, 5H), 3.01 (t, J=7.5 Hz, 2H), 2.48-2.35 (m, 3H), 2.14 (s, 3H), 1.96-1.88 (m, 1H), 1.35 (t, J=7.5 Hz, 3H). MS: (ES) m/z calculated for C$_{33}$H$_{36}$ClN$_6$O$_4$ [M+H]$^+$ 615.2. found 615.6.

Example 58: N-(2'-chloro-3'-(6-((((3R,4R)-3-hydroxytetrahydro-2H-pyran-4-yl)amino)methyl)-5-methoxypyridin-3-yl)-2-methyl-[1,1'-biphenyl]-3-yl)-1,3-dimethyl-2,4-dioxo-1,2,3,4-tetrahydropyrimidine-5-carboxamide

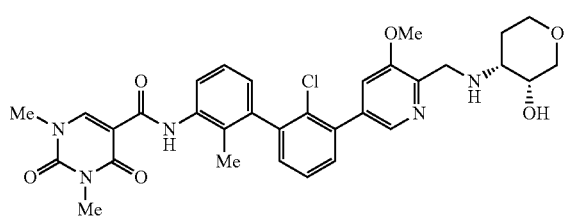 [SMILES: COc1cc(-c2cccc(-c3cccc(NC(=O)c4cn(C)c(=O)n(C)c4=O)c3C)c2Cl)cnc1CN[C@@H]1CCOC[C@@H]1O]

A mixture of N-(2'-chloro-3'-(6-formyl-5-methoxypyridin-3-yl)-2-methyl-[1,1'-biphenyl]-3-yl)-1,3-dimethyl-2,4-dioxo-1,2,3,4-tetrahydropyrimidine-5-carboxamide (32 mg, 0.061 mmol), (3R,4R)-4-aminotetrahydro-2H-pyran-3-ol hydrogen chloride (20 mg, 0.13 mmol), Et$_3$N (75 mg, 0.74 mmol) and AcOH (150 mg, 2.5 mmol) in EtOH (1.5 mL) and DCM (1.5 mL) was heated at 70° C. for 0.5 h. The contents were cooled to 0° C. and NaBH$_3$CN (30 mg, 0.44 mmol) was added. After stirring for 5 min at 0° C. the mixture was concentrated in vacuo. The obtained residue was purified by preparative HPLC to give N-(2'-chloro-3'-(6-((((3R,4R)-3-hydroxytetrahydro-2H-pyran-4-yl)amino)methyl)-5-methoxypyridin-3-yl)-2-methyl-[1,1'-biphenyl]-3-yl)-1,3- dimethyl-2,4-dioxo-1,2,3,4-tetrahydropyrimidine-5-carboxamide. $^1$H NMR (400 MHz, CD$_3$OD) δ 8.62 (s, 1H), 8.33 (d, J=1.6 Hz, 1H), 8.12 (d, J=8.4 Hz, 1H), 7.65 (d, J=1.6 Hz, 1H), 7.56-7.47 (m, 2H), 7.37 (dd, J=7.6, 1.6 Hz, 1H), 7.29 (d, J=8.2, 8.2 Hz, 1H), 6.99 (d, J=7.6 Hz, 1H), 4.47 (s, 2H), 4.08-3.94 (m, 3H), 3.99 (s, 3H), 3.62-3.54 (m, 2H), 3.55 (s, 3H), 3.50-3.42 (m, 1H), 3.38 (s, 3H), 2.20-2.10 (m, 1H), 2.14 (s, 3H), 1.96-1.88 (m, 1H). MS: (ES) m/z calculated for C$_{32}$H$_{35}$ClN$_5$O$_6$ [M+H]$^+$ 620.2. found 620.2.

Example 59: N-(2'-chloro-3'-(6-methoxy-5-((6-oxo-2,5,7-triazaspiro[3.4]octan-2-yl)methyl)pyridin-2-yl)-2-methyl-[1,1'-biphenyl]-3-yl)-1,3-dimethyl-2,4-dioxo-1,2,3,4-tetrahydropyrimidine-5-carboxamide

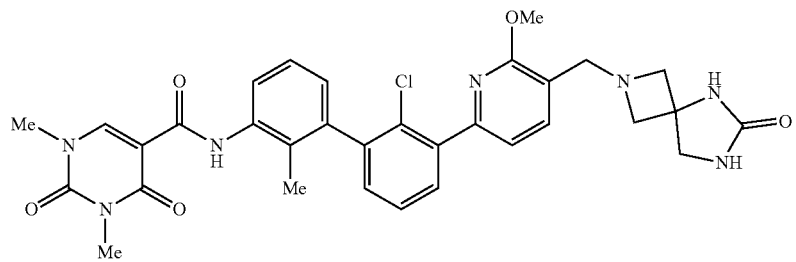 [SMILES: COc1nc(-c2cccc(-c3cccc(NC(=O)c4cn(C)c(=O)n(C)c4=O)c3C)c2Cl)ccc1CN1CC2(CNC(=O)N2)C1]

The compound was prepared from N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide and 2,5,7-triazaspiro[3.4]octan-6-one hydrochloride using a procedure similar to step d in Example 1. The crude product was purified by preparative HPLC to give N-(2'-chloro-3'-(6-methoxy-5-((6-oxo-2,5,7-triazaspiro[3.4]octan-2-yl)methyl)pyridin-2-yl)-2-methyl-[1,1'-biphenyl]-3-yl)-1,3-dimethyl-2,4-dioxo-1,2,3,4-tetrahydropyrimidine-5-carboxamide. $^1$H NMR (400 MHz, DMSO-d$_6$) δ 11.07 (s, 1H), 8.77 (s, 1H), 8.27-8.25 (m, 1H), 7.71-7.62 (m, 2H), 7.54-7.50 (m, 1H), 7.37-7.26 (m, 3H), 6.99-6.92 (m, 2H), 6.29 (s, 1H), 3.91 (s, 3H), 3.56-3.43 (m, 9H), 3.27 (s, 3H), 3.14-3.12 (m, 2H), 2.09 (s, 3H). MS: (ES) m/z calculated for C$_{32}$H$_{32}$ClN$_7$O$_5$ [M+H]$^+$ 630.2. found 630.2.

Example 60: (S)—N-(2,2'-dichloro-3'-(6-hydroxy-5-(((((5-oxopyrrolidin-2-yl)methyl)amino)methyl)pyridin-2-yl)-[1,1'-biphenyl]-3-yl)-1,3-dimethyl-2,4-dioxo-1,2,3,4-tetrahydropyrimidine-5-carboxamide

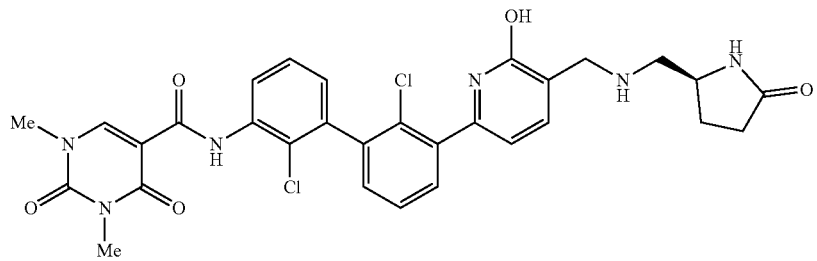 [SMILES: Cn1cc(C(=O)Nc2cccc(-c3cccc(-c4ccc(CNC[C@@H]5CCC(=O)N5)c(O)n4)c3Cl)c2Cl)c(=O)n(C)c1=O]

To a solution of (S)—N-(2,2'-dichloro-3'-(6-methoxy-5-((((5-oxopyrrolidin-2-yl)methyl)amino)methyl)pyridin-2-yl)-[1,1'-biphenyl]-3-yl)-1,3-dimethyl-2,4-dioxo-1,2,3,4-tetrahydropyrimidine-5-carboxamide (50 mg, 0.078 mmol) in 2 mL of MeOH at 0° C. was added slowly a solution of hydrochlorid acid (0.5 mL, 37% in water). The mixture was heated to 100° C. for 16 h. The crude product was purified by preparative HPLC to give the (S)—N-(2,2'-dichloro-3'-(6-hydroxy-5-((((5-oxopyrrolidin-2-yl)methyl)amino)methyl)pyridin-2-yl)-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.69 (s, 1H), 8.66 (s, 1H), 8.55 (ddd, J=8.4, 2.4, 1.5 Hz, 1H), 7.66 (d, J=7.1 Hz, 1H), 7.59-7.36 (m, 4H), 7.12-7.04 (m, 1H), 6.46 (d, J=7.1 Hz, 1H), 4.53-4.38 (m, 2H), 3.89-3.85 (m, 1H), 3.79-3.68 (m, 1H), 3.64-3.56 (m, 1H), 3.55 (s, 3H), 3.39 (s, 3H), 2.57-2.54 (m, 2H), 2.28-2.20 (m, 1H), 2.04-1.93 (m, 1H). MS: (ES) m/z calculated for C$_{30}$H$_{29}$Cl$_2$N$_6$O$_5$ [M+H]$^+$ 623.2. found 623.5.

Example 61: (S)—N-(2'-chloro-3'-(6-methoxy-5-((((1-methyl-5-oxopyrrolidin-2-yl)methyl)amino)methyl)pyridin-2-yl)-2-methyl-[1,1'-biphenyl]-3-yl)-1,3-dimethyl-2,4-dioxo-1,2,3,4-tetrahydropyrimidine-5-carboxamide

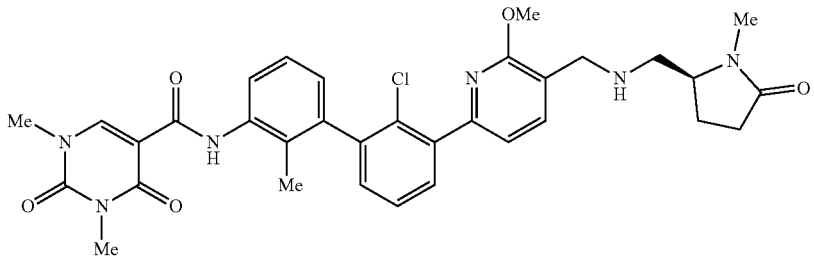 [SMILES: COc1nc(-c2cccc(-c3cccc(NC(=O)c4cn(C)c(=O)n(C)c4=O)c3C)c2Cl)ccc1CNC[C@@H]1CCC(=O)N1C]

The compound was prepared from N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide and (S)-5-(aminomethyl)-1-methylpyrrolidin-2-one hydrochloride using a procedure similar to step d in Example 1. The crude product was purified by preparative HPLC to give (S)—N-(2'-chloro-3'-(6-methoxy-5-((((1-methyl-5-oxopyrrolidin-2-yl)methyl)amino)methyl)pyridin-2-yl)-2-methyl-[1,1'-biphenyl]-3-yl)-1,3-dimethyl-2,4-dioxo-1,2,3,4-tetrahydropyrimidine-5-carboxamide. $^1$H NMR (400 MHz, DMSO-d$_6$) δ 11.07 (s, 1H), 8.77 (s, 1H), 8.27-8.25 (m, 1H), 7.80 (d, J=7.5 Hz, 1H), 7.64 (dd, J=7.7, 1.7 Hz, 1H), 7.52 (dd, J=7.6, 7.6 Hz, 1H), 7.37-7.28 (m, 3H), 6.99 (dd, J=7.7, 1.2 Hz, 1H), 3.92 (s, 3H), 3.73 (s, 2H), 3.61-3.55 (m, 1H), 3.50 (s, 3H), 3.27 (s, 3H), 2.68 (s, 5H), 2.28 (ddd, J=16.1, 9.9, 6.6 Hz, 1H), 2.20-1.98 (m, 5H), 1.91-1.79 (m, 1H). MS: (ES) m/z calculated for C$_{33}$H$_{36}$ClN$_6$O$_5$ [M+H]$^+$ 631.2. found 631.2.

Example 62: N-(3'-(5-(((3-amino-2,2-dimethyl-3-oxopropyl)amino)methyl)-6-methoxypyridin-2-yl)-2,2'-dichloro-[1,1'-biphenyl]-3-yl)-1,3-dimethyl-2,4-dioxo-1,2,3,4-tetrahydropyrimidine-5-carboxamide

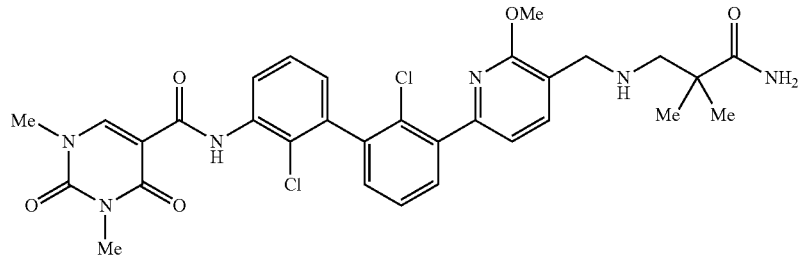 [SMILES: COc1nc(-c2cccc(-c3cccc(NC(=O)c4cn(C)c(=O)n(C)c4=O)c3Cl)c2Cl)ccc1CNCC(C)(C)C(N)=O]

The compound was prepared from N-(2,2'-dichloro-3'-(5-formyl-6-methoxypyridin-2-yl)-[1,1'-biphenyl]-3-yl)-1,3-dimethyl-2,4-dioxo-1,2,3,4-tetrahydropyrimidine-5-carboxamide and 3-amino-2,2-dimethylpropanamide using a procedure similar to step d in Example 1. The crude product was purified by preparative HPLC to give N-(3'-(5-(((3-amino-2,2-dimethyl-3-oxopropyl)amino)methyl)-6-methoxypyridin-2-yl)-2,2'-dichloro-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.68 (s, 1H), 8.65 (s, 1H), 8.53 (d, J=7.9 Hz, 1H), 7.86 (s, 1H), 7.65 (d, J=7.2 Hz, 1H), 7.50 (dd, J=7.2, 7.2 Hz, 1H), 7.42-7.36 (m, 3H), 7.09 (d, J=7.2 Hz, 1H), 4.27 (s, 2H), 4.12 (s, 3H), 3.55 (s, 3H), 3.38 (s, 3H), 3.13 (s, 2H), 1.34 (s, 6H). MS: (ES) m/z calculated for C$_{31}$H$_{33}$Cl$_2$N$_6$O$_5$ [M+H]$^+$ 639.2. found 639.2.

Example 63: (S)—N-(2,2'-dichloro-3'-(6-methoxy-5-((methyl((5-oxopyrrolidin-2-yl)methyl)amino) methyl)pyridin-2-yl)-[1,1'-biphenyl]-3-yl)-1,3-dimethyl-2,4-dioxo-1,2,3,4-tetrahydropyrimidine-5-carboxamide Example 64: (S)—N-(2,2'-dichloro-3'-(6-methoxy-5-((((5-oxopyrrolidin-2-yl)methyl)amino)methyl) pyridin-2-yl)-[1,1'-biphenyl]-3-yl)-1-methyl-2-oxo-1,2-dihydropyridine-3-carboxamide

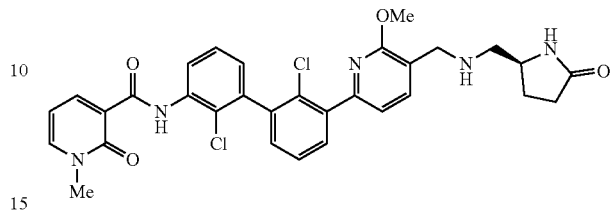

The compound was prepared from N-(2,2'-dichloro-3'-(5-formyl-6-methoxypyridin-2-yl)-[1,1'-biphenyl]-3-yl)-1-methyl-2-oxo-1,2-dihydropyridine-3-carboxamide and (S)-5-(aminomethyl)pyrrolidin-2-one hydrochloride using a procedure similar to step d in Example 1. The crude product was purified by preparative HPLC to give (S)—N-(2,2'-dichloro-3'-(6-methoxy-5-((((5-oxopyrrolidin-2-yl)methyl)

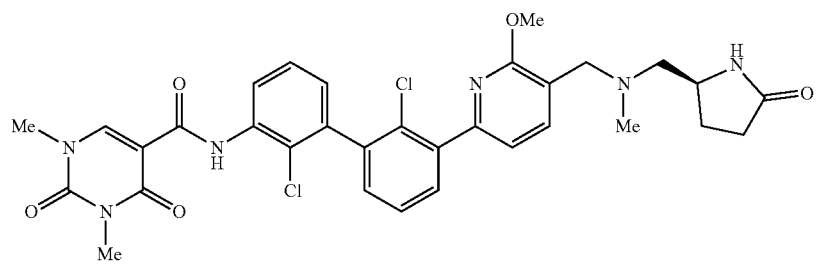 [SMILES: COc1nc(-c2cccc(-c3cccc(NC(=O)c4cn(C)c(=O)n(C)c4=O)c3Cl)c2Cl)ccc1CN(C)C[C@@H]1CCC(=O)N1]

The compound was prepared from N-(2,2'-dichloro-3'-(5-formyl-6-methoxypyridin-2-yl)-[1,1'-biphenyl]-3-yl)-1,3-dimethyl-2,4-dioxo-1,2,3,4-tetrahydropyrimidine-5-carboxamide and (S)-5-((methylamino)methyl)pyrrolidin-2-one using a procedure similar to step d in Example 1. The crude product was purified by preparative HPLC to give (S)—N-(2,2'-dichloro-3'-(6-methoxy-5-((methyl((5-oxopyrrolidin-2-yl)methyl)amino)methyl)pyridin-2-yl)-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.70 (s, 1H), 8.67 (s, 1H), 8.54 (d, J=8.2 Hz, 1H), 7.96 (d, J=7.6 Hz, 1H), 7.69-7.66 (m, 1H), 7.55-7.44 (m, 1H), 7.44-7.39 (m, 3H), 7.10 (d, J=7.5 Hz, 1H), 4.68 (s, 1H), 4.16 (s, 3H), 4.01-3.97 (m, 1H), 3.56 (s, 3H), 3.38 (s, 3H), 3.31 (s, 3H), 3.20-3.10 (m, 3H), 2.95-2.86 (m, 1H), 2.68-2.50 (m, 2H), 2.20-2.10 (m, 1H). MS: (ES) m/z calculated for C$_{32}$H$_{33}$Cl$_2$N$_6$O$_5$ [M+H]$^+$ 651.2. found 651.1.

amino)methyl)pyridin-2-yl)-[1,1'-biphenyl]-3-yl)-1-methyl-2-oxo-1,2-dihydropyridine-3-carboxamide. $^1$H NMR (400 MHz, CD$_3$OD) δ 12.66 (s, 1H), 8.62-8.61 (m, 2H), 8.03 (d, J=6.5 Hz, 1H), 7.91 (d, J=7.7 Hz, 1H), 7.68-7.66 (m, 1H), 7.53 (dd, J=7.7, 7.7 Hz, 1H), 7.42-7.38 (m, 3H), 7.12 (d, J=7.6 Hz, 1H), 6.63 (dd, J=7.0, 7.0 Hz, 1H), 4.35 (s, 2H), 4.07-4.02 (m, 4H), 3.71 (d, J=1.9 Hz, 3H), 3.29-3.25 (m, 2H), 2.48-2.35 (m, 3H), 1.98-1.89 (s, 1H). MS: (ES) m/z calculated for C$_{31}$H$_{29}$Cl$_2$N$_5$O$_4$ [M+H]$^+$ 606.2. found 606.2.

Example 65: 1-((6-(2,2'-dichloro-3'-(1,3-dimethyl-2,4-dioxo-1,2,3,4-tetrahydropyrimidine-5-carboxamido)-[1,1'-biphenyl]-3-yl)-2-methoxypyridin-3-yl) methyl)azetidine-3-carboxylic Acid

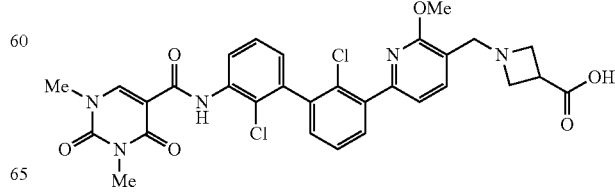

The compound was prepared from N-(2,2'-dichloro-3'-(5-formyl-6-methoxypyridin-2-yl)-[1,1'-biphenyl]-3-yl)-1,3-dimethyl-2,4-dioxo-1,2,3,4-tetrahydropyrimidine-5-carboxamide and azetidine-3-carboxylic acid using a procedure similar to step d in Example 1. The crude product was purified by preparative HPLC to give 1-((6-(2,2'-dichloro-3'-(1,3-dimethyl-2,4-dioxo-1,2,3,4-tetrahydropyrimidine-5-carboxamido)-[1,1'-biphenyl]-3-yl)-2-methoxypyridin-3-yl)methyl)azetidine-3-carboxylic acid. $^1$H NMR (400 MHz, CD$_3$OD) 11.69 (s, 1H), 8.66 (d, J=1.9 Hz, 1H), 8.57-8.49 (m, 1H), 7.89 (d, J=7.7 Hz, 1H), 7.66 (dd, J=7.8, 1.8 Hz, 1H), 7.53-7.50 (m, 1H), 7.45-7.34 (m, 3H), 7.10 (dd, J=7.6, 1.8 Hz, 1H), 4.51 (s, 2H), 4.42 (d, J=8.9 Hz, 4H), 4.09 (d, J=1.8 Hz, 3H), 3.79-3.65 (m, 1H), 3.56 (d, J=2.1 Hz, 3H), 3.39 (s, 3H). MS: (ES) m/z calculated for C$_{30}$H$_{28}$Cl$_2$N$_5$O$_6$ [M+H]$^+$ 624.1. found 624.1.

Example 66: 1-((6-(2,2'-dichloro-3'-(1,3-dimethyl-2,4-dioxo-1,2,3,4-tetrahydropyrimidine-5-carboxamido)-[1,1'-biphenyl]-3-yl)-2-methoxypyridin-3-yl)methyl)-3-methylazetidine-3-carboxylic Acid

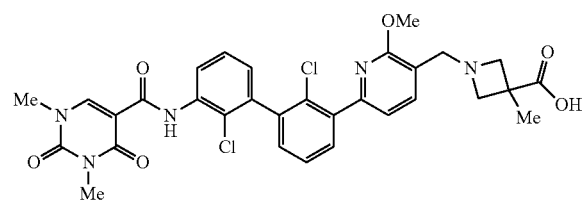 [SMILES: COc1nc(-c2cccc(-c3cccc(NC(=O)c4cn(C)c(=O)n(C)c4=O)c3Cl)c2Cl)ccc1CN1CC(C)(C(=O)O)C1]

The compound was prepared from N-(2,2'-dichloro-3'-(5-formyl-6-methoxypyridin-2-yl)-[1,1'-biphenyl]-3-yl)-1,3-dimethyl-2,4-dioxo-1,2,3,4-tetrahydropyrimidine-5-carboxamide and 3-methylazetidine-3-carboxylic acid using a procedure similar to step d in Example 1. The crude product was purified by preparative HPLC to give 1-((6-(2,2'-dichloro-3'-(1,3-dimethyl-2,4-dioxo-1,2,3,4-tetrahydropyrimidine-5-carboxamido)-[1,1'-biphenyl]-3-yl)-2-methoxypyridin-3-yl)methyl)-3-methylazetidine-3-carboxylic acid. $^1$H NMR (400 MHz, CD$_3$OD) δ 11.68 (s, 1H), 8.65 (d, J=1.7 Hz, 1H), 8.54 (dd, J=8.7, 1.8 Hz, 1H), 7.89 (d, J=7.6 Hz, 1H), 7.66 (dd, J=7.9, 1.9 Hz, 1H), 7.53-7.49 (m, 1H), 7.42-7.36 (m, 3H), 7.10 (dd, J=7.7, 1.8 Hz, 1H), 4.55-4.51 (m, 4H), 4.16-4.09 (m, 5H), 3.55 (s, 3H), 3.37 (s, 3H), 1.62 (s, 3H). MS. (ES) m/z calculated for C$_{31}$H$_{30}$Cl$_2$N$_5$O$_6$ [M+H]$^+$ 638.2. found 638.1.

Example 67: (S)-1-((5-(2,2'-dichloro-3'-(1,3-dimethyl-2,4-dioxo-1,2,3,4-tetrahydropyrimidine-5-carboxamido)-[1,1'-biphenyl]-3-yl)-3-methoxypyrazin-2-yl)methyl)piperidine-2-carboxylic Acid The compound was prepared from N-(2,2'-dichloro-3'-(5-formyl-6-methoxypyrazin-2-yl)-[1,1'-biphenyl]-3-yl)-1,3-dimethyl-2,4-dioxo-1,2,3,4-tetrahydropyrimidine-5-carboxamide and (S)-piperidine-2-carboxylic acid using a procedure similar to step d in Example 1. The crude product was purified by preparative HPLC to give (S)-1-((5-(2,2'-dichloro-3'-(1,3-dimethyl-2,4-dioxo-1,2,3,4-tetrahydropyrimidine-5-carboxamido)-[1,1'-biphenyl]-3-yl)-3-methoxypyrazin-2-yl)methyl)piperidine-2-carboxylic acid. $^1$H NMR (400 MHz, CD$_3$OD) δ 11.70 (s, 1H), 8.66 (s, 1H), 8.60-8.54 (m, 2H), 7.74 (dd, J=7.7, 1.8 Hz, 1H), 7.60-7.56 (m, 1H), 7.47-7.41 (m, 2H), 7.12 (dd, J=7.6, 1.8 Hz, 1H), 4.69 (s, 2H), 4.27-4.21 (m, 1H), 4.11 (s, 3H), 3.79 (d, J=12.6 Hz, 1H), 3.56 (s, 3H), 3.39 (s, 3H), 2.38-2.32 (m, 1H), 2.09-1.65 (m, 6H). MS: (ES) m/z calculated for C$_{31}$H$_{31}$Cl$_2$N$_6$O$_6$ [M+H]$^+$ 653.2. found 653.1.

Example 68: (R)-1-((5-(2,2'-dichloro-3'-(1,3-dimethyl-2,4-dioxo-1,2,3,4-tetrahydropyrimidine-5-carboxamido)-[1,1'-biphenyl]-3-yl)-3-methoxypyrazin-2-yl)methyl)piperidine-2-carboxylicacid

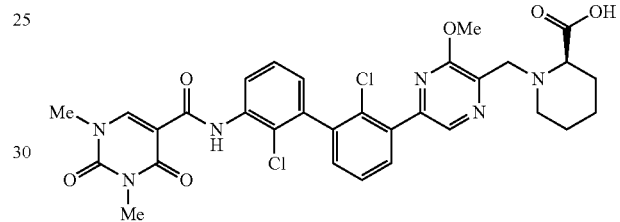

The compound was prepared from N-(2,2'-dichloro-3'-(5-formyl-6-methoxypyrazin-2-yl)-[1,1'-biphenyl]-3-yl)-1,3-dimethyl-2,4-dioxo-1,2,3,4-tetrahydropyrimidine-5-carboxamide and (R)-piperidine-2-carboxylic acid using a procedure similar to step d in Example 1. The crude product was purified by preparative HPLC to give the (R)-1-((5-(2,2'-dichloro-3'-(1,3-dimethyl-2,4-dioxo-1,2,3,4-tetrahydropyrimidine-5-carboxamido)-[1,1'-biphenyl]-3-yl)-3-methoxypyrazin-2-yl)methyl)piperidine-2-carboxylic acid. $^1$H NMR (400 MHz, CD$_3$OD) δ 11.70 (s, 1H), 8.67 (s, 1H), 8.59-8.54 (m, 2H), 7.74 (dd, J=7.7, 1.8 Hz, 1H), 7.59-7.56 (m, 1H), 7.46-7.40 (m, 2H), 7.12 (dd, J=7.6, 1.8 Hz, 1H), 4.69 (s, 2H), 4.27-4.20 (m, 1H), 4.11 (s, 3H), 3.79 (d, J=12.6 Hz, 1H), 3.56 (s, 3H), 3.39 (s, 3H), 2.38-2.33 (m, 1H), 2.09-1.65 (m, 6H). MS: (ES) m/z calculated for C$_{31}$H$_{31}$Cl$_2$N$_6$O$_6$ [M+H]$^+$ 653.2. found 653.2.

Example 69: N-(2'-chloro-3'-(5-(((3-hydroxyazetidin-1-yl)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide

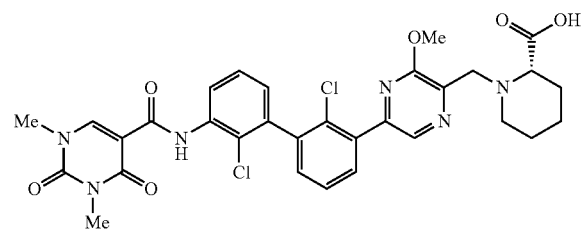 [SMILES: COc1nc(-c2cccc(-c3cccc(NC(=O)c4cn(C)c(=O)n(C)c4=O)c3Cl)c2Cl)cnc1CN1CCCC[C@H]1C(=O)O]

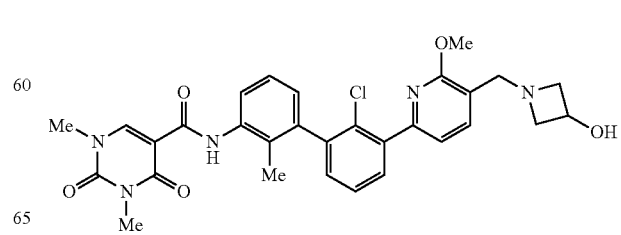

Step a: To a flask containing 2-methyl-3-(4,4,5,5-tetramethyl-1,3,2-dioxaborolan-2-yl)aniline (15 g, 65 mmol) and 1,3-dibromo-2-chlorobenzene (52.5 g, 194 mmol) in 375 mL of dioxane was added 2M $K_2CO_3$ (110 mL) and Pd(dppf)$Cl_2$ complex with DCM (5.25 g, 6.4 mmol). The mixture was degassed with $N_2$ for 10 min, then heated at 90° C. for 2 h. The reaction was quenched with sat. NaHCO$_3$ and the aqueous layer was extracted with EtOAc. The organic layers were combined, dried with sodium sulfate, filtered and concentrated. The resultant residue was purified by silica gel column chromatography to afford 3'-bromo-2'-chloro-2-methyl-[1,1'-biphenyl]-3-amine.

Step b: To a solution of 3'-bromo-2'-chloro-2-methyl-[1,1'-biphenyl]-3-amine (7 g, 23.7 mmol) in 40 mL of dioxane was added bispinacolato diboron (6.3 g, 24.9 mmol), followed by KOAc (5.8 g, 59.1 mmol) and Pd(dppf)$Cl_2$ complex with DCM (1.93 g, 2.4 mmol). The mixture was degassed with $N_2$ for 10 min, then heated at 90° C. overnight. The contents were filtered through Celite and washed with EtOAc. The filtrate was concentrated and the resultant residue was purified by silica gel column chromatography to yield 2'-chloro-2-methyl-3'-(4,4,5,5-tetramethyl-1,3,2-dioxaborolan-2-yl)-[1,1'-biphenyl]-3-amine. MS: (ES) m/z calculated for $C_{19}H_{24}BClNO_2$ [M+H]$^+$ 344.2. found 344.1.

Step c: To a solution of 2'-chloro-2-methyl-3'-(4,4,5,5-tetramethyl-1,3,2-dioxaborolan-2-yl)-[1,1'-biphenyl]-3-amine (6.4 g, 18.6 mmol) in 124 mL of DMF was added 1,3-dimethyl-2,4-dioxo-1,2,3,4-tetrahydropyrimidine-5-carboxylic acid (3.4 g, 18.6 mmol), DIPEA (4.9 mL, 27.9 mmol) and HATU (8.5 g, 22.3 mmol). The mixture was stirred at room temperature for 2 h and an additional amount of 1,3-dimethyl-2,4-dioxo-1,2,3,4-tetrahydropyrimidine-5-carboxylic acid (0.34 g, 0.99 mmol), DIPEA (0.49 mL, 2.8 mmol) and HATU (0.85 g, 2.23 mmol) was added. After stirring overnight the reaction was quenched with $H_2O$. The aqueous layer was extracted with EtOAc and the organic layers were combined, dried with sodium sulfate, filtered and concentrated. The resultant residue was purified by silica gel column chromatography to provide N-(2'-chloro-2-methyl-3'-(4,4,5,5-tetramethyl-1,3,2-dioxaborolan-2-yl)-[1,1'-biphenyl]-3-yl)-1,3-dimethyl-2,4-dioxo-1,2,3,4-tetrahydropyrimidine-5-carboxamide. MS: (ES) m/z calculated for $C_{26}H_{29}BClN_3O_5$ [M+H]$^+$ 510.2. found 510.1.

Step d: To a solution of N-(2'-chloro-2-methyl-3'-(4,4,5,5-tetramethyl-1,3,2-dioxaborolan-2-yl)-[1,1'-biphenyl]-3-yl)-1,3-dimethyl-2,4-dioxo-1,2,3,4-tetrahydropyrimidine-5-carboxamide (4.2 g, 8.3 mmol) in 82.5 mL of dioxane was added 6-chloro-2-methoxynicotinaldehyde (1.4 g, 8.3 mmol), 2 M $K_2CO_3$ (14 mL), and Pd(PPh$_3$)$_4$ (0.95 g, 0.82 mmol). The mixture was degassed with $N_2$ for 10 min, then heated at 100° C. for 2 h. The contents were filtered through Celite and the organic and aqueous layers were separated. The aqueous layer was washed with EtOAc and the combined organic layers were dried with sodium sulfate, filtered and concentrated. The resultant residue was purified by silica gel column chromatography to provide N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide. MS: (ES) m/z calculated for $C_{27}H_{24}ClN_4O_5$ [M+H]$^+$ 519.1. found 519.0.

Step e: To a solution of N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide (100 mg, 0.19 mmol) in 3.2 mL of DCM and 1.5 mL of EtOH was added azetidin-3-ol (17 mg, 0.23 mmol), Et$_3$N (0.07 mL, 0.5 mmol), and AcOH (0.04 mL, 0.70 mmol). The reaction mixture was heated at 70° C. for 1 h, then cooled to 0° C. and NaBH$_3$CN (18 mg, 0.29 mmol) was added. The reaction mixture was stirred at room temperature for 1 h, then quenched with $H_2O$. The aqueous layer was extracted with EtOAc and the organic layers were combined, dried with sodium sulfate, filtered and concentrated. The resultant residue was purified by silica gel column chromatography followed by preparative HPLC to yield N-(2'-chloro-3'-(5-((3-hydroxyazetidin-1-yl)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide. $^1$H NMR (400 MHz, DMSO-d$_6$) δ 11.05 (s, 1H), 8.74 (s, 1H), 8.24 (d, J=9.5 Hz, 1H), 7.71 (d, J=7.5 Hz, 1H), 7.61 (dd, J=7.9, 1.7 Hz, 1H), 7.50 (dd, J=7.6, 7.6 Hz, 1H), 7.40-7.16 (m, 3H), 6.96 (dd, J=7.5, 1.6 Hz, 1H), 4.45-4.13 (m, 1H), 3.90 (s, 3H), 3.70 (bs, 4H), 3.49 (s, 3H), 3.32 (s, 1H), 3.27 (s, 3H), 3.01 (bs, 2H), 2.07 (s, 3H). MS: (ES) m/z calculated for $C_{30}H_{31}ClN_5O_5$ [M+H]$^+$ 576.2. found 576.0.

Example 70: N-(2'-chloro-3'-(6-methoxy-5-((5-oxo-2,6-diazaspiro[3.4]octan-2-yl)methyl)pyridin-2-yl)-2-methyl-[1,1'-biphenyl]-3-yl)-1,3-dimethyl-2,4-dioxo-1,2,3,4-tetrahydropyrimidine-5-carboxamide

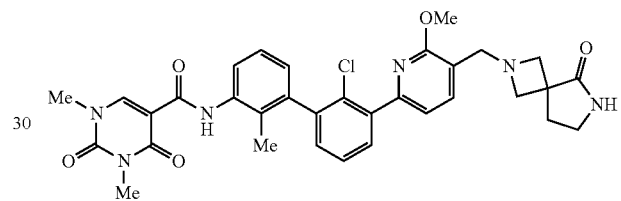

The compound was prepared from N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide and 2,6-diazaspiro[3.4]octan-5-one using a procedure similar to step d in Example 1. The crude product was purified by preparative HPLC to give N-(2'-chloro-3'-(6-methoxy-5-((5-oxo-2,6-diazaspiro[3.4]octan-2-yl)methyl)pyridin-2-yl)-2-methyl-[1,1'-biphenyl]-3-yl)-1,3-dimethyl-2,4-dioxo-1,2,3,4-tetrahydropyrimidine-5-carboxamide. $^1$H NMR (400 MHz, DMSO-d$_6$) δ 11.05 (s, 1H), 8.75 (s, 1H), 8.24 (d, J=9.7 Hz, 1H), 7.79-7.56 (m, 3H), 7.50 (dd, J=7.6, 7.6 Hz, 1H), 7.42-7.13 (m, 3H), 6.97 (d, J=7.6 Hz, 1H), 3.89 (s, 3H), 3.55 (s, 2H), 3.49 (s, 3H), 3.34-3.29 (m, 3H), 3.28-3.17 (m, 3H), 3.25 (s, 3H), 3.12 (s, 1H), 2.32 (s, 1H), 2.07 (s, 3H). MS: (ES) m/z calculated for $C_{33}H_{34}ClN_6O_5$ [M+H]$^+$ 629.2. found 629.0.

Example 71: 1-((6-(2-chloro-3'-(1,3-dimethyl-2,4-dioxo-1,2,3,4-tetrahydropyrimidine-5-carboxamido)-2'-methyl-[1,1'-biphenyl]-3-yl)-2-methoxypyridin-3-yl)methyl)azetidine-3-carboxylic Acid

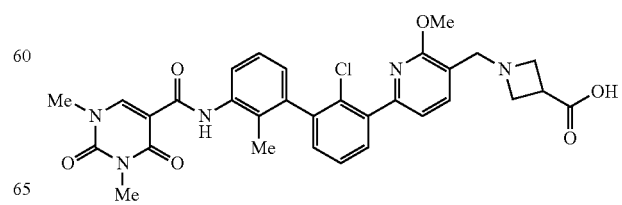

The compound was prepared from N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide and azetidine-3-carboxylic acid using a procedure similar to step d in Example 1. The crude product was purified by preparative HPLC to give 1-((6-(2-chloro-3'-(1,3-dimethyl-2,4-dioxo-1,2,3,4-tetrahydropyrimidine-5-carboxamido)-2'-methyl-[1,1'-biphenyl]-3-yl)-2-methoxypyridin-3-yl)methyl)azetidine-3-carboxylic acid. $^1$H NMR (400 MHz, CD$_3$OD) δ 8.63 (s, 1H), 8.11 (d, J=8.1 Hz, 1H), 7.86 (d, J=7.7 Hz, 1H), 7.61 (d, J=7.6 Hz, 1H), 7.49 (dd, J=7.6, 7.6 Hz, 1H), 7.35-7.23 (m, 3H), 7.01 (d, J=7.7 Hz, 1H), 4.37 (bs, 2H), 4.19 (dd, J=9.2, 2.3 Hz, 4H), 4.07 (s, 3H), 3.55 (s, 3H), 3.48-3.42 (m, 1H), 3.39 (s, 3H), 2.13 (s, 3H). MS: (ES) m/z calculated for C$_{31}$H$_{31}$ClN$_6$O$_6$ [M+H]$^+$ 604.2. found 603.9.

Example 72: (S)—N-(2'-chloro-3'-(6-methoxy-5-((((5-oxopyrrolidin-2-yl)methyl)amino)methyl)pyrazin-2-yl)-2-methyl-[1,1'-biphenyl]-3-yl)-1,3-dimethyl-2,4-dioxo-1,2,3,4-tetrahydropyrimidine-5-carboxamide Step a: To a solution of N-(2'-chloro-2-methyl-3'-(4,4,5,5-tetramethyl-1,3,2-dioxaborolan-2-yl)-[1,1'-biphenyl]-3-yl)-1,3-dimethyl-2,4-dioxo-1,2,3,4-tetrahydropyrimidine-5-carboxamide (1.0 g, 2.0 mmol) in 20 mL of dioxane was added 5-chloro-3-methoxypyrazine-2-carbaldehyde (0.42 g, 2.0 mmol), 2 M K$_2$CO$_3$ (6.7 mL), and Pd(PPh$_3$)$_4$ (0.23 g, 0.20 mmol). The mixture was degassed with N$_2$ for 10 min, then heated at 100° C. for 1 h. The reaction was quenched with H$_2$O and the aqueous layer was washed with EtOAc. The combined organic layers were dried with sodium sulfate, filtered and concentrated. The resultant residue was purified by silica gel column chromatography to provide N-(2'-chloro-3'-(5-formyl-6-methoxypyrazin-2-yl)-2-methyl-[1,1'-biphenyl]-3-yl)-1,3-dimethyl-2,4-dioxo-1,2,3,4-tetrahydropyrimidine-5-carboxamide. MS: (ES) m/z calculated for C$_{26}$H$_{23}$ClN$_5$O$_5$ [M+H]$^+$ 520.1, 519.9.

Step b: To a solution of N-(2'-chloro-3'-(5-formyl-6-methoxypyrazin-2-yl)-2-methyl-[1,1'-biphenyl]-3-yl)-1,3-dimethyl-2,4-dioxo-1,2,3,4-tetrahydropyrimidine-5-carboxamide (100 mg, 0.19 mmol) in 3.2 mL of DCM and 1.5 mL of EtOH was added (S)-5-(aminomethyl)pyrrolidin-2-one (35 mg, 0.23 mmol), Et$_3$N (0.07 mL, 0.5 mmol) and AcOH (0.04 mL, 0.70 mmol). The contents were heated at 70° C. for 1 h, then cooled to 0° C. and NaBH$_3$CN (18 mg, 0.29 mmol) was added. After stirring at room temperature for 1 h, the reaction was quenched with H$_2$O. The aqueous layer was extracted with EtOAc and the organic layers were combined, dried with sodium sulfate, filtered and concentrated. The resultant residue was purified by silica gel column chromatography followed by preparative HPLC to yield (S)—N-(2'-chloro-3'-(6-methoxy-5-((((5-oxopyrrolidin-2-yl)methyl)amino)methyl)pyrazin-2-yl)-2-methyl-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ: 8.63 (s, 1H), 8.42 (s, 1H), 8.12 (d, J=8.2 Hz, 1H), 7.65 (d, J=7.2 Hz, 1H), 7.52 (dd, J=7.6, 7.6 Hz, 1H), 7.38 (d, J=7.6 Hz, 1H), 7.30 (dd, J=8.1, 8.1 Hz, 1H), 7.01 (d, J=7.6 Hz, 1H), 4.06 (s, 3H), 4.04 (s, 2H), 3.90-3.84 (m, 1H), 3.55 (s, 3H), 3.39 (s, 3H), 2.91-2.72 (m, 2H), 2.38-2.23 (m, 3H), 2.14 (s, 3H), 1.90-1.76 (m, 1H). MS: (ES) m/z calculated for C$_{31}$H$_{33}$ClN$_7$O$_5$ [M+H]$^+$ 618.2. found 618.2.

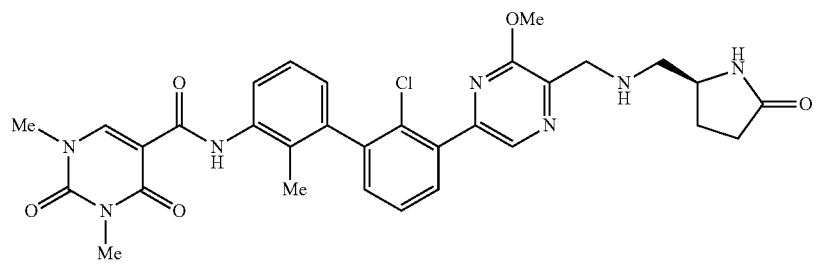

Example 73: N-(2'-chloro-3'-(5-((((3R,4R)-3-hydroxytetrahydro-2H-pyran-4-yl)amino)methyl)-6-methoxypyrazin-2-yl)-2-methyl-[1,1'-biphenyl]-3-yl)-1,3-dimethyl-2,4-dioxo-1,2,3,4-tetrahydropyrimidine-5-carboxamide

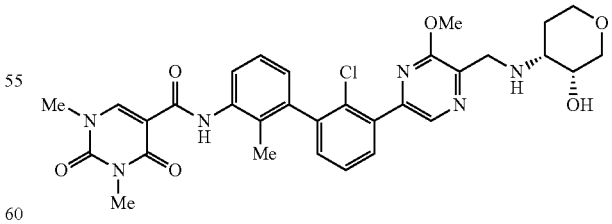

The compound was prepared from N-(2'-chloro-3'-(5-formyl-6-methoxypyrazin-2-yl)-2-methyl-[1,1'-biphenyl]-3-yl)-1,3-dimethyl-2,4-dioxo-1,2,3,4-tetrahydropyrimidine-5-carboxamide and (3R,4R)-4-aminotetrahydro-2H-pyran-3-ol using a procedure similar to step d in Example 1. The crude product was purified by preparative HPLC to give N-(2'-chloro-3'-(5-((((3R,4R)-3-hydroxytetrahydro-2H-pyran-4-yl)amino)methyl)-6-methoxypyrazin-2-yl)-2-methyl-[1,1'-biphenyl]-3-yl)-1,3-dimethyl-2,4-dioxo-1,2,3,4-tetrahydropyrimidine-5-carboxamide. $^1$H NMR (400 MHz, DMSO-$d_6$) δ 11.06 (s, 1H), 8.75 (s, 1H), 8.44 (s, 1H), 8.25 (d, J=8.2 Hz, 1H), 7.68 (d, J=7.6 Hz, 1H), 7.56 (dd, J=7.7, 7.7 Hz, 1H), 7.41 (d, J=7.5 Hz, 1H), 7.30 (dd, J=7.9, 7.9 Hz, 1H), 6.98 (d, J=7.6 Hz, 1H), 4.76 (s, 1H), 4.06-3.93 (m, 1H), 3.87 (d, J=15.6 Hz, 1H), 3.96 (s, 3H), 3.76-3.69 (m, 1H), 3.68-3.60 (m, 2H), 3.49 (s, 3H), 3.38-3.28 (m, 3H), 3.26 (s, 3H), 2.85-2.79 (m, 1H), 2.08 (s, 3H), 1.75-1.62 (m, 1H), 1.58-1.50 (m, 1H). MS: (ES) m/z calculated for $C_{31}H_{34}ClN_6O_6$ [M+H]$^+$ 621.2. found 621.2.

Example 74: (S)—N-(2'-chloro-3'-(6-methoxy-5-((((5-oxopyrrolidin-2-yl)methyl)amino)methyl)pyridin-2-yl)-[1,1'-biphenyl]-3-yl)-1,3-dimethyl-2,4-dioxo-1,2,3,4-tetrahydropyrimidine-5-carboxamide

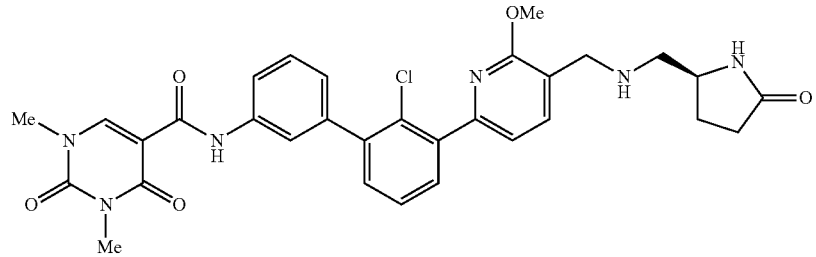 [SMILES: COc1nc(-c2cccc(-c3cccc(NC(=O)c4cn(C)c(=O)n(C)c4=O)c3)c2Cl)ccc1CNC[C@@H]1CCC(=O)N1]

Step a: To a solution of 1,3-dimethyl-2,4-dioxo-1,2,3,4-tetrahydropyrimidine-5-carboxylic acid (3.0 g, 16.3 mmol) in 110 mL of DMF was added 3-(4,4,5,5-tetramethyl-1,3,2-dioxaborolan-2-yl)aniline (3.59 g, 16.3 mmol), DIPEA (4.33 mL, 24.8 mmol) and HATU (7.53 g, 19.8 mmol). The mixture was stirred at room temperature for 2 h, then quenched with H$_2$O. The solid was filtered, washed with H$_2$O and then heptane to yield 1,3-dimethyl-2,4-dioxo-N-(3-(4,4,5,5-tetramethyl-1,3,2-dioxaborolan-2-yl)phenyl)-1,2,3,4-tetrahydropyrimidine-5-carboxamide. MS: (ES) m/z calculated for $C_{19}H_{25}BN_3O_5$ [M+H]$^+$ 386.2. found 386.4.

Step b: To a solution of 1,3-dimethyl-2,4-dioxo-N-(3-(4,4,5,5-tetramethyl-1,3,2-dioxaborolan-2-yl)phenyl)-1,2,3,4-tetrahydropyrimidine-5-carboxamide (100 mg, 0.26 mmol) in 2 mL of THF and 2 mL of H$_2$O was added 6-(3-bromo-2-chlorophenyl)-2-methoxynicotinaldehyde (85 mg, 0.26 mmol), K$_3$PO$_4$ (137 mg, 0.65 mmol), and XPhosPdG2 (20 mg, 0.03 mmol). The mixture was degassed with N$_2$ for 10 min and stirred at room temperature overnight. The solid contents were filtered and washed with EtOAc to yield N-(2'-chloro-3'-(5-formyl-6-methoxypyridin-2-yl)-[1,1'-biphenyl]-3-yl)-1,3-dimethyl-2,4-dioxo-1,2,3,4-tetrahydropyrimidine-5-carboxamide. MS: (ES) m/z calculated for $C_{26}H_{22}ClN_4O_5$ [M+H]$^+$ 505.1. found 505.4.

Step c: To a solution N-(2'-chloro-3'-(5-formyl-6-methoxypyridin-2-yl)-[1,1'-biphenyl]-3-yl)-1,3-dimethyl-2,4-dioxo-1,2,3,4-tetrahydropyrimidine-5-carboxamide (72 mg, 0.14 mmol) in 3.2 mL of DCM and 1 mL of EtOH was added (S)-5-(aminomethyl)pyrrolidin-2-one (25 mg, 0.17 mmol), Et$_3$N (0.06 mL, 0.43 mmol), and AcOH (0.04 mL, 0.70 mmol). The contents were heated at 70° C. for 1 h, then cooled to room temperature and Na(OAc)$_3$BH (90 mg, 0.42 mmol) was added. After stirring at room temperature for 20 min, the reaction was quenched with H$_2$O. The aqueous layer was extracted with EtOAc and the organic layers were combined, dried with sodium sulfate, filtered and concentrated. The resultant residue was purified by silica gel column chromatography followed by preparative HPLC to yield (S)—N-(2'-chloro-3'-(6-methoxy-5-((((5-oxopyrrolidin-2-yl)methyl)amino)methyl)pyridin-2-yl)-[1,1'-biphenyl]-3-yl)-1,3-dimethyl-2,4-dioxo-1,2,3,4-tetrahydropyrimidine-5-carboxamide. $^1$H NMR (400 MHz, DMSO-$d_6$) δ 11.12 (s, 1H), 8.69 (s, 1H), 7.82-7.78 (m, 2H), 7.74-7.60 (m, 2H), 7.60-7.52 (m, 1H), 7.52-7.39 (m, 3H), 7.23 (d, J=7.4 Hz, 1H), 7.20-7.12 (m, 1H), 3.89 (s, 3H), 3.71-3.67 (bs, 2H), 3.66-3.58 (m, 1H), 3.47 (s, 3H), 3.30-3.28 (m, 1H), 3.26 (s, 3H), 2.53 (d, J=6.1 Hz, 2H), 2.22-1.97 (m, 3H), 1.81-1.58 (m, 1H). MS: (ES) m/z calculated for $C_{31}H_{32}ClN_6O_5$ [M+H]$^+$ 603.2, found 603.5.

Example 75: (S)—N-(2'-chloro-2-fluoro-3'-(6-methoxy-5-((((5-oxopyrrolidin-2-yl)methyl)amino)methyl)pyridin-2-yl)-[1,1'-biphenyl]-3-yl)-1,3-dimethyl-2,4-dioxo-1,2,3,4-tetrahydropyrimidine-5-carboxamide

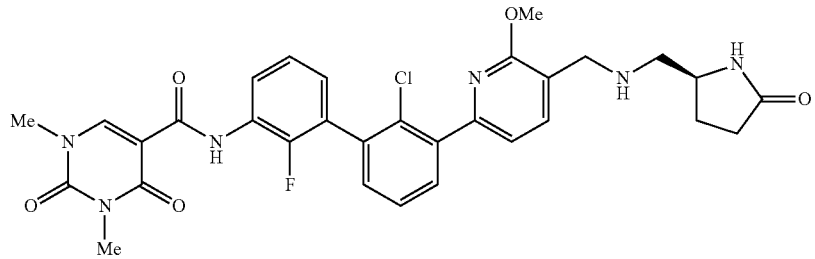 [SMILES: COc1nc(-c2cccc(-c3cccc(NC(=O)c4cn(C)c(=O)n(C)c4=O)c3F)c2Cl)ccc1CNC[C@@H]1CCC(=O)N1]

Step a: To a solution of 1,3-dimethyl-2,4-dioxo-1,2,3,4-tetrahydropyrimidine-5-carboxylic acid (1.62 g, 8.8 mmol) in 59 mL of DMF was added 3-(4,4,5,5-tetramethyl-1,3,2-dioxaborolan-2-yl)aniline (2.09 g, 8.8 mmol), DIPEA (2.3 mL, 13.2 mmol) and HATU (8.04 g, 21.2 mmol). The mixture was stirred at room temperature for 2 h, then quenched with H$_2$O. The solid was filtered, washed with H$_2$O and then heptane to yield N-(2-fluoro-3-(4,4,5,5-tetramethyl-1,3,2-dioxaborolan-2-yl)phenyl)-1,3-dimethyl-2,4-dioxo-1,2,3,4-tetrahydropyrimidine-5-carboxamide. MS: (ES) m/z calculated for C$_{19}$H$_{24}$BFN$_3$O$_5$ [M+H]$^+$ 404.2. found 404.4.

Step b: To a solution of N-(2-fluoro-3-(4,4,5,5-tetramethyl-1,3,2-dioxaborolan-2-yl)phenyl)-1,3-dimethyl-2,4-dioxo-1,2,3,4-tetrahydropyrimidine-5-carboxamide (100 mg, 0.26 mmol) in 1 mL of THF and 1 mL of H$_2$O was added 6-(3-bromo-2-chlorophenyl)-2-methoxynicotinaldehyde (81 mg, 0.25 mmol), K$_3$PO$_4$ (132 mg, 0.62 mmol), and XPhos-PdG2 (20 mg, 0.03 mmol). The mixture was degassed with N$_2$ for 10 min and stirred at room temperature for 5 h. The solid contents were filtered and washed with EtOAc to yield N-(2'-chloro-2-fluoro-3'-(5-formyl-6-methoxypyridin-2-yl)-[1,1'-biphenyl]-3-yl)-1,3-dimethyl-2,4-dioxo-1,2,3,4-tetrahydropyrimidine-5-carboxamide. MS: (ES) m/z calculated for C$_{26}$H$_{21}$ClFN$_4$O$_5$ [M+H]$^+$ 523.1. found 523.3.

Step c: To a solution N-(2'-chloro-2-fluoro-3'-(5-formyl-6-methoxypyridin-2-yl)-[1,1'-biphenyl]-3-yl)-1,3-dimethyl-2,4-dioxo-1,2,3,4-tetrahydropyrimidine-5-carboxamide (83 mg, 0.16 mmol) in 1 mL of DCM and 1 mL of EtOH was added (S)-5-(aminomethyl)pyrrolidin-2-one (28 mg, 0.19 mmol), Et$_3$N (0.07 mL, 0.5 mmol), and AcOH (0.04 mL, 0.70 mmol). The contents were heated at 70° C. for 1 h, then cooled to room temperature and Na(OAc)$_3$BH (100 mg, 0.47 mmol) was added. After stirring at at room temperature for 1 h, the reaction was quenched with H$_2$O. The aqueous layer was extracted with EtOAc and the organic layers were combined, dried with sodium sulfate, filtered and concentrated. The resultant residue was purified by silica gel column chromatography followed by preparative HPLC to yield (S)—N-(2'-chloro-2-fluoro-3'-(6-methoxy-5-((((5-oxopyrrolidin-2-yl)methyl)amino)methyl)pyridin-2-yl)-[1,1'-biphenyl]-3-yl)-1,3-dimethyl-2,4-dioxo-1,2,3,4-tetrahydropyrimidine-5-carboxamide. $^1$H NMR (400 MHz, DMSO-d$_6$) δ 11.46 (s, 1H), 8.76 (s, 1H), 8.47 (dd, J=7.8, 7.8 Hz, 1H), 7.81 (d, J=7.5 Hz, 1H), 7.69 (s, 1H), 7.64 (d, J=7.6 Hz, 1H), 7.53 (dd, J=7.3, 7.3 Hz, 1H), 7.46 (d, J=7.5 Hz, 1H), 7.30 (dd, J=8.0, 8.0 Hz, 1H), 7.25 (d, J=7.2 Hz, 1H), 7.12 (dd, J=7.2, 7.2 Hz, 1H), 3.89 (s, 3H), 3.69 (bs, 2H), 3.66-3.57 (m, 1H), 3.48 (s, 3H), 3.30-3.28 (m, 1H), 3.15 (s, 3H), 2.53 (d, J=6.0 Hz, 2H), 2.18-2.00 (m, 3H), 1.71-1.62 (m, 1H). MS: (ES) m/z calculated for C$_{31}$H$_{31}$ClFN$_6$O$_5$ [M+H]$^+$ 621.2. found 621.5.

Example 76: (S)—N-(2'-chloro-2-methyl-3'-(5-((((5-oxopyrrolidin-2-yl)methyl)amino)methyl)-6-(trifluoromethyl)pyridin-2-yl)-[1,1'-biphenyl]-3-yl)-1,3-dimethyl-2,4-dioxo-1,2,3,4-tetrahydropyrimidine-5-carboxamide

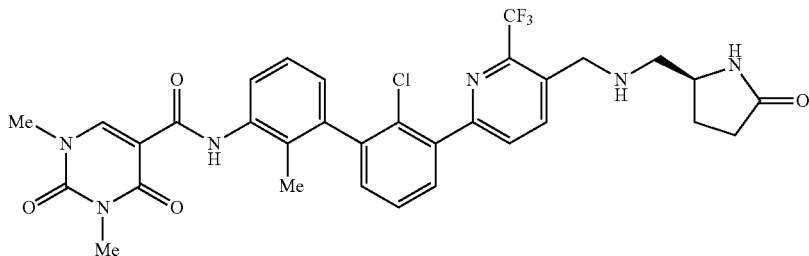 [SMILES: Cc1c(NC(=O)c2cn(C)c(=O)n(C)c2=O)cccc1-c1cccc(-c2ccc(CNC[C@@H]3CCC(=O)N3)c(C(F)(F)F)n2)c1Cl]

Step a: To a solution of (3-bromo-2-chlorophenyl)boronic acid (860 mg, 3.6 mmol) and 6-chloro-2-(trifluoromethyl)nicotinaldehyde (650 mg, 3.1 mmol) in 25.5 mL of dioxane was added 2 M K$_2$CO$_3$ (4.7 mL, 10.9 mmol), and Pd(PPh$_3$)$_4$ (420 mg, 0.36 mmol). The mixture was degassed with N$_2$ for 10 min and stirred at 100° C. for 2 h. The reaction was quenched with H$_2$O and the aqueous layer was extracted with EtOAc. The combined organic layers were combined, dried with sodium sulfate, filtered and concentrated. The resultant residue was purified by silica gel column chromatography to yield 6-(3-bromo-2-chlorophenyl)-2-(trifluoromethyl)nicotinaldehyde. MS: (ES) m/z calculated for C$_{13}$H$_7$BrClF$_3$NO [M+H]$^+$ 363.9, found 364.2.

Step b: To a solution of 1,3-dimethyl-N-(2-methyl-3-(4,4,5,5-tetramethyl-1,3,2-dioxaborolan-2-yl)phenyl)-2,4-dioxo-1,2,3,4-tetrahydropyrimidine-5-carboxamide (270 mg g, 0.68 mmol) in 10 mL of dioxane was added 6-(3-bromo-2-chlorophenyl)-2-(trifluoromethyl)nicotinaldehyde (250 mg, 0.69 mmol), 2 M K$_2$CO$_3$ (1.2 mL, 2.4 mmol), and Pd(dppf)Cl$_2$ complex with DCM (170 mg, 0.21 mmol). The mixture was degassed with N$_2$ for 10 min, then heated at 100° C. for 1 h. The contents were filtered through Celite and the filtrate was concentrated and purified by silica gel column chromatography to provide N-(2'-chloro-3'-(5-formyl-6-(trifluoromethyl)pyridin-2-yl)-2-methyl-[1,1'-biphenyl]-3-yl)-1,3-dimethyl-2,4-dioxo-1,2,3,4-tetrahydropyrimidine-5-carboxamide. MS: (ES) m/z calculated for C$_{27}$H$_{21}$ClF$_3$N$_4$O$_4$ [M+H]$^+$ 557.1. found 557.4.

Step c: To a solution N-(2'-chloro-3'-(5-formyl-6-(trifluoromethyl)pyridin-2-yl)-2-methyl-[1,1'-biphenyl]-3-yl)-1,3-dimethyl-2,4-dioxo-1,2,3,4-tetrahydropyrimidine-5-carboxamide (100 mg, 0.18 mmol) in 1 mL of DCM and 1 mL of EtOH was added (S)-5-(aminomethyl)pyrrolidin-2-one (40 mg, 0.27 mmol), Et$_3$N (0.09 mL, 0.65 mmol), and AcOH (0.06 mL, 1.0 mmol). The contents were heated at 70° C. for 1 h, then cooled to room temperature and Na(OAc)$_3$BH (114 mg, 0.54 mmol) was added. The reaction mixture was stirred at room temperature for 1 h and an additional amount of Na(OAc)₃BH (114 mg, 0.54 mmol) was added. After stirring at room temperature overnight, the contents were concentrated and the resultant residue was purified by silica gel column chromatography to yield (S)—N-(2'-chloro-2-methyl-3'-(5-((((5-oxopyrrolidin-2-yl)methyl)amino)methyl)-6-(trifluoromethyl)pyridin-2-yl)-[1,1'-biphenyl]-3-yl)-1,3-dimethyl-2,4-dioxo-1,2,3,4-tetrahydropyrimidine-5-carboxamide. ¹H NMR (400 MHz, CD₃OD) δ 8.62 (s, 1H), 8.29 (d, J=8.2 Hz, 1H), 8.12 (dd, J=8.4, 1.6 Hz, 1H), 7.93 (d, J=8.2 Hz, 1H), 7.60 (dd, J=7.7, 1.8 Hz, 1H), 7.52 (dd, J=7.6, 7.6 Hz, 1H), 7.38 (dd, J=7.5, 1.8 Hz, 1H), 7.29 (dd, J=7.9, 7.9 Hz, 1H), 7.02 (dd, J=7.4, 1.2 Hz, 1H), 4.06 (bs, 2H), 3.84 (dddd, J=6.5, 6.5, 6.5, 6.5 Hz, 1H), 3.55 (s, 3H), 3.39 (s, 3H), 2.76 (dd, J=12.0, 4.8 Hz, 1H), 2.69 (dd, J=12.0, 7.2 Hz, 1H), 2.42-2.19 (m, 3H), 2.15 (s, 3H), 1.97-1.75 (m, 1H). MS: (ES) m/z calculated for $C_{32}H_{31}CF_3N_6O_4$ [M+H]⁺ 655.2. found 655.2.

Example 77: N-(2'-chloro-3'-(5-((((1R,2S)-2-hydroxycyclopentyl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide

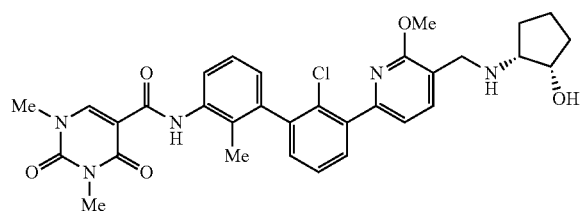 [SMILES: COc1nc(-c2cccc(-c3cccc(NC(=O)c4cn(C)c(=O)n(C)c4=O)c3C)c2Cl)ccc1CN[C@@H]1CCC[C@@H]1O]

Step a: To a stirred solution of N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide (52 mg, 0.1 mmol) and (1S,2R)-2-aminocyclopentan-1-ol hydrochloride (28 mg, 0.2 mmol) in dichloroethane (2 mL) and EtOH (1 mL) was added Et₃N (2 drops) and AcOH (2 drops). The contents were stirred at 70° C. for 1 h, then cooled to 0° C. and NaBH₃CN (13 mg, 0.2 mmol) was added slowly. After stirring at 0° C. for 10 min, the crude mixture was filtered and then purified by preparative HPLC to give N-(2'-chloro-3'-(5-((((1R,2S)-2-hydroxycyclopentyl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide. ¹H NMR (400 MHz, CDCl₃) δ 10.89 (s, 1H), 8.52 (s, 1H), 8.25-8.18 (m, 1H), 7.66-7.55 (m, 2H), 7.40 (dd, J=7.6, 7.6 Hz, 1H), 7.35-7.22 (m, 3H), 7.03 (dd, J=7.5, 1.2 Hz, 1H), 4.08 (t, J=4.8 Hz, 1H), 4.03 (s, 3H), 3.87-3.73 (m, 2H), 3.57 (s, 3H), 3.44 (s, 3H), 3.00 (m, 1H), 2.19 (s, 3H), 1.90-1.70 (m, 4H), 1.60-1.40 (m, 2H). MS: (ES) m/z calculated for $C_{32}H_{35}ClN_5O_5$ [M+H]⁺ 604.2. found 604.5.

Example 78: N-(2'-chloro-3'-(5-((((3R,4S)-3-hydroxytetrahydro-2H-pyran-4-yl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide

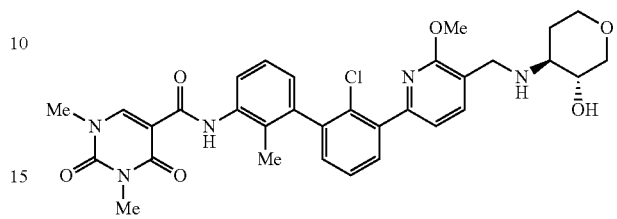

The compound was prepared from N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide and (3R,4S)-4-aminotetrahydro-2H-pyran-3-ol hydrochloride using a procedure similar to step d in Example 1. The crude product was purified by preparative HPLC to give N-(2'-chloro-3'-(5-((((3R,4S)-3-hydroxytetrahydro-2H-pyran-4-yl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide. ¹H NMR (400 MHz, CDCl₃) δ 10.89 (s, 1H), 8.53 (s, 1H), 8.22 (d, J=8.2 Hz, 1H), 7.67-7.59 (m, 2H), 7.40 (dd, J=7.6, 7.6 Hz, 1H), 7.35-7.23 (m, 3H), 7.06-6.99 (m, 1H), 4.10-3.95 (m, 2H), 4.03 (s, 3H), 3.77 (d, J=13.8 Hz, 1H), 3.58 (s, 3H), 3.53-3.35 (m, 2H), 3.44 (s, 3H), 3.22-3.12 (m, 1H), 2.63-2.55 (m, 1H), 2.19 (s, 3H), 2.09-2.01 (m, 1H), 1.90-1.70 (bs, 1H), 1.54-1.43 (m, 1H). MS: (ES) m/z calculated for $C_{32}H_{35}ClN_5O_6$ [M+H]⁺ 620.2. found 620.2.

Example 79: N-(2'-cyano-3'-(5-((((3R,4R)-3-hydroxytetrahydro-2H-pyran-4-yl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide

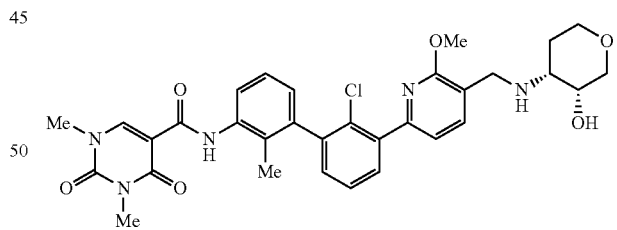

The compound was prepared from N-(2'-cyano-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide and (3R,4R)-4-aminotetrahydro-2H-pyran-3-ol hydrochloride using a procedure similar to step d in Example 1. The crude product was purified by preparative HPLC to give N-(2'-cyano-3'-(5-((((3R,4R)-3-hydroxytetrahydro-2H-pyran-4-yl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide. ¹H NMR (400 MHz, CDCl₃) δ 10.93 (s, 1H), 8.53 (s, 1H), 8.30 (d, J=7.9 Hz, 1H), 7.80 (dd, J=7.8, 1.1 Hz, 1H), 7.73-7.63 (m, 2H), 7.42-7.30 (m, 3H), 7.10 (d, J=7.8 Hz, 1H), 4.10 (s, 3H), 4.04

(dd, J=11.6, 4.1 Hz, 1H), 3.97-3.76 (m, 4H), 3.58 (s, 3H), 3.50-3.35 (m, 2H), 3.44 (s, 3H), 2.81 (dt, J=11.1, 4.1 Hz, 1H), 2.25 (s, 3H), 1.89-1.76 (m, 1H), 1.65-1.50 (m, 1H). MS: (ES) m/z calculated for $C_{33}H_{35}N_6O_6$ [M+H]$^+$ 611.3, found 611.2.

Example 80: N-(2'-chloro-3'-(5-((3-(2-hydroxypropan-2-yl)azetidin-1-yl)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide

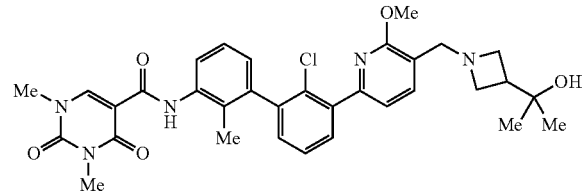 [SMILES: COc1nc(-c2cccc(-c3cccc(NC(=O)c4cn(C)c(=O)n(C)c4=O)c3C)c2Cl)ccc1CN1CC(C(C)(C)O)C1]

The compound was prepared from N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide and 2-(azetidin-3-yl)propan-2-ol hydrochloride using a procedure similar to step d in Example 1. The crude product was purified by preparative HPLC to give N-(2'-chloro-3'-(5-((3-(2-hydroxypropan-2-yl)azetidin-1-yl)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide. $^1$H NMR (400 MHz, CDCl$_3$) δ 10.89 (s, 1H), 8.53 (s, 1H), 8.21 (dd, J=7.8, 1.1 Hz, 1H), 7.65-7.57 (m, 2H), 7.38 (dd, J=7.8 Hz, 1H), 7.30 (dd, J=7.8 Hz, 1H), 7.26-7.21 (m, 2H), 7.03 (dd, J=7.8, 1.1 Hz, 1H), 4.00 (s, 3H), 3.66 (s, 2H), 3.58 (s, 3H), 3.44 (s, 3H), 3.44-3.30 (m, 4H), 2.49 (s, 1H), 2.18 (s, 3H), 1.18 (s, 6H). MS: (ES) m/z calculated for $C_{33}H_{37}ClN_5O_5$ [M+H]$^+$ 618.2, found 618.6.

Example 81: N-(2'-chloro-3'-(5-(((4-hydroxy-2-methylbutan-2-yl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide

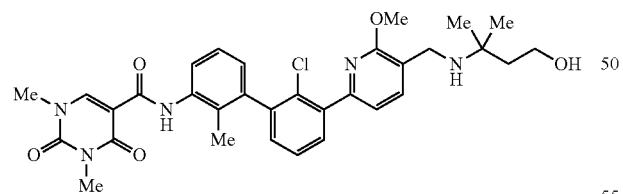

The compound was prepared from N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide and 3-amino-3-methylbutan-1-ol using a procedure similar to step d in Example 1. The crude product was purified by preparative phase HPLC to give N-(2'-chloro-3'-(5-(((4-hydroxy-2-methylbutan-2-yl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide. $^1$H NMR (400 MHz, CDCl$_3$) δ 10.89 (s, 1H), 8.52 (s, 1H), 8.22 (dd, J=7.6, 1.2 Hz, 1H), 7.64-7.56 (m, 2H), 7.39 (dd, J=7.6, 7.6 Hz, 1H), 7.30 (dd, J=7.6 Hz, 1H), 7.30-7.19 (m, 2H), 7.02 (dd, J=7.6, 1.3 Hz, 1H), 4.02 (s, 3H), 3.88 (t, J=5.6 Hz, 2H), 3.82 (s, 2H), 3.57 (s, 3H), 3.44 (s, 3H), 2.18 (s, 3H), 1.73 (t, J=5.4 Hz, 2H), 1.32 (s, 6H). MS: (ES) m/z calculated for $C_{32}H_{37}ClN_5O_5$ [M+H]$^+$ 606.2, found 606.6.

Example 82: (S)—N-(3'-(6-methoxy-5-((((5-oxopyrrolidin-2-yl)methyl)amino)methyl)pyridin-2-yl)-2,2'-dimethyl-[1,1'-biphenyl]-3-yl)-1,3-dimethyl-2,4-dioxo-1,2,3,4-tetrahydropyrimidine-5-carboxamide

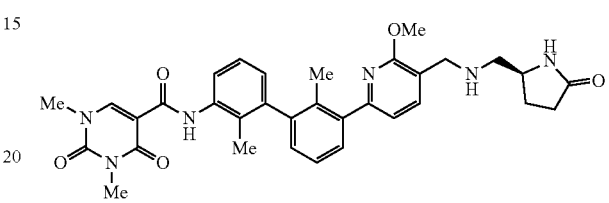

The compound was prepared from N-(3'-(5-formyl-6-methoxypyridin-2-yl)-2,2'-dimethyl-[1,1'-biphenyl]-3-yl)-1,3-dimethyl-2,4-dioxo-1,2,3,4-tetrahydropyrimidine-5-carboxamide and (S)-5-(aminomethyl)pyrrolidin-2-one hydrochloride using a procedure similar to step d in Example 1. The crude product was purified by preparative HPLC to give (S)—N-(3'-(6-methoxy-5-((((5-oxopyrrolidin-2-yl)methyl)amino)methyl)pyridin-2-yl)-2,2'-dimethyl-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.16 (s, 1H), 8.63 (d, J=1.3 Hz, 1H), 8.06 (d, J=7.9 Hz, 1H), 7.87 (d, J=7.5 Hz, 1H), 7.41 (d, J=7.8 Hz, 1H), 7.35 (dd, J=7.8 Hz, 1H), 7.28 (dd, J=7.5, 7.5 Hz, 1H), 7.28 (d, J=7.5 Hz, 1H), 7.18 (d, J=7.8 Hz, 1H), 6.98 (d, J=7.5 Hz, 1H), 4.33 (s, 2H), 4.10-4.01 (m, 1H), 4.07 (s, 3H), 3.55 (s, 3H), 3.39 (s, 3H), 3.34-3.18 (m, 2H), 2.49-2.32 (m, 3H), 2.10 (s, 3H), 2.10 (s, 3H), 1.97-1.85 (m, 1H). MS: (ES) m/z calculated for $C_{33}H_{37}N_6O_5$ [M+H]$^+$ 597.3, found 597.3.

Example 83: 1-((6-(2,2'-dichloro-3'-(1,3-dimethyl-2,4-dioxo-1,2,3,4-tetrahydropyrimidine-5-carboxamido)-[1,1'-biphenyl]-3-yl)-2-ethylpyridin-3-yl)methyl)azetidine-3-carboxylic Acid

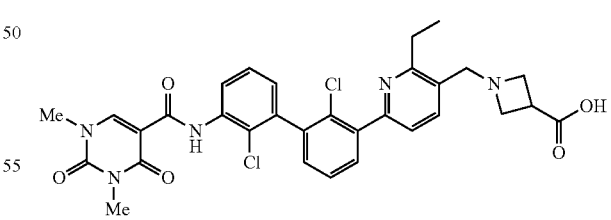

The compound was prepared from N-(2,2'-dichloro-3'-(6-ethyl-5-formylpyridin-2-yl)-[1,1'-biphenyl]-3-yl)-1,3-dimethyl-2,4-dioxo-1,2,3,4-tetrahydropyrimidine-5-carboxamide and azetidine-3-carboxylic acid using a procedure similar to step d in Example 1. The crude product was purified by preparative HPLC to give 1-((6-(2,2'-dichloro-3'-(1,3-dimethyl-2,4-dioxo-1,2,3,4-tetrahydropyrimidine-5-carboxamido)-[1,1'-biphenyl]-3-yl)-2-ethylpyridin-3-yl)methyl)azetidine-3-carboxylic acid. $^1$H NMR (400 MHz, CD₃OD) δ 11.69 (s, 1H), 8.66 (s, 1H), 8.53 (d, J=8.0 Hz, 1H), 7.92 (d, J=7.8 Hz, 1H), 7.64 (d, J=7.8 Hz, 1H), 7.60 (d, J=7.8 Hz, 1H), 7.54 (dd, J=8.0 Hz, 1H), 7.41 (dd, J=8.0 Hz, 2H), 7.10 (dd, J=7.3, 1.7 Hz, 1H), 4.65 (s, 2H), 4.49-4.42 (m, 4H), 3.82-3.68 (m, 1H), 3.55 (d, J=1.5 Hz, 3H), 3.39 (d, J=1.8 Hz, 3H), 3.05 (q, J=7.6 Hz, 2H), 1.35 (t, J=9.6 Hz, 3H). MS: (ES) m/z calculated for $C_{31}H_{30}Cl_2N_5O_5$ [M+H]⁺ 622.2. found 622.1.

Example 84: N-(2,2'-dichloro-3'-(6-ethyl-5-((3-hydroxyazetidin-1-yl)methyl)pyridin-2-yl)-[1,1'-biphenyl]-3-yl)-1,3-dimethyl-2,4-dioxo-1,2,3,4-tetrahydropyrimidine-5-carboxamide

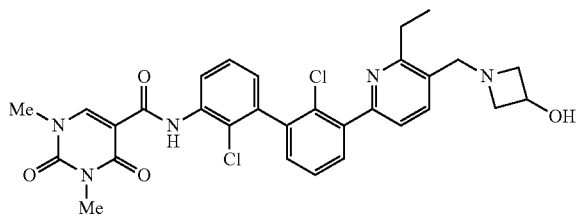 [SMILES: CCc1nc(-c2cccc(-c3cccc(NC(=O)c4cn(C)c(=O)n(C)c4=O)c3Cl)c2Cl)ccc1CN1CC(O)C1]

The compound was prepared from N-(2,2'-dichloro-3'-(6-ethyl-5-formylpyridin-2-yl)-[1,1'-biphenyl]-3-yl)-1,3-dimethyl-2,4-dioxo-1,2,3,4-tetrahydropyrimidine-5-carboxamide and azetidin-3-ol using a procedure similar to step d in Example 1. The crude product was purified by preparative HPLC to give N-(2,2'-dichloro-3'-(6-ethyl-5-((3-hydroxyazetidin-1-yl)methyl)pyridin-2-yl)-[1,1'-biphenyl]-3-yl)-1,3-dimethyl-2,4-dioxo-1,2,3,4-tetrahydropyrimidine-5-carboxamide. H NMR (400 MHz, CD₃OD) δ 11.69 (s, 1H), 8.66 (d, J=1.9 Hz, 1H), 8.54 (d, J=8.6 Hz, 1H), 7.95 (d, J=8.1 Hz, 1H), 7.64 (d, J=7.8 Hz, 1H), 7.60 (d, J=7.8 Hz, 1H), 7.54 (dd, J=8.0, 8.0 Hz, 1H), 7.41 (dd, J=8.0, 8.0 Hz, 2H), 7.13 (dd, J=7.3, 1.8 Hz, 1H), 4.63 (s, 2H), 4.45 (t, J=8.9 Hz, 2H), 4.09 (s, 2H), 3.56 (s, 3H), 3.39 (s, 3H), 3.00 (q, J=7.6 Hz, 2H), 1.36 (t, J=7.6 Hz, 3H). MS: (ES) m/z calculated for $C_{30}H_{30}Cl_2N_5O_4$ [M+H]⁺ 594.2. found 594.1.

Example 85: N-(2,2'-dichloro-3'-(6-ethyl-5-((((3R,4R)-3-hydroxytetrahydro-2H-pyran-4-yl)amino)methyl)pyridin-2-yl)-[1,1'-biphenyl]-3-yl)-1,3-dimethyl-2,4-dioxo-1,2,3,4-tetrahydropyrimidine-5-carboxamide

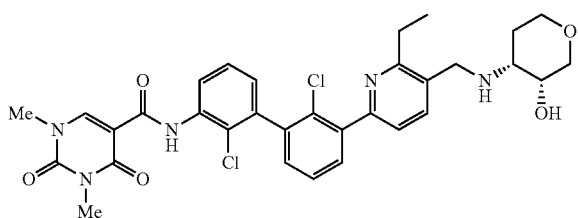 [SMILES: CCc1nc(-c2cccc(-c3cccc(NC(=O)c4cn(C)c(=O)n(C)c4=O)c3Cl)c2Cl)ccc1CN[C@@H]1CCOC[C@@H]1O]

The compound was prepared from N-(2,2'-dichloro-3'-(6-ethyl-5-formylpyridin-2-yl)-[1,1'-biphenyl]-3-yl)-1,3-dimethyl-2,4-dioxo-1,2,3,4-tetrahydropyrimidine-5-carboxamide and (3R,4R)-4-aminotetrahydro-2H-pyran-3-ol hydrochloride using a procedure similar to step d in Example 1. The crude product was purified by preparative phase HPLC to give N-(2,2'-dichloro-3'-(6-ethyl-5-((((3R,4R)-3-hydroxytetrahydro-2H-pyran-4-yl)amino)methyl)pyridin-2-yl)-[1,1'-biphenyl]-3-yl)-1,3-dimethyl-2,4-dioxo-1,2,3,4-tetrahydropyrimidine-5-carboxamide. ¹H NMR (400 MHz, CD₃OD) δ 11.69 (s, 1H), 8.66 (s, 1H), 8.54 (dd, J=8.5, 1.8 Hz, 1H), 8.00 (d, J=8.0 Hz, 1H), 7.64 (d, J=7.8 Hz, 1H), 7.60 (d, J=7.8 Hz, 1H), 7.54 (dd, J=8.0 Hz, 1H), 7.41 (dd, J=8.0 Hz, 2H), 7.10 (d, J=7.3 Hz, 1H), 4.49 (d, J=13.5 Hz, 1H), 4.30 (d, J=12.6 Hz, 1H), 4.13 (s, 1H), 4.02 (d, J=12.6 Hz, 2H), 3.62 (t, J=12.4 Hz, 2H), 3.58 (s, 3H), 3.48 (t, J=12.4 Hz, 2H), 3.39 (s, 3H), 3.15-2.29 (m, 2H), 2.21-2.07 (m, 1H), 1.86 (d, J=13.1 Hz, 1H), 1.36 (t, J=7.2 Hz, 3H). MS: (ES) m/z calculated for $C_{32}H_{34}Cl_2N_5O_5$ [M+H]⁺ 638.2, found 638.2.

Example 86: (S)—N-(2,2'-dichloro-3'-(6-ethyl-5-((((5-oxopyrrolidin-2-yl)methyl)amino)methyl)pyridin-2-yl)-[1,1'-biphenyl]-3-yl)-1,3-dimethyl-2,4-dioxo-1,2,3,4-tetrahydropyrimidine-5-carboxamide

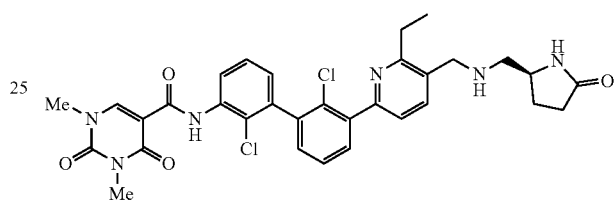

The compound was prepared from N-(2,2'-dichloro-3'-(6-ethyl-5-formylpyridin-2-yl)-[1,1'-biphenyl]-3-yl)-1,3-dimethyl-2,4-dioxo-1,2,3,4-tetrahydropyrimidine-5-carboxamide and (S)-5-(aminomethyl)pyrrolidin-2-one hydrochloride using a procedure similar to step d in Example 1. The crude product was purified by preparative HPLC to give (S)—N-(2,2'-dichloro-3'-(6-ethyl-5-((((5-oxopyrrolidin-2-yl)methyl)amino)methyl)pyridin-2-yl)-[1,1'-biphenyl]-3-yl)-1,3-dimethyl-2,4-dioxo-1,2,3,4-tetrahydropyrimidine-5-carboxamide. ¹H NMR (400 MHz, CD₃OD) δ 11.69 (s, 1H), 8.66 (s, 1H), 8.54 (d, J=8.1 Hz, 1H), 8.01 (d, J=8.1 Hz, 1H), 7.64 (d, J=7.8 Hz, 1H), 7.61 (d, J=7.8 Hz, 1H), 7.54 (dd, J=8.0 Hz, 1H), 7.42 (dd, J=8.0 Hz, 2H), 7.10 (dd, J=7.3, 1.8 Hz, 1H), 4.46 (s, 2H), 4.06 (m, 1H), 3.56 (s, 3H), 3.37 (s, 3H), 3.35 (m, 2H), 3.02 (q, J=7.6 Hz, 2H), 2.47-2.33 (m, 3H), 2.00-1.91 (m, 1H), 1.36 (t, J=7.5 Hz, 3H). MS: (ES) m/z calculated for $C_{32}H_{33}Cl_2N_6O_4$ [M+H]⁺ 635.2. found 635.2.

Example 87: 1-((5-(2,2'-dichloro-3'-(1,3-dimethyl-2,4-dioxo-1,2,3,4-tetrahydropyrimidine-5-carboxamido)-[1,1'-biphenyl]-3-yl)-3-methoxypyrazin-2-yl)methyl)-3-methylazetidine-3-carboxylic Acid

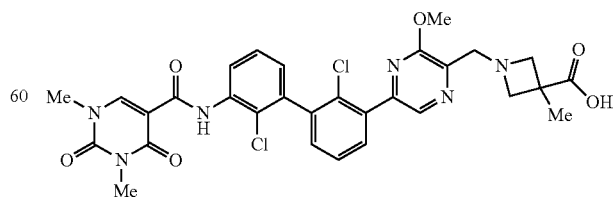

The compound was prepared from N-(2,2'-dichloro-3'-(5-formyl-6-methoxypyrazin-2-yl)-[1,1'-biphenyl]-3-yl)-1,3- dimethyl-2,4-dioxo-1,2,3,4-tetrahydropyrimidine-5-carboxamide and 3-methylazetidine-3-carboxylic acid hydrochloride using a procedure similar to step d in Example 1. The crude product was purified by preparative HPLC to give 1-((5-(2,2'-dichloro-3'-(1,3-dimethyl-2,4-dioxo-1,2,3,4-tetrahydropyrimidine-5-carboxamido)-[1,1'-biphenyl]-3-yl)-3-methoxypyrazin-2-yl)methyl)-3-methylazetidine-3-carboxylic acid. $^1$H NMR (400 MHz, CD$_3$OD) δ 11.70 (s, 1H), 8.67 (s, 1H), 8.55 (d, J=8.1 Hz, 1H), 8.49 (s, 1H), 7.70 (d, J=7.8 Hz, 1H), 7.56 (dd, J=8.0, 8.0 Hz, 1H), 7.47-7.37 (m, 2H), 7.10 (dd, J=7.3, 1.8 Hz, 1H), 4.74 (s, 2H), 4.54 (bs, 1H), 4.29-4.13 (bs, 3H), 4.11 (s, 3H), 3.56 (s, 3H), 3.39 (s, 3H), 1.65 (s, 3H). MS: (ES) m/z calculated for C$_{30}$H$_{29}$Cl$_2$N$_6$O$_6$ [M+H]$^+$ 639.1. found 639.0.

Example 88: N-(3'-(6-(((2-hydroxyethyl)amino) methyl)-5-methoxypyridin-3-yl)-2,2'-dimethyl-[1,1'-biphenyl]-3-yl)-1,3-dimethyl-2,4-dioxo-1,2,3,4-tetrahydropyrimidine-5-carboxamide

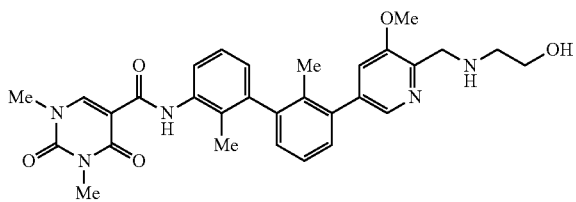 [SMILES: COc1cc(-c2cccc(-c3cccc(NC(=O)c4cn(C)c(=O)n(C)c4=O)c3C)c2C)cnc1CNCCO]

A mixture of N-(3'-(6-formyl-5-methoxypyridin-3-yl)-2,2'-dimethyl-[1,1'-biphenyl]-3-yl)-1,3-dimethyl-2,4-dioxo-1,2,3,4-tetrahydropyrimidine-5-carboxamide (40 mg, 0.080 mmol), 2-aminoethan-1-ol (60 mg, 1.0 mmol) and AcOH (90 mg, 1.5 mmol) in EtOH (2.0 mL) was heated at 70° C. for 0.5 h. The mixture was cooled to 0° C. and NaBH$_3$CN (40 mg, 0.63 mmol) was added. After stirring for 5 min at 0° C. the mixture was concentrated in vacuo. The obtained residue was purified by preparative HPLC to give N-(3'-(6-(((2-hydroxyethyl)amino)methyl)-5-methoxypyridin-3-yl)-2,2'-dimethyl-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.15 (s, 1H), 8.61 (s, 1H), 8.20 (d, J=1.6 Hz, 1H), 8.07 (ddd, J=8.4, 8.4, 1.2 Hz, 1H), 7.49 (d, J=1.6 Hz, 1H), 7.36 (dd, J=7.6, 7.6 Hz, 1H), 7.30-7.25 (m, 2H), 7.18 (dd, J=7.2, 1.2 Hz, 1H), 6.97 (dd, J=7.6, 0.8 Hz, 1H), 4.45 (s, 2H), 3.97 (s, 3H), 3.93-3.87 (m, 2H), 3.54 (s, 3H), 3.36 (s, 3H), 3.38-3.28 (m, 2H), 2.10 (s, 3H), 1.94 (s, 3H). MS: (ES) m/z calculated for C$_{30}$H$_{34}$N$_5$O$_5$ [M+H]$^+$ 544.3. found 544.3.

Example 89: (S)—N-(2'-chloro-3'-(5-((3-hydroxy-3-methylpyrrolidin-1-yl)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide

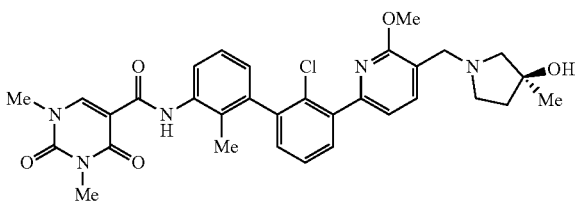 [SMILES: COc1nc(-c2cccc(-c3cccc(NC(=O)c4cn(C)c(=O)n(C)c4=O)c3C)c2Cl)ccc1CN1CC[C@](C)(O)C1]

Step a: A 3-L flask was charged with 1,3-dimethyl-2,4-dioxo-1,2,3,4-tetrahydropyrimidine-5-carboxylic acid (50.0 g, 271 mmol) and dichloromethane (800 mL). To this suspension was added oxalyl chloride (32 mL, 370 mmol) followed by DMF (0.5 mL, 6 mmol). After stirring for 90 min, the resulting yellow solution was concentrated under reduced pressure. The solid was transferred to a 3-L 3-neck flask and dissolved in anhydrous dichloromethane (800 mL). The solution was cooled to 0° C. and 2-methyl-3-(4,4,5,5-tetramethyl-1,3,2-dioxaborolan-2-yl)aniline (64.0 g, 275 mmol) was added, followed by dropwise addition of Et$_3$N (116 mL, 832 mmol). The reaction mixture was stirred for an additional 13 h. The volatiles were removed under reduced pressure and the residue was transferred to a 1-L flask and triturated with 600 mL water. The slurry was stirred for 1 d, then filtered and washed with water and dried to give 1,3-dimethyl-N-(2-methyl-3-(4,4,5,5-tetramethyl-1,3,2-dioxaborolan-2-yl)phenyl)-2,4-dioxo-1,2,3,4-tetrahydropyrimidine-5-carboxamide. $^1$H NMR (400 MHz, CDCl$_3$) δ 10.81 (s, 1H), 8.50 (s, 1H), 8.19 (d, J=8.8 Hz, 1H), 7.58 (d, J=7.6 Hz, 1H), 7.23 (dd, J=7.6, 7.6 Hz, 1H), 3.57 (s, 3H), 3.45 (s, 3H), 2.59 (s, 3H), 1.36 (s, 12H). MS: (ES) m/z calculated for C$_{20}$H$_{27}$BN$_3$O$_5$ [M+H]$^+$ 400.2. found 400.2.

Step b: To a mixture of (3-bromo-2-chlorophenyl)boronic acid (30.0 g, 127.5 mmol), 6-chloro-2-methoxynicotinaldehyde (23.0 g, 134.0 mmol), and K$_2$CO$_3$ (48.0 g, 347.8 mmol) in p-dioxane (450 mL) and DI H$_2$O (80 mL) was added Pd(PPh$_3$)$_4$ (7.4 g, 6.4 mmol). The contents were degassed and stirred under N$_2$ at 92° C. for 2 h. The reaction mixture was cooled to room temperature, diluted with DCM (1 L), washed with brine and dried over MgSO$_4$ and filtered. The solvent was removed under reduced pressure and the residue was triturated with Et$_2$O (500 mL). The solid was collected by filtration to give 6-(3-bromo-2-chlorophenyl)-2-methoxynicotinaldehyde. MS: (ES) m/z calculated for C$_{13}$H$_{10}$BrClNO$_2$ [M+H]$^+$ 326.0, found 325.9.

Step c: To a mixture of 1,3-dimethyl-N-(2-methyl-3-(4,4,5,5-tetramethyl-1,3,2-dioxaborolan-2-yl)phenyl)-2,4-dioxo-1,2,3,4-tetrahydropyrimidine-5-carboxamide (27.4 g, 68.6 mmol), 6-(3-bromo-2-chlorophenyl)-2-methoxynicotinaldehyde (22.4 g, 68.6 mmol), and K$_2$CO$_3$ (28.4 g, 205.8 mmol) in p-dioxane (500 mL) and DI H$_2$O (80 mL) was added Pd(dppf)Cl$_2$ complex with DCM (5.6 g, 6.9 mmol). The contents were degassed and stirred under N$_2$ at 92° C. for 3 h. The reaction mixture was cooled to room temperature, filtered through Celite, washed with EtOAc (300 mL×3) and the solvent was removed under reduced pressure. The residue was diluted with DCM, washed with brine and dried over MgSO$_4$. The solvent was removed under reduced pressure and the solid was triturated with MeCN, filtered and washed with MeCN to give N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide. MS: (ES) m/z calculated for C$_{27}$H$_{24}$ClN$_4$O$_5$ [M+H]$^+$ 519.1. found 519.1.

Step d: To a mixture of N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide (58 mg, 0.11 mmol) and (S)-3-methylpyrrolidin-3-ol (43 mg, 0.31 mmol) in 20% v/v MeOH in DCM (2 mL) was added trimethylamine (0.043 mL, 0.31 mmol). After stirring for 20 min at room temperature, sodium triacetoxyborohydride (91 mg, 0.43 mmol) was added, and stirring was continued for 1 d. The reaction was quenched with water (2 mL) and 2:1 CHCl$_3$/2-propanol. The organic layer was evaporated to dryness and the resulting crude material was purified by preparative HPLC to give the desired product (S)—N-(2'-chloro-3'-(5-((3-hydroxy-3-methylpyrrolidin-1-yl)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) S 11.18 (s, 1H), 8.63 (s, 1H), 8.10 (d, J=8.4 Hz, 1H), 7.91 (d, J=8.4 Hz, 1H), 7.65-7.61 (m, 1H), 7.50 (dd, J=7.6, 7.6 Hz, 1H), 7.38 (d, J=7.6 Hz, 1H), 7.35 (dd, J=7.6, 1.6 Hz, 1H), 7.29 (dd, J=8.0, 8.0 Hz, 1H), 7.00 (d, J=7.6 Hz, 1H), 4.55 (s, 1H), 4.51-4.39 (m, 1H), 4.12-4.06 (m, 3H), 3.88-3.57 (m, 1H), 3.55 (s, 3H), 3.53-3.35 (m, 1H), 3.39 (s, 3H), 3.24-3.10 (m, 1H), 2.32-2.14 (m, 1H), 2.13 (s, 3H), 2.10-1.93 (m, 1H), 1.45 (s, 3H). MS: (ES) m/z calculated for C$_{32}$H$_{35}$ClN$_5$O$_5$ [M+H]$^+$ 604.2. found 604.5.

Example 90: N-(2'-fluoro-3'-(5-((((3R,4R)-3-hydroxytetrahydro-2H-pyran-4-yl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide

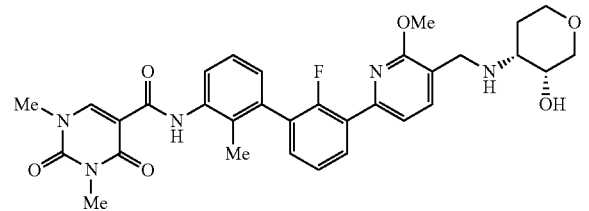

This compound was prepared from N-(2'-fluoro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide and (3R,4R)-4-aminooxan-3-ol hydrochloride using a procedure similar to step d in Example 89. The crude product was purified by preparative HPLC to give the desired product N-(2'-fluoro-3'-(5-((((3R,4R)-3-hydroxytetrahydro-2H-pyran-4-yl)amino)methyl)-6-methoxypyridin-2-yl)-2-methyl-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.19 (s, 1H), 8.63 (s, 1H), 8.16-8.08 (m, 2H), 7.86 (d, J=7.6 Hz, 1H), 7.55 (dd, J=7.6, 1.6 Hz, 1H), 7.43-7.28 (m, 3H), 7.10 (d, J=7.6 Hz, 1H), 4.38-4.20 (m, 2H), 4.14 (s, 3H), 4.06-3.93 (m, 3H), 3.60-3.53 (m, 1H), 3.55 (s, 3H), 3.52-3.41 (m, 2H), 3.39 (s, 3H), 2.20 (s, 3H), 2.17-2.05 (m, 1H), 1.90-1.82 (m, 1H). MS: (ES) m/z calculated for C$_{32}$H$_{35}$FN$_5$O$_6$ [M+H]$^+$ 604.3. found 604.5.

Example 91: (S)—N-(2-chloro-3'-(6-methoxy-5-((((5-oxopyrrolidin-2-yl)methyl)amino)methyl)pyridin-2-yl)-[1,1'-biphenyl]-3-yl)-1,3-dimethyl-2,4-dioxo-1,2,3,4-tetrahydropyrimidine-5-carboxamide

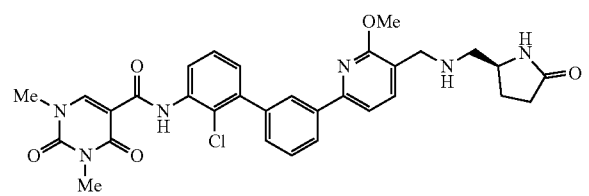 [SMILES: COc1nc(-c2cccc(-c3cccc(NC(=O)c4cn(C)c(=O)n(C)c4=O)c3Cl)c2)ccc1CNC[C@@H]1CCC(=O)N1]

This compound was prepared from N-(2-chloro-3'-(5-formyl-6-methoxypyridin-2-yl)-[1,1'-biphenyl]-3-yl)-1,3-dimethyl-2,4-dioxo-1,2,3,4-tetrahydropyrimidine-5-carboxamide and (S)-5-aminomethylpyrrolidin-2-one using a procedure similar to step d in Example 89. The crude product was purified by preparative HPLC to give (S)—N-(2-chloro-3'-(6-methoxy-5-((((5-oxopyrrolidin-2-yl)methyl)amino)methyl)pyridin-2-yl)-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.71 (s, 1H), 8.66 (s, 1H), 8.50 (d, J=8.8 Hz, 1H), 8.19 (s, 1H), 8.16 (d, J=8.0 Hz, 1H), 7.87 (d, J=7.6 Hz, 1H), 7.64 (d, J=7.6 Hz, 1H), 7.58 (dd, J=7.6, 7.6 Hz, 1H), 7.49 (d, J=7.6 Hz, 1H), 7.41 (dd, J=7.6, 7.6 Hz, 1H), 7.19 (d, J=7.6 Hz, 1H), 4.37-4.27 (m, 2H), 4.15 (s, 3H), 4.10-4.00 (m, 1H), 3.55 (s, 3H), 3.38 (s, 3H), 3.27-3.19 (m, 2H), 2.48-2.31 (m, 3H), 1.97-1.86 (m, 1H). MS: (ES) m/z calculated for C$_{31}$H$_{32}$ClN$_6$O$_5$ [M+H]$^+$ 603.2. found 602.8.

Example 92: (S)—N-(2-chloro-3'-(6-methoxy-5-((((5-oxopyrrolidin-2-yl)methyl)amino)methyl)pyridin-2-yl)-2'-methyl-[1,1'-biphenyl]-3-yl)-1,3-dimethyl-2,4-dioxo-1,2,3,4-tetrahydropyrimidine-5-carboxamide

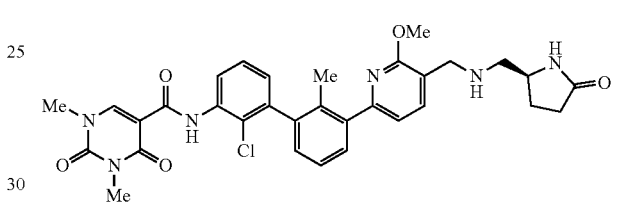

The compound was prepared from N-(2-chloro-3'-(5-formyl-6-methoxypyridin-2-yl)-2'-methyl-[1,1'-biphenyl]-3-yl)-1,3-dimethyl-2,4-dioxo-1,2,3,4-tetrahydropyrimidine-5-carboxamide and (S)-5-aminomethylpyrrolidin-2-one using a procedure similar to step d in Example 89. The crude product was purified by preparative HPLC to give (S)—N-(2-chloro-3'-(6-methoxy-5-((((5-oxopyrrolidin-2-yl)methyl)amino)methyl)pyridin-2-yl)-2'-methyl-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.69 (s, 1H), 8.67 (s, 1H), 8.51 (d, J=8.4 Hz, 1H), 7.88 (d, J=7.6 Hz, 1H), 7.45 (d, J=7.2 Hz, 1H), 7.43-7.34 (m, 2H), 7.25-7.19 (m, 2H), 7.07 (d, J=7.2 Hz, 1H), 4.38-4.29 (m, 2H), 4.11-4.02 (m, 1H), 4.08 (s, 3H), 3.56 (s, 3H), 3.38 (s, 3H), 3.29-3.20 (m, 2H), 2.50-2.33 (m, 3H), 2.11 (s, 3H), 1.99-1.86 (m, 1H). MS: (ES) m/z calculated for C$_{32}$H$_{34}$ClN$_6$O$_5$ [M+H]$^+$ 617.2. found 617.5.

Example 93: (S)-2-(((6-(2,2'-dichloro-3'-(1,3-dimethyl-2,4-dioxo-1,2,3,4-tetrahydropyrimidine-5-carboxamido)-[1,1'-biphenyl]-3-yl)-2-methoxypyridin-3-yl)methyl)amino)-3-hydroxy-2-methylpropanoic Acid

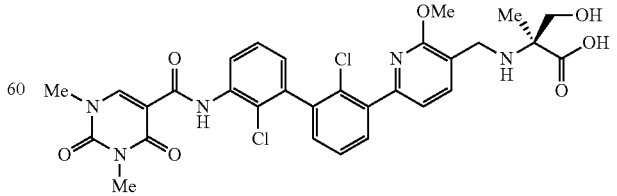

The compound was prepared from N-(2,2'-dichloro-3'-(5-formyl-6-methoxypyridin-2-yl)-[1,1'-biphenyl]-3-yl)-1,3- dimethyl-2,4-dioxo-1,2,3,4-tetrahydropyrimidine-5-carboxamide and (S)-2-amino-3-hydroxy-2-methylpropanoic acid using a procedure similar to step d in Example 89. The crude product was purified by preparative HPLC to give (S)-2-(((6-(2,2'-dichloro-3'-(1,3-dimethyl-2,4-dioxo-1,2,3,4-tetrahydropyrimidine-5-carboxamido)-[1,1'-biphenyl]-3-yl)-2-methoxypyridin-3-yl)methyl)amino)-3-hydroxy-2-methylpropanoic acid. $^1$H NMR (400 MHz, CD$_3$OD) δ 11.69 (s, 1H), 8.66 (s, 1H), 8.53 d, J=8.4 Hz, 1H), 7.91 (d, J=7.6 Hz, 1H), 7.65 (d, J=7.6 Hz, 1H), 7.51 (t, J=7.6 Hz, 1H), 7.44-7.33 (m, 3H), 7.10 (d, J=7.6 Hz, 1H), 4.41-4.29 (m, 2H), 4.09 (s, 3H), 4.11-4.05 (m, 1H), 3.88 (d, J=12 Hz, 1H), 3.56 (s, 3H), 3.39 (s, 3H), 1.63 (s, 3H). MS: (ES) m/z calculated for C$_{30}$H$_{30}$Cl$_2$N$_5$O$_7$ [M+H]$^+$ 642.2. found 642.5.

Example 94: N-(2,2'-dichloro-3'-(6-methoxy-5-((3-(methylsulfonamido)azetidin-1-yl)methyl)pyridin-2-yl)-[1,1'-biphenyl]-3-yl)-1,3-dimethyl-2,4-dioxo-1,2,3,4-tetrahydropyrimidine-5-carboxamide

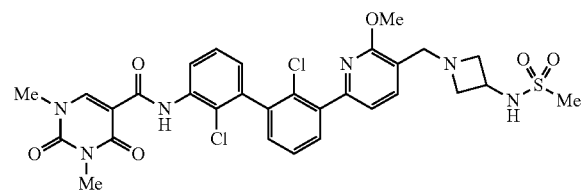 [SMILES: COc1nc(-c2cccc(-c3cccc(NC(=O)c4cn(C)c(=O)n(C)c4=O)c3Cl)c2Cl)ccc1CN1CC(NS(C)(=O)=O)C1]

The compound was prepare from N-(2,2'-dichloro-3'-(5-formyl-6-methoxypyridin-2-yl)-[1,1'-biphenyl]-3-yl)-1,3-dimethyl-2,4-dioxo-1,2,3,4-tetrahydropyriimidine-5-carboxamide and N-(azetidinyl)methanesulfonamide hydrochloride using a procedure similar to step d in Example 89. The crude product was purified by preparative HPLC to give N-(2,2'-dichloro-3'-(6-methoxy-5-((3-(methylsulfonamido)azetidin-1-yl)methyl)pyridin-2-yl)-[1,1'-biphenyl]-3-yl)-1,3-dimethyl-2,4-dioxo-1,2,3,4-tetrahydropyriimidine-5-carboxamide. $^1$H NMR (400 MHz, CD$_3$OD) δ 11.69 (s, 1H), 8.66 (s, 1H), 8.53 (d, J=8.0 Hz, 1H), 7.87 (d, J=7.2 Hz, 1H), 7.65 (d, J=7.6 Hz, 1H), 7.51 (dd, J=7.6, 7.6 Hz, 1H), 7.44-7.36 (m, 3H), 7.10 (d, J=7.6 Hz, 1H), 4.61-4.34 (m, 5H), 4.32-4.13 (m, 2H), 4.10 (s, 3H), 3.56 (s, 3H), 3.39 (s, 3H), 2.99 (s, 3H). MS: (ES) m/z calculated for C$_{30}$H$_{31}$Cl$_2$N$_6$O$_6$S [M+H]$^+$ 673.1. found 672.7.

Example 95: (R)-1-((6-(2,2'-dichloro-3'-(1,3-dimethyl-2,4-dioxo-1,2,3,4-tetrahydropyrimidine-5-carboxamido)-[1,1'-biphenyl]-3-yl)-2-methoxypyridin-3-yl)methyl)pyrrolidine-3-carboxylic Acid The compound was prepared from N-(2,2'-dichloro-3'-(5-formyl-6-methoxypyridin-2-yl)-[1,1'-biphenyl]-3-yl)-1,3-dimethyl-2,4-dioxo-1,2,3,4-tetrahydropyrimidine-5-carboxamide and (R)-pyrrolidine-3-carboxylic acid using a procedure similar to step d in Example 89. The crude product was purified by preparative HPLC to give (R)-1-((6-(2,2'-dichloro-3'-(1,3-dimethyl-2,4-dioxo-1,2,3,4-tetrahydropyrimidine-5-carboxamido)-[1,1'-biphenyl]-3-yl)-2-methoxypyridin-3-yl)methyl)pyrrolidine-3-carboxylic acid. $^1$H NMR (400 MHz, CD$_3$OD) δ 11.69 (s, 1H), 8.66 (s, 1H), 8.54 (d, J=6.8 Hz, 1H), 7.92 (d, J=7.2 Hz, 1H), 7.67 (d, J=8.4 Hz, 1H), 7.52 (dd, J=8.0, 8.0 Hz, 1H), 7.44-7.36 (m, 3H), 7.10 (d, J=7.6 Hz, 1H), 4.49 (s, 2H), 4.11 (s, 3H), 3.95-3.34 (m, 5H), 3.55 (s, 3H), 3.38 (s, 3H), 2.66-2.18 (m, 2H). MS: (ES) m/z calculated for C$_{31}$H$_{30}$Cl$_2$N$_5$O$_6$ [M+H]$^+$ 638.2. found 637.8.

Example 96: N-(2,2'-dichloro-3'-(5-((3-hydroxyazetidin-1-yl)methyl)-4-methoxypyridin-2-yl)-[1,1'-biphenyl]-3-yl)-1,3-dimethyl-2,4-dioxo-1,2,3,4-tetrahydropyrimidine-5-carboxamide

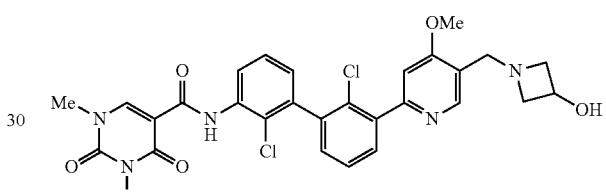

The compound was prepared from N-(2,2'-dichloro-3'-(5-formyl-4-methoxypyridin-2-yl)-[1,1'-biphenyl]-3-yl)-1,3-dimethyl-2,4-dioxo-1,2,3,4-tetrahydropyrimidine-5-carboxamide and azetidin-3-ol hydrochloride using a procedure similar to step d in Example 89. The crude product was purified by preparative HPLC to give N-(2,2'-dichloro-3'-(5-((3-hydroxyazetidin-1-yl)methyl)-4-methoxypyridin-2-yl)-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.69 (s, 1H), 8.66 (s, 1H), 8.59 (s, 1H), 8.55 (d, J=8.4 Hz, 1H), 7.64-7.54 (m, 2H), 7.53 (s, 1H), 7.48 (d, J=6.4 Hz, 1H), 7.42 (dd, J=8.0, 8.0 Hz, 1H), 7.10 (d, J=7.2 Hz, 1H), 4.65 (bs, 1H), 4.55 (s, 2H), 4.11-4.38 (m, 2H), 4.13-4.02 (m, 2H), 4.10 (s, 3H), 3.55 (s, 3H), 3.38 (s, 3H). MS: (ES) m/z calculated for C$_{29}$H$_{28}$Cl$_2$N$_5$O$_5$ [M+H]$^+$ 596.1. found 595.8.

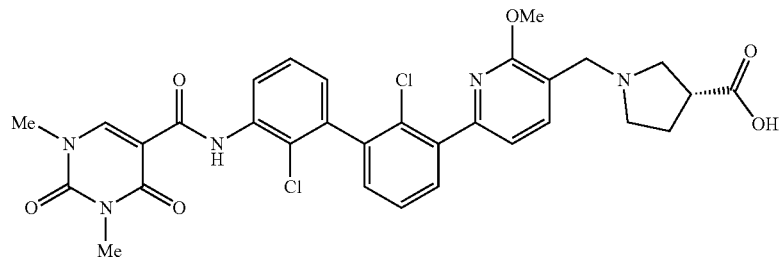 [SMILES: COc1nc(-c2cccc(-c3cccc(NC(=O)c4cn(C)c(=O)n(C)c4=O)c3Cl)c2Cl)ccc1CN1CC[C@@H](C(=O)O)C1]

Example 97: (S)—N-(2,2'-dichloro-3'-(4-methoxy-5-((((5-oxopyrrolidin-2-yl)methyl)amino)methyl)pyrimidin-2-yl)-[1,1'-biphenyl]-3-yl)-1,3-dimethyl-2,4-dioxo-1,2,3,4-tetrahydropyrimidine-5-carboxamide

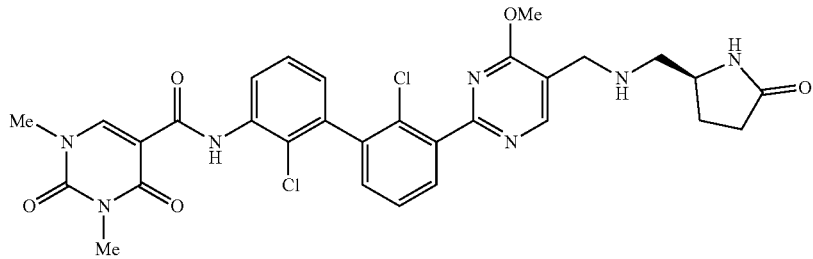 [SMILES: COc1nc(-c2cccc(-c3cccc(NC(=O)c4cn(C)c(=O)n(C)c4=O)c3Cl)c2Cl)ncc1CNC[C@@H]1CCC(=O)N1]

The compound was prepared from N-(2,2'-dichloro-3'-(5-formyl-4-methoxypyrimidin-2-yl)-[1,1'-biphenyl]-3-yl)-1,3-dimethyl-2,4-dioxo-1,2,3,4-tetrahydropyrimidine-5-carboxamide and (S)-5-aminomethylpyrrolidin-2-one hydrochloride using a procedure similar to step d in Example 89. The crude product was purified by preparative HPLC to give (S)—N-(2,2'-dichloro-3'-(4-methoxy-5-((((5-oxopyrrolidin-2-yl)methyl)amino)methyl)pyrimidin-2-yl)-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.70 (s, 1H), 8.71 (s, 1H), 8.66 (s, 1H), 8.55 (d, J=8.0 Hz, 1H), 7.78 (d, J=8.0 Hz, 1H), 7.75 (dd, J=8.0, 8.0 Hz, 1H), 7.48-7.38 (m, 2H), 7.10 (d, J=7.6 Hz, 1H), 4.37 (s, 2H), 4.19 (s, 3H), 4.09-4.01 (m, 1H), 3.55 (s, 3H), 3.38 (s, 3H), 3.30-3.27 (m, 2H), 2.49-2.32 (m, 3H), 2.00-1.88 (m, 1H). MS: (ES) m/z calculated for C$_{30}$H$_{30}$Cl$_2$N$_7$O$_5$ [M+H]$^+$ 638.2, found 638.2.

Example 98: 1-((6-(2,2'-dichloro-3'-(1,3-dimethyl-2,4-dioxo-1,2,3,4-tetrahydropyrimidine-5-carboxamido)-[1,1'-biphenyl]-3-yl)-4-methoxypyridin-3-yl)methyl)-3-methylazetidine-3-carboxylic Acid

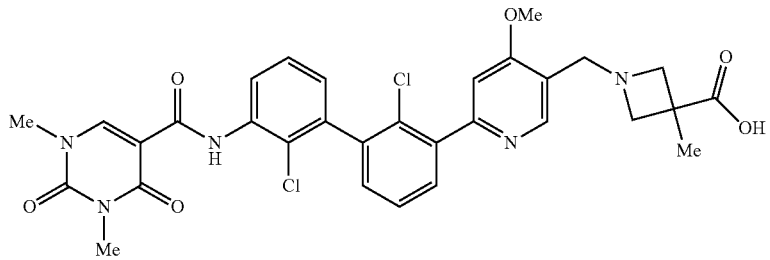 [SMILES: COc1cc(-c2cccc(-c3cccc(NC(=O)c4cn(C)c(=O)n(C)c4=O)c3Cl)c2Cl)ncc1CN1CC(C)(C(=O)O)C1]

The compound was prepared from N-(2,2'-dichloro-3'-(5-formyl-4-methoxypyridin-2-yl)-[1,1'-biphenyl]-3-yl)-1,3-dimethyl-2,4-dioxo-1,2,3,4-tetrahydropyrimidine-5-carboxamide and 3-methyl-3-azetidine carboxylic acid using a procedure similar to step d in Example 89. The crude product was purified by preparative HPLC to give 1-((6-(2,2'-dichloro-3'-(1,3-dimethyl-2,4-dioxo-1,2,3,4-tetrahydropyrimidine-5-carboxamido)-[1,1'-biphenyl]-3-yl)-4-methoxypyridin-3-yl)methyl)-3-methylazetidine-3-carboxylic acid. $^1$H NMR (400 MHz, CD$_3$OD) δ 11.70 (s, 1H), 8.67 (s, 1H), 8.57 (s, 1H), 8.55 (d, J=8.8 Hz, 1H), 7.62-7.54 (m, 2H), 7.50 (s, 1H), 7.47 (d, J=7.2 Hz, 1H), 7.41 (dd, J=7.2, 7.2 Hz, 1H), 7.10 (d, J=7.2 Hz, 1H), 4.62-4.51 (m, 4H), 4.15 (d, J=10.8 Hz, 2H), 4.09 (s, 3H), 3.55 (s, 3H), 3.39 (s, 3H), 1.62 (s, 3H). MS: (ES) m/z calculated for C$_{31}$H$_{30}$Cl$_2$N$_5$O$_6$ [M+H]$^+$ 638.2. found 638.0.

Example 99: 1-((6-(2,2'-dichloro-3'-(1,3-dimethyl-2, 4-dioxo-1,2,3,4-tetrahydropyrimidine-5-carboxamido)-[1,1'-biphenyl]-3-yl)-4-methoxypyridin-3-yl) methyl)azetidine-3-carboxylic Acid

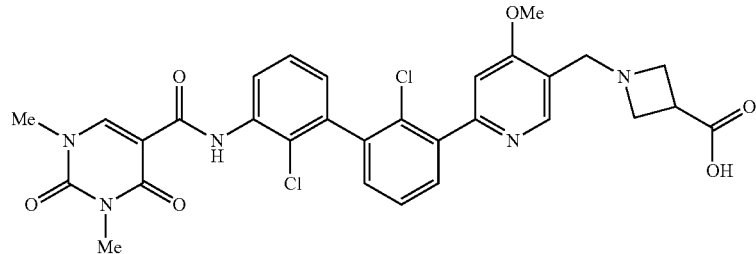 [SMILES: COc1cc(-c2cccc(-c3cccc(NC(=O)c4cn(C)c(=O)n(C)c4=O)c3Cl)c2Cl)ncc1CN1CC(C(=O)O)C1]

The compound was prepared from N-(2,2'-dichloro-3'-(5-formyl-4-methoxypyridin-2-yl)-[1,1'-biphenyl]-3-yl)-1,3-dimethyl-2,4-dioxo-1,2,3,4-tetrahydropyrimidine-5-carboxamide and 3-azetidine carboxylic acid using a procedure similar to step d in Example 89. The crude product was purified by preparative HPLC to give 1-((6-(2,2'-dichloro-3'-(1,3-dimethyl-2,4-dioxo-1,2,3,4-tetrahydropyrimidine-5-carboxamido)-[1,1'-biphenyl]-3-yl)-4-methoxypyridin-3-yl) methyl)azetidine-3-carboxylic acid. $^1$H NMR (400 MHz, CD$_3$OD) δ 11.70 (s, 1H), 8.66 (s, 1H), 8.59 (s, 1H), 8.55 (d, J=8.0 Hz, 1H), 7.64-7.54 (m, 2H), 7.52 (s, 1H), 7.48 (d, J=7.6 Hz, 1H), 7.42 (dd, J=8.0, 8.0 Hz, 1H), 7.10 (d, J=7.2 Hz, 1H), 4.57 (s, 2H), 4.49-4.38 (m, 4H), 4.10 (s, 3H), 3.78-3.66 (m, 1H), 3.55 (s, 3H), 3.39 (s, 3H). MS: (ES) m/z calculated for C$_{30}$H$_{28}$Cl$_2$N$_5$O$_6$ [M+H]$^+$ 624.1. found 623.9.

Example 100: (S)—N-(2,2'-dichloro-3'-(4-methoxy-5-((((5-oxopyrrolidin-2-yl)methyl)amino)methyl) pyridin-2-yl)-[1,1'-biphenyl]-3-yl)-1,3-dimethyl-2,4-dioxo-1,2,3,4-tetrahydropyrimidine-5-carboxamide

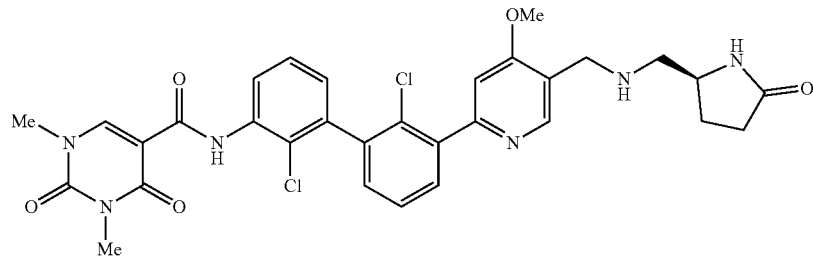 [SMILES: COc1cc(-c2cccc(-c3cccc(NC(=O)c4cn(C)c(=O)n(C)c4=O)c3Cl)c2Cl)ncc1CNC[C@@H]1CCC(=O)N1]

The compound was prepared from N-(2,2'-dichloro-3'-(5-formyl-4-methoxypyridin-2-yl)-[1,1'-biphenyl]-3-yl)-1,3-dimethyl-2,4-dioxo-1,2,3,4-tetrahydropyrimidine-5-carboxamide and (S)-5-aminomethylpyrrolidin-2-one hydrochloride using a procedure similar to step d in Example 89. The crude product was purified by preparative HPLC to give (S)—N-(2,2'-dichloro-3'-(4-methoxy-5-((((5-oxopyrrolidin-2-yl)methyl)amino)methyl)pyridin-2-yl)-[1, 1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.70 (s, 1H), 8.67 (s, 1H), 8.59 (s, 1H), 8.55 (d, J=8.4 Hz, 1H), 7.63-7.55 (m, 2H), 7.53 (s, 1H), 7.47 (d, J=6.8 Hz, 1H), 7.42 (dd, J=8.0, 8.0 Hz, 1H), 7.10 (d, J=8.0 Hz, 1H), 4.41 (s, 2H), 4.11 (s, 3H), 4.09-4.02 (m, 1H), 3.56 (s, 3H), 3.39 (s, 3H), 3.30-3.27 (m, 2H), 2.48-2.33 (m, 3H), 1.99-1.86 (m, 1H). MS: (ES) m/z calculated for C$_{31}$H$_{31}$Cl$_2$N$_6$O$_5$ [M+H]$^+$ 637.2. found 636.9.

Example 101: N-(2,2'-dichloro-3'-(5-((((3R,4R)-3-hydroxytetrahydro-2H-pyran-4-yl)amino)methyl)-4-methoxypyridin-2-yl)-[1,1'-biphenyl]-3-yl)-1,3-dimethyl-2,4-dioxo-1,2,3,4-tetrahydropyrimidine-5-carboxamide

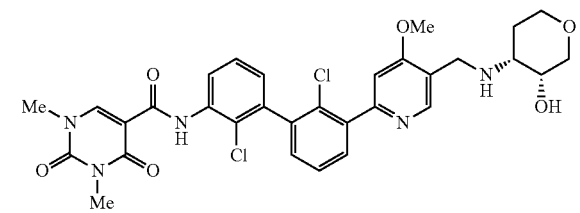 [SMILES: COc1cc(-c2cccc(-c3cccc(NC(=O)c4cn(C)c(=O)n(C)c4=O)c3Cl)c2Cl)ncc1CN[C@@H]1CCOC[C@@H]1O]

The compound was prepared from N-(2,2'-dichloro-3'-(5-formyl-4-methoxypyridin-2-yl)-[1,1'-biphenyl]-3-yl)-1,3-dimethyl-2,4-dioxo-1,2,3,4-tetrahydropyrimidine-5-carboxamide and (3R,4R)-4-aminotetrahydro-2H-pyran-3-ol hydrochloride using a procedure similar to step d in Example 89. The crude product was purified by preparative HPLC to give N-(2,2'-dichloro-3'-(5-((((3R,4R)-3-hydroxytetrahydro-2H-pyran-4-yl)amino)methyl)-4-methoxypyridin-2-yl)-[1,1'-biphenyl]-3-yl)-1,3-dimethyl-2,4-dioxo-1,2,3,4-tetrahydropyrimidine-5-carboxamide. $^1$H NMR (400 MHz, CD$_3$OD) δ 11.70 (s, 1H), 8.67 (s, 1H), 8.58 (s, 1H), 8.55 (d, J=8.4 Hz, 1H), 7.63-7.54 (m, 2H), 7.50 (s, 1H), 7.47 (d, J=7.6 Hz, 1H), 7.42 (dd, J=7.6, 7.6 Hz, 1H), 7.10 (d, J=7.6 Hz, 1H), 4.46-4.26 (m, 2H), 4.10 (s, 3H), 4.08-3.95 (m, 3H), 3.61-3.42 (m, 3H), 3.56 (s, 3H), 3.39 (s, 3H), 2.18-2.04 (m, 1H), 1.90-1.83 (m, 1H). MS: (ES) m/z calculated for C$_{31}$H$_{32}$Cl$_2$N$_5$O$_6$ [M+H]$^+$ 640.2. found 639.9.

Example 102: N-(2'-chloro-3'-(6-methoxy-5-((6-oxo-2,5-diazaspiro[3.4]octan-2-yl)methyl)pyridin-2-yl)-2-methyl-[1,1'-biphenyl]-3-yl)-1,3-dimethyl-2,4-dioxo-1,2,3,4-tetrahydropyrimidine-5-carboxamide

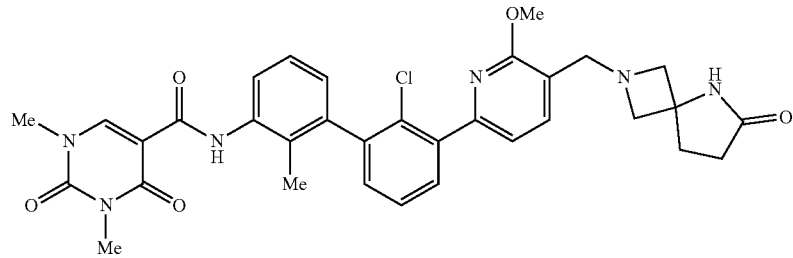 [SMILES: COc1nc(-c2cccc(-c3cccc(NC(=O)c4cn(C)c(=O)n(C)c4=O)c3C)c2Cl)ccc1CN1CC2(CCC(=O)N2)C1]

The compound was prepared from N-(2'-chloro-3'-(5-formyl-6-methoxypyridin-2-yl)-2-methyl-[1,1'-biphenyl]-3-yl)-1,3-dimethyl-2,4-dioxo-1,2,3,4-tetrahydropyrimidine-5-carboxamide and 2,5-diazaspiro[3.4]octan-6-one using a procedure similar to step d in Example 89. The product was purified by preparative HPLC to give N-(2'-chloro-3'-(6-methoxy-5-((6-oxo-2,5-diazaspiro[3.4]octan-2-yl)methyl)pyridin-2-yl)-2-methyl-[1,1'-biphenyl]-3-yl)-1,3-dimethyl-2,4-dioxo-1,2,3,4-tetrahydropyrimidine-5-carboxamide. $^1$H NMR (400 MHz, DMSO-$d_6$) δ: 11.05 (s, 1H), 8.75 (s, 1H), 8.24 (d, J=8.0 Hz, 1H), 8.18 (bs, 1H), 7.62 (d, J=7.6 Hz, 1H), 7.52 (dd, J=7.6, 7.6 Hz, 1H), 7.36 (d, J=7.4 Hz, 1H), 7.30 (dd, J=7.8, 7.8 Hz, 1H), 6.97 (d, J=7.5 Hz, 1H), 3.93 (s, 3H), 3.49 (s, 3H), 3.32 (s, 6H), 3.25 (s, 3H), 2.34-2.24 (m, 2H), 2.20-2.12 (m, 2H), 2.07 (s, 3H). MS: (ES) m/z calculated for $C_{33}H_{34}ClN_6O_5$ $[M+H]^+$ 629.2, found 629.0.

Biological Example: Enzyme-Linked Immunosorbent Assay—ELISA

96 Well plates were coated with 1 µg/mL of human PD-L1 (obtained from R&D) in PBS overnight at 4° C. The wells were then blocked with 2% BSA in PBS (W/V) with 0.05% TWEEN-20 for 1 hour at 37° C. The plates were washed 3 times with PBS/0.05% TWEEN-20 and the compounds were serial diluted (1:5) in dilution medium and added to the ELISA plates. Human PD-1 and biotin 0.3 µg/mL (ACRO Biosystems) were added and incubated for 1 hour at 37° C. then washed 3 times with PBS/0.05% TWEEN-20. A second block was performed with 2% BSA in PBS (W/V)/0.05% TWEEN-20 for 10 min at 37° C. and the plates were washed 3 times with PBS/0.05% TWEEN-20. Streptavidin-HRP was added for 1 hour at 37° C. then the plates were washed 3 times with PBS/0.05% TWEEN-20. TMB substrate was added and reacted for 20 min at 37° C. A stop solution (2 N aqueous $H_2SO_4$) was added. The absorbance was read at 450 nm using a micro-plate spectrophotometer. The results are shown in Table 1: $IC_{50}$ values are provided as follows: from 1000 to 10,000 nM (+); from 10 up to 1000 nM (++); less than 10 nM (+++).

TABLE 1

| Compound | Structure | ELISA $IC_{50}$ |
|---|---|---|
| 1.001 | 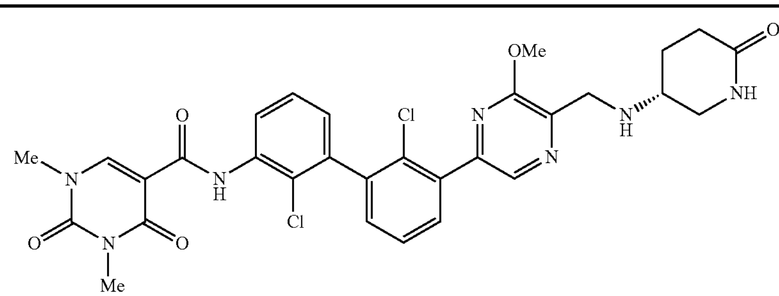 | +++ |
| 1.002 | 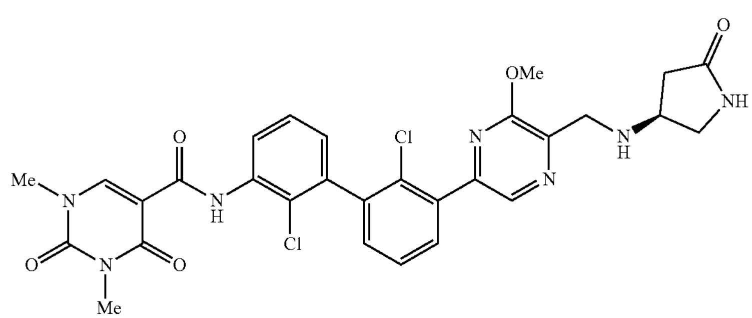 [SMILES: COc1nc(-c2cccc(-c3cccc(NC(=O)c4cn(C)c(=O)n(C)c4=O)c3Cl)c2Cl)cnc1CN[C@@H]1CNC(=O)C1] | +++ |

TABLE 1-continued

| Compound | Structure | ELISA IC$_{50}$ |
|---|---|---|
| 1.003 | 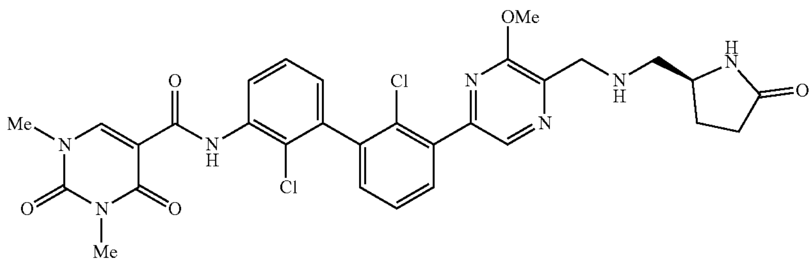 | +++ |
| 1.004 | 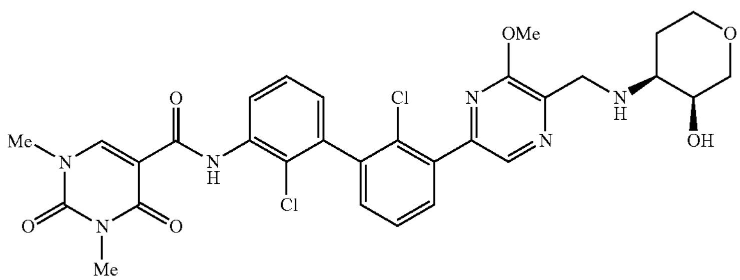 [SMILES: COc1nc(-c2cccc(-c3cccc(NC(=O)c4cn(C)c(=O)n(C)c4=O)c3Cl)c2Cl)cnc1CN[C@H]1CCOC[C@H]1O] | +++ |
| 1.005 | 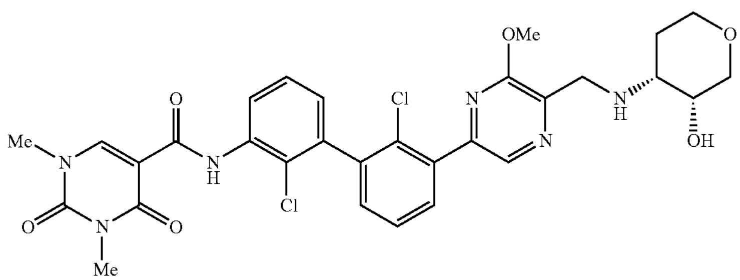 [SMILES: COc1nc(-c2cccc(-c3cccc(NC(=O)c4cn(C)c(=O)n(C)c4=O)c3Cl)c2Cl)cnc1CN[C@@H]1CCOC[C@@H]1O] | +++ |
| 1.006 | 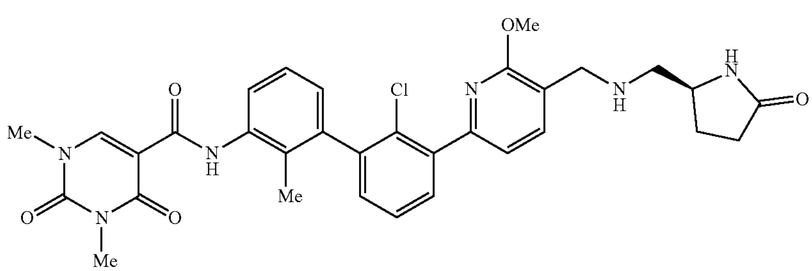 [SMILES: COc1nc(-c2cccc(-c3cccc(NC(=O)c4cn(C)c(=O)n(C)c4=O)c3C)c2Cl)ccc1CNC[C@@H]1CCC(=O)N1] | +++ |
| 1.007 | 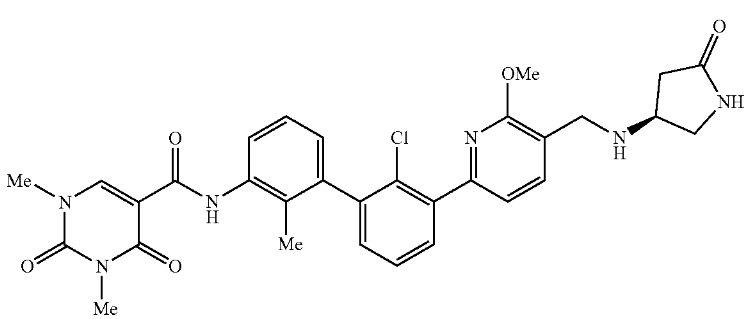 [SMILES: COc1nc(-c2cccc(-c3cccc(NC(=O)c4cn(C)c(=O)n(C)c4=O)c3C)c2Cl)ccc1CN[C@@H]1CNC(=O)C1] | +++ |

TABLE 1-continued

| Compound | Structure | ELISA IC$_{50}$ |
|---|---|---|
| 1.008 | 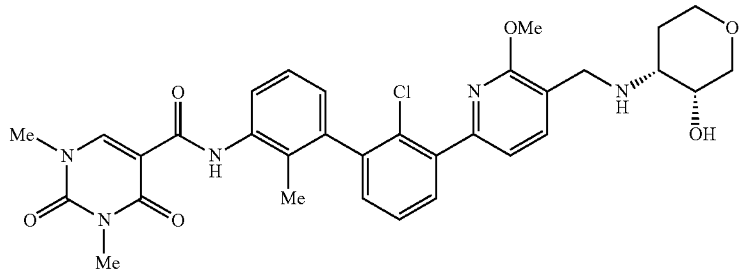 | +++ |
| 1.009 | 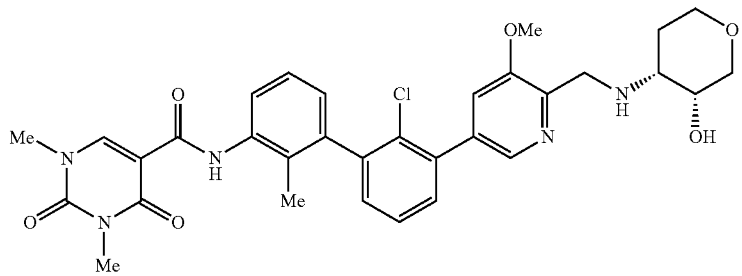 [SMILES: COc1cc(-c2cccc(-c3cccc(NC(=O)c4cn(C)c(=O)n(C)c4=O)c3C)c2Cl)cnc1CN[C@@H]1CCOC[C@@H]1O] | +++ |
| 1.010 | 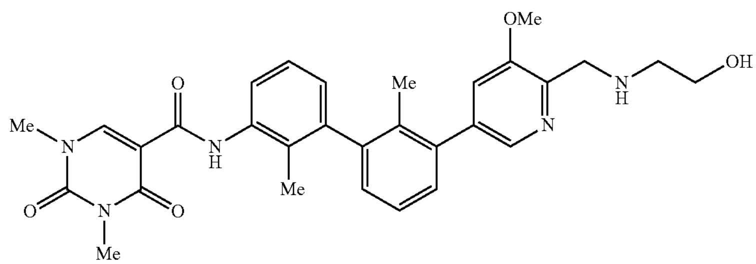 [SMILES: COc1cc(-c2cccc(-c3cccc(NC(=O)c4cn(C)c(=O)n(C)c4=O)c3C)c2C)cnc1CNCCO] | +++ |
| 1.011 | 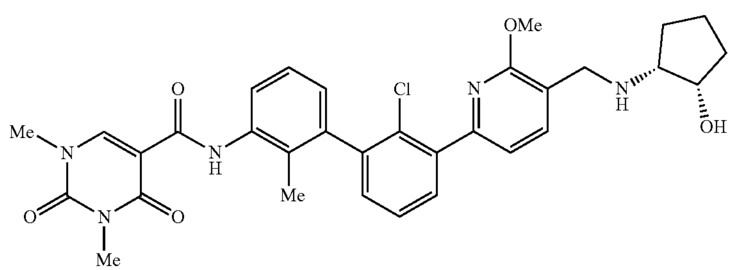 [SMILES: COc1nc(-c2cccc(-c3cccc(NC(=O)c4cn(C)c(=O)n(C)c4=O)c3C)c2Cl)ccc1CN[C@@H]1CCC[C@@H]1O] | +++ |
| 1.012 | 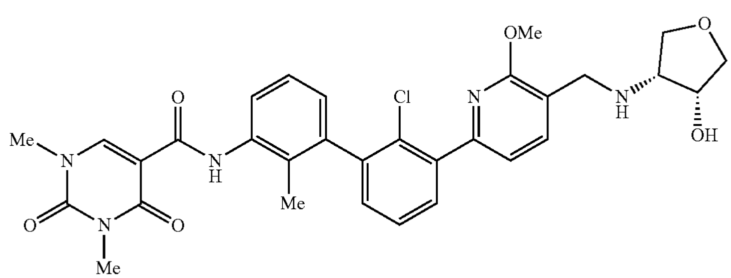 [SMILES: COc1nc(-c2cccc(-c3cccc(NC(=O)c4cn(C)c(=O)n(C)c4=O)c3C)c2Cl)ccc1CN[C@@H]1COC[C@@H]1O] | +++ |

TABLE 1-continued

| Compound | Structure | ELISA IC$_{50}$ |
|---|---|---|
| 1.013 | 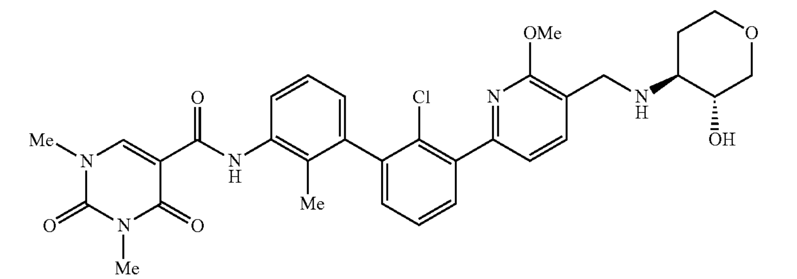 [SMILES: COc1nc(-c2cccc(-c3cccc(NC(=O)c4cn(C)c(=O)n(C)c4=O)c3C)c2Cl)ccc1CN[C@H]1CCOC[C@@H]1O] | +++ |
| 1.014 | 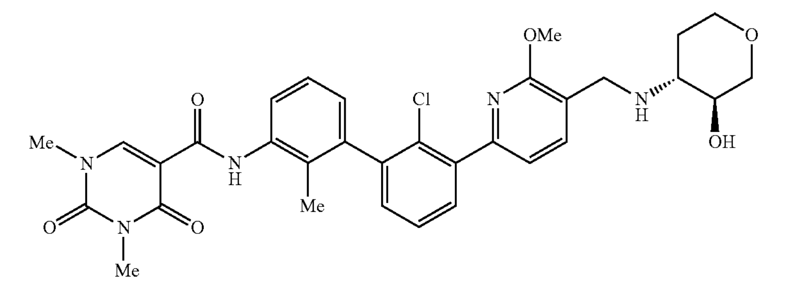 [SMILES: COc1nc(-c2cccc(-c3cccc(NC(=O)c4cn(C)c(=O)n(C)c4=O)c3C)c2Cl)ccc1CN[C@@H]1CCOC[C@H]1O] | +++ |
| 1.015 | 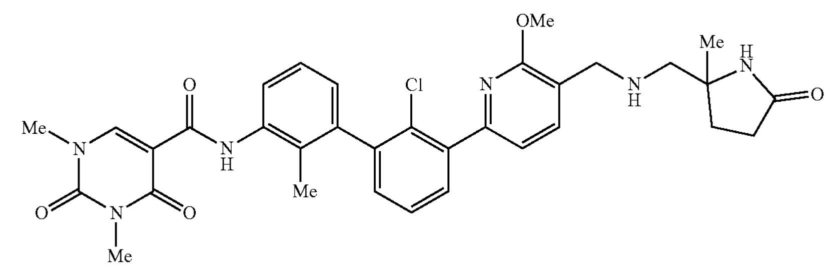 [SMILES: COc1nc(-c2cccc(-c3cccc(NC(=O)c4cn(C)c(=O)n(C)c4=O)c3C)c2Cl)ccc1CNCC1(C)CCC(=O)N1] | +++ |
| 1.016 | 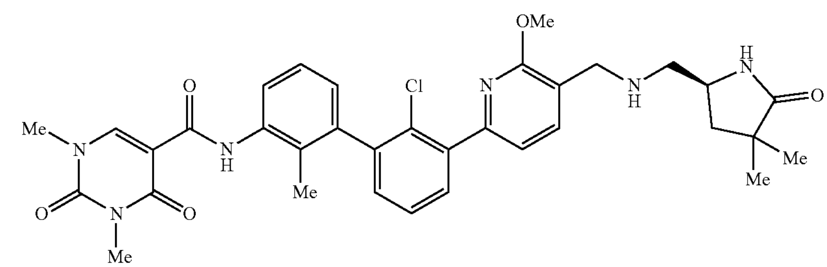 [SMILES: COc1nc(-c2cccc(-c3cccc(NC(=O)c4cn(C)c(=O)n(C)c4=O)c3C)c2Cl)ccc1CNC[C@@H]1CC(C)(C)C(=O)N1] | +++ |
| 1.017 | 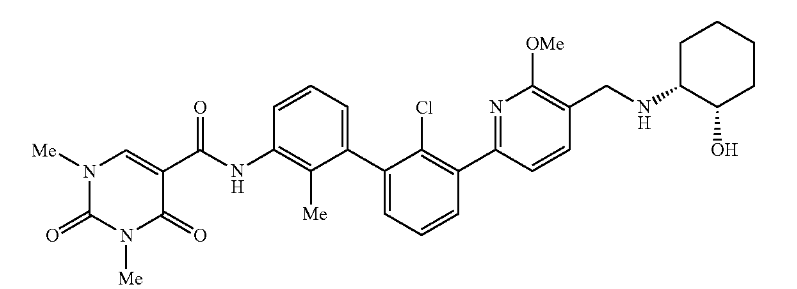 [SMILES: COc1nc(-c2cccc(-c3cccc(NC(=O)c4cn(C)c(=O)n(C)c4=O)c3C)c2Cl)ccc1CN[C@@H]1CCCC[C@@H]1O] | +++ |

TABLE 1-continued

| Compound | Structure | ELISA IC$_{50}$ |
|---|---|---|
| 1.018 | 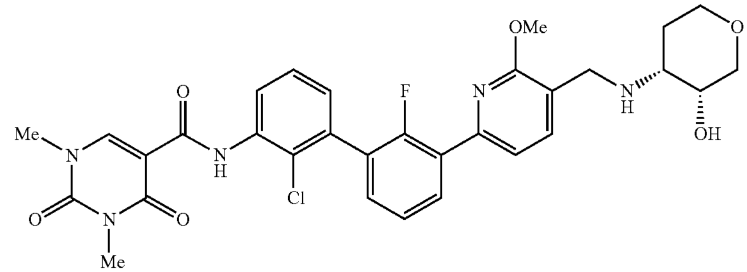 [SMILES: COc1nc(-c2cccc(-c3cccc(NC(=O)c4cn(C)c(=O)n(C)c4=O)c3Cl)c2F)ccc1CN[C@@H]1CCOC[C@@H]1O] | +++ |
| 1.019 | 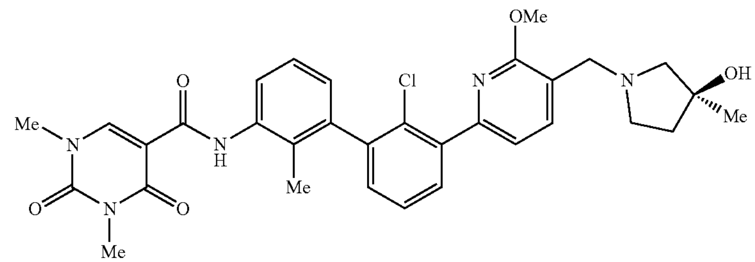 [SMILES: COc1nc(-c2cccc(-c3cccc(NC(=O)c4cn(C)c(=O)n(C)c4=O)c3C)c2Cl)ccc1CN1CC[C@](C)(O)C1] | +++ |
| 1.020 | 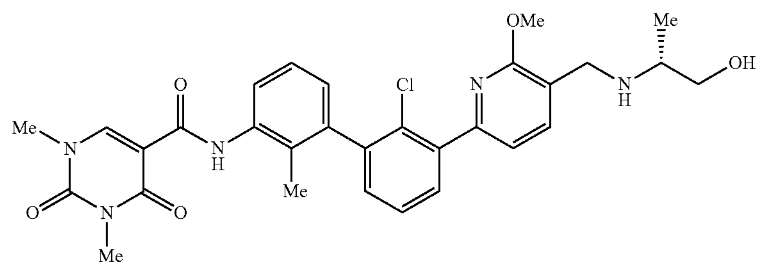 [SMILES: COc1nc(-c2cccc(-c3cccc(NC(=O)c4cn(C)c(=O)n(C)c4=O)c3C)c2Cl)ccc1CN[C@H](C)CO] | +++ |
| 1.021 | 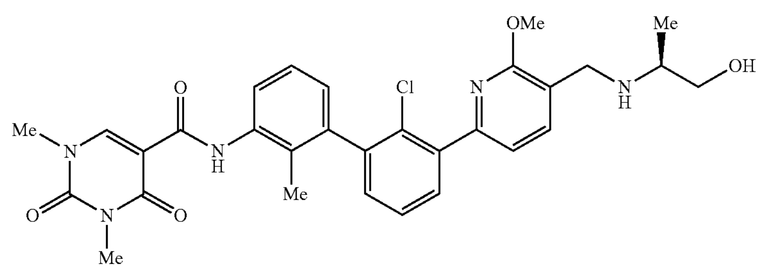 [SMILES: COc1nc(-c2cccc(-c3cccc(NC(=O)c4cn(C)c(=O)n(C)c4=O)c3C)c2Cl)ccc1CN[C@@H](C)CO] | +++ |
| 1.022 | 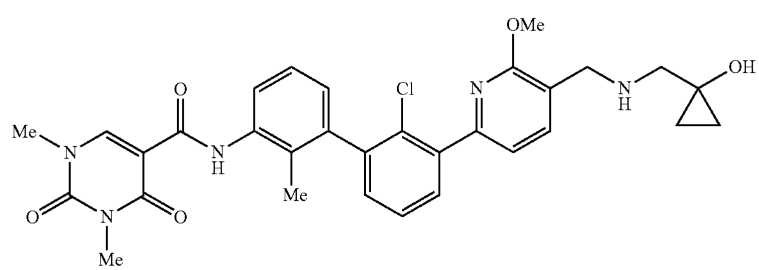 [SMILES: COc1nc(-c2cccc(-c3cccc(NC(=O)c4cn(C)c(=O)n(C)c4=O)c3C)c2Cl)ccc1CNCC1(O)CC1] | + |
| 1.023 | 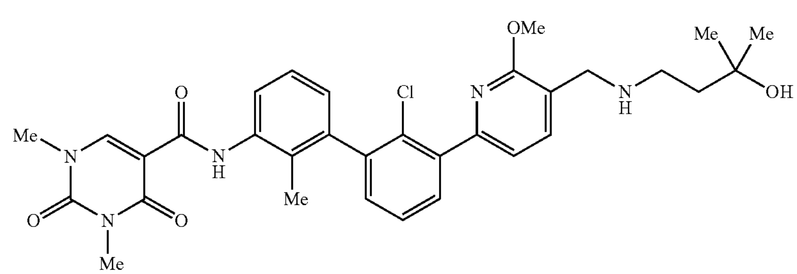 [SMILES: COc1nc(-c2cccc(-c3cccc(NC(=O)c4cn(C)c(=O)n(C)c4=O)c3C)c2Cl)ccc1CNCCC(C)(C)O] | +++ |

//

TABLE 1-continued

| Compound | Structure | ELISA IC$_{50}$ |
|---|---|---|
| 1.024 | 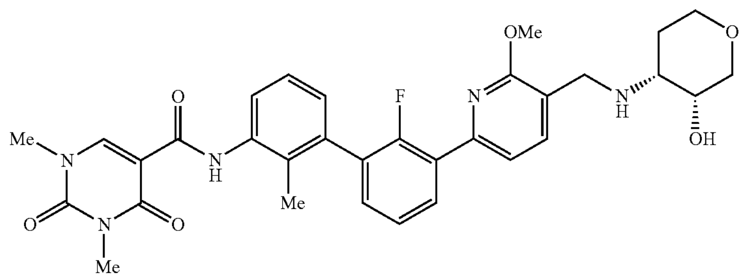 [SMILES: COc1nc(-c2cccc(-c3cccc(NC(=O)c4cn(C)c(=O)n(C)c4=O)c3C)c2F)ccc1CN[C@@H]1CCOC[C@@H]1O] | +++ |
| 1.025 | 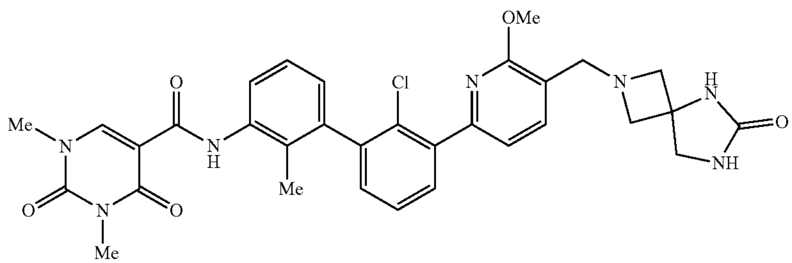 [SMILES: COc1nc(-c2cccc(-c3cccc(NC(=O)c4cn(C)c(=O)n(C)c4=O)c3C)c2Cl)ccc1CN1CC2(CNC(=O)N2)C1] | +++ |
| 1.026 | 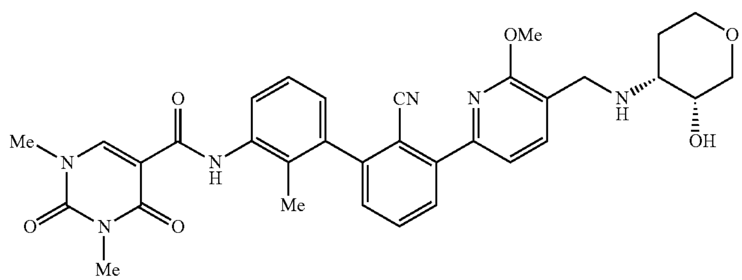 | +++ |
| 1.027 | 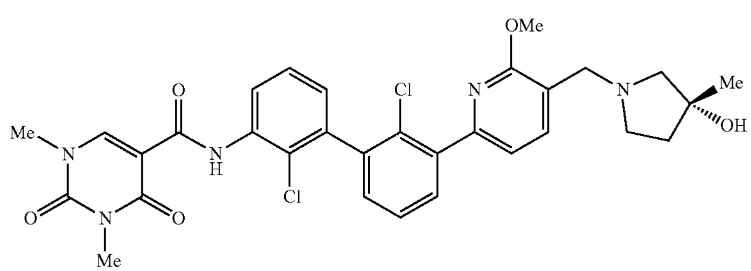 [SMILES: COc1nc(-c2cccc(-c3cccc(NC(=O)c4cn(C)c(=O)n(C)c4=O)c3Cl)c2Cl)ccc1CN1CC[C@@](C)(O)C1] | +++ |
| 1.028 | 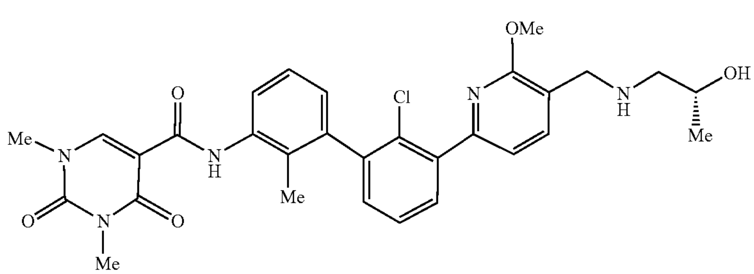 [SMILES: COc1nc(-c2cccc(-c3cccc(NC(=O)c4cn(C)c(=O)n(C)c4=O)c3C)c2Cl)ccc1CNC[C@@H](C)O] | +++ |

TABLE 1-continued

| Compound | Structure | ELISA IC$_{50}$ |
|---|---|---|
| 1.029 | 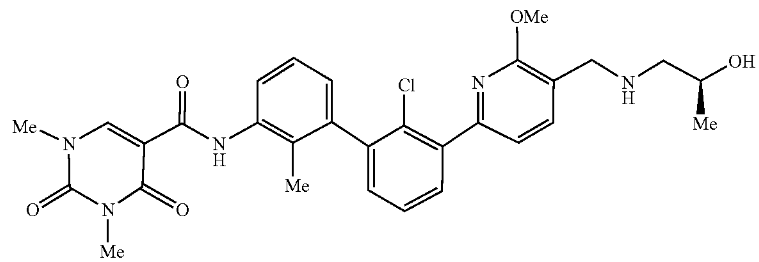 [SMILES: COc1nc(-c2cccc(-c3cccc(NC(=O)c4cn(C)c(=O)n(C)c4=O)c3C)c2Cl)ccc1CNC[C@H](C)O] | +++ |
| 1.030 | 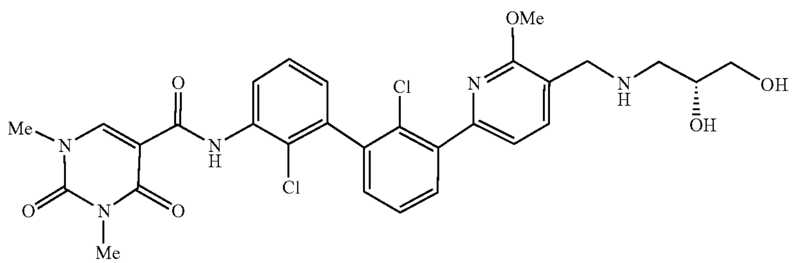 [SMILES: COc1nc(-c2cccc(-c3cccc(NC(=O)c4cn(C)c(=O)n(C)c4=O)c3Cl)c2Cl)ccc1CNC[C@@H](O)CO] | +++ |
| 1.031 | 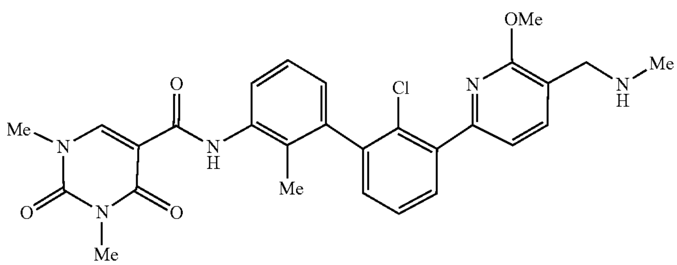 [SMILES: CNCc1ccc(-c2cccc(-c3cccc(NC(=O)c4cn(C)c(=O)n(C)c4=O)c3C)c2Cl)nc1OC] | +++ |
| 1.032 | 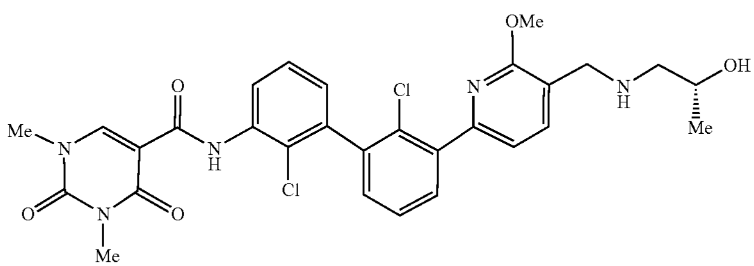 [SMILES: COc1nc(-c2cccc(-c3cccc(NC(=O)c4cn(C)c(=O)n(C)c4=O)c3Cl)c2Cl)ccc1CNC[C@@H](C)O] | +++ |
| 1.033 | 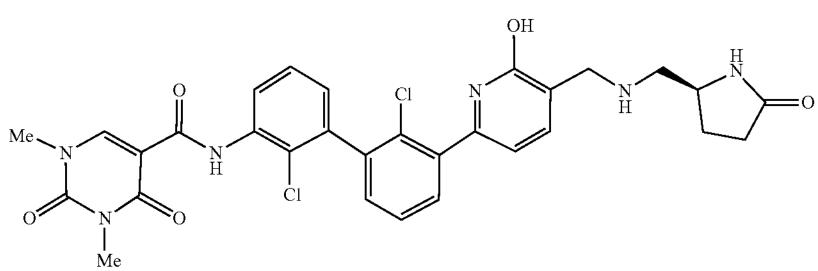 [SMILES: Cn1cc(C(=O)Nc2cccc(-c3cccc(-c4ccc(CNC[C@@H]5CCC(=O)N5)c(O)n4)c3Cl)c2Cl)c(=O)n(C)c1=O] | ++ |
| 1.034 | 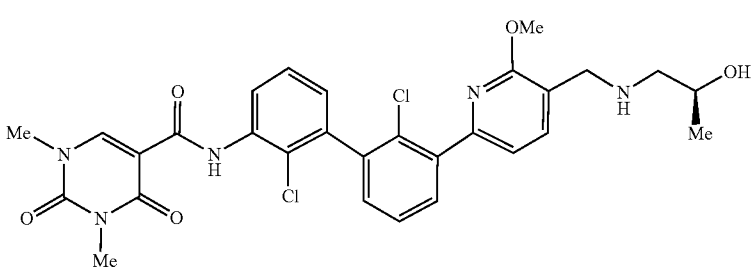 [SMILES: COc1nc(-c2cccc(-c3cccc(NC(=O)c4cn(C)c(=O)n(C)c4=O)c3Cl)c2Cl)ccc1CNC[C@H](C)O] | +++ |

TABLE 1-continued

| Compound | Structure | ELISA IC$_{50}$ |
|---|---|---|
| 1.035 | 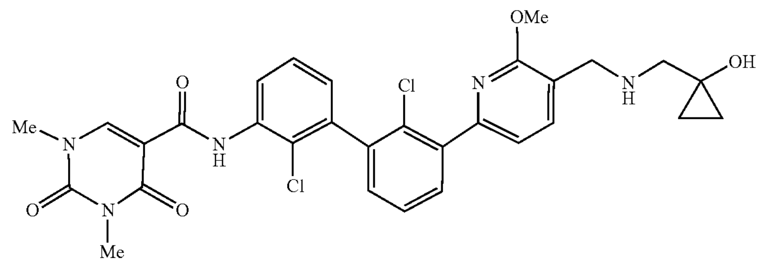 [SMILES: COc1nc(-c2cccc(-c3cccc(NC(=O)c4cn(C)c(=O)n(C)c4=O)c3Cl)c2Cl)ccc1CNCC1(O)CC1] | +++ |
| 1.036 | 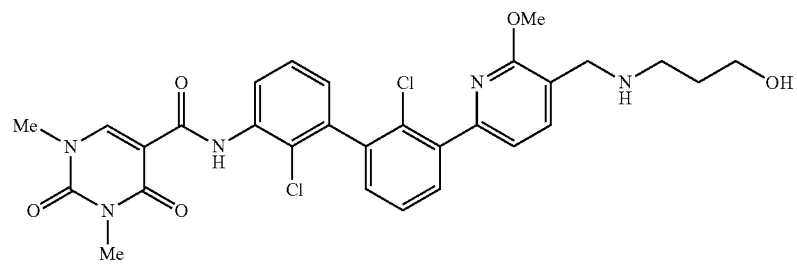 [SMILES: COc1nc(-c2cccc(-c3cccc(NC(=O)c4cn(C)c(=O)n(C)c4=O)c3Cl)c2Cl)ccc1CNCCCO] | +++ |
| 1.037 | 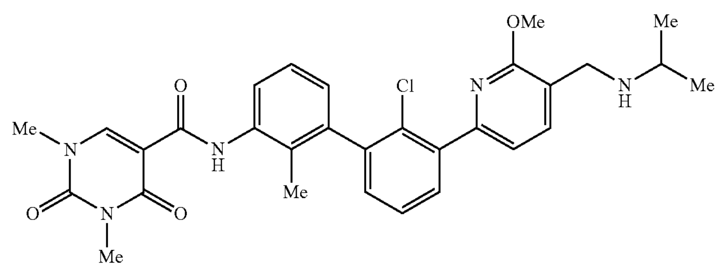 [SMILES: COc1nc(-c2cccc(-c3cccc(NC(=O)c4cn(C)c(=O)n(C)c4=O)c3C)c2Cl)ccc1CNC(C)C] | +++ |
| 1.038 | 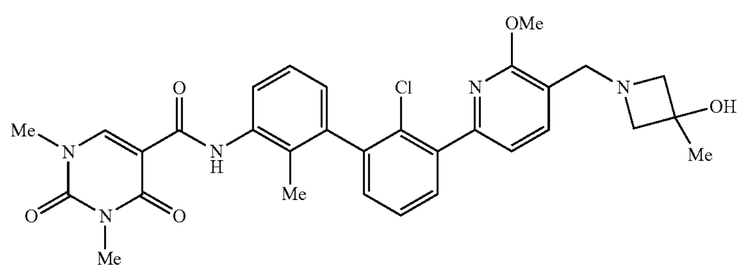 [SMILES: COc1nc(-c2cccc(-c3cccc(NC(=O)c4cn(C)c(=O)n(C)c4=O)c3C)c2Cl)ccc1CN1CC(C)(O)C1] | +++ |
| 1.039 | 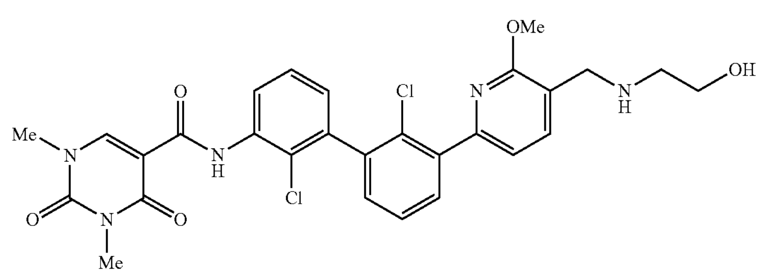 [SMILES: COc1nc(-c2cccc(-c3cccc(NC(=O)c4cn(C)c(=O)n(C)c4=O)c3Cl)c2Cl)ccc1CNCCO] | +++ |
| 1.040 | 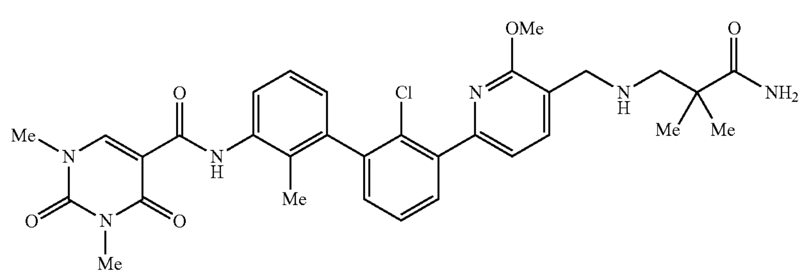 [SMILES: COc1nc(-c2cccc(-c3cccc(NC(=O)c4cn(C)c(=O)n(C)c4=O)c3C)c2Cl)ccc1CNCC(C)(C)C(N)=O] | +++ |

TABLE 1-continued

| Compound | Structure | ELISA IC$_{50}$ |
|---|---|---|
| 1.041 | 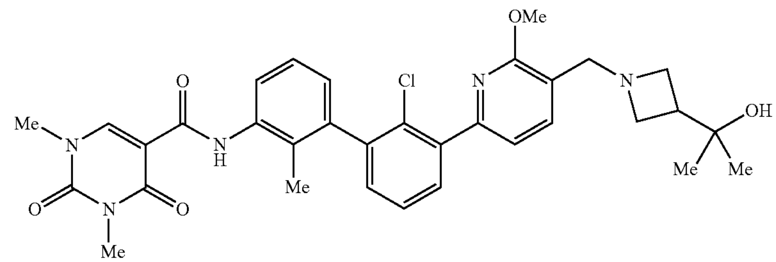 [SMILES: COc1nc(-c2cccc(-c3cccc(NC(=O)c4cn(C)c(=O)n(C)c4=O)c3C)c2Cl)ccc1CN1CC(C(C)(C)O)C1] | +++ |
| 1.042 | 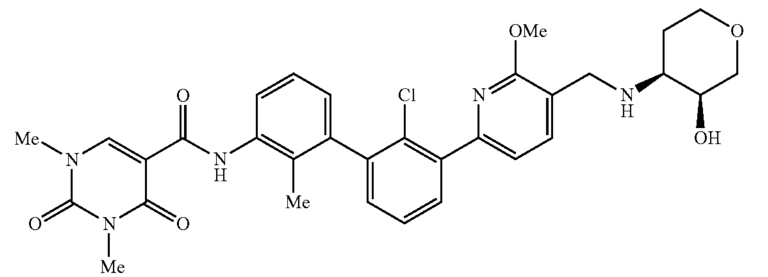 [SMILES: COc1nc(-c2cccc(-c3cccc(NC(=O)c4cn(C)c(=O)n(C)c4=O)c3C)c2Cl)ccc1CN[C@H]1CCOC[C@H]1O] | +++ |
| 1.043 | 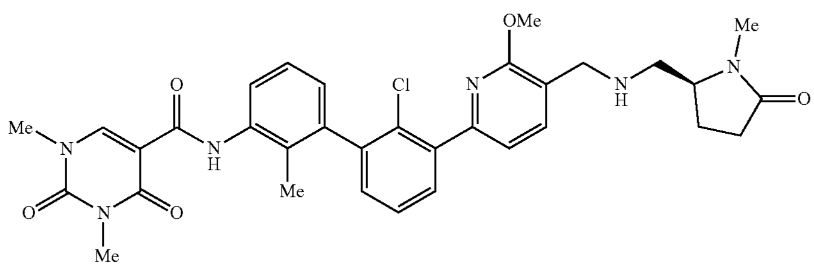 [SMILES: COc1nc(-c2cccc(-c3cccc(NC(=O)c4cn(C)c(=O)n(C)c4=O)c3C)c2Cl)ccc1CNC[C@@H]1CCC(=O)N1C] | +++ |
| 1.044 | 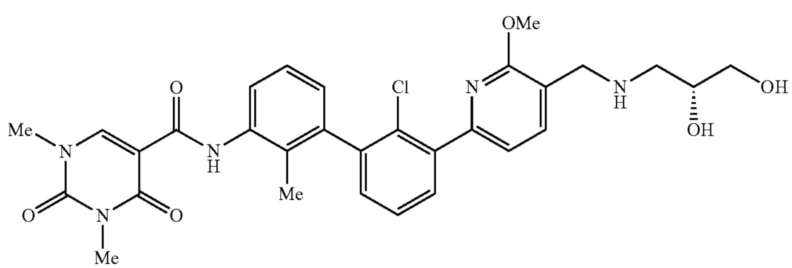 | +++ |
| 1.045 | 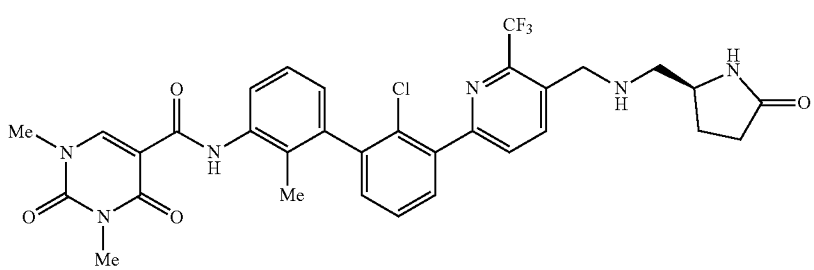 [SMILES: Cc1c(NC(=O)c2cn(C)c(=O)n(C)c2=O)cccc1-c1cccc(-c2ccc(CNC[C@@H]3CCC(=O)N3)c(C(F)(F)F)n2)c1Cl] | +++ |
| 1.046 | 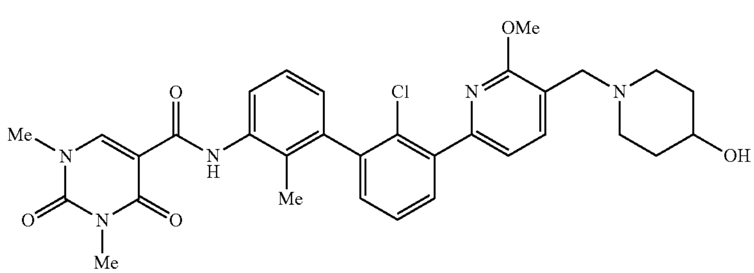 [SMILES: COc1nc(-c2cccc(-c3cccc(NC(=O)c4cn(C)c(=O)n(C)c4=O)c3C)c2Cl)ccc1CN1CCC(O)CC1] | +++ |

TABLE 1-continued

| Compound | Structure | ELISA IC$_{50}$ |
|---|---|---|
| 1.047 | 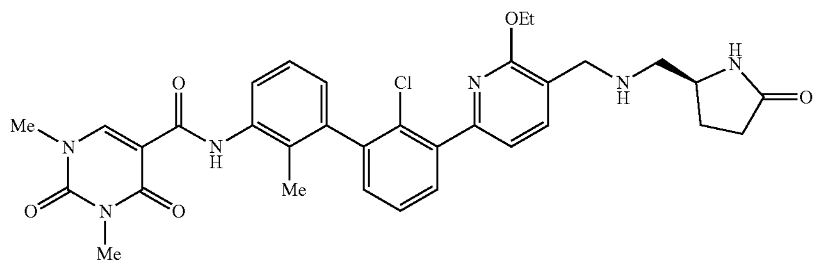 [SMILES: CCOc1nc(-c2cccc(-c3cccc(NC(=O)c4cn(C)c(=O)n(C)c4=O)c3C)c2Cl)ccc1CNC[C@@H]1CCC(=O)N1] | +++ |
| 1.048 | 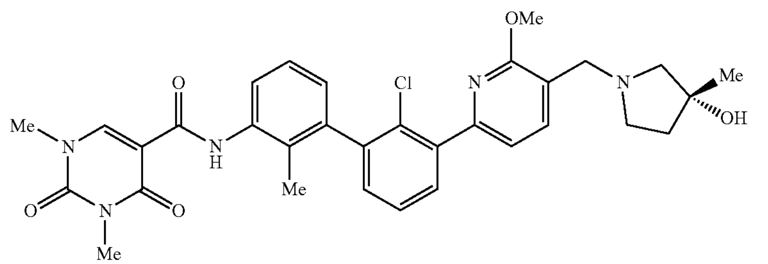 [SMILES: COc1nc(-c2cccc(-c3cccc(NC(=O)c4cn(C)c(=O)n(C)c4=O)c3C)c2Cl)ccc1CN1CC[C@@](C)(O)C1] | +++ |
| 1.049 | 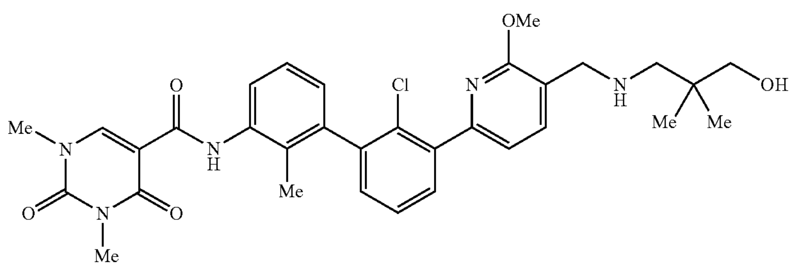 [SMILES: COc1nc(-c2cccc(-c3cccc(NC(=O)c4cn(C)c(=O)n(C)c4=O)c3C)c2Cl)ccc1CNCC(C)(C)CO] | +++ |
| 1.050 | 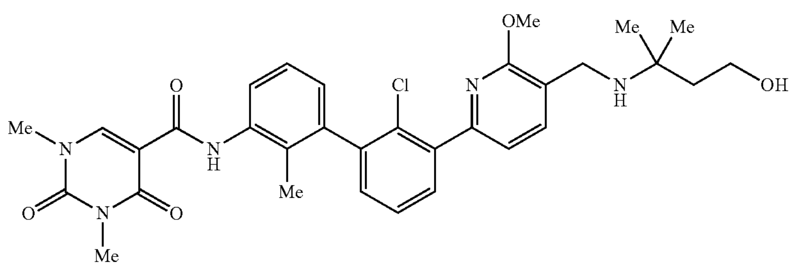 [SMILES: COc1nc(-c2cccc(-c3cccc(NC(=O)c4cn(C)c(=O)n(C)c4=O)c3C)c2Cl)ccc1CNC(C)(C)CCO] | +++ |
| 1.051 | 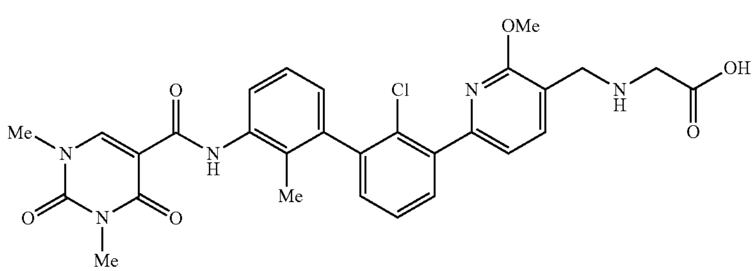 [SMILES: COc1nc(-c2cccc(-c3cccc(NC(=O)c4cn(C)c(=O)n(C)c4=O)c3C)c2Cl)ccc1CNCC(=O)O] | +++ |
| 1.052 | 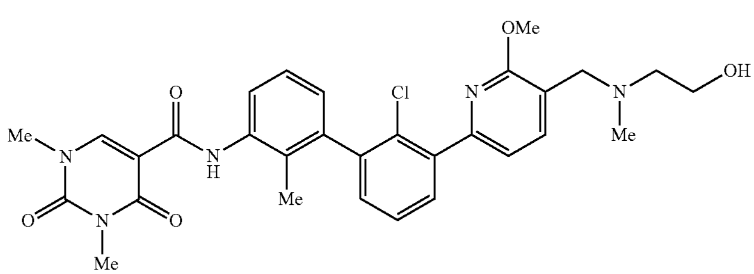 [SMILES: COc1nc(-c2cccc(-c3cccc(NC(=O)c4cn(C)c(=O)n(C)c4=O)c3C)c2Cl)ccc1CN(C)CCO] | +++ |

TABLE 1-continued

| Compound | Structure | ELISA IC$_{50}$ |
|---|---|---|
| 1.053 | 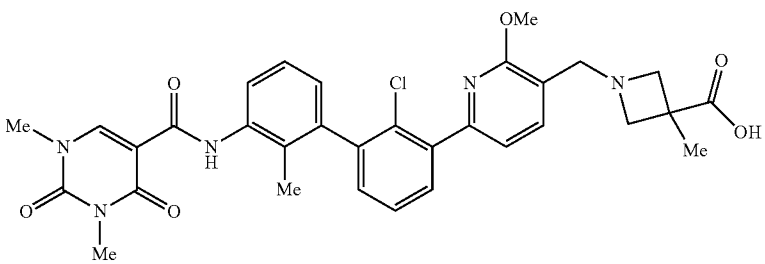 [SMILES: COc1nc(-c2cccc(-c3cccc(NC(=O)c4cn(C)c(=O)n(C)c4=O)c3C)c2Cl)ccc1CN1CC(C)(C(=O)O)C1] | +++ |
| 1.054 | 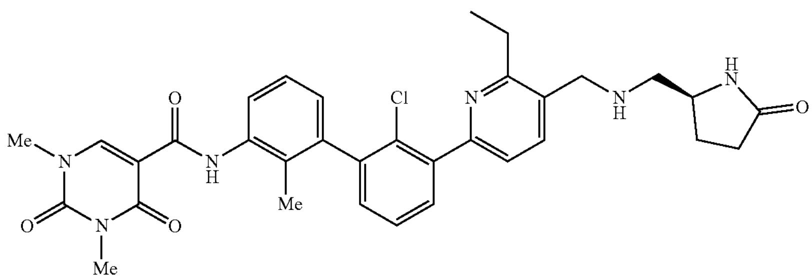 | +++ |
| 1.055 | 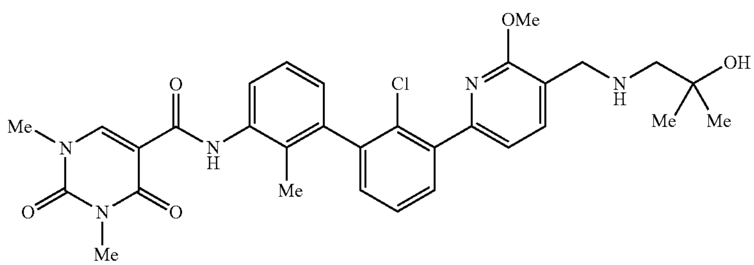 [SMILES: COc1nc(-c2cccc(-c3cccc(NC(=O)c4cn(C)c(=O)n(C)c4=O)c3C)c2Cl)ccc1CNCC(C)(C)O] | +++ |
| 1.056 | 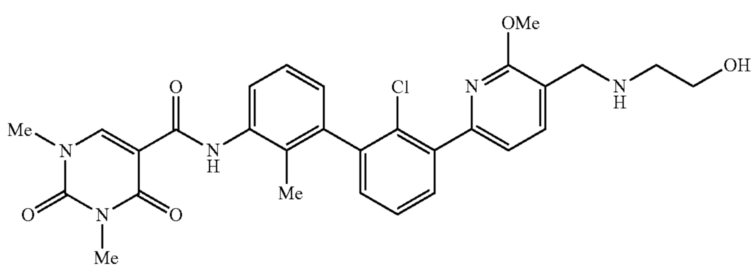 | +++ |
| 1.057 | 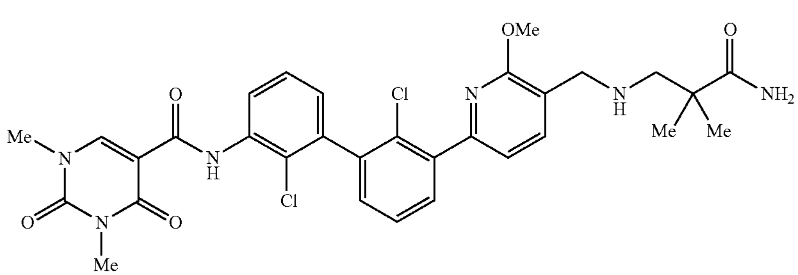 [SMILES: COc1nc(-c2cccc(-c3cccc(NC(=O)c4cn(C)c(=O)n(C)c4=O)c3Cl)c2Cl)ccc1CNCC(C)(C)C(N)=O] | +++ |

TABLE 1-continued

| Compound | Structure | ELISA IC$_{50}$ |
|---|---|---|
| 1.058 | 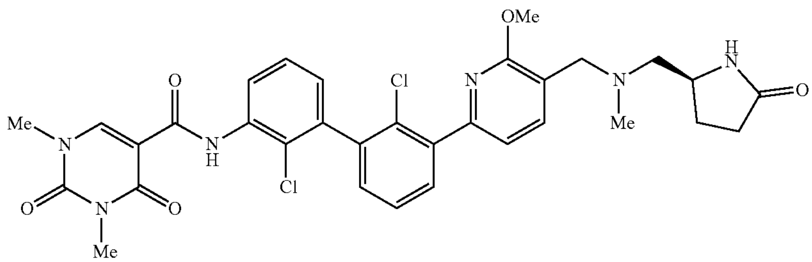 [SMILES: COc1nc(-c2cccc(-c3cccc(NC(=O)c4cn(C)c(=O)n(C)c4=O)c3Cl)c2Cl)ccc1CN(C)C[C@@H]1CCC(=O)N1] | ++ |
| 1.059 | 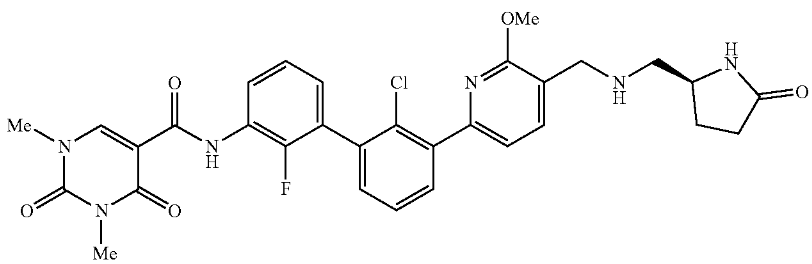 [SMILES: COc1nc(-c2cccc(-c3cccc(NC(=O)c4cn(C)c(=O)n(C)c4=O)c3F)c2Cl)ccc1CNC[C@@H]1CCC(=O)N1] | +++ |
| 1.060 | 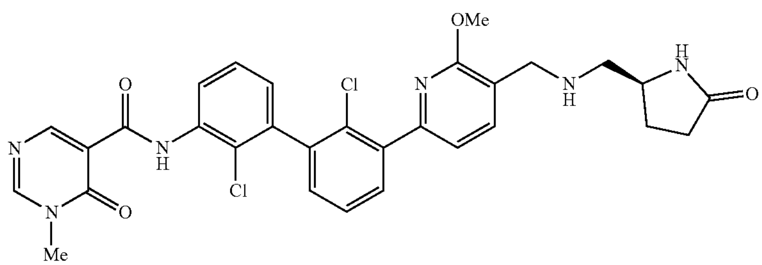 [SMILES: COc1nc(-c2cccc(-c3cccc(NC(=O)c4cncn(C)c4=O)c3Cl)c2Cl)ccc1CNC[C@@H]1CCC(=O)N1] | +++ |
| 1.061 | 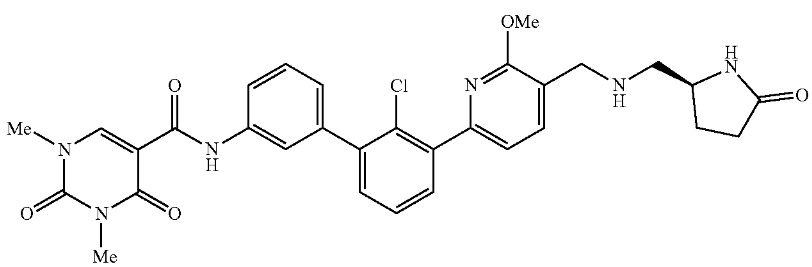 [SMILES: COc1nc(-c2cccc(-c3cccc(NC(=O)c4cn(C)c(=O)n(C)c4=O)c3)c2Cl)ccc1CNC[C@@H]1CCC(=O)N1] | +++ |
| 1.062 | 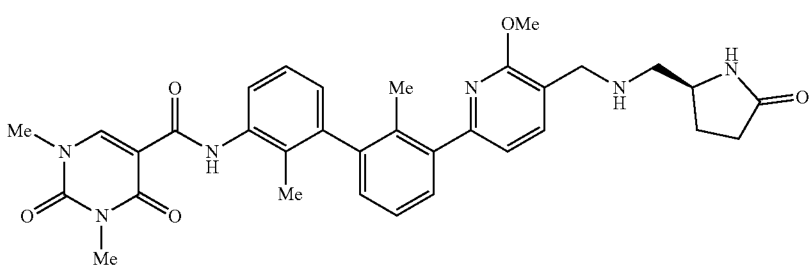 | +++ |
| 1.063 | 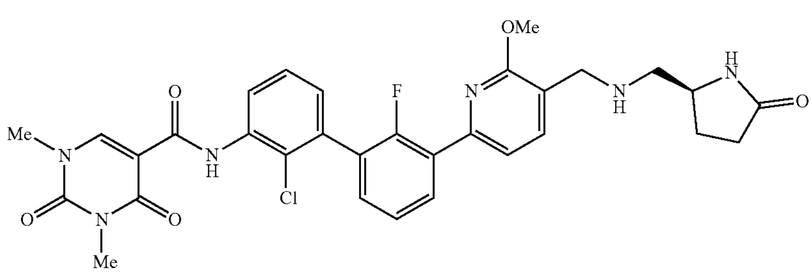 [SMILES: COc1nc(-c2cccc(-c3cccc(NC(=O)c4cn(C)c(=O)n(C)c4=O)c3Cl)c2F)ccc1CNC[C@@H]1CCC(=O)N1] | +++ |

TABLE 1-continued

| Compound | Structure | ELISA IC$_{50}$ |
|---|---|---|
| 1.064 | 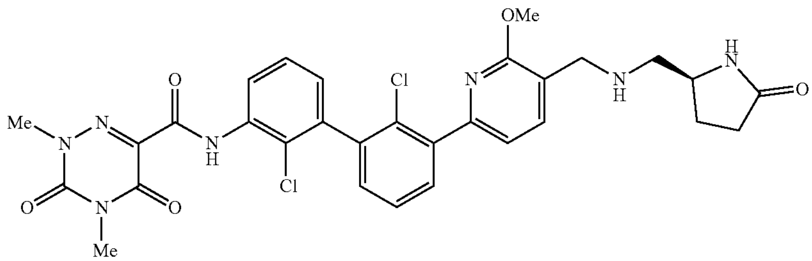 [SMILES: COc1nc(-c2cccc(-c3cccc(NC(=O)c4nn(C)c(=O)n(C)c4=O)c3Cl)c2Cl)ccc1CNC[C@@H]1CCC(=O)N1] | +++ |
| 1.065 | 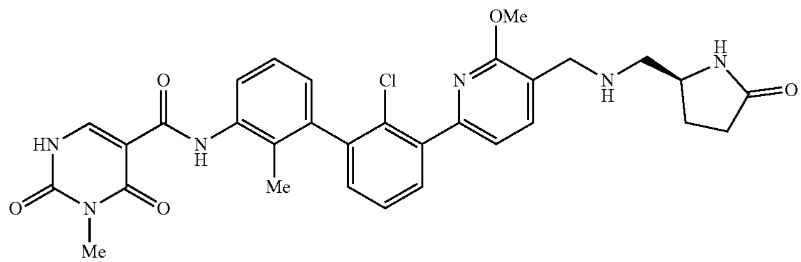 [SMILES: COc1nc(-c2cccc(-c3cccc(NC(=O)c4c[nH]c(=O)n(C)c4=O)c3C)c2Cl)ccc1CNC[C@@H]1CCC(=O)N1] | +++ |
| 1.066 | 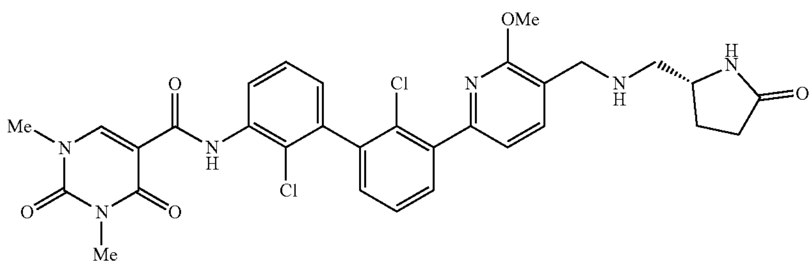 [SMILES: COc1nc(-c2cccc(-c3cccc(NC(=O)c4cn(C)c(=O)n(C)c4=O)c3Cl)c2Cl)ccc1CNC[C@H]1CCC(=O)N1] | +++ |
| 1.067 | 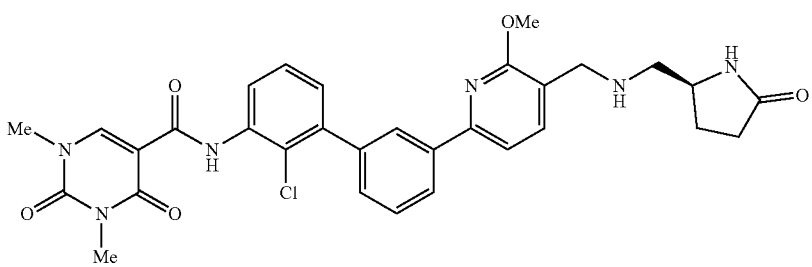 [SMILES: COc1nc(-c2cccc(-c3cccc(NC(=O)c4cn(C)c(=O)n(C)c4=O)c3Cl)c2)ccc1CNC[C@@H]1CCC(=O)N1] | +++ |
| 1.068 | 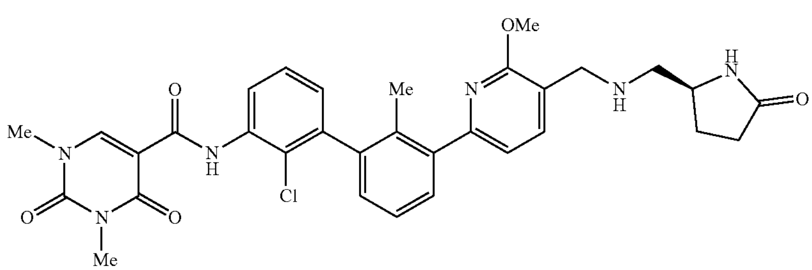 | +++ |
| 1.069 | 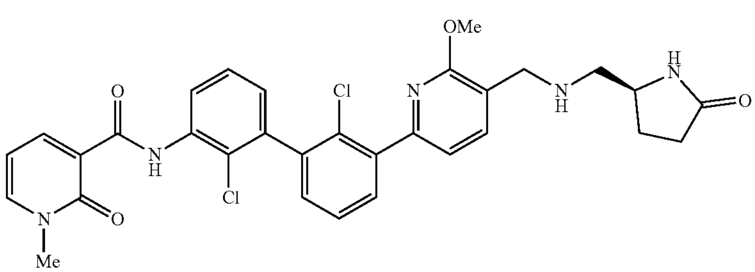 [SMILES: COc1nc(-c2cccc(-c3cccc(NC(=O)c4cccn(C)c4=O)c3Cl)c2Cl)ccc1CNC[C@@H]1CCC(=O)N1] | +++ |

TABLE 1-continued

| Compound | Structure | ELISA IC$_{50}$ |
|---|---|---|
| 1.070 | 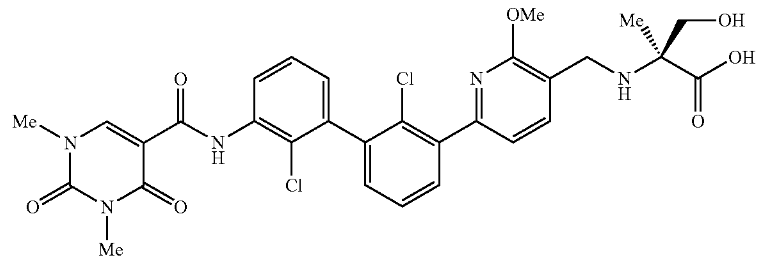 [SMILES: COc1nc(-c2cccc(-c3cccc(NC(=O)c4cn(C)c(=O)n(C)c4=O)c3Cl)c2Cl)ccc1CN[C@@](C)(CO)C(=O)O] | +++ |
| 1.071 | 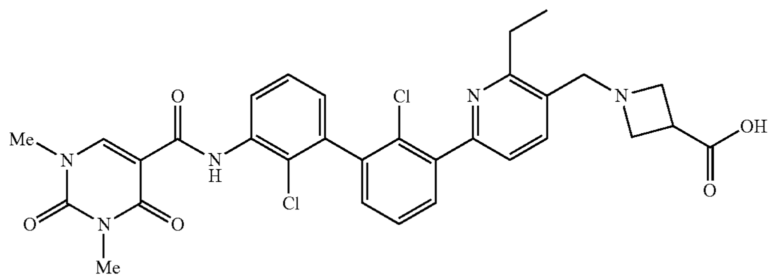 [SMILES: CCc1nc(-c2cccc(-c3cccc(NC(=O)c4cn(C)c(=O)n(C)c4=O)c3Cl)c2Cl)ccc1CN1CC(C(=O)O)C1] | +++ |
| 1.072 | 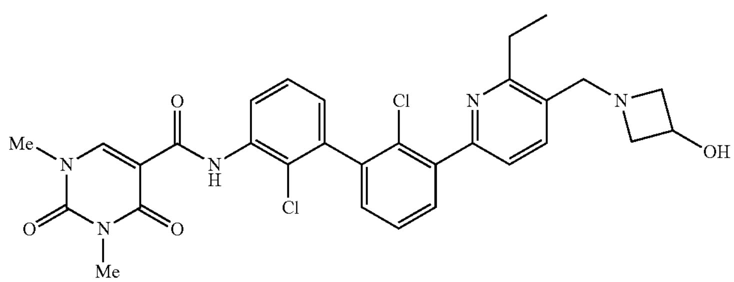 [SMILES: CCc1nc(-c2cccc(-c3cccc(NC(=O)c4cn(C)c(=O)n(C)c4=O)c3Cl)c2Cl)ccc1CN1CC(O)C1] | ++ |
| 1.073 | 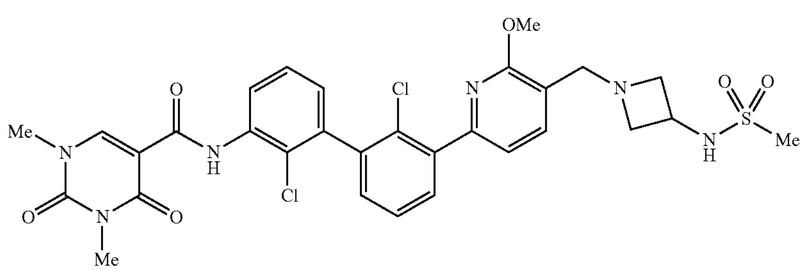 [SMILES: COc1nc(-c2cccc(-c3cccc(NC(=O)c4cn(C)c(=O)n(C)c4=O)c3Cl)c2Cl)ccc1CN1CC(NS(C)(=O)=O)C1] | +++ |
| 1.074 | 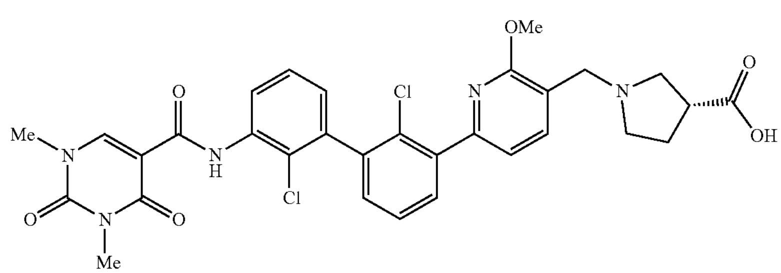 [SMILES: COc1nc(-c2cccc(-c3cccc(NC(=O)c4cn(C)c(=O)n(C)c4=O)c3Cl)c2Cl)ccc1CN1CC[C@@H](C(=O)O)C1] | +++ |

TABLE 1-continued

| Compound | Structure | ELISA IC$_{50}$ |
|---|---|---|
| 1.075 | 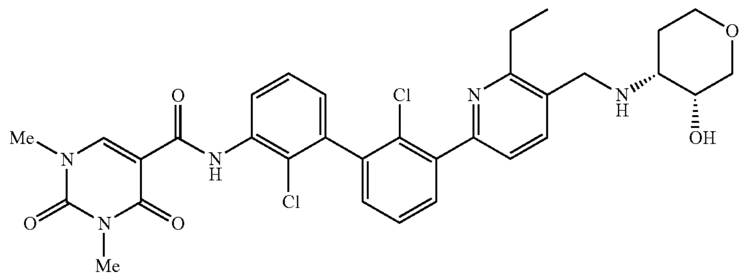 [SMILES: CCc1nc(-c2cccc(-c3cccc(NC(=O)c4cn(C)c(=O)n(C)c4=O)c3Cl)c2Cl)ccc1CN[C@@H]1CCOC[C@@H]1O] | +++ |
| 1.076 | 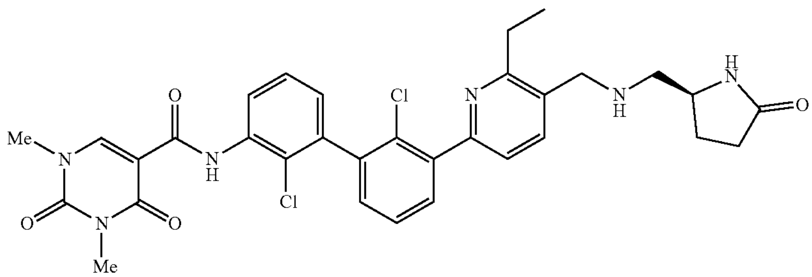 [SMILES: CCc1nc(-c2cccc(-c3cccc(NC(=O)c4cn(C)c(=O)n(C)c4=O)c3Cl)c2Cl)ccc1CNC[C@@H]1CCC(=O)N1] | +++ |
| 1.077 | 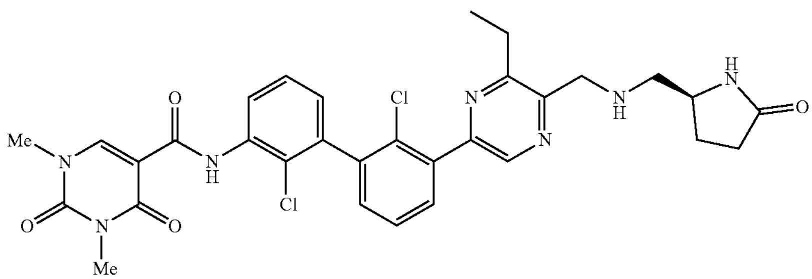 [SMILES: CCc1nc(-c2cccc(-c3cccc(NC(=O)c4cn(C)c(=O)n(C)c4=O)c3Cl)c2Cl)cnc1CNC[C@@H]1CCC(=O)N1] | +++ |
| 1.078 | 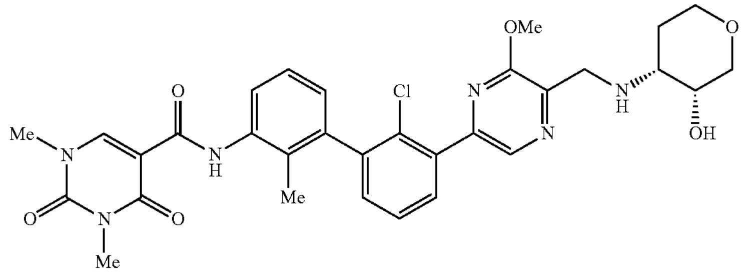 [SMILES: COc1nc(-c2cccc(-c3cccc(NC(=O)c4cn(C)c(=O)n(C)c4=O)c3C)c2Cl)cnc1CN[C@@H]1CCOC[C@@H]1O] | +++ |
| 1.079 | 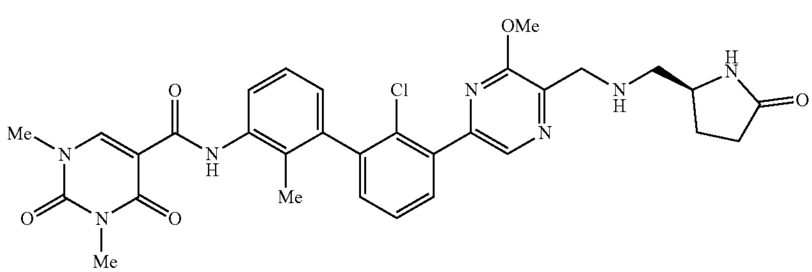 [SMILES: COc1nc(-c2cccc(-c3cccc(NC(=O)c4cn(C)c(=O)n(C)c4=O)c3C)c2Cl)cnc1CNC[C@@H]1CCC(=O)N1] | +++ |

TABLE 1-continued

| Compound | Structure | ELISA IC$_{50}$ |
|---|---|---|
| 1.080 | 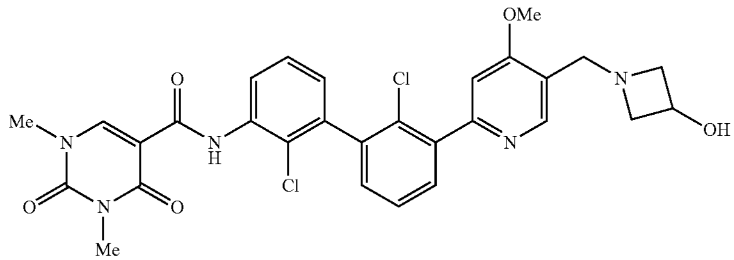 [SMILES: COc1cc(-c2cccc(-c3cccc(NC(=O)c4cn(C)c(=O)n(C)c4=O)c3Cl)c2Cl)ncc1CN1CC(O)C1] | ++ |
| 1.081 | 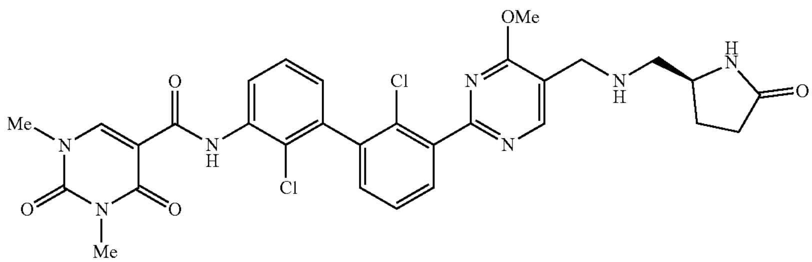 | +++ |
| 1.082 | 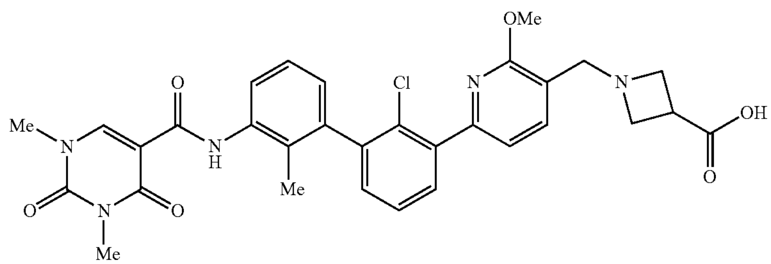 [SMILES: COc1nc(-c2cccc(-c3cccc(NC(=O)c4cn(C)c(=O)n(C)c4=O)c3C)c2Cl)ccc1CN1CC(C(=O)O)C1] | +++ |
| 1.083 | 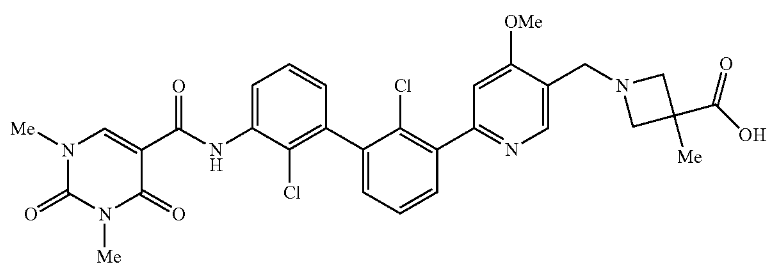 [SMILES: COc1cc(-c2cccc(-c3cccc(NC(=O)c4cn(C)c(=O)n(C)c4=O)c3Cl)c2Cl)ncc1CN1CC(C)(C(=O)O)C1] | +++ |
| 1.084 | 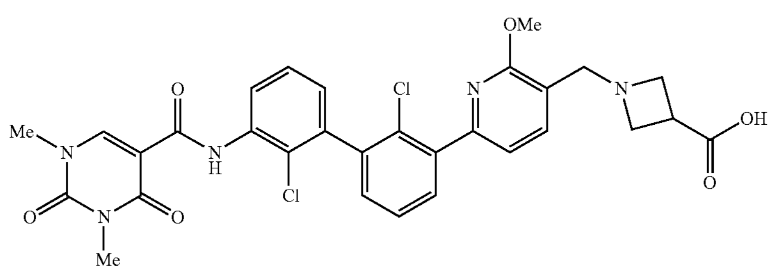 [SMILES: COc1nc(-c2cccc(-c3cccc(NC(=O)c4cn(C)c(=O)n(C)c4=O)c3Cl)c2Cl)ccc1CN1CC(C(=O)O)C1] | +++ |
| 1.085 | 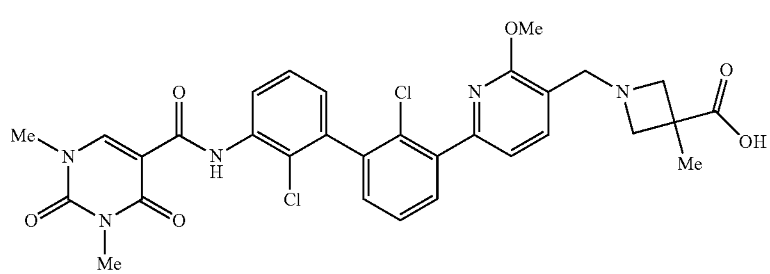 [SMILES: COc1nc(-c2cccc(-c3cccc(NC(=O)c4cn(C)c(=O)n(C)c4=O)c3Cl)c2Cl)ccc1CN1CC(C)(C(=O)O)C1] | +++ |

TABLE 1-continued

| Compound | Structure | ELISA IC$_{50}$ |
|---|---|---|
| 1.086 | 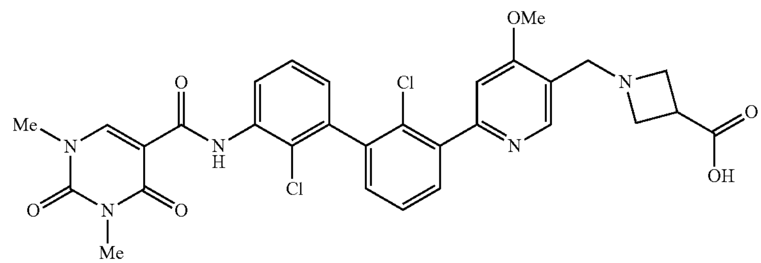 [SMILES: COc1cc(-c2cccc(-c3cccc(NC(=O)c4cn(C)c(=O)n(C)c4=O)c3Cl)c2Cl)ncc1CN1CC(C(=O)O)C1] | +++ |
| 1.087 | 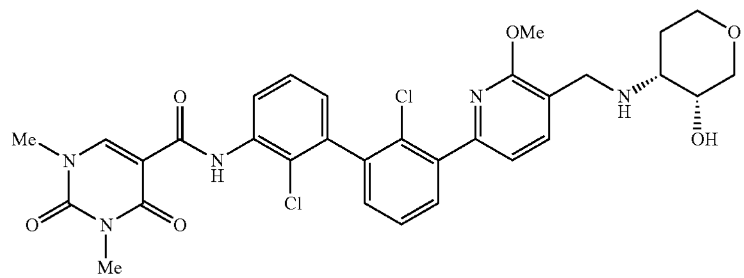 [SMILES: COc1nc(-c2cccc(-c3cccc(NC(=O)c4cn(C)c(=O)n(C)c4=O)c3Cl)c2Cl)ccc1CN[C@@H]1CCOC[C@@H]1O] | +++ |
| 1.088 | 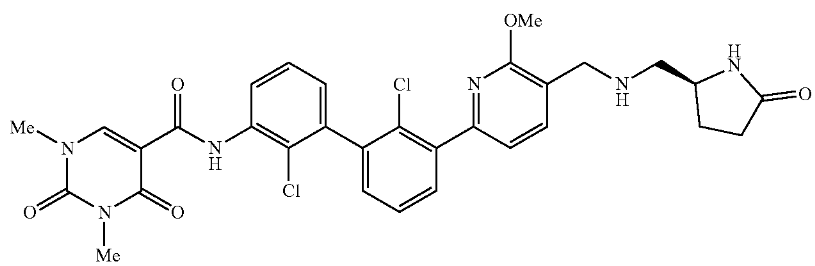 [SMILES: COc1nc(-c2cccc(-c3cccc(NC(=O)c4cn(C)c(=O)n(C)c4=O)c3Cl)c2Cl)ccc1CNC[C@@H]1CCC(=O)N1] | +++ |
| 1.089 | 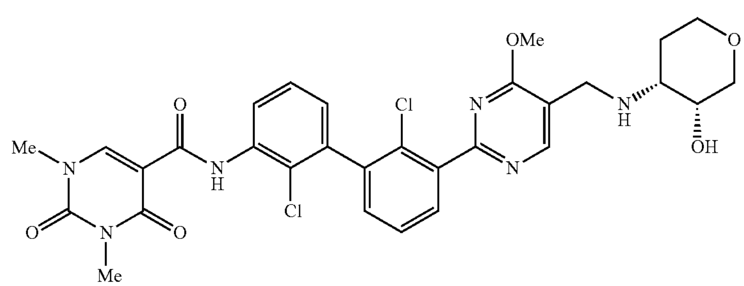 [SMILES: COc1nc(-c2cccc(-c3cccc(NC(=O)c4cn(C)c(=O)n(C)c4=O)c3Cl)c2Cl)ncc1CN[C@@H]1CCOC[C@@H]1O] | +++ |
| 1.090 | 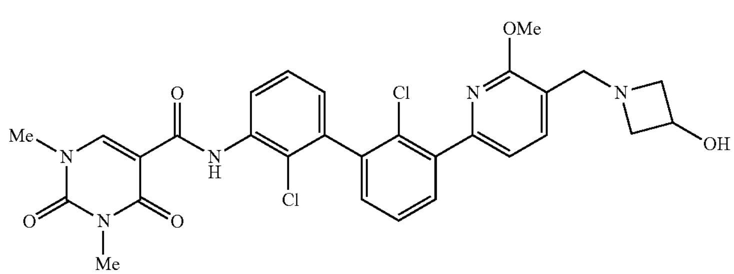 [SMILES: COc1nc(-c2cccc(-c3cccc(NC(=O)c4cn(C)c(=O)n(C)c4=O)c3Cl)c2Cl)ccc1CN1CC(O)C1] | +++ |

TABLE 1-continued

| Compound | Structure | ELISA IC$_{50}$ |
|---|---|---|
| 1.091 | 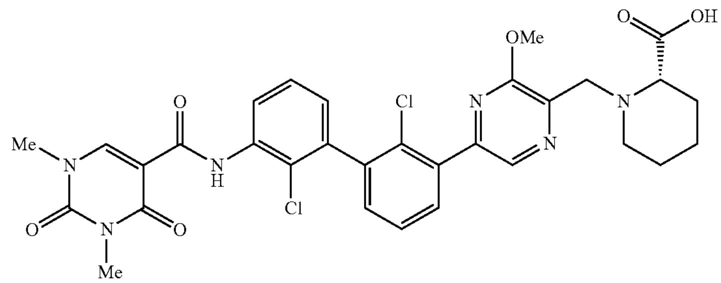 [SMILES: COc1nc(-c2cccc(-c3cccc(NC(=O)c4cn(C)c(=O)n(C)c4=O)c3Cl)c2Cl)cnc1CN1CCCC[C@H]1C(=O)O] | +++ |
| 1.092 | 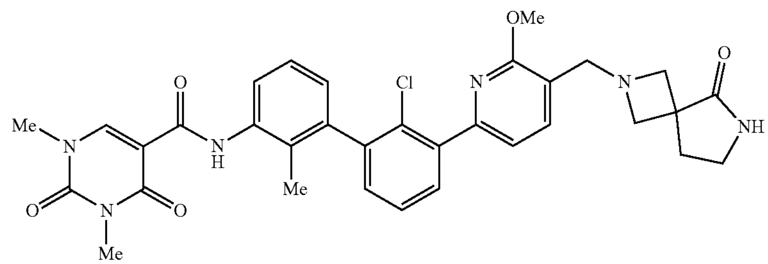 [SMILES: COc1nc(-c2cccc(-c3cccc(NC(=O)c4cn(C)c(=O)n(C)c4=O)c3C)c2Cl)ccc1CN1CC2(CCNC2=O)C1] | +++ |
| 1.093 | 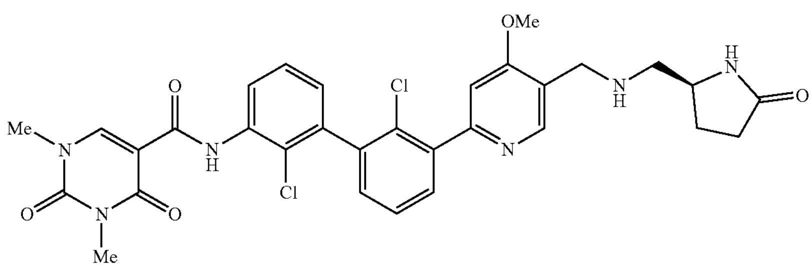 | +++ |
| 1.094 | 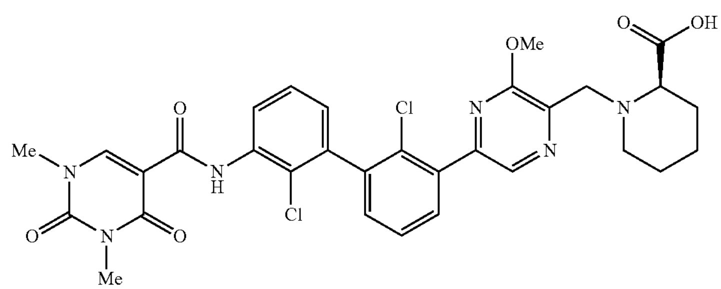 [SMILES: COc1nc(-c2cccc(-c3cccc(NC(=O)c4cn(C)c(=O)n(C)c4=O)c3Cl)c2Cl)cnc1CN1CCCC[C@@H]1C(=O)O] | +++ |
| 1.095 | 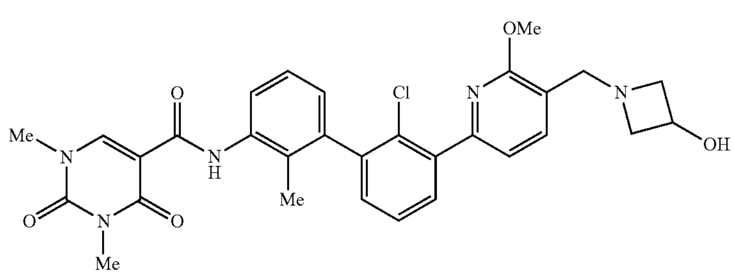 [SMILES: COc1nc(-c2cccc(-c3cccc(NC(=O)c4cn(C)c(=O)n(C)c4=O)c3C)c2Cl)ccc1CN1CC(O)C1] | +++ |

TABLE 1-continued

| Compound | Structure | ELISA IC$_{50}$ |
|---|---|---|
| 1.096 | 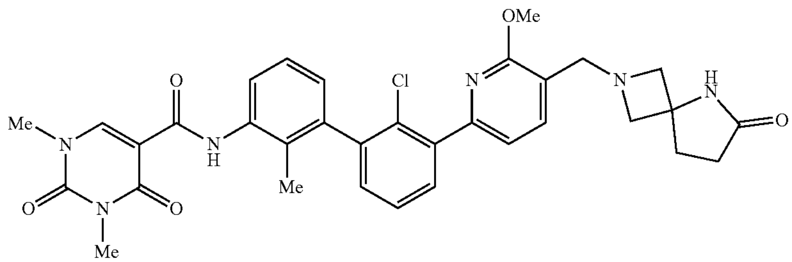 [SMILES: COc1nc(-c2cccc(-c3cccc(NC(=O)c4cn(C)c(=O)n(C)c4=O)c3C)c2Cl)ccc1CN1CC2(CCC(=O)N2)C1] | +++ |
| 1.097 | 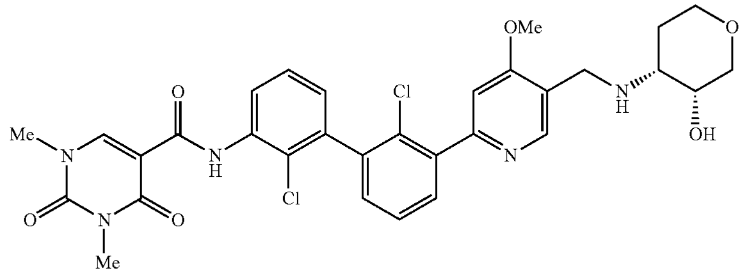 [SMILES: COc1cc(-c2cccc(-c3cccc(NC(=O)c4cn(C)c(=O)n(C)c4=O)c3Cl)c2Cl)ncc1CN[C@@H]1CCOC[C@@H]1O] | +++ |
| 1.098 | 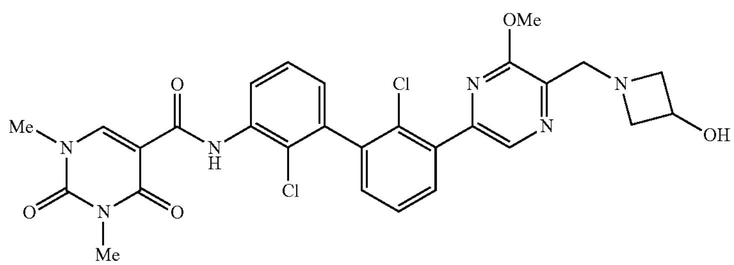 [SMILES: COc1nc(-c2cccc(-c3cccc(NC(=O)c4cn(C)c(=O)n(C)c4=O)c3Cl)c2Cl)cnc1CN1CC(O)C1] | +++ |
| 1.099 | 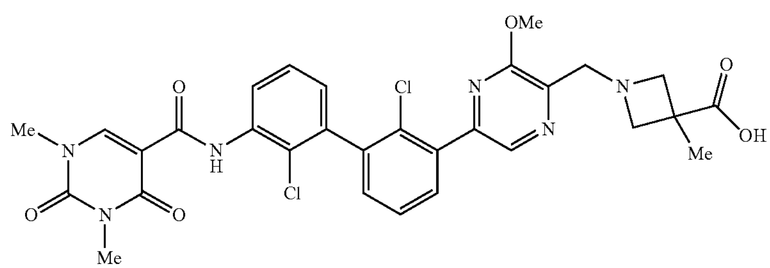 [SMILES: COc1nc(-c2cccc(-c3cccc(NC(=O)c4cn(C)c(=O)n(C)c4=O)c3Cl)c2Cl)cnc1CN1CC(C)(C(=O)O)C1] | +++ |
| 1.100 | 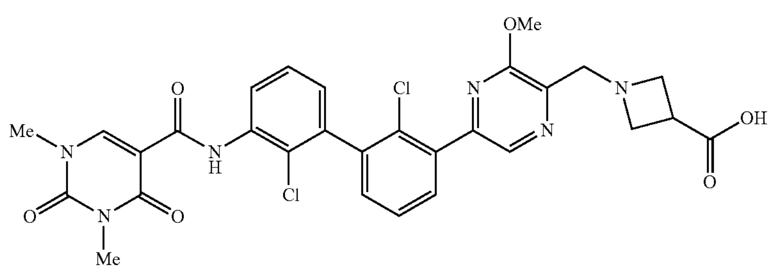 [SMILES: COc1nc(-c2cccc(-c3cccc(NC(=O)c4cn(C)c(=O)n(C)c4=O)c3Cl)c2Cl)cnc1CN1CC(C(=O)O)C1] | +++ |
| 1.101 | 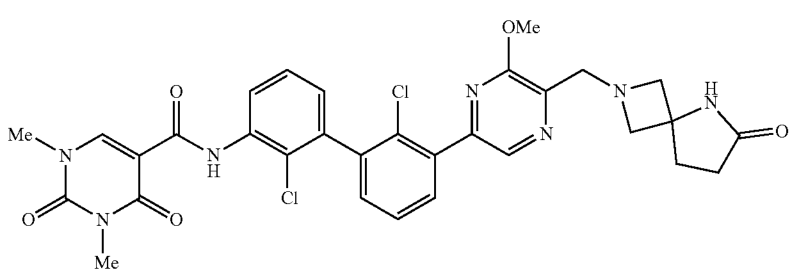 [SMILES: COc1nc(-c2cccc(-c3cccc(NC(=O)c4cn(C)c(=O)n(C)c4=O)c3Cl)c2Cl)cnc1CN1CC2(CCC(=O)N2)C1] | +++ |

TABLE 1-continued

| Compound | Structure | ELISA IC$_{50}$ |
|---|---|---|
| 1.102 | 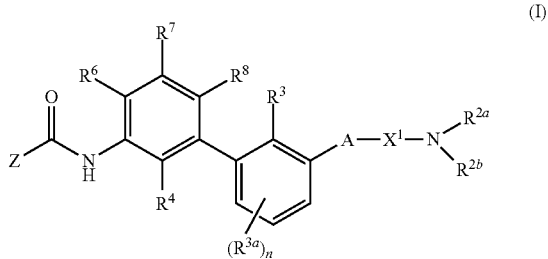 | +++ |

Particular embodiments of this invention are described herein, including the best mode known to the inventors for carrying out the invention. Upon reading the foregoing, description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

What is claimed is:

1. A compound of Formula (I):

(I)

or a pharmaceutically acceptable salt, or a stereoisomer thereof, wherein:

A is a 5- to 10-membered heteroaryl group which is unsubstituted or substituted with from one to five members independently selected from the group consisting of halogen, $C_{1-3}$ alkyl, $C_{1-3}$ haloalkyl, $C_{1-3}$ alkoxy, $C_{1-3}$ haloalkoxy and CN;

$X^1$ is $C_{1-3}$ alkylene, which is unsubstituted or substituted with one or two members independently selected from the group consisting of $C_{1-2}$ alkyl and $CO_2H$;

$R^{2a}$ and $R^{2b}$ are each independently selected from the group consisting of H, $C_{1-8}$ alkyl, $C_{1-8}$ haloalkyl, —Y, —$X^2$—$CO_2R^a$, —$X^2$—$OR^a$, —$X^2$—$NR^aR^b$, —$X^2$—C(O)$NR^aR^b$, —$X^2$—$SO_2R^a$, —$X^2$—$SO_2NR^aR^b$, —$X^2$—$SO_3R^a$ and —$X^2$—Y, wherein each $X^2$ is $C_{1-6}$ alkylene, any $C_{1-8}$ alkyl or $C_{1-6}$ alkylene is unsubstituted or substituted with one or two members independently selected from the group consisting of OH, $SO_2NH_2$, C(O)$NH_2$, C(O)NHOH, $PO_3H_2$, $CO_2$—$C_{1-8}$ alkyl and $CO_2H$, and each Y is selected from the group consisting of $C_{3-6}$ cycloalkyl, $C_{4-8}$ heterocyclyl and 5- to 6-membered heteroaryl, each of which is unsubstituted or substituted with one to four substituents independently selected from the group consisting of oxo, OH, $C_{1-4}$ alkyl, $C_{1-4}$ haloalkyl, $C_{1-4}$ hydroxyalkyl, $C_{1-4}$ alkoxy, $C_{1-4}$ haloalkoxy, $C_{1-4}$ hydroxyalkoxy, $SO_2NH_2$, C(O)$NH_2$, C(O)NHOH, $PO_3H_2$, $CO_2C_{1-8}$ alkyl, $SO_3H$ and $CO_2H$;

or $R^{2a}$ and $R^{2b}$ are combined to form a 4- to 9-membered ring or spirocyclic ring, having from zero to two additional heteroatom ring vertices selected from O, N or S;

wherein the ring formed by combining $R^{2a}$ and $R^{2b}$, is unsubstituted or substituted with 1 to 4 substituents independently selected from the group consisting of oxo, $C_{1-8}$ alkyl, $C_{1-8}$ haloalkyl, $C_{1-8}$ hydroxyalkyl, —$X^3$—$CO_2R_a$, —$X^3$—$OR^a$, —$X^3$—$NR^aR^b$, —$X^3$—C(O)$NR^aR^b$, —$X^3$—$SO_2R^a$, —$X^3$—$SO_2NR^aR^b$, and —$X^3$—$SO_3R^a$; wherein $X^3$ is a bond or $C_{1-6}$ alkylene;

$R^3$ and $R^4$ are each independently selected from the group consisting of F, Cl, CN, $CH_3$, $OCH_3$, $CH_2CH_3$ and $CF_3$;

the subscript n is 0, 1, 2 or 3;

each $R^{3'}$ is independently selected from the group consisting of H, F, Cl, $C_{1-3}$ alkyl, $C_{1-3}$ alkoxy, $C_{1-3}$ haloalkyl, $C_{1-3}$ haloalkoxy, $C_{2-3}$ alkenyl and CN;

$R^6$, $R^7$ and $R^8$ are each independently selected from the group consisting of H, F, Cl, CN, $CH_3$, $OCH_3$, $CH_2CH_3$ and $CF_3$;

Z is a 6-membered monocyclic non-aromatic heterocyclic ring, optionally substituted with one or two oxo groups and optionally substituted with up to four $R^a$ and/or $R^b$;

each $R^a$ is independently selected from the group consisting of H, $C_{1-6}$ alkyl, $C_{3-6}$ cycloalkyl, $C_{1-6}$ haloalkyl, $C_{1-6}$ hydroxyalkyl, $C_{1-6}$ alkylene-$CO_2H$, and $C_{1-6}$ alkylene-$SO_3H$;

each $R^b$ is independently selected from the group consisting of H, $C_{1-6}$ alkyl, $C_{3-6}$ cycloalkyl, $C_{1-6}$ haloalkyl, $C_{1-6}$ hydroxyalkyl, $C_{1-6}$ alkylene-$CO_2H$, and $C_{1-6}$ alkylene-$SO_3H$, each of which is unsubstituted or substituted with one or two members independently selected from OH, $SO_2NH_2$, C(O)$NH_2$, C(O)NHOH, $PO_3H_2$, $CO_2C_{1-8}$ alkyl and $CO_2H$;

and $R^a$ and $R^b$, when attached to the same nitrogen atom, are optionally combined to form a 4- to 8-membered ring or spirocyclic ring, which is unsubstituted or substituted with halogen, OH, $SO_2NH_2$, $C(O)NH_2$, $C(O)NHOH$, $PO_3H_2$, $CO_2C_{1-8}$ alkyl or $CO_2H$.

2. The compound of claim 1, or a pharmaceutically acceptable salt thereof, having formula (Ia):

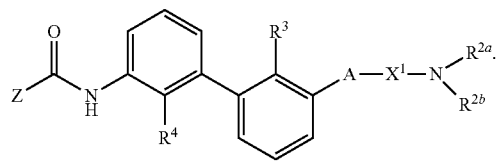
(Ia)

3. The compound of claim 1, or a pharmaceutically acceptable salt thereof, wherein A is a 5- or 6-membered heteroaryl group which is unsubstituted or substituted with from one to three members independently selected from the group consisting of halogen, $C_{1-3}$ alkyl, $C_{1-3}$ haloalkyl, $C_{1-3}$ alkoxy, and CN.

4. The compound of claim 1, or a pharmaceutically acceptable salt thereof, wherein A is a 6-membered heteroaryl group which is unsubstituted or substituted with from one to three members independently selected from the group consisting of halogen, $C_{1-3}$ alkyl, $C_{1-3}$ haloalkyl, $C_{1-3}$ alkoxy, and CN.

5. The compound of claim 1, or a pharmaceutically acceptable salt thereof, having formula (Ib):

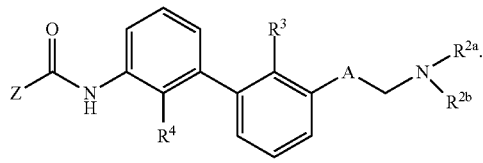
(Ib)

6. The compound of claim 1, or a pharmaceutically acceptable salt thereof, wherein A is unsubstituted or substituted with one or two members independently selected from the group consisting of $OCH_3$ and F.

7. The compound of claim 1, or a pharmaceutically acceptable salt thereof, wherein A is a 6-membered heteroaryl selected from the group consisting of pyridine, pyrimidine, pyrazine and 1,2,4-triazine, each of which is unsubstituted or substituted with one or two members independently selected from the group consisting of $OCH_3$ and F.

8. The compound of claim 1, or a pharmaceutically acceptable salt thereof, wherein Z is a 6-membered monocyclic non-aromatic heterocyclic ring having a formula selected from the group consisting of:

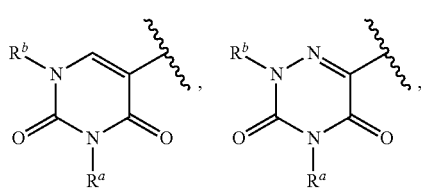

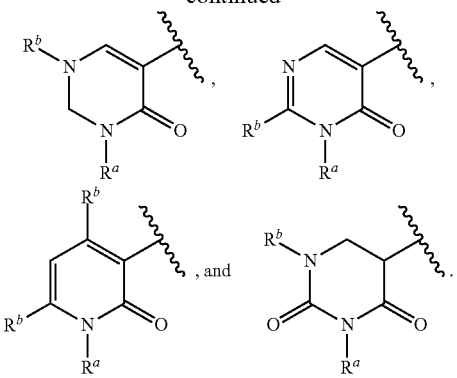

9. The compound of claim 1, or a pharmaceutically acceptable salt thereof, wherein Z is a 6-membered monocyclic non-aromatic heterocyclic ring selected from the group consisting of piperidinyl, morpholinyl, and tetrahydropyranyl each of which is optionally substituted with up to four $R^a$ and/or $R^b$.

10. The compound of claim 1, or a pharmaceutically acceptable salt thereof, wherein $—N(R^{2a})(R^{2b})$ is selected from the group consisting of:

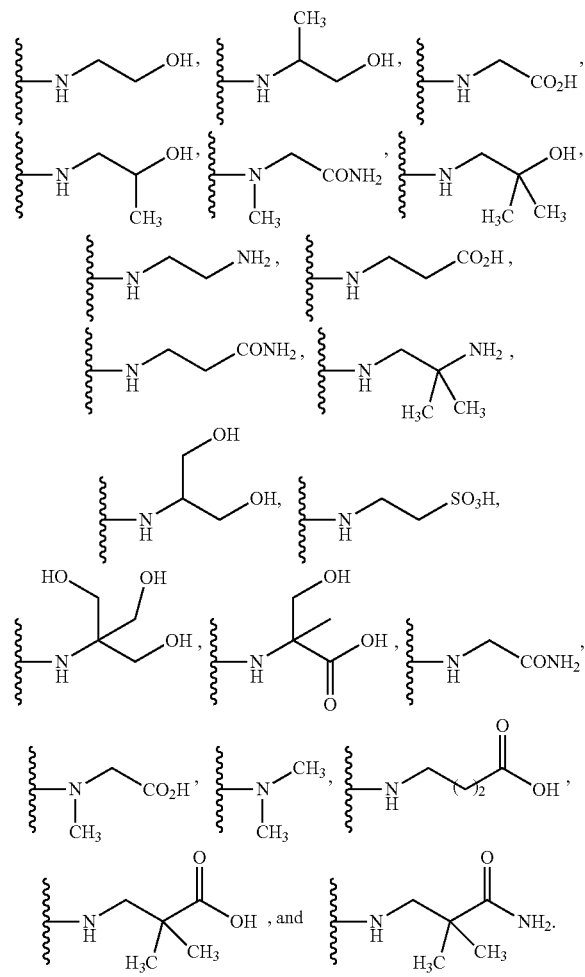

11. The compound of claim 1, or a pharmaceutically acceptable salt thereof, wherein —N(R$^{2a}$)(R$^{2b}$) is selected from the group consisting of:

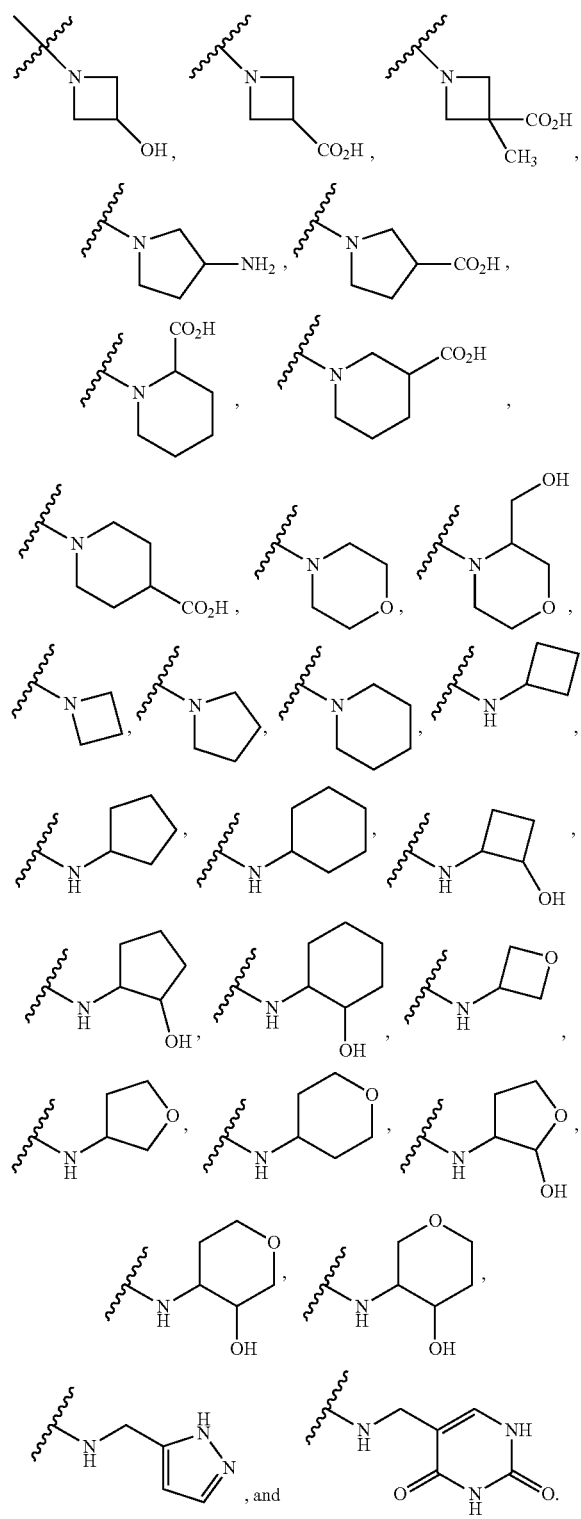

12. The compound of claim 1, or a pharmaceutically acceptable salt thereof, wherein —N(R$^{2a}$)(R$^{2b}$) is selected from the group consisting of:

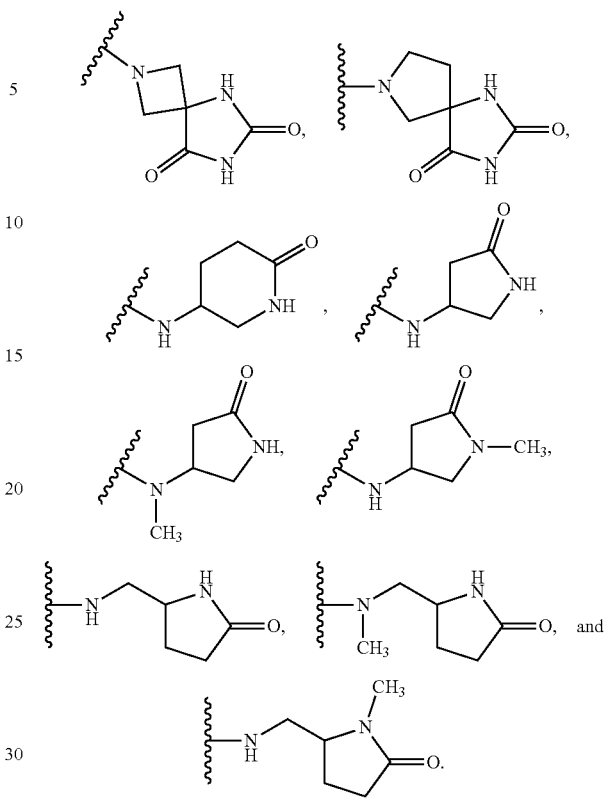

13. The compound of claim 1, or a pharmaceutically acceptable salt thereof, wherein the compound is an optically pure or enriched stereoisomer.

14. The compound of claim 1, or a pharmaceutically acceptable salt thereof, wherein Y is selected from the group consisting of C$_{3-6}$ cycloalkyl and C$_{4-8}$ heterocyclyl, each of which is unsubstituted or substituted with one to four substituents independently selected from the group consisting of oxo, OH, C$_{1-4}$ alkyl, C$_{1-4}$haloalkyl, C$_{1-4}$ hydroxyalkyl, C$_{1-4}$alkoxy, C$_{1-4}$haloalkoxy, C$_{1-4}$ hydroxyalkoxy, SO$_2$NH$_2$, C(O)NH$_2$, C(O)NHOH, PO$_3$H$_2$, CO$_2$C$_{1-8}$alkyl, SO$_3$H and CO$_2$H.

15. The compound of claim 1, or a pharmaceutically acceptable salt thereof, wherein Z is a 6-membered monocyclic non-aromatic heterocyclic ring, optionally substituted with one or two oxo groups and optionally substituted with one R$^a$ and/or one R$^b$.

16. The compound of claim 1, or a pharmaceutically acceptable salt thereof, wherein Z is a 6-membered monocyclic non-aromatic heterocyclic ring, optionally substituted with one or two oxo groups and optionally substituted with one R$^a$ and/or one R$^b$; and each of R$^6$, R$^7$ and R$^8$ is H.

17. The compound of claim 1, or a pharmaceutically acceptable salt thereof, wherein Z is a 6-membered monocyclic non-aromatic heterocyclic ring selected from the group consisting of piperidinyl, morpholinyl, and tetrahydropyranyl, optionally substituted with one or two oxo groups and optionally substituted with one R$^a$ and/or one R$^b$.

18. The compound of claim 1, wherein said compound is selected from the group consisting of

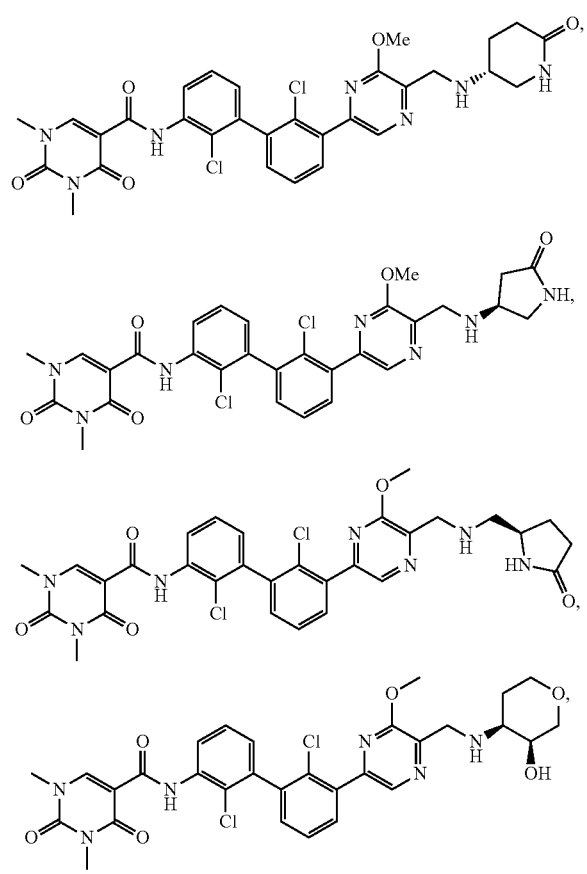

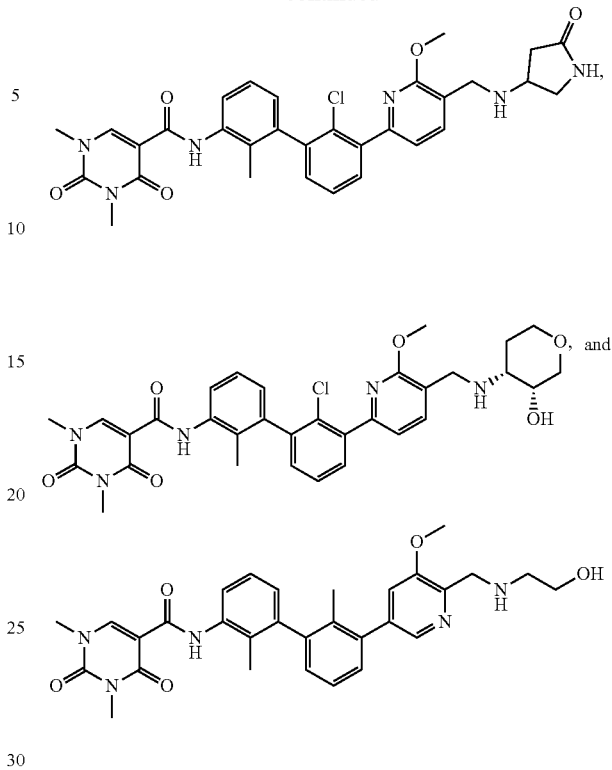

or a pharmaceutically acceptable salt thereof.

19. A pharmaceutical composition comprising a compound of claim 1, or a pharmaceutically acceptable salt thereof, and a pharmaceutically acceptable excipient.

20. The compound of claim 1, having the formula

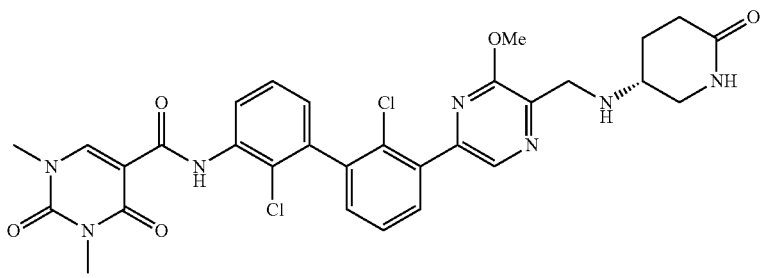 [SMILES: COc1nc(-c2cccc(-c3cccc(NC(=O)c4cn(C)c(=O)n(C)c4=O)c3Cl)c2Cl)cnc1CN[C@@H]1CCC(=O)NC1]

or a pharmaceutically acceptable salt thereof.

21. The compound of claim 1, having the formula

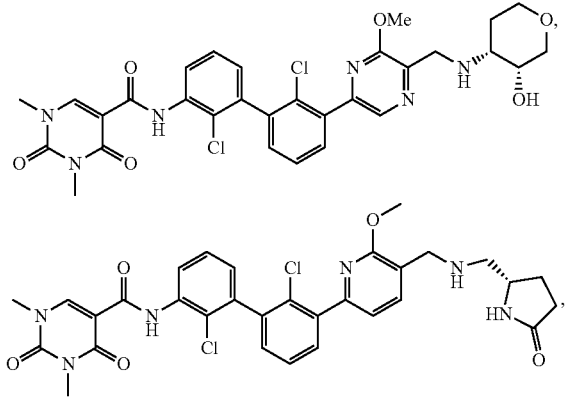

or a pharmaceutically acceptable salt thereof.

22. The compound of claim 1, having the formula

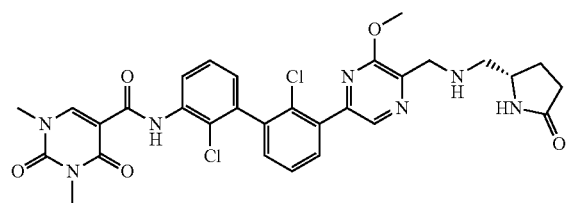 [SMILES: COc1nc(-c2cccc(-c3cccc(NC(=O)c4cn(C)c(=O)n(C)c4=O)c3Cl)c2Cl)cnc1CNC[C@@H]1CCC(=O)N1]

or a pharmaceutically acceptable salt thereof.

23. The compound of claim 1, having the formula

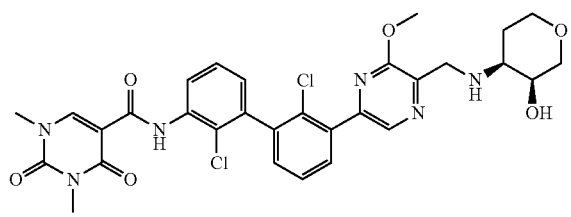 [SMILES: COc1nc(-c2cccc(-c3cccc(NC(=O)c4cn(C)c(=O)n(C)c4=O)c3Cl)c2Cl)cnc1CN[C@H]1CCOC[C@H]1O]

or a pharmaceutically acceptable salt thereof.

24. The compound of claim 1, having the formula

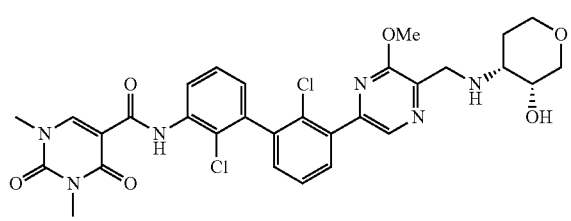 [SMILES: COc1nc(-c2cccc(-c3cccc(NC(=O)c4cn(C)c(=O)n(C)c4=O)c3Cl)c2Cl)cnc1CN[C@@H]1CCOC[C@@H]1O]

or a pharmaceutically acceptable salt thereof.

25. The compound of claim 1, having the formula

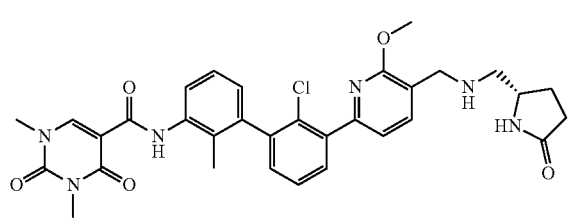 [SMILES: COc1nc(-c2cccc(-c3cccc(NC(=O)c4cn(C)c(=O)n(C)c4=O)c3C)c2Cl)ccc1CNC[C@@H]1CCC(=O)N1]

or a pharmaceutically acceptable salt thereof.

26. The compound of claim 1, having the formula

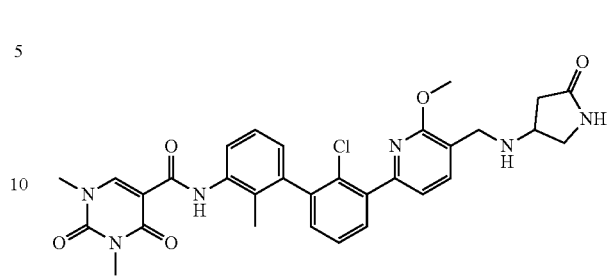

or a pharmaceutically acceptable salt thereof.

27. The compound of claim 1, having the formula

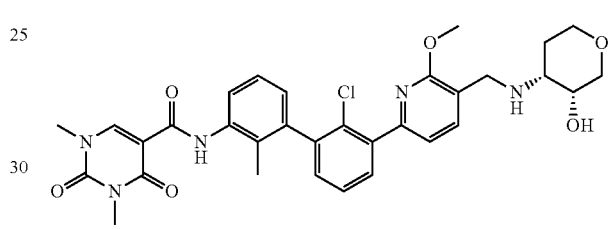

or a pharmaceutically acceptable salt thereof.

28. The compound of claim 1, having the formula

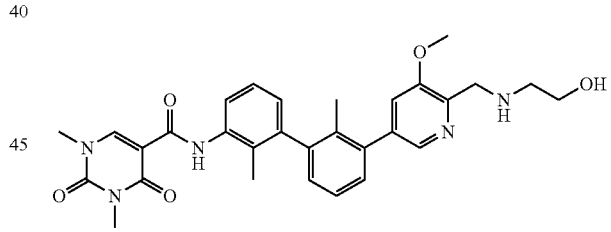

or a pharmaceutically acceptable salt thereof.

* * * * *